US012692288B2

(12) United States Patent
Miksztal et al.

(10) Patent No.: US 12,692,288 B2
(45) Date of Patent: Jul. 28, 2026

(54) CRYSTALLINE AND LIQUID CRYSTALLINE 25-HYDROXY-CHOLEST-5-EN-3-SULFATE SODIUM AND METHODS FOR PREPARING SAME

(71) Applicant: Medicis Pharmaceutical Corporation, Bridgewater, NJ (US)

(72) Inventors: Andrew R. Miksztal, Palo Alto, CA (US); Shawn Johnstone, Saint-Lazare (CA); Michael Holtz-Mulholland, Lachine (CA); Flavio Lopez, Florence, SC (US); Howard Sard, Arlington, MA (US); Jie Li, Winchester, MA (US); Mario Gonzalez, Winchester, MA (US); Stephan D. Parent, West Lafayette, IN (US); Travis Lee Houston, Lafayette, IN (US); Robert Wenslow, Cranbury, NJ (US)

(73) Assignee: Medicis Pharmaceutical Corporation, Bridgewater, NJ (US)

( * ) Notice: Subject to any disclaimer, the term of this patent is extended or adjusted under 35 U.S.C. 154(b) by 797 days.

(21) Appl. No.: 17/783,248

(22) PCT Filed: Dec. 23, 2020

(86) PCT No.: PCT/US2020/066947
§ 371 (c)(1),
(2) Date: Jun. 7, 2022

(87) PCT Pub. No.: WO2021/133976
PCT Pub. Date: Jul. 1, 2021

(65) Prior Publication Data
US 2023/0056273 A1      Feb. 23, 2023

Related U.S. Application Data

(60) Provisional application No. 62/954,279, filed on Dec. 27, 2019.

(51) Int. Cl.
| | |
|---|---|
| *C07J 31/00* | (2006.01) |
| *A61K 31/56* | (2006.01) |
| *A61P 1/16* | (2006.01) |
| *A61P 3/00* | (2006.01) |
| *A61P 3/06* | (2006.01) |

(52) U.S. Cl.
CPC ......... *C07J 31/006* (2013.01); *C07B 2200/13* (2013.01)

(58) Field of Classification Search
CPC ...... C07J 31/006; C07J 31/00; C07B 2200/13
See application file for complete search history.

(56) References Cited

U.S. PATENT DOCUMENTS

| | | | |
|---|---|---|---|
| 3,868,396 | A | 2/1975 | Ikekawa et al. |
| 4,046,760 | A | 9/1977 | Jones et al. |
| 4,427,668 | A | 1/1984 | Javitt |
| 4,743,597 | A | 5/1988 | Javitt et al. |
| 6,923,988 | B2 | 8/2005 | Patel et al. |
| 7,524,493 | B2 | 4/2009 | Flugelman et al. |
| 8,399,441 | B2 | 3/2013 | Ren et al. |
| 8,697,678 | B2 | 4/2014 | Goodchild et al. |
| 8,975,245 | B2 | 3/2015 | Goodchild et al. |
| 9,034,859 | B2 | 5/2015 | Ren et al. |
| 9,321,802 | B2 | 4/2016 | Ren et al. |
| 9,480,692 | B2 | 11/2016 | Ren |
| 9,757,391 | B2 | 9/2017 | Goodchild et al. |
| 10,144,759 | B2 | 12/2018 | Ren et al. |
| 10,272,097 | B2 | 4/2019 | Ren et al. |
| 10,786,517 | B2 | 9/2020 | Ren et al. |
| 10,844,089 | B2 | 11/2020 | Ren et al. |
| 11,384,115 | B2 | 7/2022 | Ren et al. |
| 11,406,646 | B2 | 8/2022 | Ren et al. |
| 11,612,609 | B2 | 3/2023 | Ren et al. |
| 2002/0107233 | A1 | 8/2002 | Liao et al. |
| 2003/0077297 | A1 | 4/2003 | Chen et al. |
| 2007/0197484 | A1 | 8/2007 | Song et al. |

(Continued)

FOREIGN PATENT DOCUMENTS

| | | |
|---|---|---|
| CA | 3165765 | 7/2021 |
| EP | 0005653 | 11/1979 |
| EP | 3639828 | 4/2020 |
| GB | 1592170 | 7/1981 |
| WO | WO 1995015165 | 6/1995 |
| WO | WO 2006047022 | 5/2006 |
| WO | WO 2013036835 | 3/2013 |
| WO | WO 2013154752 | 10/2013 |
| WO | WO 2015100312 | 7/2015 |
| WO | WO 2016057713 | 4/2016 |
| WO | WO 2016058000 | 4/2016 |

(Continued)

OTHER PUBLICATIONS

PubChem, Larsucosterol, CID 11583880, entered 2006, https://pubchem.ncbi.nlm.nih.gov/compound/11583880 (Year: 2006).*

(Continued)

*Primary Examiner* — Bruck Kifle
*Assistant Examiner* — Kevin S Martin
(74) *Attorney, Agent, or Firm* — Morgan, Lewis & Bockius LLP

(57) ABSTRACT

Crystalline and liquid crystalline forms of 25HC3S sodium are described herein. The disclosure includes Forms I, II, III, V, IX, XI, and XIII of 25HC3S sodium and combinations thereof. Pharmaceutical formulations of said forms, or combinations thereof, and methods of treating or preventing disease such as hypercholesterolemia, hypertriglyceridemia, and conditions related to fat accumulation and inflammation (e.g., non-alcoholic fatty liver disease (NAFLD), non-alcoholic steatohepatitis (NASH), alcoholic hepatitis, acute kidney injury (AKI), psoriasis, and atherosclerosis) are further disclosed herein. Methods for preparing 25HC3S are also provided.

20 Claims, 58 Drawing Sheets

(56) References Cited

U.S. PATENT DOCUMENTS

| | | |
|---|---|---|
| 2007/0275939 A1 | 11/2007 | Ren et al. |
| 2009/0143279 A1 | 6/2009 | Mootha et al. |
| 2010/0273761 A1 | 10/2010 | Ren et al. |
| 2011/0160174 A1 | 6/2011 | Song et al. |
| 2012/0172324 A1 | 7/2012 | Liu et al. |
| 2012/0264816 A1 | 10/2012 | Ren et al. |
| 2013/0143854 A1 | 6/2013 | Ren et al. |
| 2015/0072962 A1 | 3/2015 | Ren |
| 2015/0320769 A1 | 11/2015 | Ren |
| 2016/0264615 A1 | 9/2016 | Ren et al. |
| 2016/0355544 A1 | 12/2016 | Ren |
| 2017/0014429 A1 | 1/2017 | Ren et al. |
| 2017/0136038 A1 | 5/2017 | Ren |
| 2017/0252355 A1 | 9/2017 | Ren et al. |
| 2018/0127457 A1 | 5/2018 | Ren |
| 2018/0346509 A9 | 12/2018 | Ren et al. |
| 2019/0083509 A1 | 3/2019 | Ren et al. |
| 2019/0135856 A1 | 5/2019 | Ren |
| 2019/0169225 A1 | 6/2019 | Ren et al. |
| 2019/0269695 A1 | 9/2019 | Ren et al. |
| 2019/0350945 A1 | 11/2019 | Ren et al. |
| 2019/0374554 A1 | 12/2019 | Ren et al. |
| 2020/0009158 A1 | 1/2020 | Ren |
| 2020/0138831 A1 | 5/2020 | Ren et al. |
| 2020/0157140 A1 | 5/2020 | Ren |
| 2020/0222430 A1 | 7/2020 | Miksztal et al. |
| 2021/0046091 A1 | 2/2021 | Ren et al. |
| 2021/0147469 A1 | 5/2021 | Ren et al. |
| 2021/0161913 A1 | 6/2021 | Ren et al. |
| 2021/0169898 A1 | 6/2021 | Ren et al. |
| 2021/0169902 A1 | 6/2021 | Ren et al. |
| 2021/0238219 A1 | 8/2021 | Ren |
| 2022/0054505 A1 | 2/2022 | Ren |
| 2022/0175798 A1 | 6/2022 | Miksztal et al. |
| 2022/0378802 A1 | 12/2022 | Lin et al. |
| 2023/0047788 A1 | 2/2023 | Ren et al. |
| 2023/0056273 A1 | 2/2023 | Miksztal et al. |
| 2023/0141965 A1 | 5/2023 | Ren et al. |
| 2023/0181601 A1 | 6/2023 | Lin |
| 2023/0181602 A1 | 6/2023 | Lin et al. |
| 2023/0218639 A1 | 7/2023 | Ren et al. |
| 2023/0233580 A1 | 7/2023 | Ren et al. |
| 2023/0285416 A1 | 9/2023 | Ren et al. |
| 2023/0293551 A1 | 9/2023 | Ren et al. |
| 2023/0310458 A1 | 10/2023 | Ren et al. |
| 2023/0372361 A1 | 11/2023 | Ren et al. |

FOREIGN PATENT DOCUMENTS

| | | | | |
|---|---|---|---|---|
| WO | WO 2017218379 | 12/2017 | | |
| WO | WO-2018026837 A1 * | 2/2018 | ............. | A61K 47/32 |
| WO | WO 2020072656 | 4/2020 | | |
| WO | WO 2020150136 | 7/2020 | | |
| WO | WO 2021067297 | 4/2021 | | |
| WO | WO 2021133796 | 7/2021 | | |
| WO | WO 2021154796 | 8/2021 | | |
| WO | WO 2022272103 | 12/2022 | | |
| WO | WO 2024136884 | 6/2024 | | |
| WO | WO 2024138203 | 6/2024 | | |

OTHER PUBLICATIONS

Itoh, et al (1999) "Synthesis of 6- and 7-hydroxyestradiol 17-sulfates: The potential metabolites of estradiol 17-sulfate by female rat liver microsomes"; Steroids 64; pp. 363-370.

Li et al. (1999) "Sterol synthesis. Preparation and characterization of fluorinated and deuterated analogs of oxygenated derivatives of cholesterol"; Chemistry and Physics of Lipids 99; pp. 33-71.

Ogawa et al., "A facile synthesis of C-24 and C-25 oxysterols by in situ generated ethyl(trifluoromethyl)dioxirane", Steroids, 2009, pp. 81-87, vol. 74, Elsevier.

Pascher et al, (1977) "The Crystal Structure of Sodium Cholesteryl Sulfate Dihydrate"; Acta Chemica Scandinavica A, vol. 31, No. 9; p. 767-774.

Pierce and Hilinski, Chemoselective Hydroxylation of Aliphatic sp3 C—H Bonds Using a Ketone Catalyst and Aqueous H2O2, Org. Lett., 2014, 16, 6504-6507.

Ren S., et al., "Sulfated oxsterol, 25HC3S, is a potent regulator of lipid metabolism in human hepatocytes", ScienceDirect, BBRC, 360 (2007) pp. 802-808.

Sobel et al. 'Steryl Sulfates. I. Preparation and Properties'. Journal of the American Chemical Society, vol. 63, No. 5, May 1, 1941 (May 1, 1941). p. 1259-1261.

Taber, D. F. et al. (2013) Simplified Preparation of Dimethyldioxirane (DMDO), Org. Synth., , 90, 350-357.

Zou, et al., (2013) "Enhanced Reactivity in Dioxirane C—H Oxidations via Strain Release: A Computational and Experimental Study", J. Org. Chem., 78; pp. 4037-4048.

Akriviadis et al., "Pentoxifylline Improves Short-term Survival in Severe Acute Alcoholic Hepatitis: A Double-Blind, Placebo-Controlled Trial," Gastroenerology, 119: 1637-1648 (2000).

Argemi et al. (2019) "Defective HNF4alpha-dependent gene expression as a driver of hepatocellular failure in alcoholic hepatitis"; Nature Communications, 10 (3126); pp. 1-19.

Arora, et al.(2011) "Acute renal dysfunction in patients with alcoholic hepatitis"; World J Hepatol 3(5): pp. 121-124.

Barve et al., "Development, Prevention, and Treatment of Alcohol-Induced Organ Injury: The Role of Nutrition," Curr Rev., 38:289-302 (2017).

Basra and Anand (2011) "Definition, epidemiology and magnitude of alcoholic hepatitis"; World J Hepatol. 3(5); pp. 108-113.

Bataller et al., "Alcohol-Associated Hepatitis," N Engl J Med, 387:2436-2448 (2022).

Bentley, Ortner NJ. 2020 U.S. organ and tissue transplant: cost estimates, discussion, and emerging issues. Feb. 18, 2020. Accessed Apr. 9, 2022. https://www.milliman.com/-/media/milliman/pdfs/articles/2020-US-organ-tissue-transplants.ashxtorn.

Bittermann et al., "Rising Trend in Waitlisting for Alcoholic Hepatitis With More Favorable Outcomes Than Other High Model for End-stage Liver Disease in the Current Era," Transplantation, 10.1097/TP.0000000000004049. doi:10.1097/TP.0000000000004049 (2022) (18 pages).

Bittermann et al., "Trends in Liver Transplantation for Acute Alcohol-Associated Hepatitis During the COVID-19 Pandemic in the US," JAMA Network Open., 4:e2118713. doi:10.1001/jamanetworkopen.2021.18713 (2021) (4 pages).

Cal, et al.(2008) "Use of cyclodextrins in topical formulations: practical aspects"; Eur J Pharm Biopharm 68(3); pp. 467-478.

Cambridge MedChem Consulting, Formulations, 5 pages (2012).

Carpenter et al., "Safety of Parenteral Hydroxypropyl β-Cyclodextrin," Journal of Pharmaceutical Sciences, 84(2):222-225 (1995).

Chayanupatkul and Liangpunsakul (2014) "Alcoholic hepatitis: a comprehensive review of pathogenesis and treatment"; World J Gastroenterol. 20(20); pp. 6279-6286.

Cheng et al., "Targeting epigenetic regulators for cancer therapy:mechanisms and advances in clinical trials", Signal Transduct Target Ther., 4:62 (2019).

Cholankeril et al., "Alcoholic Liver Disease Replaces Hepatitis C Virus Infection as the Leading Indication for Liver Transplantation in the United States," Clin Gastroenterol Hepatol, 16:1356-1358 (2018).

Cotter et al., "Liver transplantation for alcoholic hepatitis in the United States: Excellent outcomes with profound temporal and geographic variation in frequency," Am J Transplant, 21:1039-1055 (2021).

Crabb DW, et al (2016) "Standard Definitions and Common Data Elements for Clinical Trials in Patients With Alcoholic Hepatitis: Recommendation From the NIAAA Alcoholic Hepatitis Consortia"; Gastroenterology.150(4); pp. 785-790.

Crabb DW, et al (2020) "Diagnosis and Treatment of Alcohol-Associated Liver Diseases: 2019 Practice Guidance from the American Association for the Study of Liver Diseases"; Hepatology 71(1); pp. 306-333.

(56)  References Cited

OTHER PUBLICATIONS

Dao and Rangnekar (2018) "Steroids for Severe Alcoholic Hepatitis: More Risk Than Reward?"; Clin Liver Dis (Hoboken) 12(6); pp. 151-153.

Deutsch et al., "Alcohol-associated liver disease mortality increased from 2017 to 2020 and accelerated during the COVID-19 pandemic," Clin Gastroenterol Hepatology, 20:2142-2144 (2022).

Drinane and Shah (2013) "Alcoholic Hepatitis: Diagnosis and Prognosis"; Clinical Liver Disease, vol. 2, No. 2, pp. 80-83.

Dubuquoy et al., "Progenitor cell expansion and impaired hepatocyte regeneration in explanted livers from alcoholic hepatitis," Gut, 64:1949-1960 (2015).

Duvnjak et al., "Pathogenesis and management issues for non-alcoholic fatty liver disease"; World journal of gastroenterology, 13(34). pp. 4539-4550. 2007.

European Association for the Study of Liver (2012) "EASL Clinical Practical Guidelines: Management of Alcoholic Liver Disease"; Journal of Hepatology vol. 57; pp. 399-420.

European Association for the Study of Liver (2018) "EASL Clinical Practical Guidelines: Management of Alcoholic-Related Liver Disease"; Journal of Hepatology vol. 69; pp. 154-181.

Fuda et al., "Mutational Analysis of Human Hydroxysteroid Sulfotransferase SULT2B1 Isoforms Reveals That Exon 1B of the SULT2B1 Gene Produces Cholesterol Sulfotransferase, whereas Exon 1A Yields Pregnenolone Sulfotransferase", The Journal of Biological Chemistry, Sep. 27, 2002, pp. 36161-36166, vol. 277, No. 39, American Society for Biochemistry and Molecular Biology, Inc.

Fuda et al., "Oxysterols are substrates for cholesterol sulfotransferase", The Journal of Lipid Research, Mar. 2007, pp. 1343-1352, vol. 48, American Society for Biochemistry and Molecular Biology, Inc.

Gawrieh et al., "Randomized trial of anakinra plus zinc vs. prednisone for severe alcohol-associated hepatitis," J Hepatol., 80(5):684-693 (2024).

Geese and Raftogianis, "Biochemical Characterization and Tissue Distribution of Human SULT2B1", Biochemical and Biophysical Research Communications, 2001, pp. 280-289, vol. 288, Academic Press.

Gibney et al., "Epigenetics and gene expression," Heredity (Edinb), 105(1):4-13 (2010).

Gill et al., "Sterol regulators of cholesterol homeostasis and beyond: The oxysterol hypothesis revisited and revised", Progress in Lipid Research, 2008, pp. 391-404, vol. 47, Elsevier.

Ginotra et al. (2004) "Efficient Oxidizing Methods for the Synthesis of Oxandrolone Intermediates"; Chem. Pharm. Bull. 52(8); pp. 989-991.

Gougol et al., "Alcoholic Hepatitis," Clinical Liver Disease, 18(2), 90-95 (2021).

Gould et al., "Hydroxypropyl-beta-cyclodextrin (HP-beta-CD): a toxicology review," Food Chem Toxicol., 43(10):1451-1459 (2005).

Guerra Ruiz et al., "Measurement and clinical usefulness of bilirubin in liver disease," Adv Lab Med., 2:352-361 (2021).

Gustot, et al (2017) "Sepsis in alcohol-related liver disease"; *Journal of Hepatology* vol. 67; pp. 1031-1050.

Habka et al., "Future Economics of Liver Transplantation: A 20-Year Cost Modeling Forecast and the Prospect of Bioengineering Autologous Liver Grafts"; Plos One. 10:e0131764. doi:10.1371/journal.pone.0131764 (2015) (21 pages).

Handy et al., "Epigenetic Modifications Basic Mechanisms and Role in Cardiovascular Disease," Circulation, 123:2145-2156 (2011).

Herman et al., "Epigenetic dysregulation in cardiovascular aging and disease," J Cardiovasc Aging. 2021;1:10. doi:10.20517/jca. 2021.16.

Hoffmann et al., "Are German family practitioners and psychiatrists sufficiently trained to diagnose and treat patients with alcohol problems?," BMC Family Practice, 20:115 (2019) (7 pages).

Hosseini et al., "Alcoholic Hepatitis: A Review," Alcohol and Alcoholism, 54(4):408-416 (2019).

https://exploreahepigenetics.com/ (2023).

Hughes, et al. (2018) "Survival from alcoholic hepatitis has not improved over time"; PLOS One; pp. 1-10.

Irie et al., "Hydroxypropylcyclodextrins in Parenteral Use. II: Effects on Transport and Disposition of Lipids in Rabbit and Humans," Journal of Pharmaceutical Sciences, 81(6):524-528 (1992).

Jiang et al., "Sophocarpine Attenuates LPS-Induced Liver Injury and Improves Survival of Mice through Suppressing Oxidative Stress, Inflammation, and Apoptosis," Mediators Inflamm., 2018:5871431 (12 pages) (2018).

Jiang et al., "The Role of Diverse Liver Cells in Liver Transplantation Tolerance," Front Immunol, 11:1-16 (2020).

Jinjuvadia and Liangpunsakul (2015) "Trends in Alcoholic Hepatitis-related Hospitalizations, Financial Burden, and Mortality in the United States"; J Clin Gastroenterol. 49(6);pp. 506-511.

Johnson, "Managing medicines in alcohol-associated liver disease: a practical review," Aust Prescr., 44:96-106 (2021).

Julien et al., "Effect of increased alcohol consumption during COVID-19 pandemic on alcohol-associated liver disease: A modeling study," Hepatology, 00:1-11 (2022).

Kezer et al., "The Mortality Index for Alcohol-Associated Hepatitis: A Novel Prognostic Score," Mayo Clin Proc., 97(3):480-490 (2022).

Kim and Kim (2014) "Severe alcoholic hepatitis-current concepts, diagnosis and treatment options"; World J Hepatol. 6(10); pp. 688-695.

Kunutsor et al., "Circulating total bilirubin and risk of non-alcoholic fatty liver disease in the PREVEND study: observational findings and a Mendelian randomization study," European Journal of Epidemiology, 35:123-137 (2020).

Kwong et al., "OPTN/SRTR 2021 Annual Data Report: Liver," Am J Transplant., 23(2 Suppl 1):S178-S263 (2023).

Lee et al., "Designing clinical trials to address alcohol use and alcohol-associated liver disease: an expert panel Consensus Statement," Nature Reviews Gastroenterology & Hepatology (2024); 20 pages.

Lee et al., "National Trends and Long-term Outcomes of Liver Transplant for Alcohol-Associated Liver Disease in the United States," JAMA Internal Medicine, 179(3):340-348 (2019).

Lee et al., "Retail Alcohol and Tobacco Sales During COVID-19," Ann Intern Med., 174:1027-1029 (2021).

Lee YC. et al., "Sp1 elements in SULT2B1b promoter and 5'-untranslated region of mRNA: Sp1/Sp2 induction and augmentation by histone deacetylase inhibition"; FEBS Lett. 579:3639-3645, 2005.

Liu et al., "TLR3/4 Signaling is Mediated via the NFκB-CXCR4/7 Pathway in Human Alcoholic Hepatitis and Non Alcoholic Steatohepatitis Which Formed Mallory-Denk Bodies," Exp Mol Pathol., 97(2): 234-240 (2014).

Louvet et al., "Corticosteroids Reduce Risk of Death Within 28 Days for Patients with Severe Alcoholic Hepatitis, Compared With Pentoxifylline or Placebo—a Meta-analysis of Individual Data From Controlled Trials," Gastroenterology, 155:458-468 (2018).

Louvet et al., "The Lille model: a new tool for therapeutic strategy in patients with severe alcoholic hepatitis treated with steroids," Hepatology, 45:1348-1354 (2007).

Lucey, et al (2009) "Alcoholic hepatitis"; N Engl J Med. 360(26); 2758-2769.

Mandrekar et al., "Alcoholic Hepatitis: Translational Approaches to Develop Targeted Therapies," Hepatology, 64(4):1343-1355 (2016).

Marlowe et al (2022) "Prevalence, co-morbidities, and in-hospital mortality of patients hospitalized with alcohol-associated hepatitis in the United States from 2015 to 2019"; *Alcohol Clin Exp Res.*; pp. 1-10.

Marlowe et al., "Alcohol-associated Hepatitis as a Secondary Diagnosis: Comparisons of Medicare Patient Outcomes and Hospital Financial Performance, 2017-2019," JMCP, 29(10-a), p. S80, Abstract (2023).

Marlowe et al., "Alcohol-Associated Hepatitis as a Secondary Diagnosis: Comparisons of Medicare Patient Outcomes and Hospital Financial Performance, 2017-2019," AMCP, Poster (2023).

Marlowe et al., "Epidemic within a pandemic: Alcohol-related hepatitis and COVID-19," Alcohol Clin Exp Res., 47:1883-1889 (2023).

Marlowe et al., "Epidemic within pandemic: Alcohol-related hepatitis and COVID-19," EASL, Abstract (2023).

(56)                References Cited

OTHER PUBLICATIONS

Marlowe et al., "Epidemic within pandemic: Alcohol-related hepatitis and COVID-19," EASL, Poster (2023).

Marlowe et al., "Reporting the cases of alcohol-associated hepatitis using the National Inpatient Sample data"; World J Gastroenterol; 29(10): 1648-1650 (2023).

Marlowe et al., Prevalence, Co-Morbidities And In-Hospital Mortality of Hospitalized Alcohol-Associated Hepatitis In US In 2015-2018. AASLD The Liver Meeting®; Nov. 12-15, 2021.

Marlowe et al., The Inpatient Cost and Utilization Impact of Alcohol-Associated Hepatitis (AH) Among Traditional Medicare Beneficiaries, 2017-2019. AASLD The Liver Meeting®; Nov. 2022.

Marroni et al., "Liver Transplantation and Alcoholic Liver Disease: History, Controversies, and Considerations," World J Gastroenterol., 24(26):2785-2805 (2018).

Mathurin et al., "Trends in the management and burden of alcoholic liver disease," Journal of Hepatology, 62:S38-S46 (2015).

Mazzone et al., "The emerging role of epigenetics in human autoimmune disorders," Clinical Epigenetics, 11:34 (2019) (15 pages).

Michelena et al., "Systemic Inflammatory Response and Serum Lipopolysaccharide Levels Predict Multiple Organ Failure and Death in Alcoholic Hepatitis," Hepatology, 62:762-772 (2015).

Millipore Sigma, "1X Phosphate-Buffered Saline (PBS) Recipe Calculator," https://www.sigmaaldrich.com/US/en/support/calculators-and-apps/1x-phosphate-buffered-saline (2023).

Moon et al., "Alcohol-Associated Liver Disease Before and After COVID-19—An Overview and Call for Ongoing Investigation," Hepatol Commun., 5:1616-1621 (2021).

Morales-Arraez et al., "The MELD Score Is Superior to the Maddrey Discriminant Function Score to Predict Short-Term Mortality in Alcohol-Associated Hepatitis: A Global Study," Am J Gastroenterol., 117(2):301-310 (2022).

Musto et al., "Recovery and outcomes of patients denied early liver transplantation for severe alcohol-associated hepatitis," Hepatology, 75:104-114 (2022).

Nguyen-Khac et al., "Glucocorticoids plus N-Acetylcysteine in Severe Alcoholic Hepatitis," N Engl J Med., 365:1781-1789 (2011).

Nguyen-Louie et al., "Learning and Memory in Adolescent Moderate, Binge, and Extreme-binge Drinkers," Alcohol Clin Exp Res, 40(9):1895-1904 (2016).

Niinep et al., "Repeated Ethanol Exposure Alters DNA Methylation Status and Dynorphin/Kappa-Opioid Receptor Expression in Nucleus Accumbens of Alcohol-Preferring AA Rats," Frontiers in Genetics, vol. 12, Article 750142 (2021); 11 pages.

O'Shea, et al.(2010) "Alcoholic Liver Disease"; Hepatology, vol. 51, No. 1; pp. 307-328.

Owens, et al.(2016) "Pharmacologic Treatment of Alcoholic Hepatitis: Examining Outcomes Based on Disease Severity Stratification"; J Clin Exp Hepatol. 6(4); pp. 275-281.

Parker and McCune (2013) "Diagnosis and treatment of alcoholic hepatitis"; Frontline Gastroenterology; pp. 1-7.

Philips et al., "Severe alcoholic hepatitis: current perspectives," Hepatic Medicine: Evidence and Research, 11:97-108 (2019).

Prado et al., "Alcoholic hepatitis: How far are we and where are we going?," Annals of Hepatology, 15(4):463-473 (2016).

Rutledge et al., "COVID-19 Aftershocks on Alcohol-Associated Liver Disease: An Early Cross-Sectional Report From the U.S. Epicenter," Hepatol Commun., 5:1151-1155 (2021).

Saberi et al., "Current Management of Alcoholic Hepatitis and Future Therapies," J Clin Transl Hepatol, 4(2):113-22 (2016).

Schroepfer, "Oxysterols: Modulators of Cholesterol Metabolism and Other Processes," Physiological Reviews, 80(1): 361-554 (2000).

Sehrawat et al., "The Knowns and Unknowns of Treatment for Alcoholic Hepatitis," Lancet Gastroenterol Hepatol., 5:494-506 (2020).

Serrazina et al., "Shaping new paths in clinical trial design to address alcohol use disorders and alcohol-associated liver disease," Nat. Rev. Gastroenterol. Hepatol. (2024); 2 pages.

Shen et al., "Increased DNA methylation in the livers of patients with alcoholic hepatitis," Exp Mol Pathol., 99(2): 326-329 (2015).

Shipley et al., "Liver transplantation for alcoholic hepatitis," Transl Gastroenterol Hepatol, 5:26 (2020) http://dx.doi.org/10.21037/tgh.2019.11.17.

Shukla, et al.(2013) "Epigenetic Effects of Ethanol on the Liver and Gastrointestinal System"; Alcohol Research: Current Reviews; pp. 47-55.

Singal et al., "ACG Clinical Guideline: Alcoholic Liver Disease," Am J Gastroenterol, 113:175-194 (2018).

Singal et al., "Alcoholic Hepatitis: Current challenges and future directions," Clin Gastroenterol Hepatol, 12:555-564 (2014).

Singal et al., "Diagnosis and Treatment of Alcohol-Associated Liver Disease: A Review," JAMA, 326:165-176 (2021).

Singal et al., "Grand Rounds: Alcoholic Hepatitis," Journal of Hepatology, 69:534-543 (2018).

Singal et al., "Management practices of hepatitis C virus infected alcoholic hepatitis patients: A survey of physicians," World J Gastrointest Pharmacol Ther, 4(2):16-22 (2013).

Sohal et al., "The Pandemic Within the Pandemic Unprecedented Rise in Alcohol-related Hepatitis During the COVID-19 Pandemic," J Clin Gastro., 56;171-175 (2022).

Spahr et al. (2011) "Early liver biopsy, intraparenchymal cholestasis, and prognosis in patients with alcoholic steatohepatitis"; BMC Gastroenterology, 11:115; pp. 2-9.

Sun et al., "The changing epidemiology of liver diseases in Asia," Liver International, 42: 1926-1929 (2022).

Szabo et al., "IL-1 receptor antagonist plus pentoxifylline and zinc for severe alcohol-associated hepatitis," Hepatology. 2022. doi:10.1002/hep.32478.

Tan et al., "Leptin Deficiency contributes to the pathogenesis of alcoholic fatty liver disease in mice", The American Journal of Pathology, 2012, vol. 181, No. 10, pp. 1279-1286 (Year: 2012).

Tapper et al., "Mortality due to cirrhosis and liver cancer in the United States, 1999-2016: observational study," BMJ, 362:1-11 (2018).

Thanda Han et al., "Emerging therapies for alcoholic hepatitis," Clin Liver Dis. 2021;25:603-624.

Thompson, et al (2018) "Mortality and costs associated with alcoholic hepatitis: A claims analysis of a commercially insured population"; Alcohol.71; pp. 57-63.

Thursz et al. (2016) "Treatment of Severe Alcoholic Hepatitis," Gastroenterology, 150(8): 1823-1834.

Thursz, et al. (2015) "Prednisolone or Pentoxifylline for Alcoholic Hepatitis" N Engl J 372(17); pp. 1619-1628.

Tu et al., "Decreased Mortality in Patients with Severe Alcohol-associated Hepatitis (SAH) Treated with Corticosteroids During the COVID Pandemic," AASLD, Abstract 169 (2023) 3 pages.

Tu et al., "Decreased Mortality in Patients with Severe Alcohol-associated Hepatitis (SAH) Treated with Corticosteroids During the COVID Pandemic," AASLD, Oral Session 169 (2023) 18 pages.

Ventura-Cots et al., "Clinical, histological and molecular profiling of different stages of alcohol-related liver disease," Gut. 2022. doi: 10.1136/gutinl-2021-324295.

Vergis et al., "The future of therapy for alcoholic hepatitis—beyond corticosteroids," The Journal of Hepatology, 70:785-787 (2019).

Wang et al., "Concise Clinical Hepatology," pp. 81-82 (2010) with partial English language translation.

You, et al.(2002) "Ethanol Induces Fatty Acid Synthesis Pathways by Activation of Sterol Regulatory Element-binding Protein (SREBP)"; The Journal Of Biological Chemistry, vol. 277, No. 32, pp. 29342-29347.

Zhao, "Dysregulated Epigenetic Modifications in the Pathogenesis of NAFLD-HCC," Adv Exp Med Biol. 2018;1061:79-93. doi: 10.1007/978-981-10-8684-7_7. PMID: 29956208.

Zheng et al., "DNA Methylation in Alcohol Use Disorder," Int. J. Mol. Sci., 24, 130 (2023); 16 pages.

Australian New Zealand Clinical Trials Registry (ANZCTR), "A Multiple Daily Oral Dose Study of DUR-928 in Healthy Volunteers", Trial ID ACTRN 12615000267550, Mar. 20, 2015, web.

Australian New Zealand Clinical Trials Registry (ANZCTR), "A Single Infusion of DUR-928 in Healthy Volunteers", Trial ID ACRTN 12616000856415, Jun. 30, 2016, web.

(56)         References Cited

OTHER PUBLICATIONS

Australian New Zealand Clinical Trials Registry (ANZCTR), "A Single Injection Dose Study of DUR-928 in Patients with Impaired Kidney Function and Healthy Volunteers" Trial ID ACTRN 12616000389404, Jun. 24, 2016, web.

Australian New Zealand Clinical Trials Registry (ANZCTR), "A Single Oral Dose Study of DUR-928 in Nonalcoholic Steatohepatitis (NASH) Patients and Healthy Volunteers", Trial ID ACTRN 12515001355561, Dec. 14, 2015, web.

Australian New Zealand Clinical Trials Registry (ANZCTR), "A Single and Multiple Daily Injection Study of DUR-928 in Healthy Volunteers", Trial ID ACTRN 12615000903583, Aug. 28, 2015, web.

Australian New Zealand Clinical Trials Registry (ANZCTR), "An Intralesional Injection Study of DUR-928 in Psoriasis Patients" Trial ID ACRTN 12616001077459, Aug. 10, 2016, web.

Australian New Zealand Clinical Trials Registry (ANZCTR), "First-in-Human, Single Ascending Oral Dose Study of DV-928 in Healthy Volunteers", Trial ID ACTRN 12614001022651, Sep. 24, 2014, web.

Bai et al., "Oxysterol sulfation by cytosolic sulfotransferase suppresses liver X receptor/sterol regulatory element binding protein-lc signaling pathway and reduces serum and hepatic lipids in mouse models of nonalcoholic fatty liver disease", Metabolism, 2012, pp. 836-845, vol. 61.

Bai et al., "Sulfation of 25-hydroxycholesterol by SULT2B1b decreases cellular lipids via the LXR/SREBP-1c signaling pathway in human aortic endothelial cells"; Atherosclerosis. Feb. 2011; 214(2): 350-356.

Bai et al (2011) "In Vivo Overexpression of Hydroxysteroid Sulfotransferase SULT2B1b in Mice Reduces Hepatic Lipids and Suppresses SREBP Signaling: Further Evidence for Oxysterol Sulfates as Endogenous Regulators of Hepatic Lipid Metabolism"; *Gastroenterology* 140(5); abstract.

Bai et al "Overexpression of Oxysterol Sulfotransferase (Sult2B1 b) Decreases Intracellular Lipid Levels via SREBPs Signaling Pathway in Primary Human Aorta Endothelial Cells"; Abstract, Arteriosclerosis, Thrombosis, and Vascular Biology 2010 Scientific Sessions, American Heart Association; Apr. 8-10, 2010.

Bi et al (2018) "Regulation of Cholesterol Sulfotransferase SULT2B1b by Hepatocyte Nuclear Factor 4α Constitutes a Negative Feedback Control of Hepatic Gluconeogenesis"; Molecular and Cellular Biology, vol. 38 Issue 7; pp. 1-15.

Blevins et al., "A Phase 2B Trial in Alcohol-Associated Hepatitis to Evaluate the Safety and Efficacy of Larsucosterol Treatment (AHFIRM);" (poster) SCSG GI Symposium (2022).

Cha and Kim "Sulfated oxysterol 25HC3S as a therapeutic target of non-alcoholic fatty liver disease", Metabolism, 2012, pp. 1055-1057, vol. 61, Elsevier.

Clinicaltrials.gov: NCT03432260; "A Research Study to Assess the Safety, Pharmacokinetics and Pharmacodynamicsof DUR-928 in Patients with Alcoholic Hepatitis (AH)"; Full Text View; Durect Corporation; Dec. 14, 2022; 9 pages.

Clinicaltrials.gov: NCT03432260; "A Research Study to Assess the Safety, Pharmacokinetics and Pharmacodynamicsof DUR-928 in Patients With Alcoholic Hepatitis (AH)"; Tabular View; Durect Corporation; Dec. 14, 2022; 10 pages.

Clinicaltrials.gov: NCT03432260; "A Research Study to Assess the Safety, Pharmacokinetics and Pharmacodynamicsof DUR-928 in Patients With Alcoholic Hepatitis (AH)"; Study Results; Durect Corporation; Dec. 14, 2022; 16 pages.

Clinicaltrials.gov: NCT03917407; "DUR-928 in Patients With Alcoholic Hepatitis (DUR-928/AH)"; Full Text View; Craig James McClain; Nov. 9, 2022; 11 pages.

Clinicaltrials.gov: NCT03917407; "DUR-928 in Patients With Alcoholic Hepatitis (DUR-928/AH)"; Tabular View; Craig James McClain; Nov. 9, 2022; 11 pages.

Clinicaltrials.gov: NCT03917407; "DUR-928 in Patients With Alcoholic Hepatitis (DUR-928/AH)"; Study Results; Craig James McClain; Nov. 9, 2022; 2 pages.

Clinicaltrials.gov: NCT04447404; DUR-928 in Subjects With SARS-CoV-2 With Acute Lung, Liver or Kidney Injury; Study Results; Durect Corporation; Aug. 5, 2022; 9 pages.

ClinicalTrials.gov: NCT04563026; "A Phase 2b Study in Subjects With Alcoholic Hepatitis to Evaluate Safety and Efficacy of DUR-928 Treatment (AHFIRM)"; Tabular View; Durect Corporation; Sep. 24, 2020; 8 pages.

ClinicalTrials.gov: NCT04563026; "A Phase 2b Study in Subjects With Alcoholic Hepatitis to Evaluate Safety and Efficacy of DUR-928 Treatment (AHFIRM)"; Study Details; Durect Corporation; Sep. 24, 2020; 8 pages.

ClinicalTrials.gov: NCT04563026; "A Phase 2b Study in Subjects With Alcoholic Hepatitis to Evaluate Safety and Efficacy of DUR-928 Treatment (AHFIRM)"; Tabular View; Durect Corporation; (update) Aug. 10, 2022; 8 pages.

Clinicaltrials.gov: NCT04563026; A Phase 2b Study in Subjects With Alcoholic Hepatitis to Evaluate Safety and Efficacy of DUR-928 Treatment (AHFIRM); Full Text View; Durect Corporation; (update) Aug. 10, 2022; 7 pages.

Cook et al. (2009) "24-Hydroxycholesterol Sulfation by Human Cytosolic Sulfotransferases: Formation of Monosulfates and Disulfates, Molecular Modeling, Sulfatase Sensitivity, and Inhibition of Liver X Receptor Activation", Drug Metabolism and Disposition, vol. 37, No. 10; pp. 2069-2078, The American Society for Pharmacology and Experimental Therapeutics.

DePass, et al; "A 14-Day Intravenous Infusion Toxicity and Toxicokinetic Study of DUR-928, a Novel, First in Class, Investigational Therapeutic in Sprague-Dawley Rats"; American College of Toxicology's 39th Annual Meeting, West Palm Beach, Florida, Nov. 4-7, 2018.

DePass, et al; "In Vivo Tissue Distribution and Elimination of DUR-928, a First in Class Therapeutic for Treatment of Hepatic and Renal Disease"; Abstract #3355/Poster Board #P137, Late Breaking SOT Poster, Toxicokinetics, 57thAnnual Meeting of the Society of Toxicology, San Antonio, Texas, Mar. 11-15, 2018.

Durect (2015) "Durect Announces Epigenomic Regulator Program including a New NAFLD/NASH and Acute Organ Injury Product Candidate in Development"; News Release, Mar. 2, 2015; 4 pages.

Durect (2015) "Durect Announces Positive Results from DUR-928 Multi-Dose Phase 1 Study"; News Release, May 18, 2015; 4 pages.

Durect (2016) "Durect Announces Positive Phase 1 Data for DUR-928"; News Release, Jan. 6, 2016; 3 pages.

Durect (2016) "Durect Corporation Announces Update on DUR-928 Development Program"; News Release, Oct. 31, 2016; 5 pages.

Durect (2017) "Durect Corporation Announces Update on DUR-928 Development Program"; News Release, Jan. 30, 2017; 4 pages.

Durect (2018) "A Research Study to Evaluate Safety and Efficacy of DUR-928 in Subjects with Primary Sclerosing Cholangitis (PSC)"; U.S. National Library of Medicine, ClinicalTrials.gov Identifier: NCT03394781; 13 pages.

Durect (2018) "Durect Announces Amendment to Accelerate Ongoing Phase 2a Trial of DUR-928 in Alcoholic Hepatitis (AH) by Allowing Dosing of Severe AH Patients in Parallel to Moderate AH Patients" News Release, Nov. 19, 2018; 4 pages.

Durect (2018) "Durect Announces Patient Dosing in Phase 2a Trial ofDUR-928 in Alcoholic Hepatitis"; News Release, Apr. 25, 2018; 3 pages.

Durect (2019) "Durect Announces Positive Data from its Phase 2a Clinical Trial of DUR-928 in Alcoholic Hepatitis"; News Release, Sep. 17, 2019; 3 pages.

Durect (2019) "Durect Corporation Announces Preliminary Data from the Ongoing DUR-928 Alcoholic Hepatitis Phase 2a Trial"; News Release, May 7, 2019; 6 pages.

Durect (2020) "Durect Corporation Announces Positive Topline Data from Phase 1b Study of DUR-928 in NASH"; News Release, May 26, 2020; 6 pages.

Durect (2020) "Durect Corporation Announces Top-Line Results from Phase 2a Clinical Trial in Patients with Psoriasis"; News Release, Jan. 2, 2020; 3 pages.

Durect (2023), "Durect Corporation Announces Topline Results from Phase 2b AHFIRM Trial of Larsucosterol in Alcohol-Associated Hepatitis with Promising Effect on Mortality," News Release, Nov. 7, 2023; 5 pages.

(56) References Cited

OTHER PUBLICATIONS

Durect (2023), "Durect Corporation Reports Third Quarter 2023 Financial Results and Business Update," News Release, Nov. 13, 2023; 6 pages.

Durect Corporation (DRRX) Q3 2023 Earnings Call Transcript, 13 pages (2023).

Durect (2018) "A Research Study to Assess the Safety, Pharmacokinetics and Pharmacodynamics of DUR-928 in Patients With Alcoholic Hepatitis (AH)"; U.S. National Library of Medicine, ClinicalTrials. gov Identifier: NCT03432260; 14 pages.

Hassanein et al., "Safety, Pharmacokinetics, & Efficacy Signals of Larsucosterol (DUR-928) in Alcohol-associated Hepatitis," Am J Gastroenterol (2023) 25 pages.

Hassanein, et al (2019) "Safety and Efficacy of DUR-928: A Potential New Therapy for Acute Alcoholic Hepatitis" AASLD; Abstract LB-09 (Durect C928-010 Trial); 1 page.

Hassanein, et al (2019) "Safety and Efficacy of DUR-928: A Potential New Therapy for Acute Alcoholic Hepatitis"; AASLD; 22 pages.

He D., et al., "Inhibition of SULT2B1B expression alters effects of 3 beta-hydroxysteroids on cell proliferation and steroid hormone receptor in human LNCaP prostate cancer cells"; Prostate 67-1318-1329, 2007.

He et al., "Identification and immunohistochemical localization of Sulfotransferase 2B1b (SULT2B1b) in human lung", Biochimica et Biophysica Acta, Apr. 12, 2005, pp. 119-126, vol. 1724, Elsevier.

Higashi et al., "Expression of Cholesterol Sulfotransferase (SULT2B1b) in Human Skin and Primary Cultures of Human Epidermal Keralinocytes", The Journal of Investigative Dermatology, 2004, pp. 1207-1212, vol. 122, The Society for Investigative Dermatology.

Javitt et al., "Cholesterol and hydroxycholesterol sulfotransferases: Identification, distinction from dehydroepiandrosterone sulfotransferase, and differential tissue expression". Endocrinology, vol. 142, pp. 2978-2984, 2001.

Ji et al., "Human Hydroxysteroid Sulfotransferase SULT2B1 Pharmacogenomics: Gene Sequence Variation and Functional Genomics", The Journal of Pharmacology and Experimental Therapeutics, 2007, pp. 529-540, vol. 322, No. 2, The American Society for Pharmacology and Experimental Therapeutics.

Kakiyama, et al.(2011) "Characterization of Oxysterols and Their Sulfates in Primary Rat Hepatocytes (Prh) Following Increased Expression of the Mitochondrial Cholesterol Delivery Protein, StarD1"; Gastroenterology 140(5); Abstract; 1 page.

Kemp, W., "Safety and pharmacokinetics of DUR-928 in patients with non-alcoholic steatohepatitis—A Phase 1b study", EASL The International Liver Congress; Apr. 2017.

Kim et al; "Attenuation of Renal Ischemic Reperfusion Injury in Rats with DUR-928, a Novel, First-in-Class Therapeutic in Development for Renal Disease"; Poster #: SA-PO650, Kidney Week, San Diego, CA—Oct. 23-28, 2018.

Kim, "DUR-928, an endogenous regulatory molecule, exhibits anti-inflammatory and antifibrotic activity in a mouse model of NASH", AASLD's Emerging Trends in NAFLD, Washington DC,; Mar. 17-18, 2017.

Lawitz et al., "Efficacy Signals of 4-Week Oral DUR-928 in NASH Subjects;" ePoster at EASL the International Liver Congress; Jun. 23, 2021.

Lawitz et al., "Safety and Efficacy Signals of Daily Oral DUR-928 for 4-Weeks in F1-F3 NASH;" ePoster at AASLD The Liver Meeting; Nov. 13, 2020.

Li et al., (2006) "A Novel Metabolic Pathway for the Synthesis of the Newly Discovered Nuclear 5-cholesten-3β,25-Diol3-sulphate", Abstract; 1 page.

Li et al., "Biosynthesis of the regulatory oxysterol, 5-cholesten-3β,25-diol 3-sulfate, in hepatocytes", Journal of Lipid Research, Sep. 21, 2007, pp. 2587-2596, vol. 48.

Li, et al (2007) "Discovery of a novel regulatory pathway in cholesterol metabolism"; The FASEB Journal 21(5); Abstract; 1 page. https://doi.org/10.1096/fasebj_21.5.A239-a.

Li, et al (2008) "25-Hydroxycholesterol 3-sulfate regulates lipid metabolism via SREBP-1 in human macrophages"; The FASEB Journal 22(S1); Abstract; 1 page. https://doi.org/10.1096/fasebj.22. 1_supplement.807.6.

Ma et al., "25-Hydroxycholesterol-3-sulfate regulates macrophage lipid metabolism via the LXR/SREBP-1 signaling pathway", Am J Physiol Endocrinol Metab, Oct. 14, 2008, pp. E1369-E1379, vol. 295.

Ma, et al (2009) "Inhibition of cellular lipid biosynthesis by sulfated oxysterol is mediated via the LXR pathway"; The FASEB Journal 23(S1); Abstract; 1 page. https://doi.org/10.1096/fasebi.23.1_ supplement.522.1.

McClain, et al.(2019) "DUR-928 Therapy For Acute Alcoholic Hepatitis: A Pilot Study"; AASLD; Poster (Durect Corporation); 1 page.

Napodano et al., "Zacks Small-Cap Research", Mar. 4, 2015, pp. (1-14).

Ning et al.(2009) "Overexpression of mitochondrial cholesterol delivery protein, StAR, decreases intracellular lipids and inflammatory factors secretion in macrophages"; Atherosclerosis. 204(1): pp. 114-120.

Ning et al.(2009) "StAR overexpression decreases serum and tissue lipids in apolipoprotein E-deficient mice"; Lipids 44(6); pp. 511-519.

Ning, "Cholesterol metabolites alleviate injured liver function and decrease mortality in an LPS-induced mouse model", Metabolism Clinical and Experimental, 71 (2017), 83-93.

Olkkonen et al., "Oxysterols and Their Cellular Effectors," Biomolecules, 2:76-103 (2012).

Pandak, et al., "The cholesterol metabolite, 5-cholesten-3beta, 25-diol 3-sulfate, promotes hepatic proliferation in mice"; Poster Abstract, XXII International Bile Acid Meeting: Hepatic and Extrahepatic Targets of Bile Acid Signalling, Falk Symposium 184; Sep. 14-15, 2012.

Polyzos, et al. "Sulfated oxysterols as candidates for the treatment of nonalcoholic fatty liver disease"; Metabolism, 2012, pp. 755-758, vol. 61.

Ren and Ning, "Sulfation of 25-hydroxycholesterol regulates lipid metabolism, inflammatory responses, and cell proliferation", Am J Physiol Endocrinol Metab, Dec. 3, 2013, pp. E123-E130, vol. 306.

Ren et al. (2018) "Novel oxysterol sulfates alleviate injured liver function and decrease mortality in LPS-induced mouse model," J Clin Gastroenterol Hepatol vol. 2; 1 page.

Ren et al. "Identification of a novel sulfonated oxysterol, 5-cholesten-3β,25-diol 3-sulfonate, in hepatocyte nuclei and mitochondria"; Journal of Lipid Research, Feb. 27, 2006, pp. 1081-1090, vol. 47, American Society for Biochemistry and Molecular Biology, Inc.

Ren et al., "Identification of A Novel Regulatory Nuclear Oxysterol", Abstract, 56th Annual Meeting of the American Association for the Study of Liver Diseased, Nov. 11-15, 2005.

Ren et al., "25HC3S Alleviates Injured Liver Function and Decreases Mortality by Promoter 5mCpG Demethylation Signaling Pathways," AASLD, The Liver Meeting, Boston, Massachusetts (2023); Abstract, 3 pages.

Ren et al., "25HC3S Alleviates Injured Liver Function and Decreases Mortality by Promoter [5m]CpG Demethylation Signaling Pathways," AASLD, The Liver Meeting, Boston, Massachusetts (2023); Poster, 1 page.

Ren et al., "25-hydroxycholesterol and 25-hydroxycholesterol 3-sulfate reciprocally regulate lipid metabolism and inflammation in hepatocytes and macrophages", Abstract, The Liver Meeting, the 60th Annual Meeting of the American Association for the Study of Liver Diseases, Oct. 30-Nov. 3, 2009.

Ren et al., "25-Hydroxycholesterol sulfation regulates lipid metabolism in vivo in mice", Jun. 13-14, 2008; Abstract.

Ren et al., "25-Hydroxycholesterol-3-sulfate (25HC3S) regulates lipid metabolism by activation/inactivation of receptors in hepatocytes and macrophages", Abstract, XX International Bile Acid Meeting, Falk Symposium 165; Jun. 13-14, 2008.

Ren et al., "Discovery of a Novel Oxysterol, 5-Cholesten-3β,25-Diol3-Sulfonate, in Nuclei and Mitochondria Following Over-

(56)        References Cited

OTHER PUBLICATIONS expression of the Gene Encoding StarD1", Bile Acids: Biological Actions and Clinical Relevance, 2007 pp. 20-35, Kluwer Academic Publishers.

Ren et al., "Discovery of a Novel Oxysterol, 5-Cholesten-3β,25-Diol3-Sulfonate, in Nuclei and Mitochondria Following Over-expression of the Gene Encoding StarD1", Abstract, International Bile Acid Meeting, XIII Falk Liver Week, Falk Symposia 155, Oct. 6-11, 2006.

Ren et al., "Discovery of a Novel Regulatory Pathway for Maintenance of Intracellular Cholesterol Homeostasis", Abstract, DOW Annual Meeting 2007, May 19-25, 2007.

Ren et al., "Identification of Novel Regulatory Cholesterol Metabolite, 5-Cholesten, 3β,25-Diol, Disulfate" PLOS One, 2014, vol. 9. No. 7, p. 1-11.

Ren et al., "Overexpression of Cholesterol Transporter StAR Increases In Vivo Rates of Bile Acid Synthesis in the Rat and Mouse"; Liver Biology and Pathobiology, Aug. 20, 2004, pp. 910-917, vol. 40, No. 4.

Ren et al., "Regulation of Hepatocyte Lipid Metabolism by 25-Hydroxycholesterol-3-Sulfate (25HC3S) Is Mediated Via the LXR/SREBP-1 Signaling Pathway"; Abstract, DOW Annual Meeting 2008, May 17-23, 2008.

Ren S., et al.; "The acidic pathway of bile acid biosynthesis: Role in oxysterol sulfation, lipid metabolism and inflammatory responses"; Poster Abstract, XXII International Bile Acid Meeting, Falk Symposia 184; Sep. 14-15, 2012.

Ren, "Oxysterol Sulfation as Regulatory Signaling Pathway"; McGuire VA Medical CenterNirginia Commonwealth University; (Apr. 2014) 1 page.

Ren, "Sulfation of 25-Hydroxycholesterol Regulates Lipid Metabolism and Inflammatory Responses in Human Aortic Endothelial Cells, Macrophages, and Hepatocytes"; Abstract; Departments of Medicine, McGuire Veterans Affairs Medical Center Virginia Commonwealth University; (Jan. 2014) 1 page.

Ren, A Novel Regulatory Pathway: Oxysterol Sulfation in Lipid Metabolism and Inflammatory Responses, presentation (Nov. 2011); pp. 1-63.

Ren, et al (2007) "The Nuclear Oxysterol, 5-Cholesten-3β, 25-Diol 3-Sulfate, Decreases Cholesterol Biosynthesis by Inhibiting Expression of HMG CoA Reductase in HepG2 Cells"; *The FASEB Journal* 21(5); Abstract; 1 page. https://doi.org/10.1096/fasebj.21.5.A454-C.

Ren, et al (2010) "Is 25-Hydroxycholesterol 3Sulfate an Endogenous Ligand of Ppargamma?"; *Gastroenterology*, 138(5); Abstract; 1 page.

Ren, et al (2011) "In vivo Oxysterol Sulfation by SULT2B1b Reduces Hepatic Lipid Accumulation and Suppresses SREBP-1c Signaling: Evidence for the Sulfation as a Regulatory Pathway in Lipid Metabolism"; Departments of Medicine, Virginia Commonwealth University/McGuire Veterans Affairs Medical Center; poster; 1 page.

Ren, et al (2021) "Oxysterol Sulfation"; Encyclopedia Publication; 13 pages.

Ren, et al "25-Hydroxycholesterol-3-Sulfate Activates PPARγ and Attenuates Inflammatory Responses in Human Macrophages"; Poster Abstract, Arteriosclerosis, Thrombosis, and Vascular Biology Annual Conference 2009, American Heart Association; Apr. 29-May 1, 2009.

Ren, et al; "Oxysterol sulfates alleviate injured liver function and decrease mortality in mouse models"; Poster Abstract, XXV International Bile Acid Meeting:Bile Acids in Health and Disease, Symposium 211; Jul. 6-7, 2018.

Ren, Shunlin, "Novel Oxysterol Sulfates Alleviate Injured Liver Function and Decrease Mortality in Mouse Models", Nov. 2017; 2 pages.

Shah et al., "Pharmacokinetics of DUR-928 in Alcoholic Hepatitis Patients—A Phase 2a Study;" ePoster at EASL The European Association for the Study of the Liver; Aug. 27, 2020.

Shah et al., "Safety and Pharmacokinetics of DUR-928 in Hepatic Function Impaired Subjects," ePoster at EASL the International Liver Congress; Jun. 23, 2021.

Shah, et al; "A Clinical Drug-Drug Interaction Study with Midazolam to Assess the Effect of DUR-928 on CYP3A4"; Meeting of the American College of Clinical Pharmacology, Bethesda, Maryland, Sep. 23-25, 2018; 1 page.

Shah, et al; "Pharmacokinetic and Pharmacodynamic Response in Individual NASH Patients Receiving Two Dose Levels of DUR-928"; Nash Summit—2019, Apr. 22-25, 2019. 1 page.

Shah, et al; "Safety and Single Ascending Dose Pharmacokinetic Study of DUR-928 in Patients with Chronic Kidney Disease versus Matched Control Subjects"; Poster #: SA-PO63; Kidney Week, San Diego, CA—Oct. 23-28, 2018; 1 page.

Shen, et al (2011) "25-Hydroxycholesterol-3Sulfate (25HC3S): A Physiological Ligand of PPARγ?"; *Gastroenterology* 140(5); Abstract; 1 page.

Therapeutics, Inc. (2019) "Safety and Efficacy Study of DUR-928 Topical Solution in Subjects With Plaque Psoriasis"; U.S. National Library of Medicine, ClinicalTrials.gov Identifier: NCT03837743; 14 pages.

Wang and Ren "25-Hydroxycholesterol is a Potent Epigenetic Regulator: High Glucose Induces Lipid Accumulation via 25-Hydroxycholesterol DNA-CpG Methylation in Human Hepatocytes"; Department of Internal Medicine, Virginia Commonwealth University/ McGuire VA Medical Centre; AASLD Annual Meeting, Nov. 13-16, 2020. 1 page.

Wang et al. (2021) "25-Hydroxycholesterol 3-sulfate is an endogenous ligand of DNA methyltransferases in hepatocytes"; Journal of Lipid Research. 2021; 62: 100063 (14 pages).

Wang, et al (2020) "High Glucose Induces Lipid Accumulation via 25-Hydroxycholesterol DNA-CpG Methylation"; iScience 23(5); pp. 1-28.

Wang, et al (2021) "25-Hydroxycholesterol 3-Sulfate Recovers Acetaminophen Induced Acute Liver Injury via Stabilizing Mitochondria in Mouse Models"; Cells 10, 3027; pp. 1-17.

Wang, et al (2021) "Cholesterol Metabolites 25-Hydroxycholesterol and 25-Hydroxycholesterol 3-Sulfate Are Potent Paired Regulators: From Discovery to Clinical Usage"; *Metabolites* 11(1); pp. 2-14.

Wikipedia, "Acebrochol," last edited Jan. 5, 2021.

Xu et al. "Reversal of Diet-induced Serum and Hepatic Lipid Accumulation by 5-cholesten-3beta.25-diol 3-sulfate in Mouse Models of Nonalcoholic Fatty Liver Diseases"; Hepatology, Jun. 9, 2011.

Xu et al., "25-Hydroxycholesterol (25HC) and 25HC-3-Sulfate (25HC3S) Mediate Nuclear Orphan Receptors in Opposite Direction in Hepatocytes", Abstract, XX International Bile Acid Meeting, Falk Symposia 165, Jun. 13-14, 2008.

Xu et al., "25-Hydroxycholesterol-3-sulfate (25HC3S) Attenuates Hepatocyte Intracellular Lipid Levels and Inflammatory Response via LXR/SREBPs and IKBa/NF-KB Pathways", Abstract, DOW Annual Meeting 2008, May 3, 2010.

Xu et al., "25-Hydroxycholesterol-3-Sulfate (25HC3S) Suppresses NF-κB Activation and Inflammatory Response in Human Macrophages and Hepatocytes", Abstract, Arteriosclerosis, Thrombosis, and Vascular Biology 2010 Scientific Sessions, American Heart Association; Apr. 8-10, 2010.

Xu et al., "25-Hydroxycholesterol-3-sulfate attenuates inflammatory response via PPARγ signaling in human THP-1 macrophages", Am J Physiol Endocrinol Metab, Jan. 24, 2012, pp. E788-E799, vol. 302.

Xu et al., "5-Cholesten-3β,25-Diol 3-Sulfate Decreases Lipid Accumulation in Diet-Induced Nonalcoholic Fatty Liver Disease Mouse Model", Molecular Pharmacology, Mar. 2013, 648-658, vol. 83.

Xu et al., "Induction of IκBα Expression as a Mechanism Contributing to the Anti-inflammatory Activities of Peroxisome Proliferator-activated Receptor-αActivators", Abstract, DOW Annual Meeting 2011, May 7-10, 2011.

Xu et al., "Induction of IKBα Expression Mediates the Anti-Inflammatory Response to 25-Hydroxycholesterol-3-Sulfate (25HC3S) in Primary Rat Hepatocytes and THP-1 Macrophages"; AASLD Abstract; 2011.

(56) References Cited

OTHER PUBLICATIONS

Xu et al., "Regulation of Hepatocyte Lipid Metabolism and inflammatory Response by 25-Hydroxycholesterol and 25-Hydroxycholesterol-3-sulfate", Lipids, 2010, pp. 821-832, vol. 45, AOCS.

Xu et al.., "25-Hydroxycholesterol-3-Sulfate Decreases Hepatic Steatosis and Inflammation In Mouse Models of Nonalcoholic Fatty Liver Disease by Down-Regulating Sterol Regulatory Element Binding Protein-1c", Abstract, DOW Annual Meeting 2011, May 7-10, 2011.

Xu, et al (2009) "Nuclear Oxysterols, 25HC and 25HC3S, Regulate Nuclear Orphan Receptor Activities and Attenuate Intracellular Lipid Levels"; *The FASEB Journal* 23(S1); Abstract; 1 page. https://doi.org/10.1096/fasebj.23.1_supplement.871.1.

Yang et al., "Bindings of PPARγ ligand-binding domain with 5-cholesten-3β, 25-diol, 3-sulfate: accurate prediction by molecular simulation"; *Journal of Biomlecular Structure and Dynamics*, pp. 1-9 (2019).

Zhang et al., (2011) "SULT2B1b overexpression promotes liver regeneration via inhibiting LXR signaling pathway in mouse with or without Partial Hepatectomy", Poster; Departments of Medicine, Virginia Commonwealth University/McGuire Veterans Affairs Medical Center, Richmond, Virginia.; 1 page.

Zhang et al., (2012) "Cytosolic sulfotransferase 2B1b promotes hepatocyte proliferation gene expression in vivo and in vitro", Am J Physiol Gastrointest Liver Physiol, vol. 303; pp. G344-G355.

Zhang et al., "Cholesterol metabolite, 5-cholesten-3β-25-diol-3-sulfate, promotes hepatic proliferation in mice"; Journal of Steroid Biochemistry and Molecular Biology, 2012, pp. 262-270, vol. 132, Elsevier.

Zhang et al., "Effects of 25-hydroxycholesterol sulfation on liver regeneration in normal and partial hepatectomy (PHX) mouse models", Abstract, DOW Annual Meeting 2011, May 7-10, 2011.

Zhang et al., "Effects of 25-Hydroxycholesterol Sulfation on Liver Regeneration in Normal and Partial Hepatectomy (PHX) Mouse Models"; May 2011, Gastroenterology vol. 140, Issue 5, Supplement 1, p. S-967.

Al Idrus, "AASLD: Durect's alcoholic hepatitis med repairs liver, cuts mortality in phase 2," Fierce Biotech (2019).

Annual Report, Bringing Ideas to Life (2014).

Clinicaltrials.gov: NCT03432260; "A Research Study to Assess the Safety, Pharmacokinetics and Pharmacodynamicsof DUR-928 in Patients With Alcoholic Hepatitis (AH)"; History of Changes; Durect Corporation; Nov. 18, 2022; 4 pages.

Clinicaltrials.gov: NCT04447404; DUR-928 in Subjects With SARS-CoV-2 With Acute Lung, Liver or Kidney Injury; Tabular View; Durect Corporation; Mar. 2, 2022; 6 pages.

Clinicaltrials.gov: NCT04447404; DUR-928 in Subjects With SARS-CoV-2 With Acute Lung, Liver or Kidney Injury; Full Text View; Durect Corporation; Mar. 2, 2022; 6 pages.

Clinicaltrials.gov: NCT04563026; A Phase 2b Study in Subjects With Alcoholic Hepatitis to Evaluate Safety and Efficacy of DUR-928 Treatment (AHFIRM); Durect Corporation; (update) Feb. 23, 2024; 9 pages.

Durect (2024), "Durect Corporation Receives FDA Breakthrough Therapy Designation for Larsucosterol in Alcohol-Associated Hepatitis," News Release, May 21, 2024; 3 pages.

Durect Corporate Presentation, 43 pages, Mar. 2, 2015.

Durect Corporation presenting at Oppenheimer 34th Annual Healthcare Life Sciences Conference, Feb. 14, 2024 (partial transcript).

Durect Corporation, Epigenomic Regulator Program, Presentation, 17 pages, Mar. 2, 2015.

English Translation of Japanese Office Action dated Jul. 23, 2019 for Japanese Patent Application No. 2017-518508.

Flamm et al., "Drinking Behavior in the AHFIRM Trial as Measured by Phosphatidyl Ethanol," AASLD abstract, S1194-S1195 (2024).

Flamm et al., "Drinking Behavior in the AHFIRM trial as measured by Phosphatidyl Ethanol (PEth)," AASLD poster, 1 page (2024).

Goel et al., "A Balancing Act: The Life-Saving Potential and Dilemma of Liver Transplantation as an Endpoint in Alcohol-Associated Hepatitis Trials," AASLD abstract, S1116-S1117 (2024).

Goel et al., "3040: A Balancing Act: Liver Transplantation as an Endpoint in Alcohol-Associated Hepatitis (AH) Trials," AASLD poster, 1 page (2024).

Hagler, "Get to Know Norman Sussman, Chief Medical Officer at Durect," BioSpace (2021).

Healio, "Alcoholic hepatitis drug candidate shows 'life-saving potential'" (2019).

Healio, "Q&A: DUR-928 'well tolerated' for NASH in Phase 1b study" (2020).

Hirayama, Handbook of production of organic compound crystals, pp. 17-23, 37-40, 45-51, and 57 to 65 (2008) (along with English language translation).

Kemp, "Safety and pharmacokinetics of DUR-928 in patients with nonalcoholic steatohepatitis—A phase 1b study," Journal of Hepatology, 66:S596, abstract (2017).

McClain, Craig J., "Which Therapeutic Targets Will Be The Most Attractive In The Future?", Oct. 2017.

Mitchell et al., "Current Management and Future Treatment of Alcoholic Hepatitis," Gastroenterology & Hepatology, 16(4):178-189 (2020).

Pandak, et al., "Reversal of NAFLD through selective increased intracellular hepatic cholesterol catabolism"; Poster Abstract, XXIII International Bile Acid Meeting: Bile Acids as Signal Integrators and Metabolic Modulators, Falk Symposium 194; Oct. 8-9, 2014.

Ren et al., "25HC and 25HC3S are Paired Endogenous Ligands of DNA Methyltransferases: Implication for Its Role in Development and Recovery of Non-Alcoholic Fatty Liver Diseases (NAFLD)," Abstract, AASLD Liver meeting, Nov. 4-8, 2022, Washington, DC, USA.

Ren, "5-Cholesten-3, 25-diol 3-sulfate has potential to serve as new medication for therapy of inflammatory diseases," BIT Life Sciences' 7th Annual Congress of International Drug Discovery Science and Technology (IDDST), Shanghai, China, Oct. 22-25, 2009.

Ren, "5-cholesten-3beta, 25-diol 3-sulfate serves as a new medicine for therapy of hyperlipidemia," 2nd World Congress on Bioavailability & Bioequivalence: Pharmaceutical R & D Summit, Las Vegas, Jun. 6-8, 2011.

Ren, "5-Cholesten-3β, 25-diol 3-sulfate decreases lipid accumulation in diet-induced nonalcoholic fatty liver disease mouse model," 3nd World Congress on Bioavailability & Bioequivalence: Pharmaceutical R & D Summit, Beijing, China, May 20-22, 2013.

Ren, "Novel cholesterol metabolites for therapy of nonalcoholic fatty liver diseases," BIT's 5th Annual World Congress of Molecular & Cell Biology 2015, Nanjing, China, Apr. 25-28, 2015.

Ren, "Novel Regulatory Pathway in Prevention of Atherosclerosis," Project No. 1101BX001874-01, 7 pages (2013).

Ren, "Novel Regulatory Pathway in Prevention of Atherosclerosis," Project No. 5101BX001874-02, 7 pages (2014).

Ren, "Novel Regulatory Pathway in Prevention of Atherosclerosis," Project No. 5101BX001874-03, 7 pages (2014).

Ren, "Novel Regulatory Pathway in Prevention of Atherosclerosis," Project No. 5101BX001874-04, 7 pages (2016).

Ren, "Regulation of Cholesterol Metabolism," Project No. 1R01HL078898-01A2, 7 pages (2006).

Ren, "Regulation of Cholesterol Metabolism," Project No. 5R01HL078898-02, 7 pages (2007).

Ren, "Regulation of Cholesterol Metabolism," Project No. 5R01HL078898-03, 7 pages (2008).

Ren, "Regulation of Cholesterol Metabolism," Project No. 5R01HL078898-04, 7 pages (2009).

Ren, "Regulation of Cholesterol Metabolism," Project No. 5R01HL078898-05, 7 pages (2010).

Ren, "Role of oxysterol sulfation in lipid metabolism," Experimental Biology Annual Meeting. Washington D.C., Apr. 9-12, 2011.

Ren, "Study the role of oxysterol sulfates in NAFLD development," Project No. 5101BX003656-01A2, 7 pages (2018).

Ren, "Study the role of oxysterol sulfates in NAFLD development," Project No. 5101BX003656-02, 7 pages (2020).

Ren, "Study the role of oxysterol sulfates in NAFLD development," Project No. 5101BX003656-03, 7 pages (2021).

Ren, "Study the role of oxysterol sulfates in NAFLD development," Project No. 5101BX003656-04, 7 pages (2022).

(56) References Cited

OTHER PUBLICATIONS

Serizawa, Chemistry of polymorphism phenomena and crystallization of pharmaceuticals, pp. 273, 278, and 305 to 317 (2002) (along with English language translation).

Shiffman et al., "Results of a phase 2b multicenter randomized trial of larsucosterol for the treatment of severe alcohol-associated hepatitis (AHFIRM trial)," EASL abstract (2024); 2 pages.

Shiffman et al., "Results of a Phase 2b multicenter randomized trial of larsucosterol for the treatment of severe alcohol-associated hepatitis (AHFIRM Trial)," EASL presentation (2024); 18 pages.

Stein et al., "Effects of Timely Treatment on Outcomes of Larsucosterol for Severe Alcohol-Associated Hepatitis (AHFIRM Trial)," AASLD abstract, S548-S549 (2024).

Stein et al., "Larsucosterol for Treatment of Severe Alcohol-associated Hepatitis—Impact of Hospitalization-to-Treat Time," AASLD presentation, 16 slides (2024).

Sussman, "Alcohol-associated HepatitisResults of a recent trial and remaining questions," BASL/BSG meeting (24 pages).

Tornai and Szabo (2020) "Emerging medical therapies for severe alcoholic hepatitis"; *Clinical and Molecular Hepatology*, 26; pp. 686-696.

Wang et al., "25HC3S Decreases Insulin Resistance (IR) via DNA 5mCpG in the promoter region Demethylation in Non-Alcoholic Fatty Liver Disease (NAFLD) Mouse Model," Abstract, AASLD Liver meeting, Nov. 4-8, 2022. Washington, DC, USA.

Wang et al., "25-Hydroxycholesterol 3-Sulfate Recovers Acetaminophen Induced Acute Liver Injury via Stabilizing Mitochondria in Mouse Models," Abstract, AASLD Liver meeting, Nov. 4-8, 2022, Washington, DC, USA.

Wang et al., "High Glucose Increases DNA CpG Methylation in Promoter Regions of Insulin Signaling Pathway and Induces Lipid Accumulation in Hepatocytes," South East Lipid Research Conference, Conjunction with University Cincinnati, Sep. 10-13, 2019.

Wang et al., "Larsucosterol: endogenous epigenetic regulator for treating chronic and acute liver diseases," Am J Physiol Endocrinol Metab, 326: E577-E587 (2024).

Xu et al., "25HC3S Regulates Lipid Metabolism via LXRs-independent Pathway in An MASLD In Vitro Model," Poster, DDW (2024).

Xu et al., "Induction of IκBα Expression as a Mechanism Contributing to the Anti-inflammatory Activities of Peroxisome Proliferator-activated Receptor-a Activators", Abstract, DDW Annual Meeting 2011, May 7-10, 2011.

Search Opinion for European Patent Application No. 20907564.7 dated Feb. 5, 2024, 9 pages.

Examination Report dated Oct. 17, 2025 for Australian Patent Application No. 2020415462, 5 pages.

Substantive Examination Adverse Report dated Jan. 29, 2025 for Malaysian Patent Application No. PI2022003403, 4 pages.

First Office Action dated May 19, 2025 for Vietnam Patent Application No. 1-2022-04726, 4 pages.

Narayanan, et al.; Larsucosterol Moves Forward as a Treatment Contender for Alcohol-Associated Hepatitis; NEJM Evidence; Published Jan. 28, 2025; 2 pages.

Shiffman, et al.; Larsucosterol for the Treatment of Alcohol-Associated Hepatitis; NEJM Evidence; Published Jan. 28, 2025; 11 pages.

Pang, et al.; Risk factors for mortality in patients with alcoholic hepatitis and assessment of prognostic models: A population-based study; Can J Gastroenterol Hepatol, vol. 29, No. 3, Apr. 2015, 8 pages.

Tujios, et al.; Clinical and pathological spectrum of disease severity among patients with acute liver failure (ALF) undergoing deceased donor liver transplantation; American Association for the Study of Liver Diseases; Published by Wolters Kluwer Health, Inc.; 2025; 24 pages.

Wang et al.; Cholestenoic acid as endogenous epigenetic regulator decreases hepatocyte lipid accumulation in vitro and in vivo; Am J Physiol Gastrointest Liver Physiol 326: G147-G162, 2024; First published Nov. 14, 2023; 16 pages.

Liangpunsakul, et al.; The impact of liver transplantation on end-point selection in alcohol-associated hepatitis trials; AASLD; Hepatology Communications, 2025; 11 pages.

Durect Corporation (DRRX) Q4 2024 Earnings Call Transcript; Mar. 26, 2025; 9 pages.

First Office Action and its translation for Chile Patent Application No. 202201742 dated Jul. 2, 2024, 19 pages.

Translation of First Office Action Search Report for Chile Patent Application No. 202201742 dated Jul. 2, 2024, 3 pages.

Second Office Action and its translation for Chile Patent Application No. 202201742 dated Apr. 3, 2025, 15 pages.

Translation of Second Office Action Search Report for Chile Patent Application No. 202201742 dated Apr. 3, 2025, 3 pages.

Translation of First Office Action dated Sep. 6, 2023 for Chinese Application for Invention No. 202080095990.5, 6 pages.

Translation of Second Office Action dated Aug. 27, 2024 for Chinese Application for Invention No. 202080095990.5, 4 pages.

Translation of Third Office Action dated Aug. 20, 2025 for Chinese Application for Invention No. 202080095990.5, 11 pages.

Search Report and written Opinion dated May 27, 2024 for Singapore Patent Application No. 11202250530R, 11 pages.

Search Report for Taiwan Patent Application No. 109145999 dated Dec. 26, 2024; 15 page.

International Search Report and Written Opinion dated Apr. 29, 2021 for International Application No. PCT/US2020/066947, 13 pages. (all references cited, ISR/WO not previously cited).

Translation of Office Action dated Aug. 5, 2024 for Thailand Patent Application No. 2201004056, 5 pages. (no references cited).

Examiner's Report dated Dec. 11, 2025 for Canadian Patent Application No. 3165765, 6 pages.

Translation of Office Action dated Dec. 9, 2025 for Japanese Patent Application No. 2025-076809, 1 page.

First Examination Report dated Aug. 18, 2025 for Indian Patent Application No. 202217034039, 9 pages.

Byrn et al., Pharm. Res., 12(7), pp. 945-954, 1995 (1995), "Pharmaceutical solids—A strategic approach to regulatory considerations".

Caira, Topics in Current Chemistry, 198, pp. 163-208, Jan. 1998 (Jan. 1998). "Crystalline Polymorphism of Organic Compounds".

Notice of Grounds for Rejection dated Jun. 19, 2025 for Korean Patent Application No. 10-2022-70205318; 6 pages.

Ogawa et al.; A Facile synthesis of C-24 and C-25 oxysterols by in situ generated ethyl(trifluoromethyl)dioxirane; Steroids 74; 2009; pp. 81-87.

Office action dated Jun. 7, 2026 for Israel Patent Application No. 294286, 6 pages.

Subsequent Substantive Examination Report dated May 6, 2026 for Philippines Application No. Jan. 2022/551596, 6 pages.

Notice of Examination as to Substance dated May 7, 2026 for Vietnamese Application No. 1-2022-04726, 1 page.

Decision for Grant of Patent dated May 14, 2026 for Korean Patent Application No. 10-2022-7025318, 6 pages.

\* cited by examiner

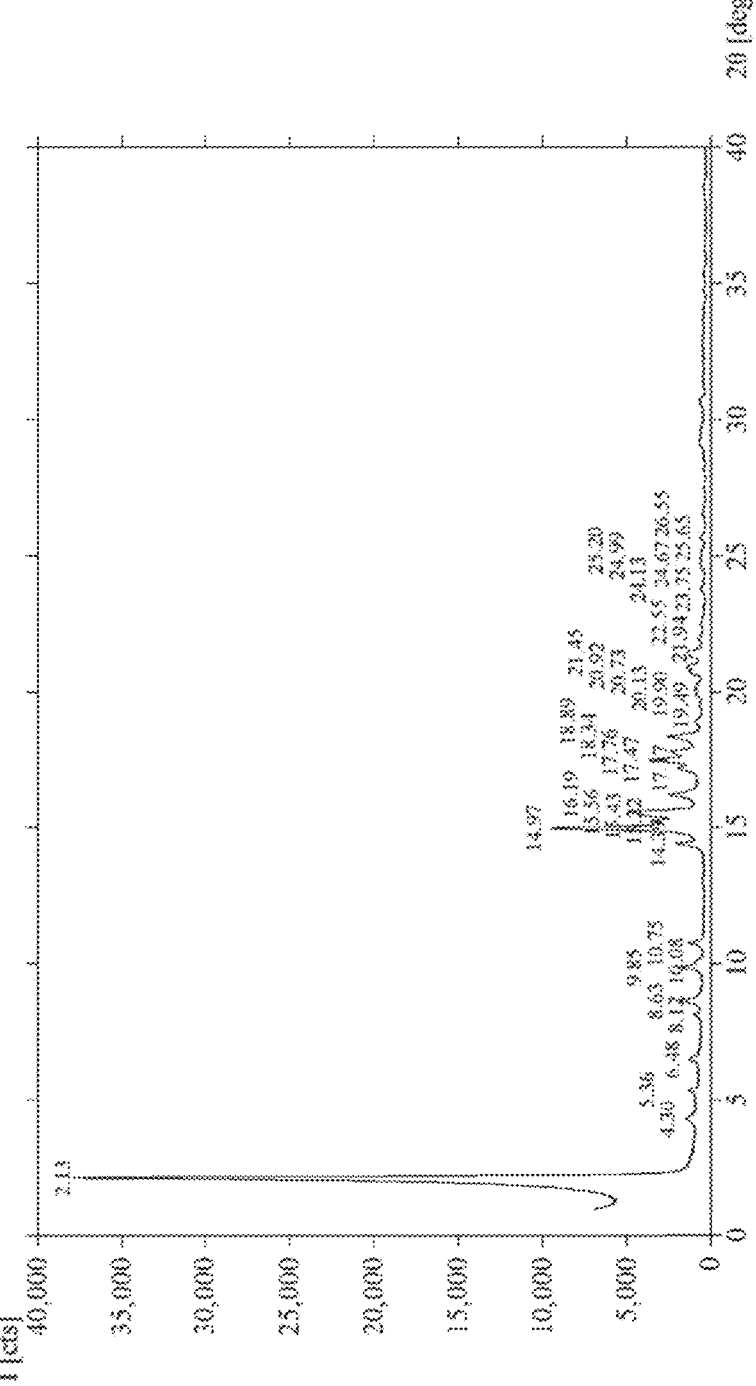
Figure 1 – Form I XRPD Diffractogram

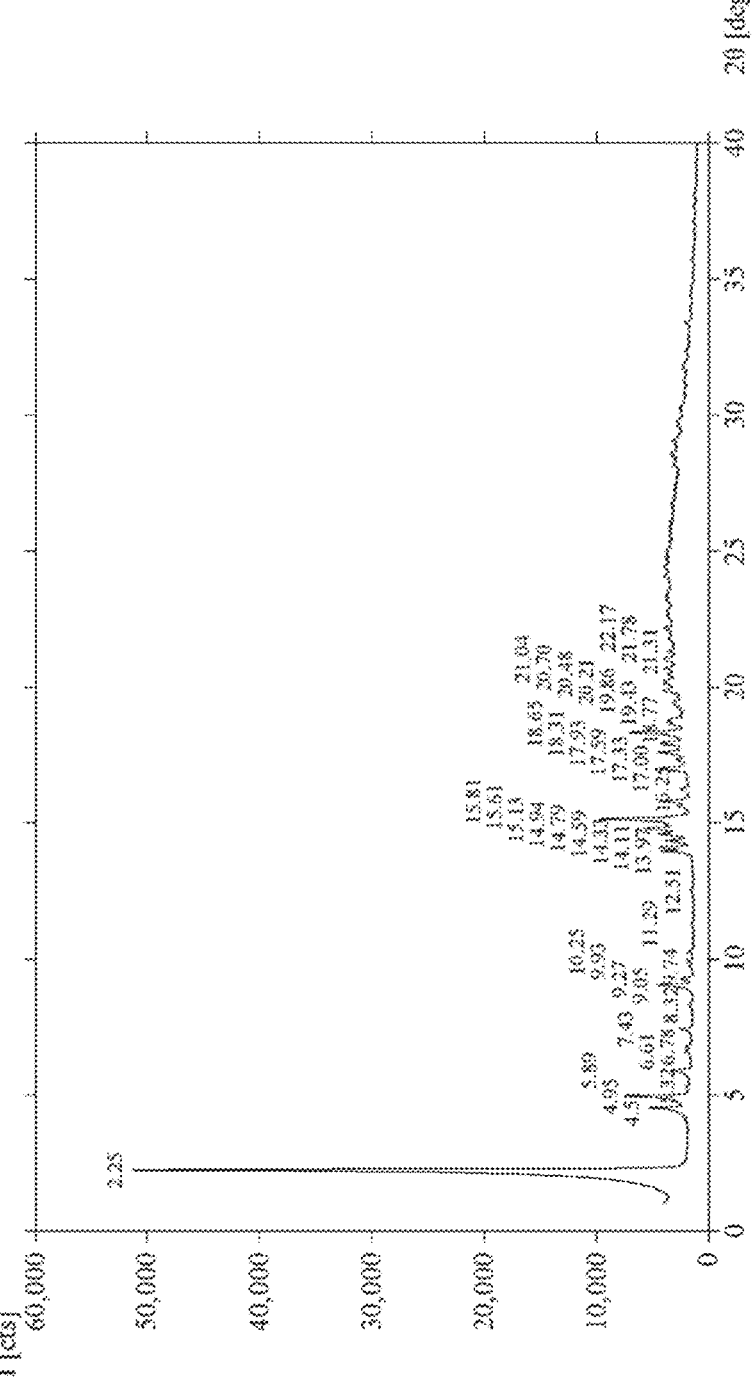
Observed peaks for XRPD file 916673 collected with Cu-Kα radiation.
Figure 2 – Form II XRPD Diffractogram
Output rendered using Triads™ v2.1

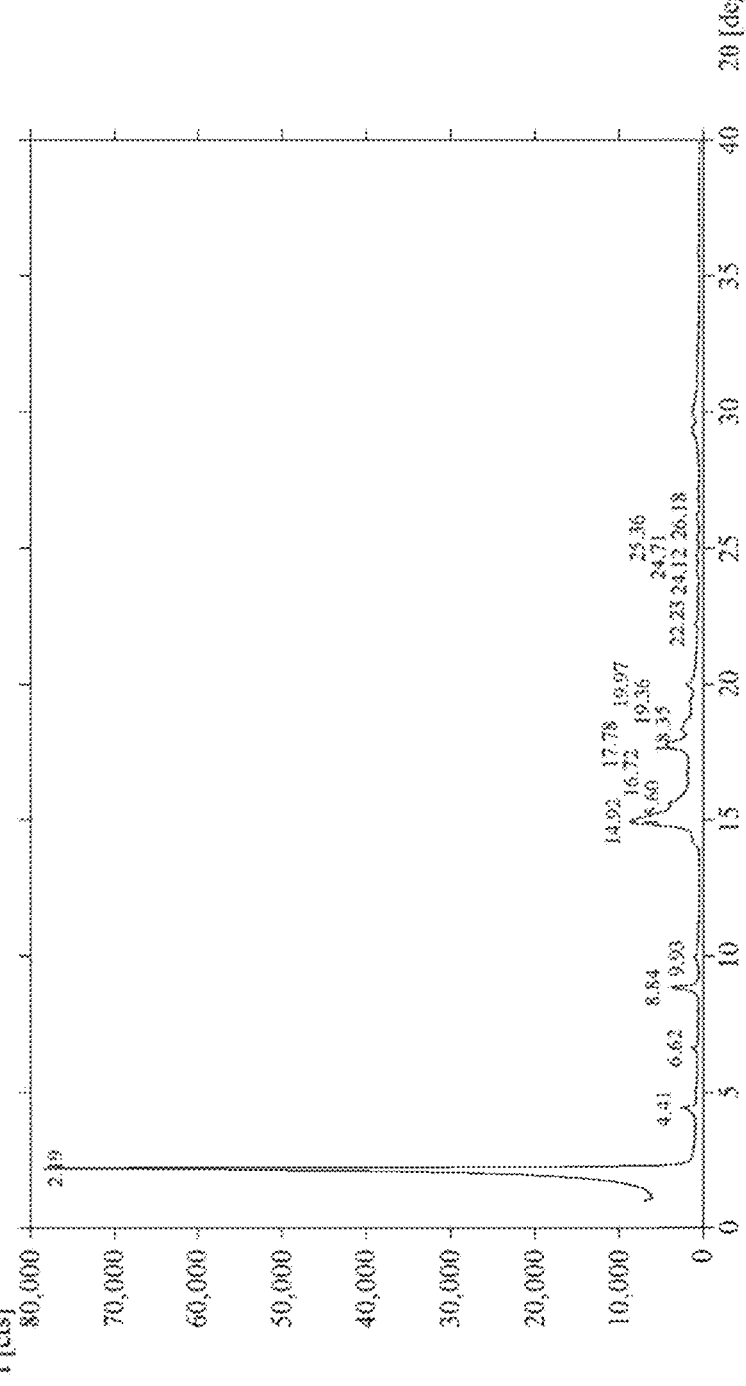
Observed peaks for XRPD file 614895 collected with Cu-Kα radiation.
Figure 3 – Form V XRPD Diffractogram
Output rendered using Triads™ v2.1

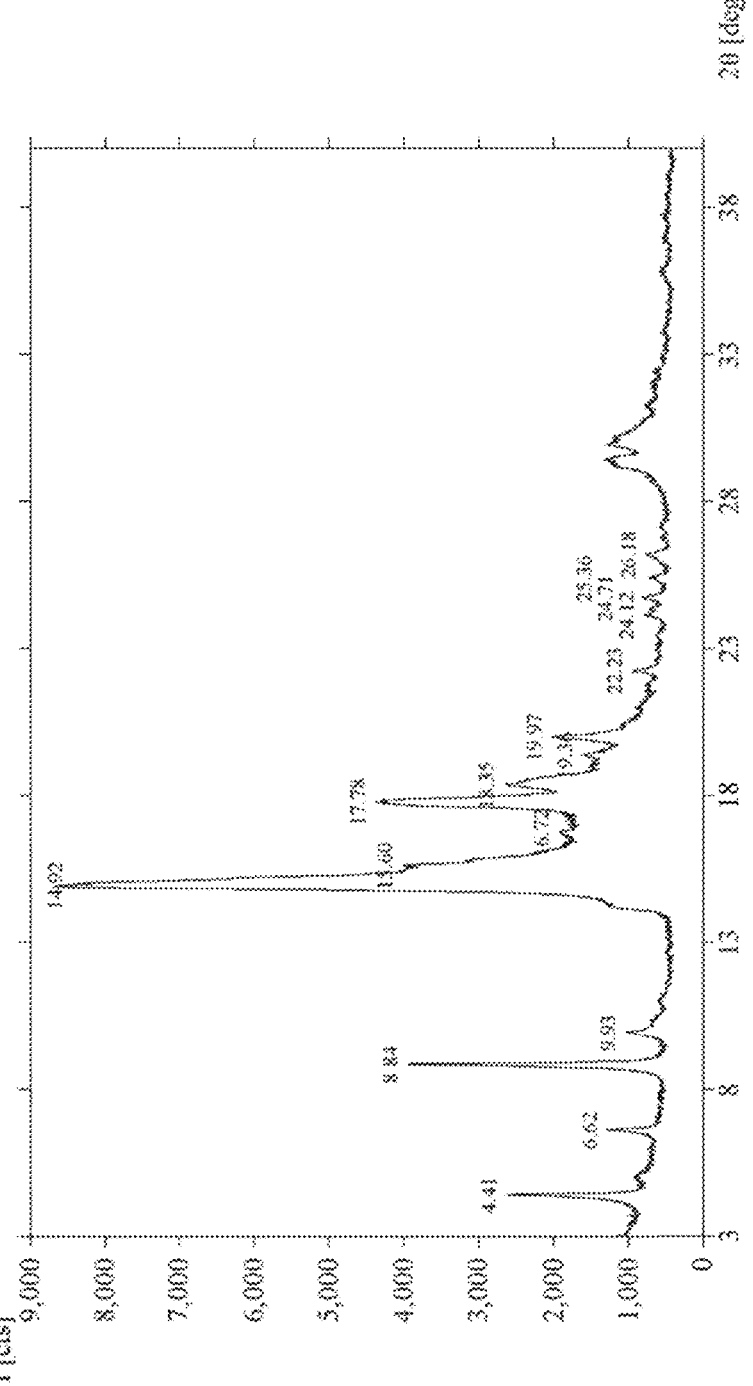
Figure 4 – Form V XRPD Diffractogram

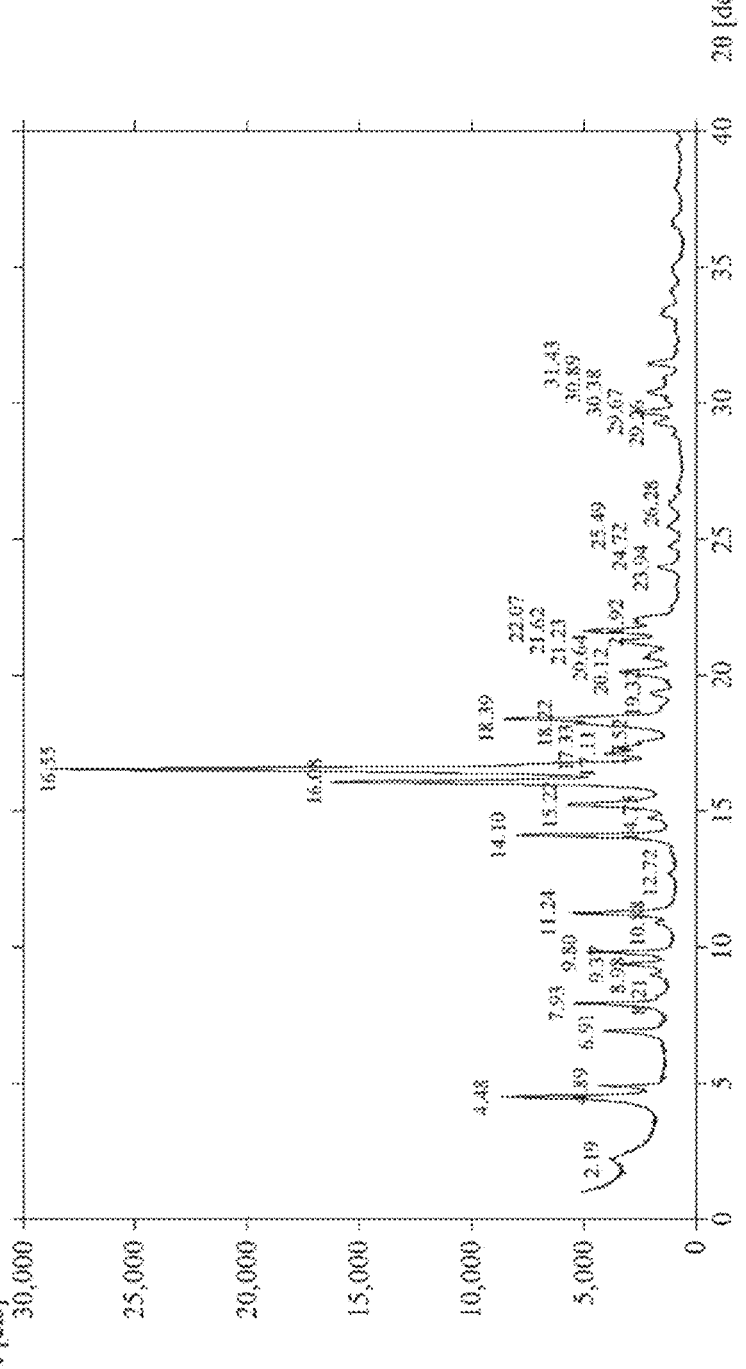
Figure 5 – Form IX XRPD Diffractogram

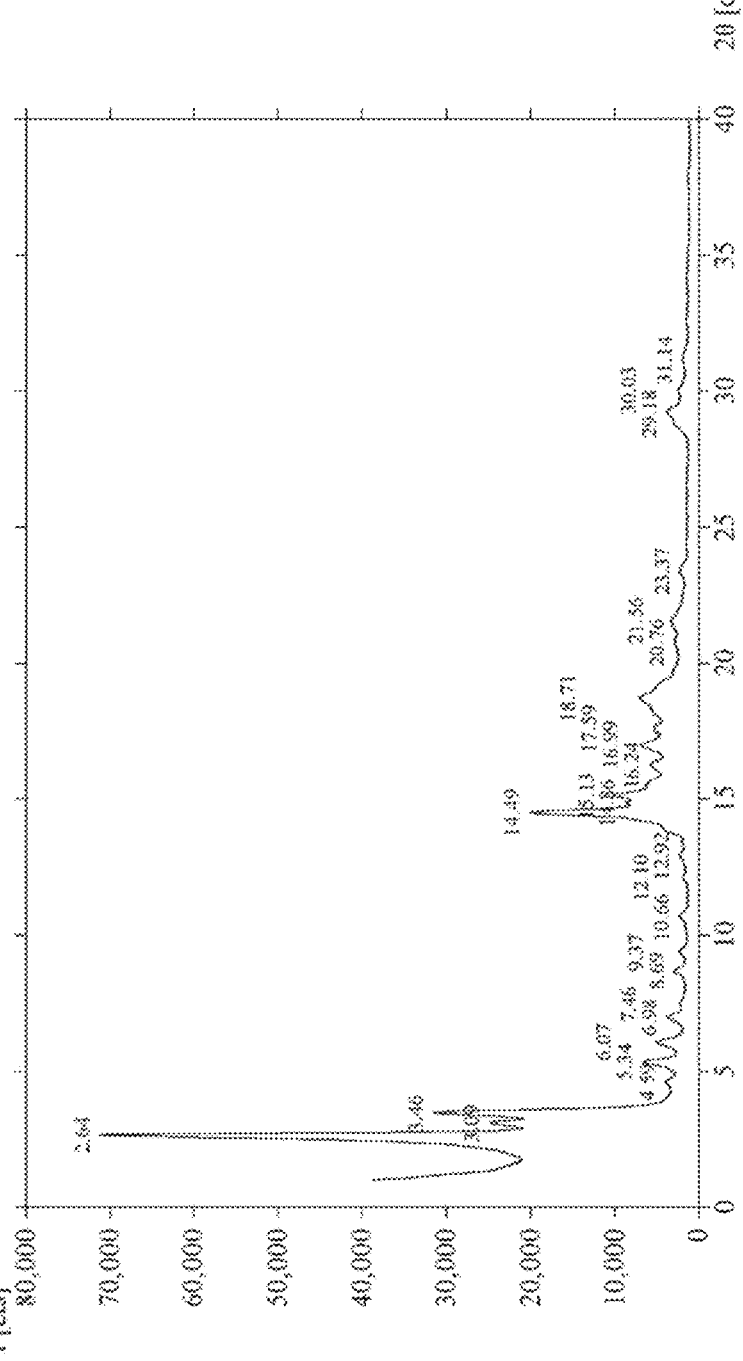
Figure 6 – Form XI XRPD Diffractogram

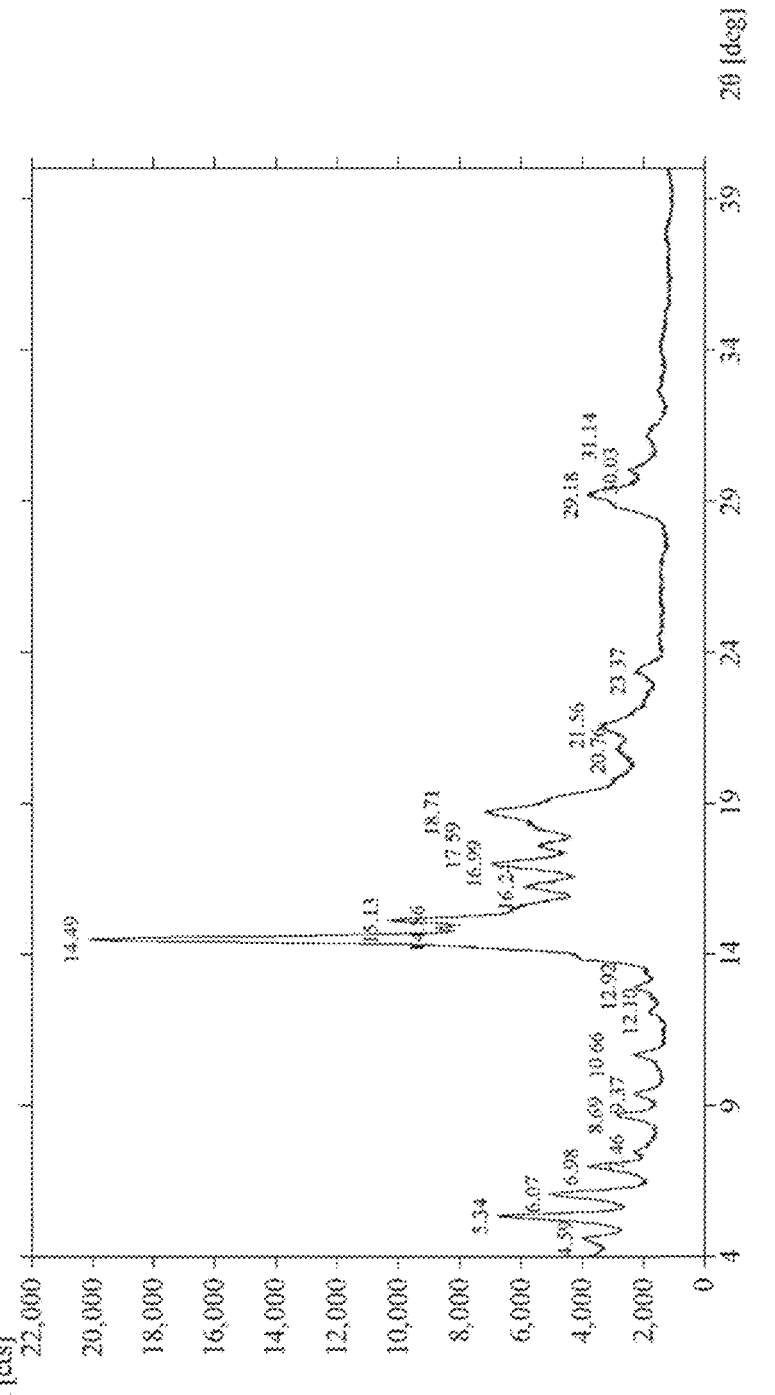
Observed peaks for XRPD file 920831 collected with Cu-Kα radiation.
Figure 7 – Form X1 XRPD Diffractogram
Output rendered using triadsTM v2.1

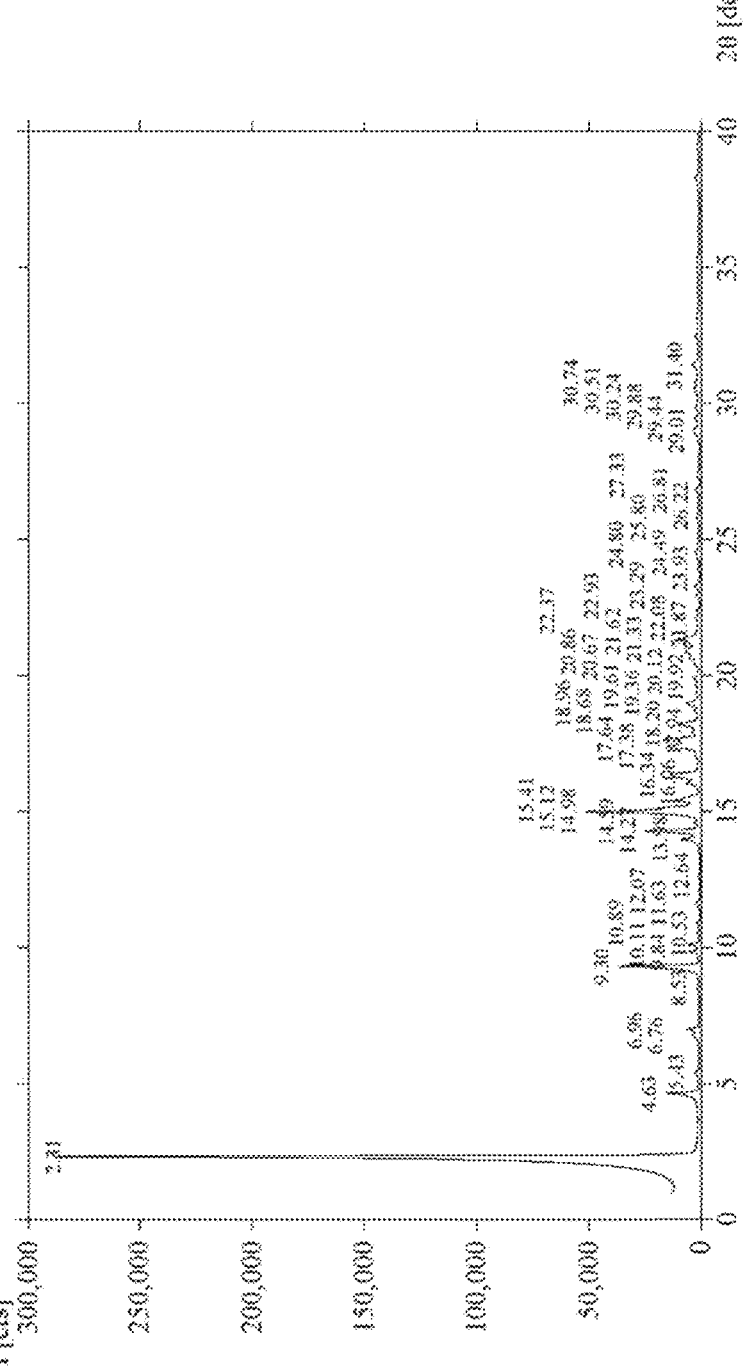
Figure 8 -- Form XIII XRPD Diffractogram

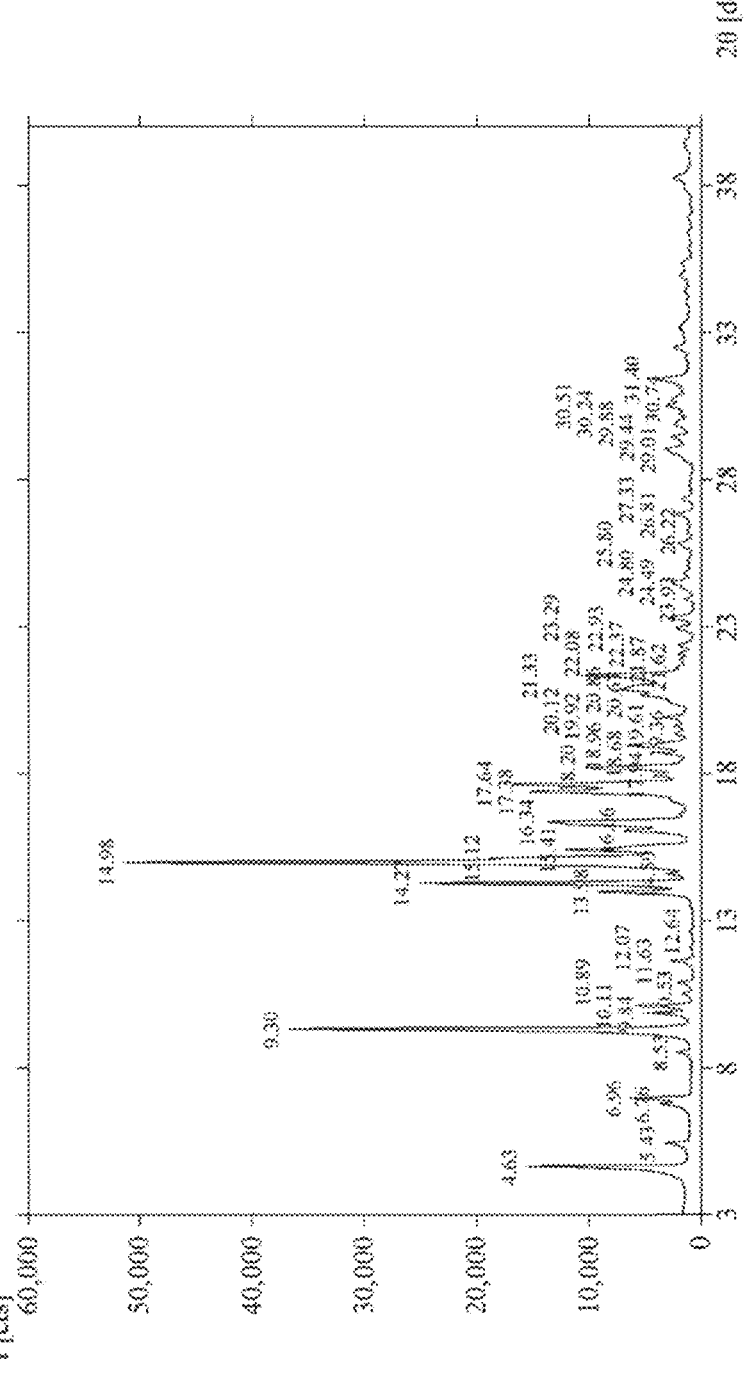
Figure 9 – Form XIII XRPD Diffractogram

Figure 10 – Indexing results for Form 1
Indexing results for XRPD file 614894 collected with Cu-Kα radiation.
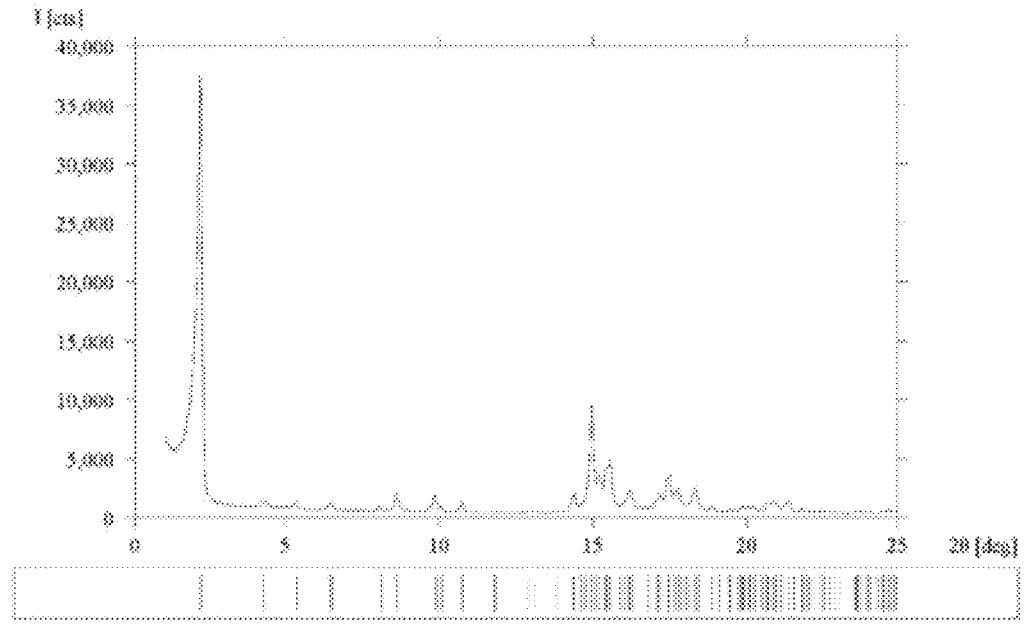
| Bravais Type | Primitive Monoclinic |
|---|---|
| a [Å] | 6.175 |
| b [Å] | 17.937 |
| c [Å] | 41.693 |
| α [deg] | 90 |
| β [deg] | 93.14 |
| γ [deg] | 90 |
| Volume [Å³/cell] | 4,544.7 |
| Chiral Contents? | Chiral |
| Extinction Symbol | P 1 2₁ 1 |
| Space Group(s) | P2₁ (4) |
| Source | Manual Input |

Indexing is conducted under the "Procedures for SSCI Non-cGMP Activities." Output rendered using Triads v1.0

Figure 11 _ Thermograms for Form I
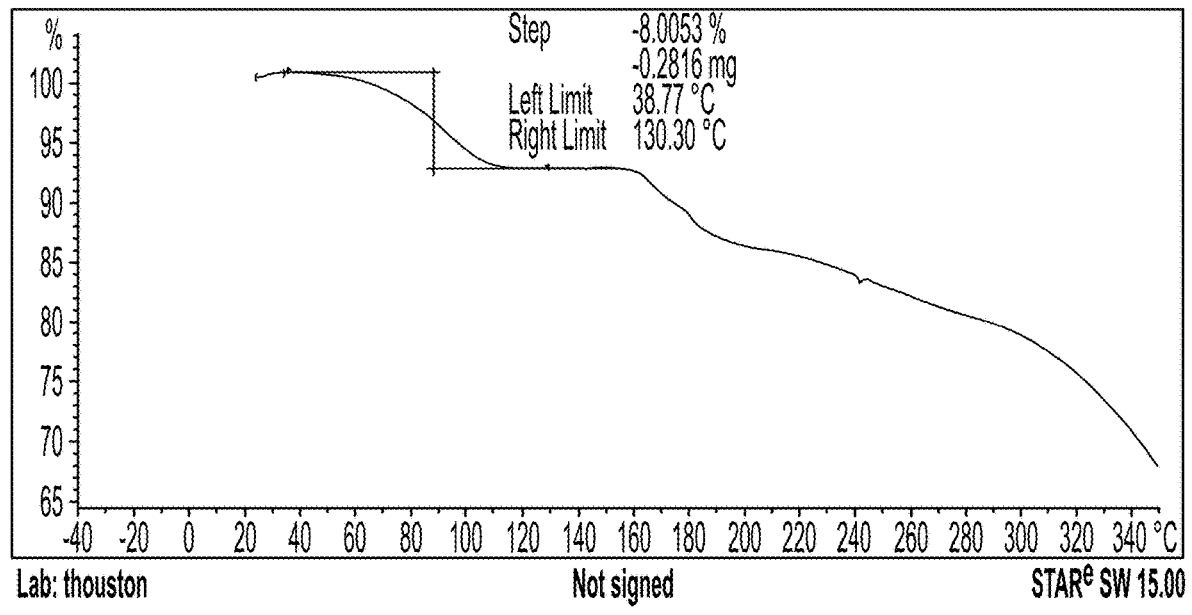
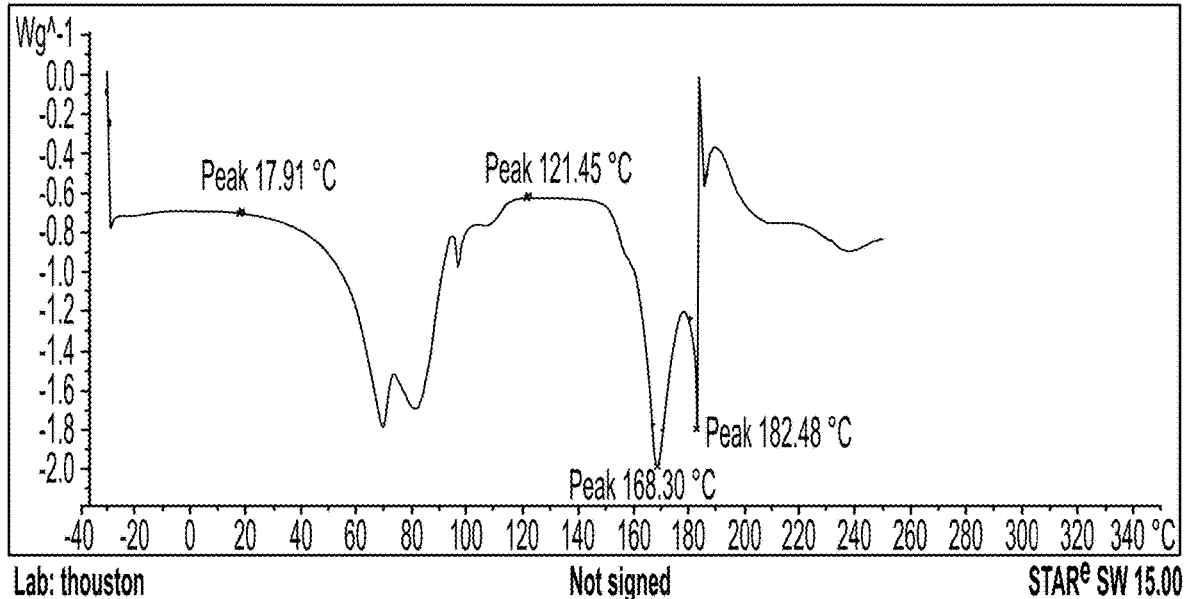

Figure 12 – VT-XRPD experiment for Form I
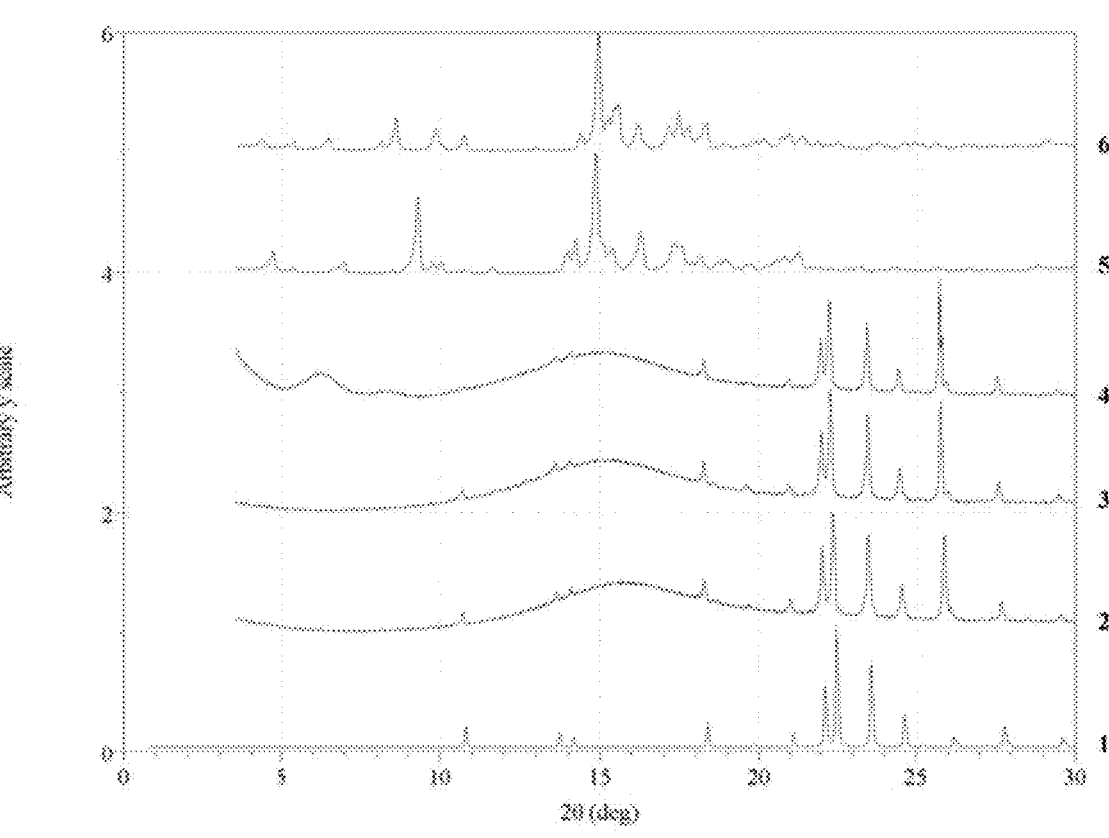
1 = Reference pattern of $HNa_3(SO_4)_2$ calculated from Cambridge Structural Database single crystal data
2 = $HNa_3(SO_4)_2$ (30°C)
3 = $HNa_3(SO_4)_2$ (135°C)
4 = Broad reflections + $HNa_3(SO_4)_2$ (170°C)
5 = Form XIII (135°C)
6 = Form I + peak at 9.0° (30°C)

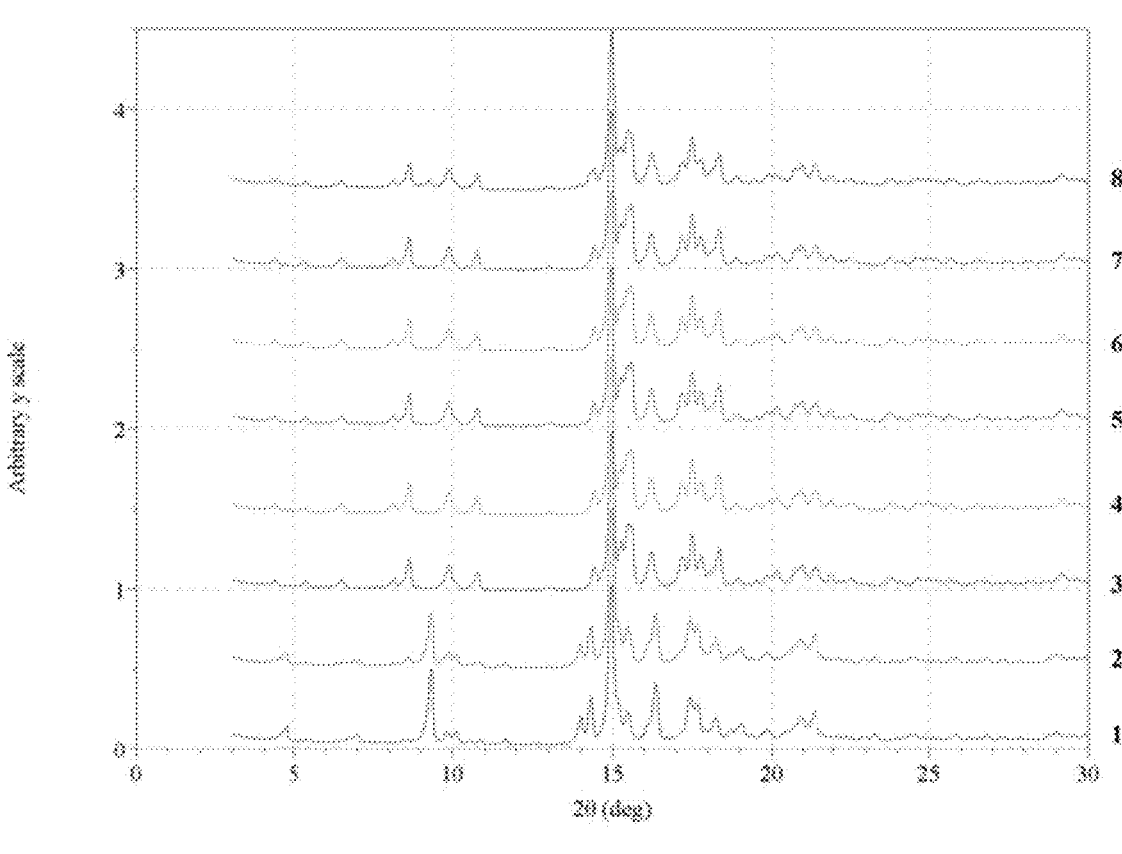
Figure 13 – VRH-XRPD experiment for Form I and Form XIII
1 = Form XIII, 0% RH
2 = Forms XIII + I, 0% RH
3 = Form I, 25% RH
4 = Form I, 75% RH
5 = Form I, 85% RH
6 = Form I, 75% RH
7 = Form I, 55% RH
8 = Forms I + XIII, lab humidity 14.7% RH, initial XRPD

Figure 14 – XRPD Diffractograms from dehydration of Form I
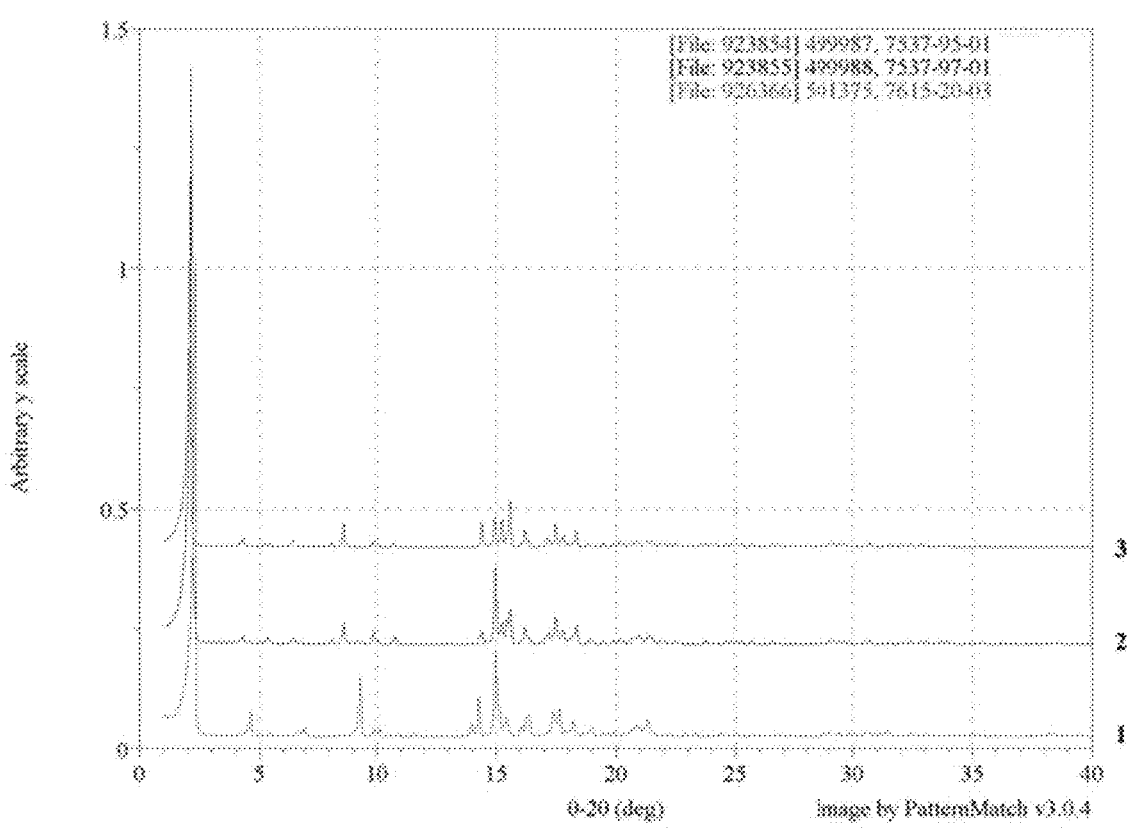
1 = Dried @ 70 °C vacuum for 2 days; Form XIII
2 = Dried under N₂ for 30 min, Forms I + XIII
3 = 0.50 aₗ ACN/H₂O slurry 4 days, Form I + peak @ 9.0°

Figure 15 – XRPD Diffractograms from dehydration of Form I (expanded)
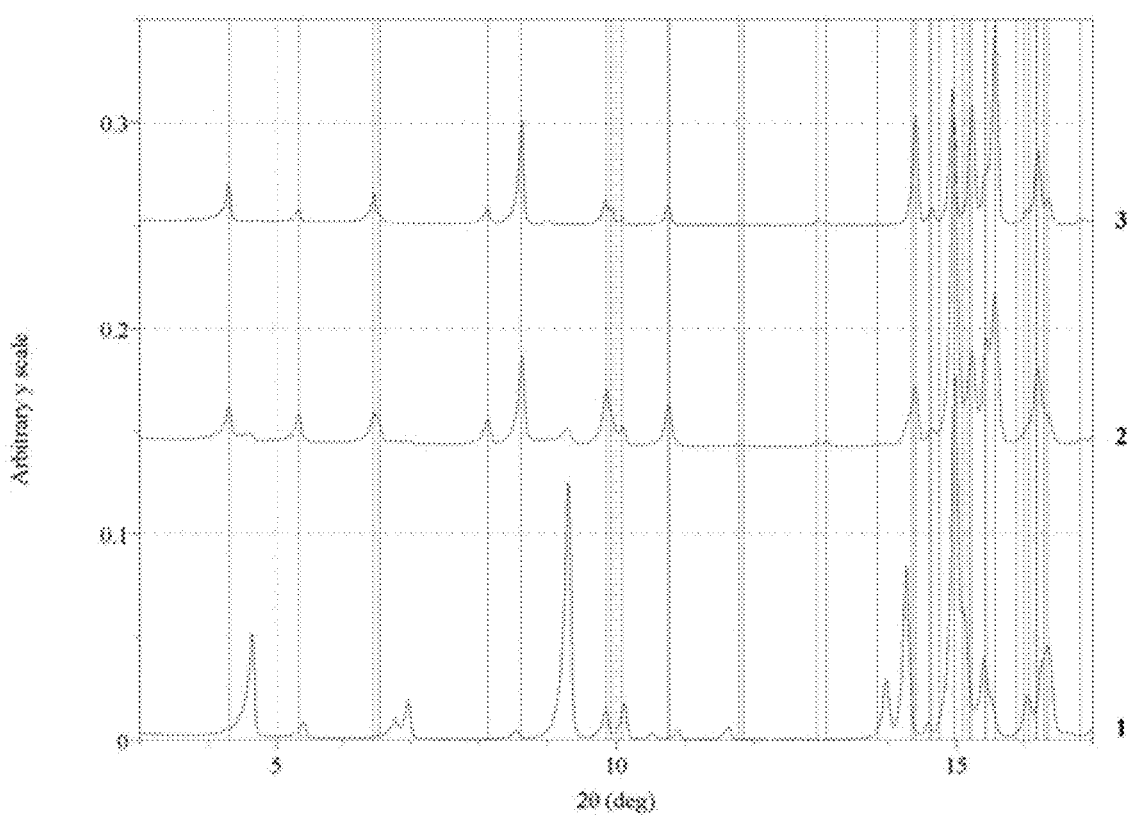
1 = Dried @ 70 °C vacuum for 2 days; Form XIII
2 = Dried under N2 for 30 min, Forms I + XIII
3 = 0.50 a$_w$ ACN/H$_2$O slurry 4 days, Form I + peak @ 9.0°

Figure 16 – DVS Isotherm for Form II
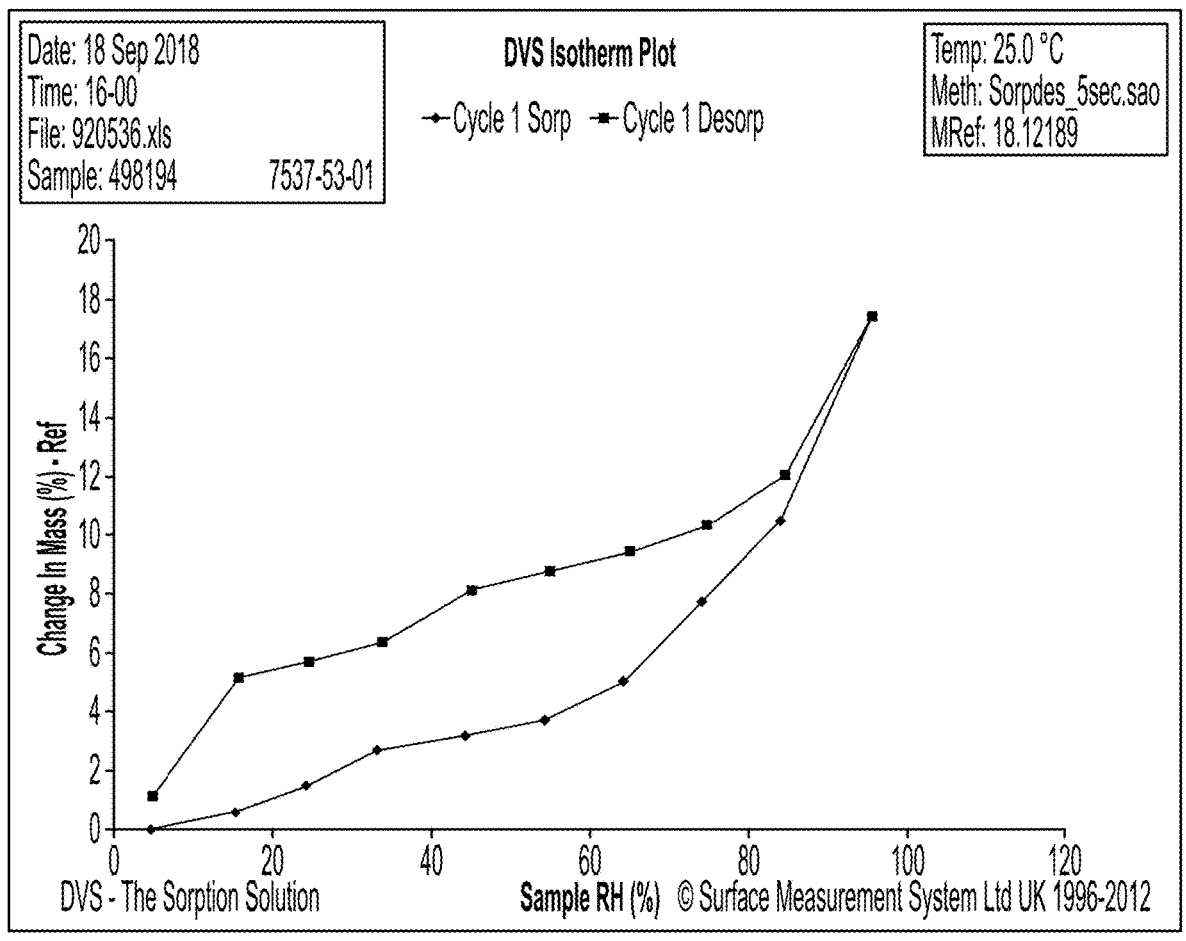

Figure 17 – Indexing results for Form II (99:01 ACN/H₂O slurry, 0.21 a$_w$, 3 days)
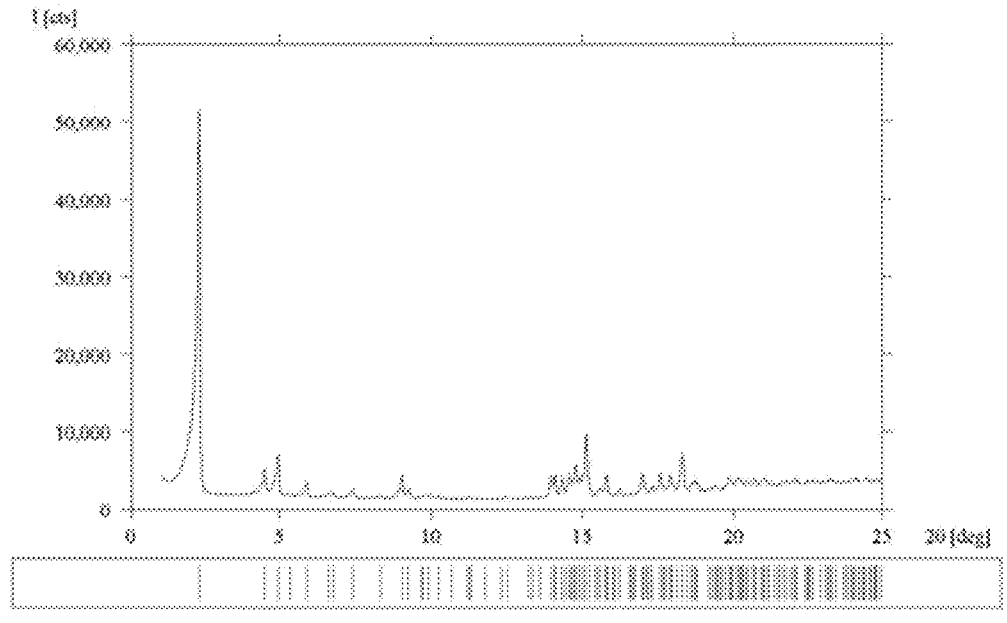
Indexing results for XRPD file 916672 collected with Cu-Kα radiation.
| Bravais Type | Primitive Orthorhombic |
|---|---|
| a [Å] | 6.353 |
| b [Å] | 18.289 |
| c [Å] | 78.133 |
| α [deg] | 90 |
| β [deg] | 90 |
| γ [deg] | 90 |
| Volume [Å³/cell] | 9,066.5 |
| Chiral Contents? | Chiral |
| Extinction Symbol | P 2₁ 2₁ 2₁ |
| Space Group(s) | P2₁2₁2₁ (19) |
| Source | Manual Input |

Indexing is conducted under the "Procedure for SSCI Non-cGMP Activities."      Output rendered using Triads™ v2.0

Figure 18 – Indexing results for Form II (95:05 EtOH/H₂O slurry, 0.30aₓ, 10 days)

Indexing results for XRPD file 916677 collected with Cu-Kα radiation.

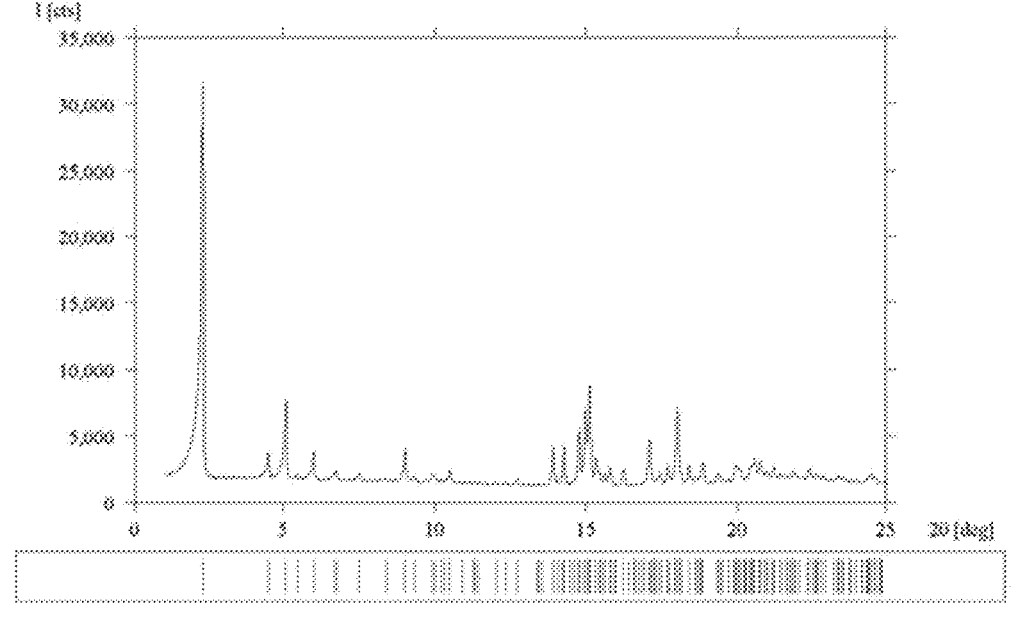

| Bravais Type | Primitive Orthorhombic |
|---|---|
| a [Å] | 6.375 |
| b [Å] | 17.766 |
| c [Å] | 78.215 |
| α [deg] | 90 |
| β [deg] | 90 |
| γ [deg] | 90 |
| Volume [Å³/cell] | 8,858.5 |
| Chiral Contents? | Chiral |
| Extinction Symbol | P 2₁ 2₁ 2₁ |
| Space Group(s) | P2₁2₁2₁ (19) |
| Source | Manual Input |

Indexing is conducted under the "Procedure for 33C1 Non-cGMP Activities."          Output rendered using Triads™ v2.0

Figure 19 – Indexing results for Form II (Acetone slurry, 55°C, 1 day)

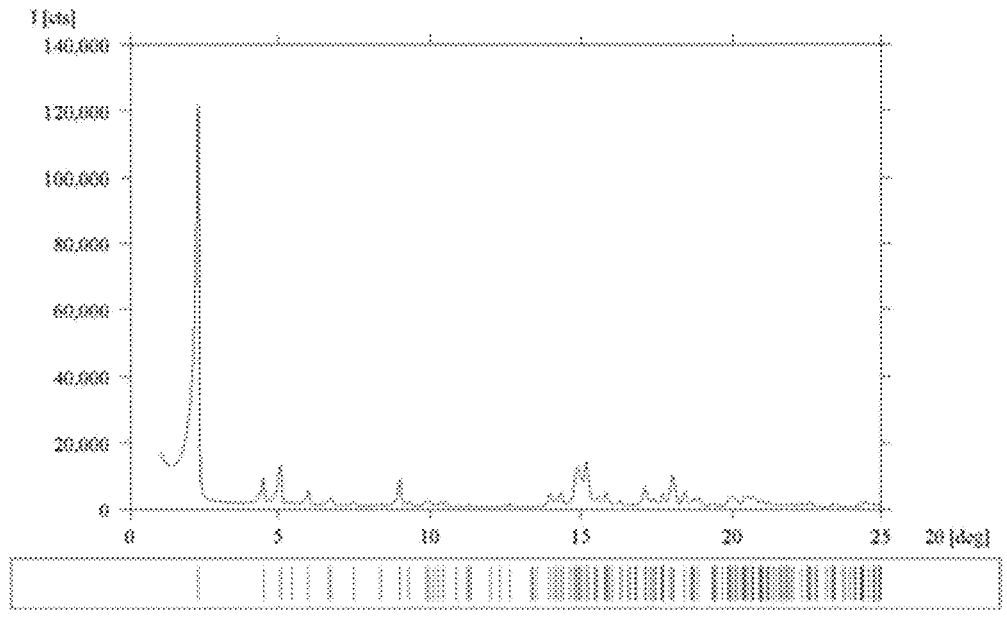

Indexing results for XRPD file 916689 collected with Cu-Kα radiation.

| Bravais Type | Primitive Orthorhombic |
|---|---|
| a [Å] | 6.353 |
| b [Å] | 17.863 |
| c [Å] | 78.433 |
| α [deg] | 90 |
| β [deg] | 90 |
| γ [deg] | 90 |
| Volume (Å³/cell) | 8,900.9 |
| Chiral Contents? | Chiral |
| Extinction Symbol | P 2₁ 2₁ 2₁ |
| Space Group(s) | P2₁2₁2₁ (19) |
| Source | Manual Input |

Indexing is conducted under the "Procedures for SSCI Non-cGMP Activities."     Output rendered using Triads™ v2.0

Figure 20 – XRPD peak position variability for Form II for slurries indexed in Figures 17 –
19, shown from approximately 4°2θ to approximately 11°2θ
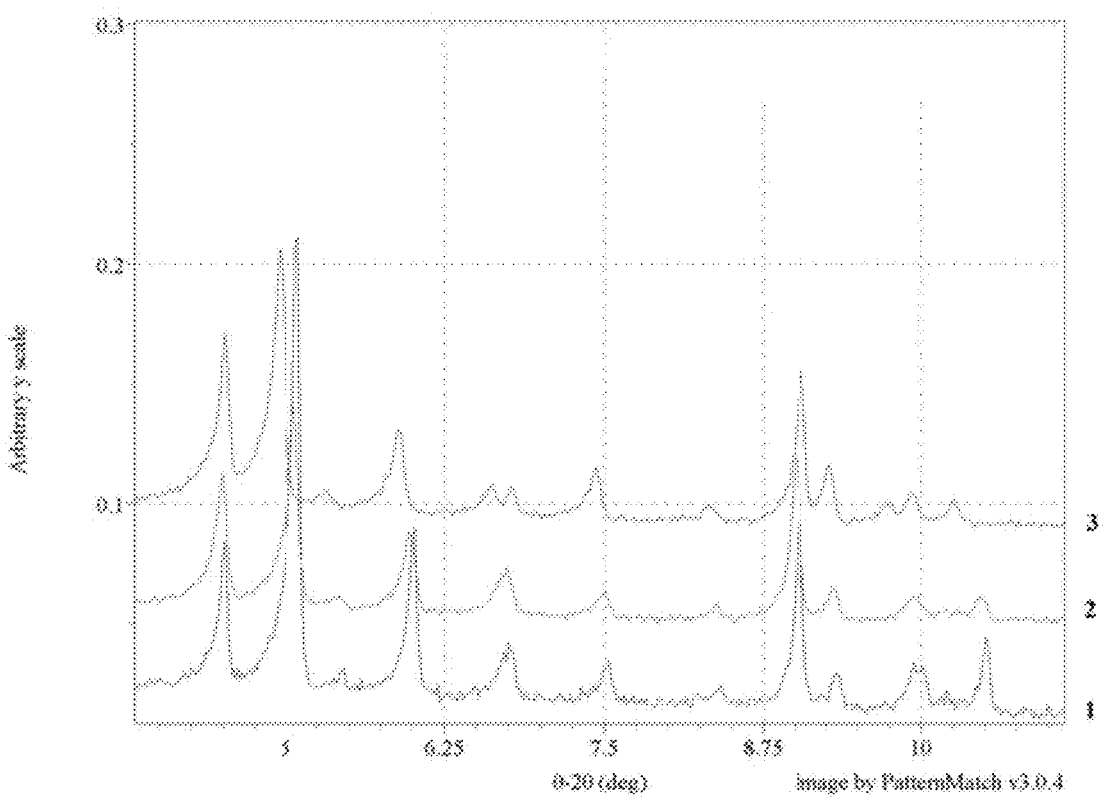
1 = 95:05 (EtOH/H₂O slurry, 0.30a<sub>w</sub>)
1 = 95:05 (EtOH/H₂O slurry, 0.30a_w)
2 = Acetone slurry
3 = 99:01 (ACN/H₂O slurry, 0.21a_w)

Figure 21 – XRPD peak position variability for Form II for slurries indexed in Figures 17 – 19, shown from approximately 13°2θ to approximately 21.5°2θ
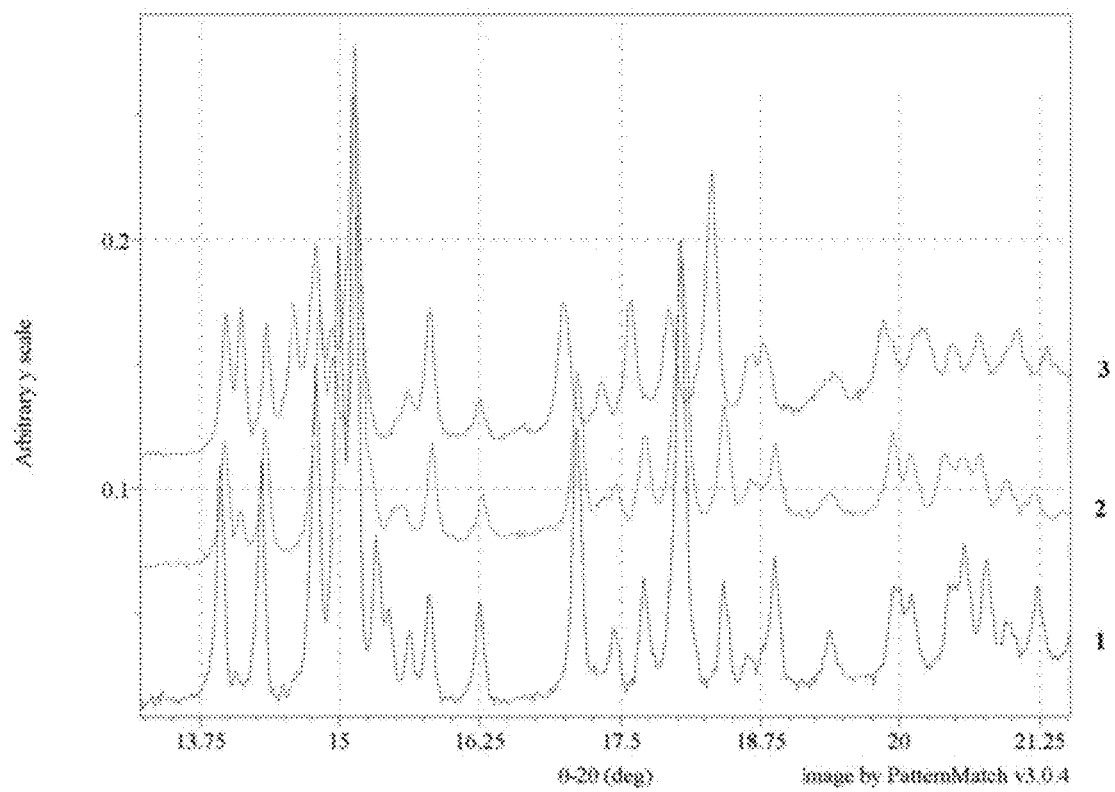
1 = 95:05 (EtOH/H₂O slurry, 0.30aₐ)
2 = Acetone slurry
3 = 99:01 (ACN/H₂O slurry, 0.21aₐ)

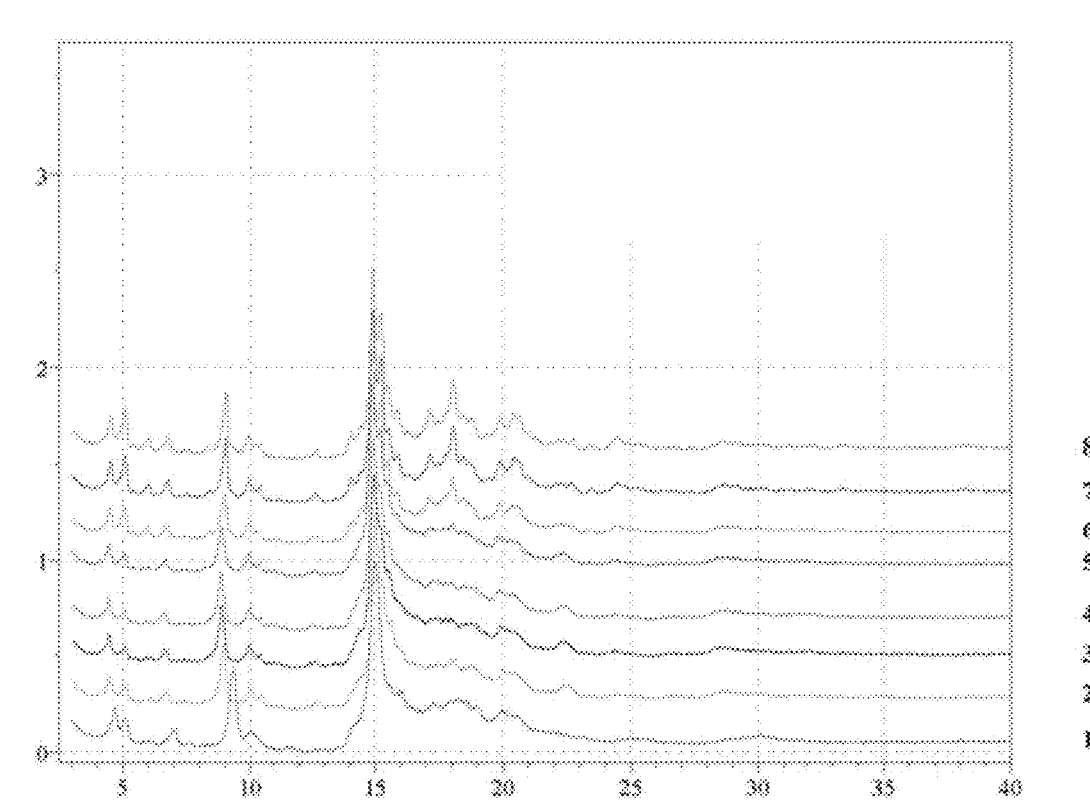
Figure 22 – VRH-XRPD experiment for Form II
1 = Form II, 0% RH
2 = Form II, 25% RH
3 = Form II, 55% RH
4 = Form II, 75% RH
5 = Form II, 85% RH
6 = Form II, 75% RH
7 = Form II, 55% RH
8 = Form II, initial, 40% RH Figure 23 – XRPD peak position variability for Form II observed by VH-XRPD, shown from approximately 7.5°2θ to approximately 10.2°2θ
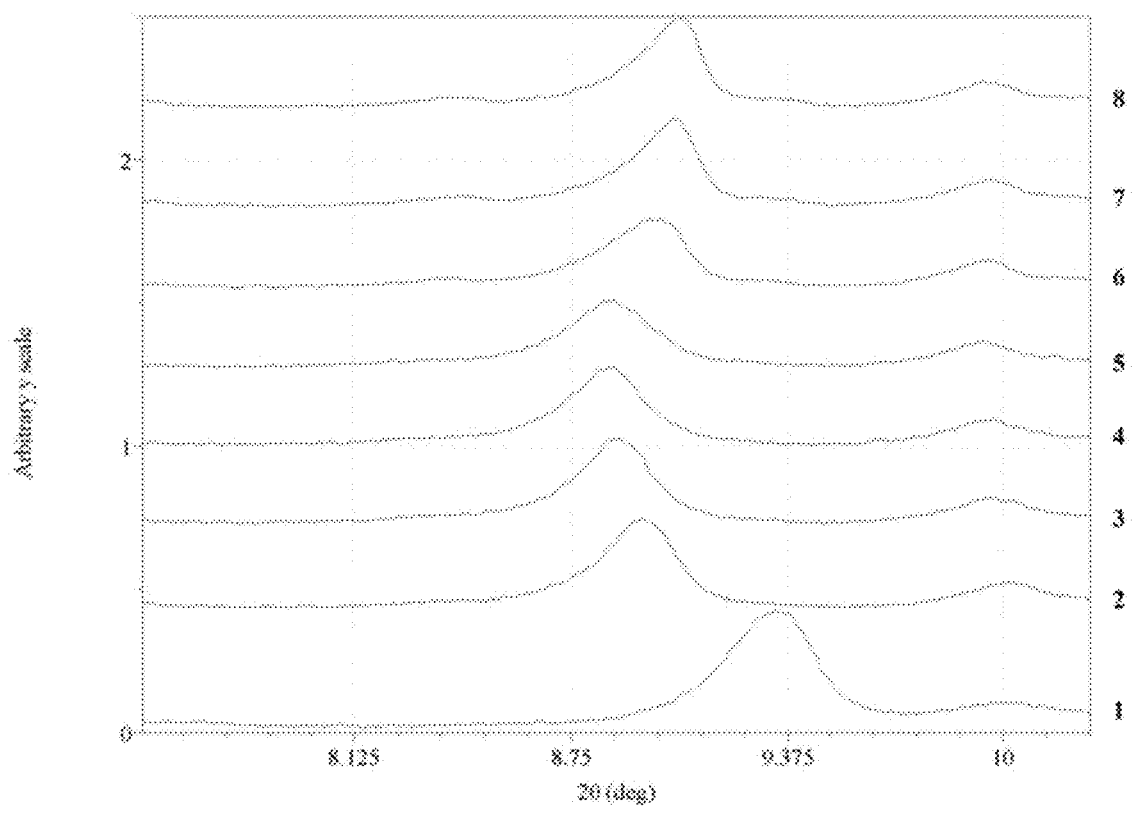
1 = Form II, 0% RH
2 = Form II, 25% RH
3 = Form II, 55% RH
4 = Form II, 75% RH
5 = Form II, 85% RH
6 = Form II, 75% RH
7 = Form II, 55% RH
8 = Form II, initial, 40% RH Figure 24 – TGA thermograms for Form II
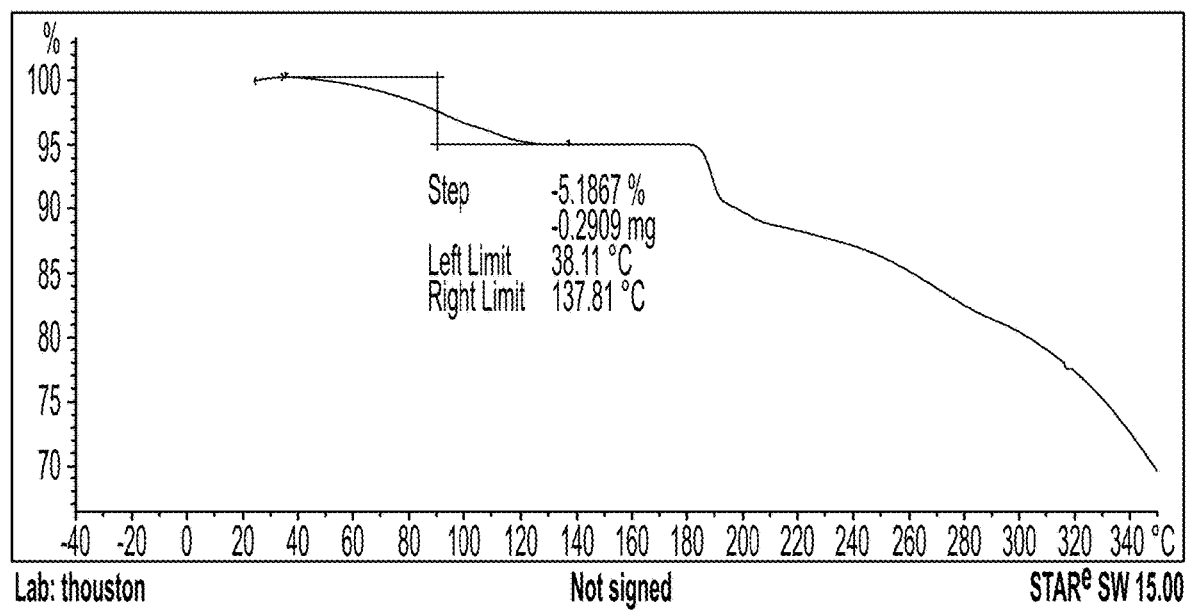
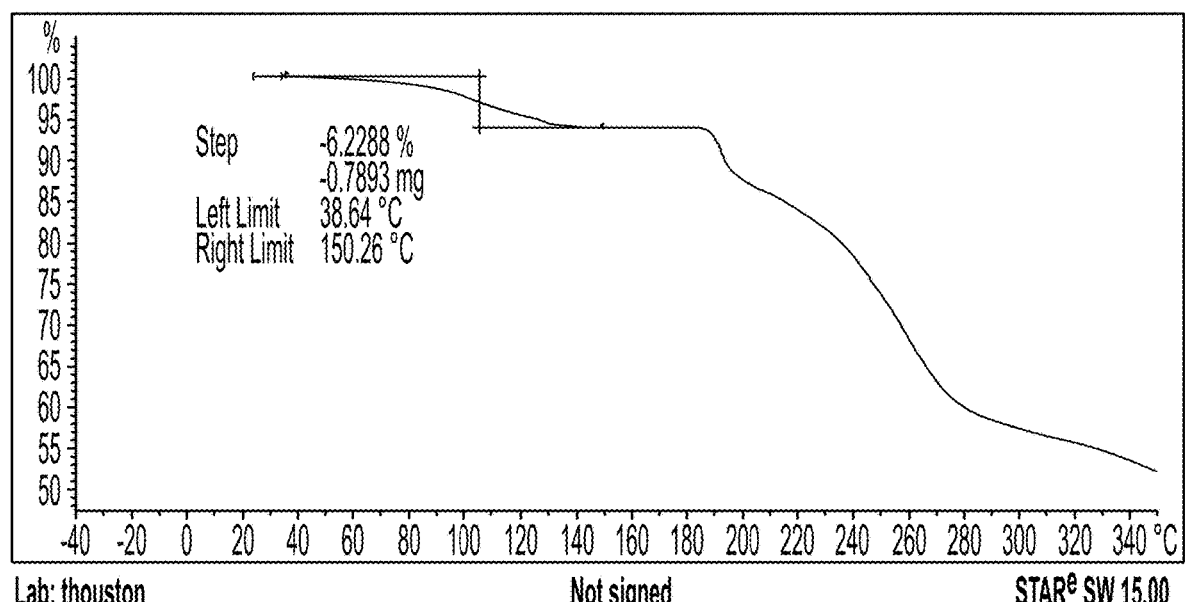

Figure 25 – DSC thermograms for Form II
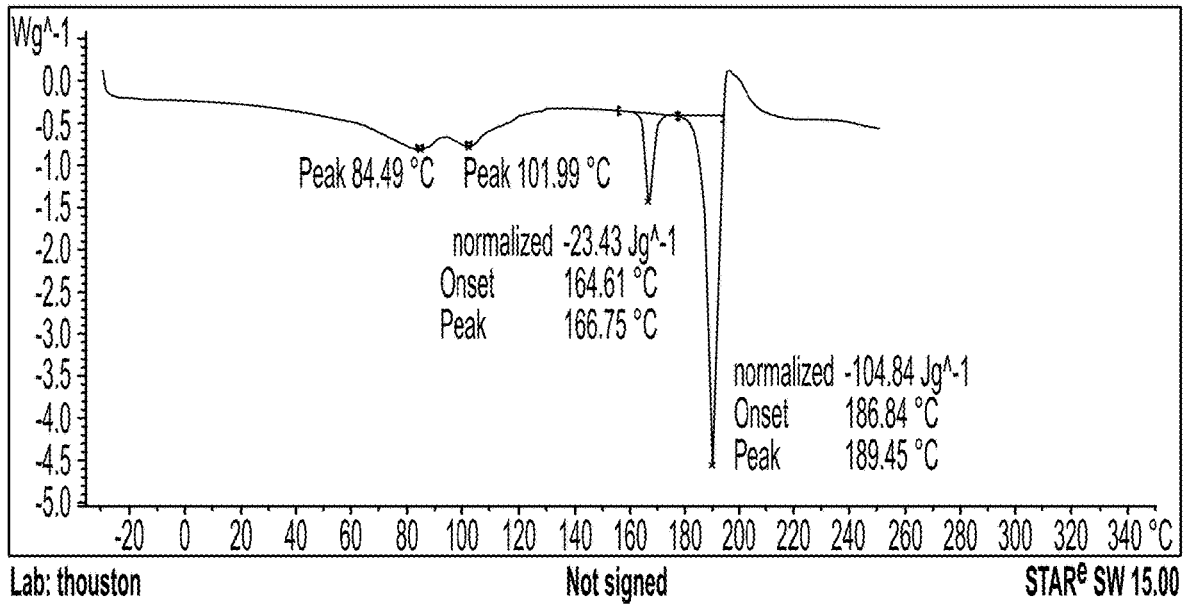
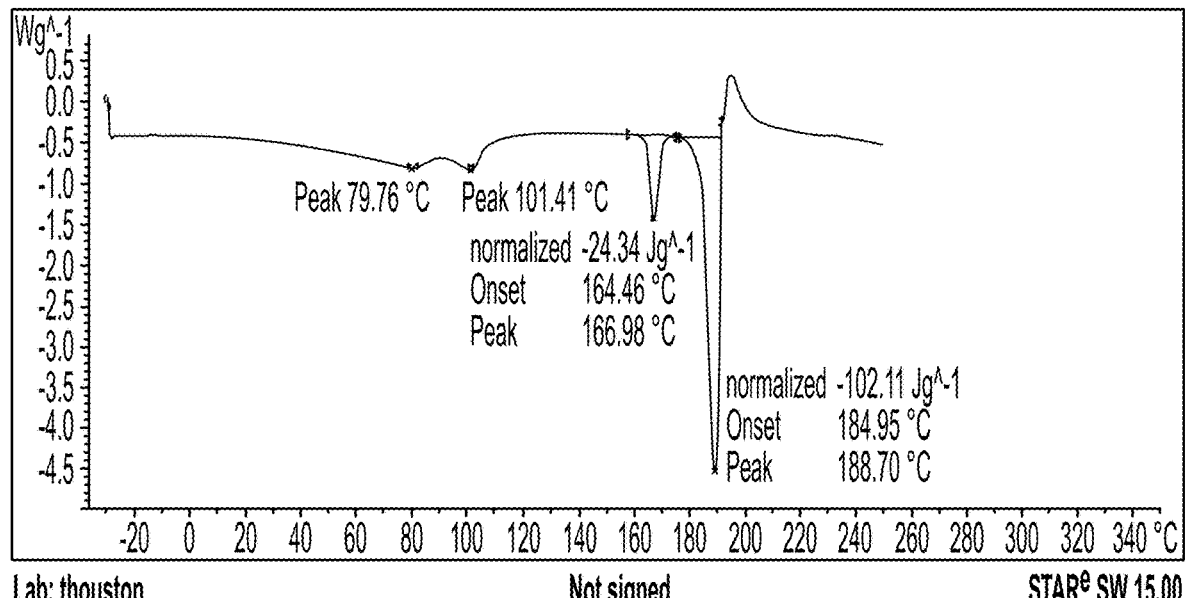

Figure 26 – Cycling DSC experiment for Form II
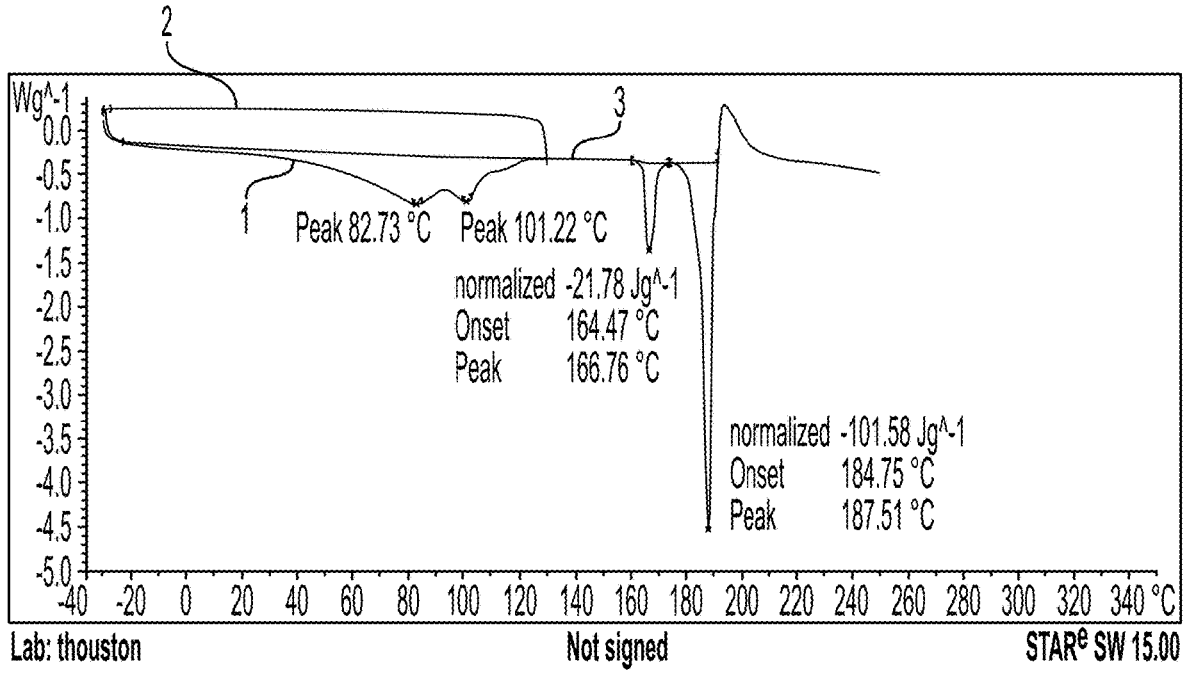
Lab: thouston                    Not signed                    STAR$^e$ SW 15.00
1 = Trace 1 (-30°C to 130°C)
2 = Trace 2 (130°C to -30°C)
3 = Trace 3 (-30°C to 250°C)

Figure 27:
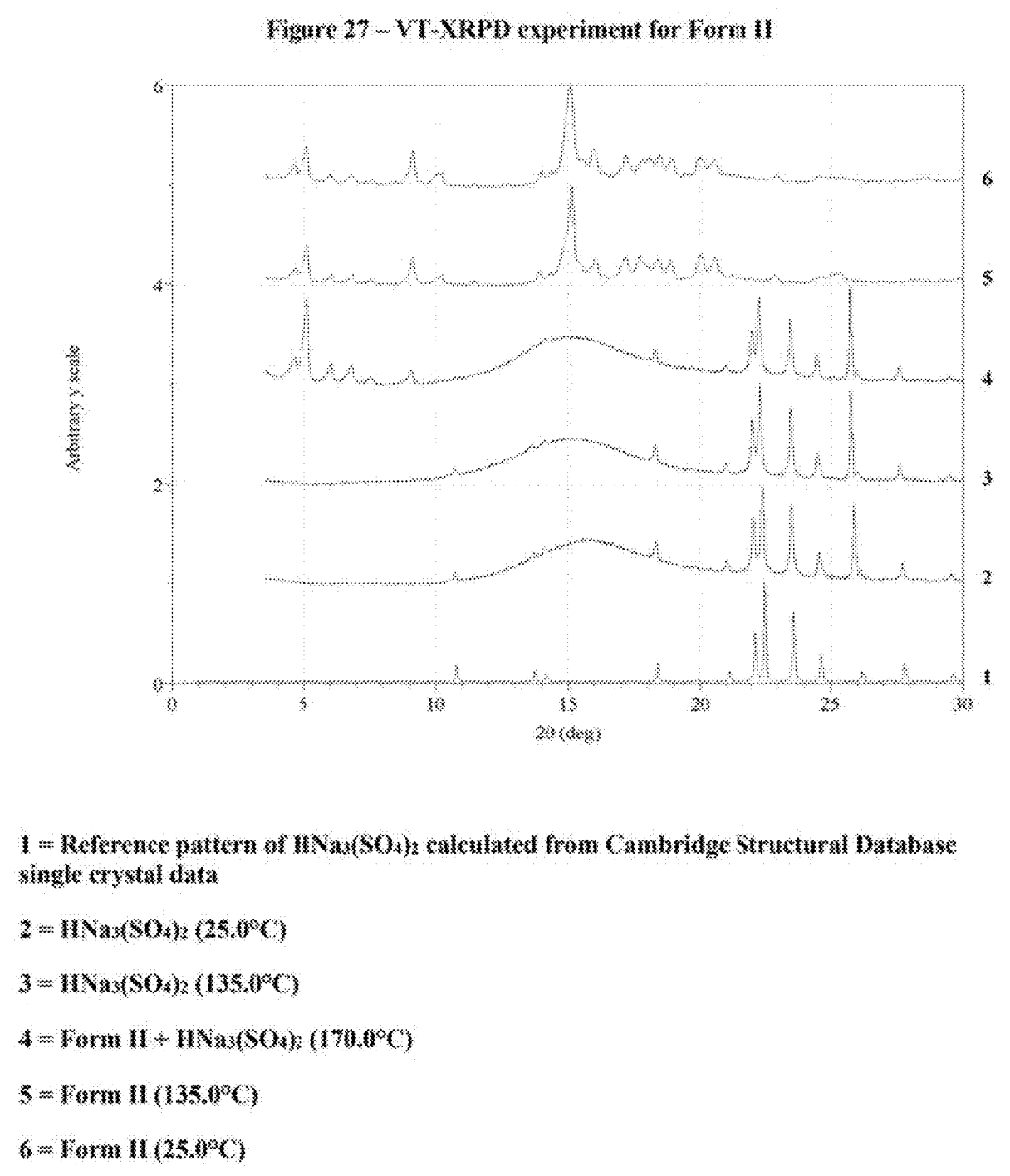

Figure 27 – VT-XRPD experiment for Form II

1 = Reference pattern of HNa₃(SO₄)₂ calculated from Cambridge Structural Database single crystal data 2 = HNa₃(SO₄)₂ (25.0°C)

3 = HNa₃(SO₄)₂ (135.0°C)

4 = Form II + HNa₃(SO₄)₂ (170.0°C)

5 = Form II (135.0°C)

6 = Form II (25.0°C)

Figure 28 – TGA thermogram for Form V
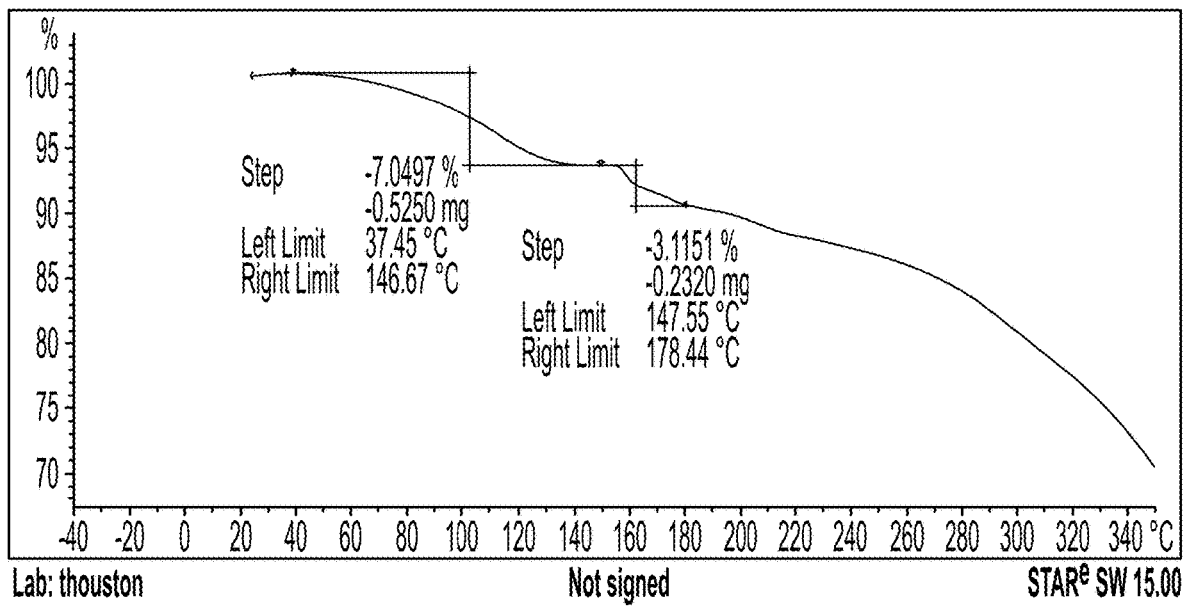

Figure 29 – DSC thermogram for Form V
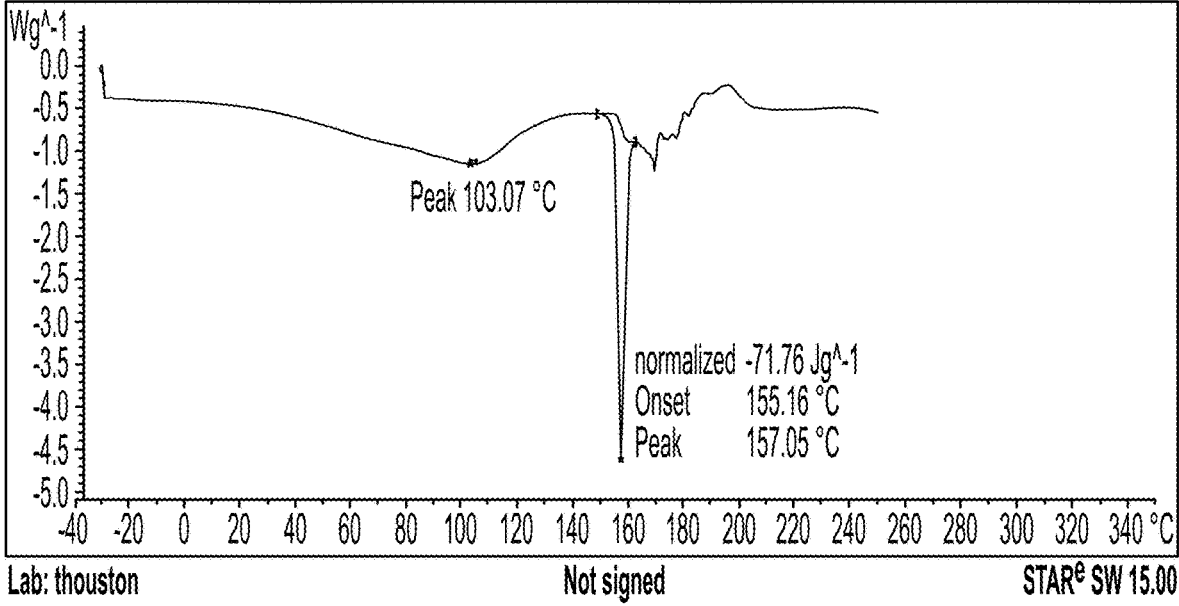
Lab: thouston                     Not signed                     STARᵉ SW 15.00

Figure 30 – Indexing results for Form XIII
(generated from a mixture of Form I and Form XIII exposed to 70°C vacuum for 2 days)

Indexing results for XRPD file 926366 collected with Cu-Kα radiation.

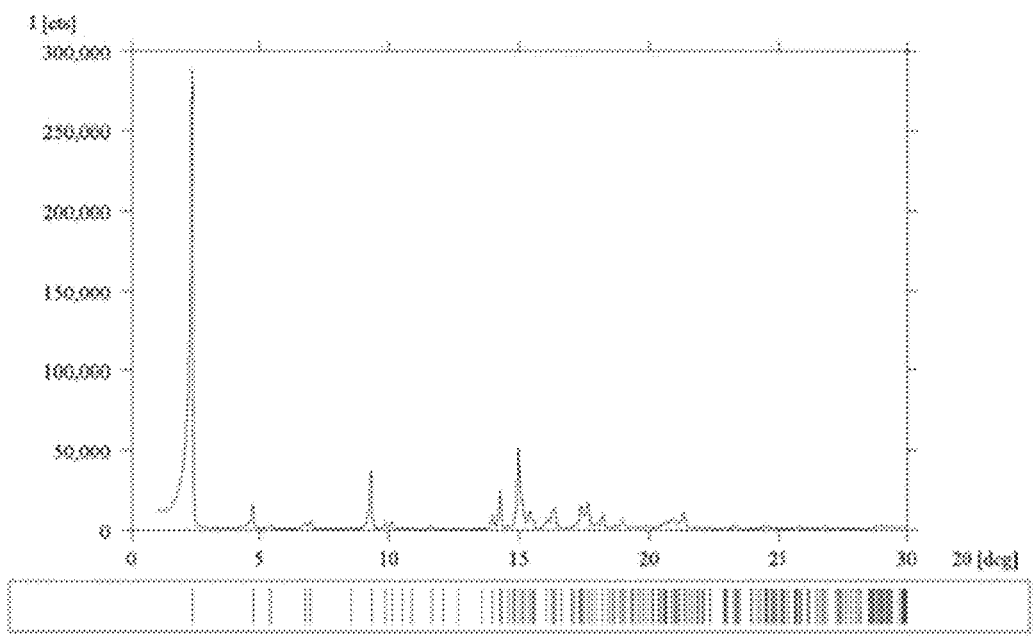

| Bravais Type | Primitive Monoclinic |
|---|---|
| a [Å] | 6.208 |
| b [Å] | 17.944 |
| c [Å] | 38.049 |
| α [deg] | 90 |
| β [deg] | 93.22 |
| γ [deg] | 90 |
| Volume [Å³/cell] | 4,230.8 |
| Chiral Content? | Chiral |
| Extinction Symbol | P 1 2₁ 1 |
| Space Group(s) | P2₁ (4) |
| Source | Manual Input |

Indexing is conducted under the "Procedures for SSCI Free-dANP Activities."          Output rendered using Triads™ v2.0

Figure 31 – XRPD Diffractograms of Form III and Form IX

1 = Form IX

2 = Form III

Figure 32 – Indexing results for Form III
Indexing results for XRPD file 914954 collected with Cu-Kα radiation.
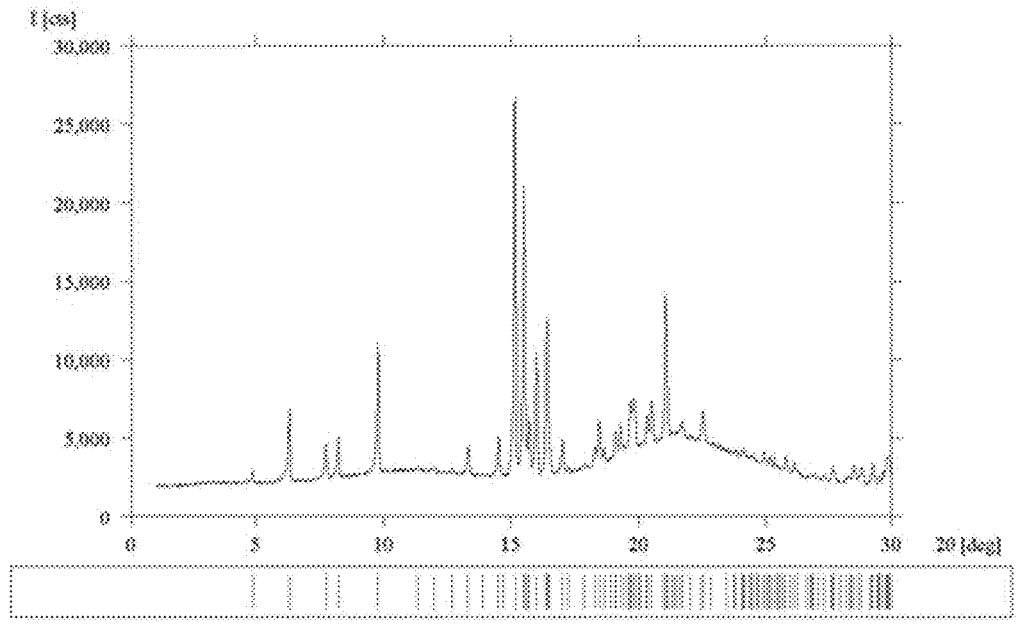
| Bravais Type | Triclinic |
|---|---|
| a [Å] | 6.699 |
| b [Å] | 13.982 |
| c [Å] | 18.099 |
| α [deg] | 93.42 |
| β [deg] | 92.09 |
| γ [deg] | 91.25 |
| Volume [Å³/cell] | 1,536.2 |
| Chiral Contents? | Chiral |
| Extinction Symbol | P - |
| Space Group(s) | P1 (1) |
| Source | Triads™ Algorithm |
Indexing is conducted under the "Procedures for SSCI Non-cGMP Activities."                    Output rendered using Triads™ v2.0

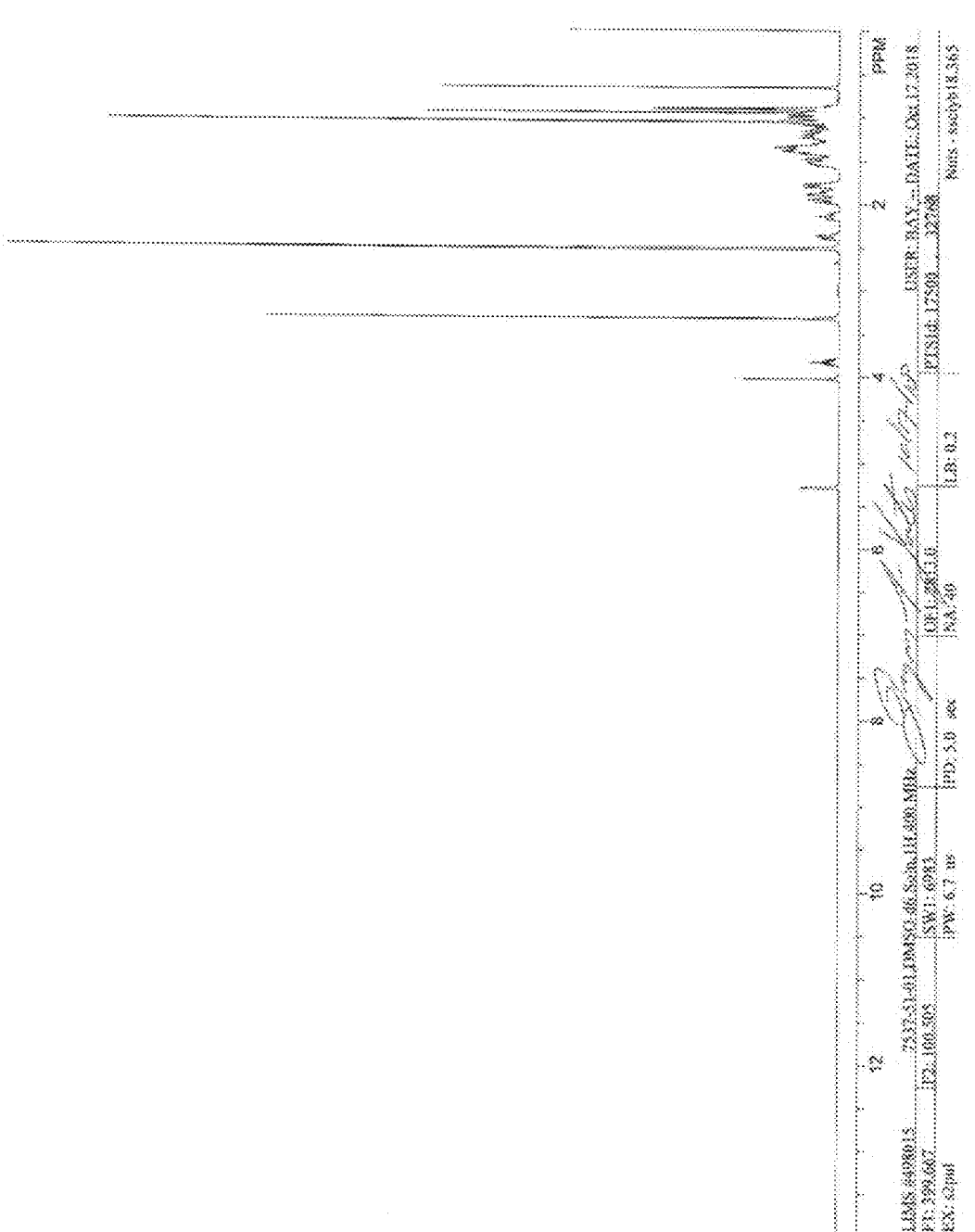
Figure 33—¹H-NMR spectrum of Form IX

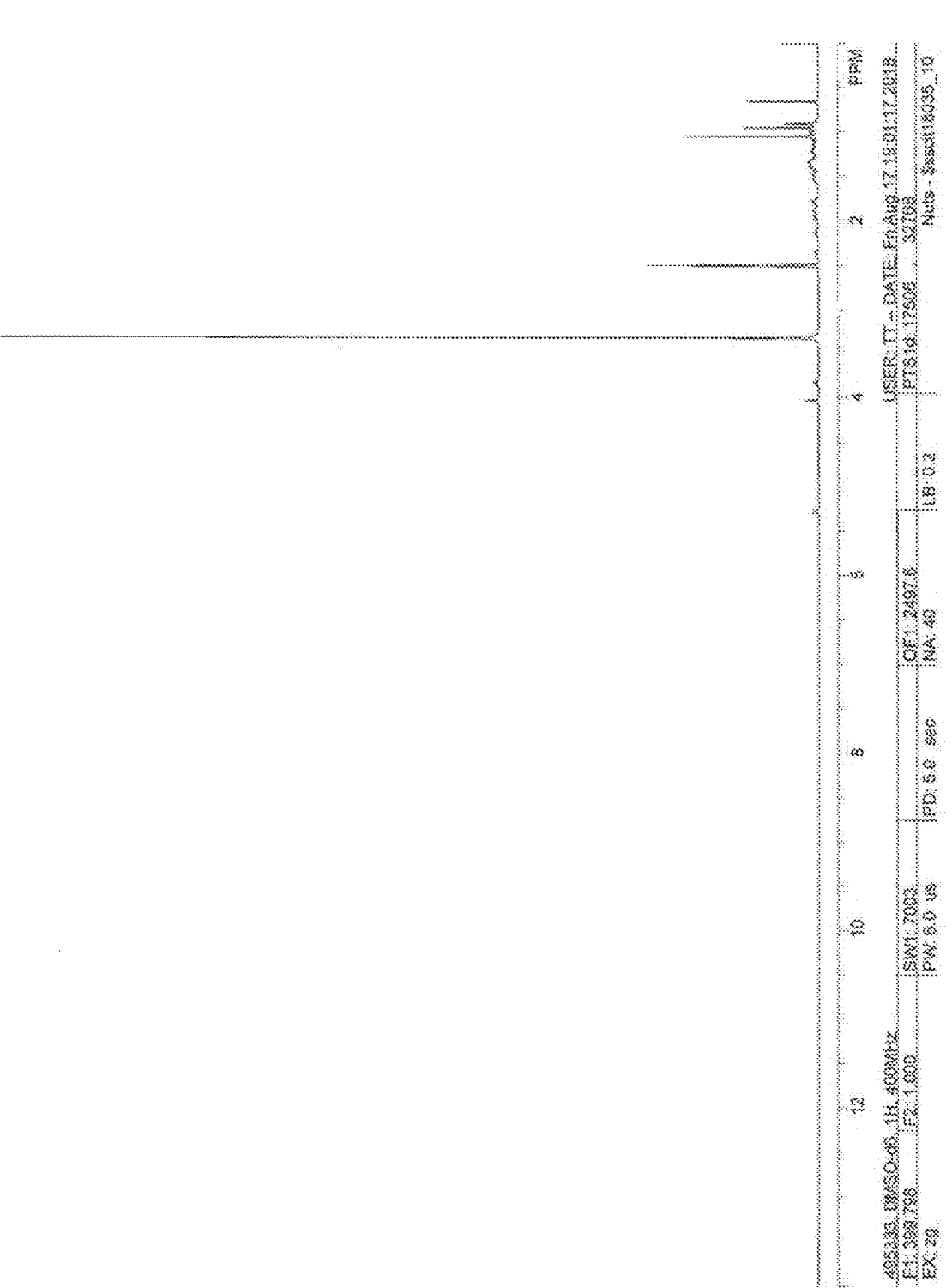
Figure 34 – 1H-NMR spectrum of 2SHC3S sodium

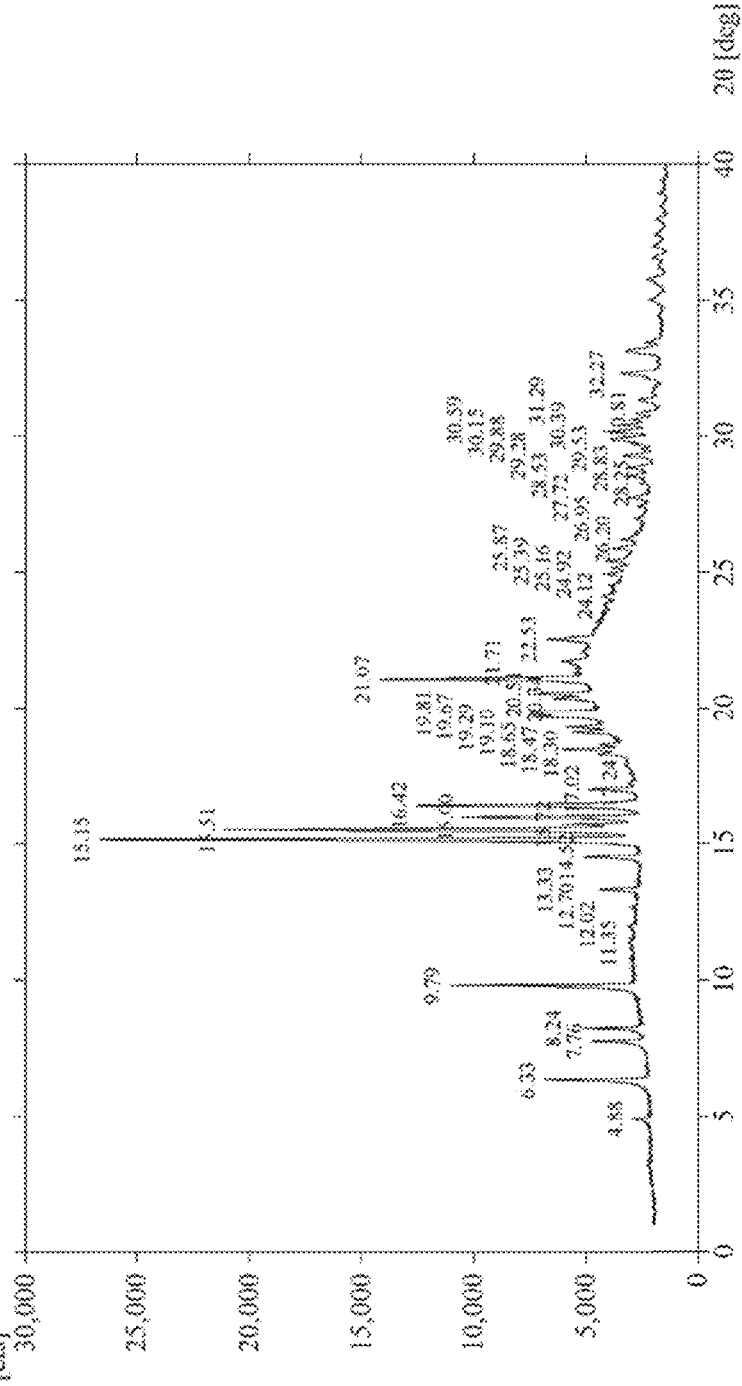
Figure 35 – Form III XRPD Diffractogram

Figure 36 – Form I XRPD Diffractogram
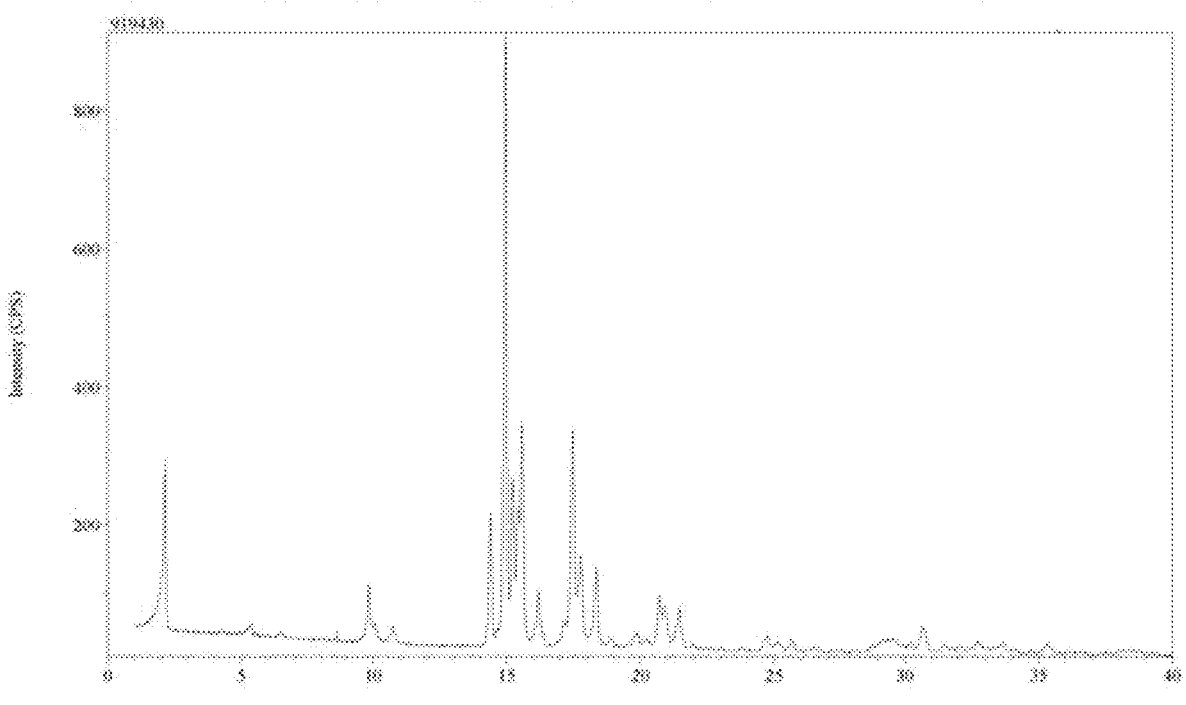

Figure 37 – Form 1 XRPD Diffractogram
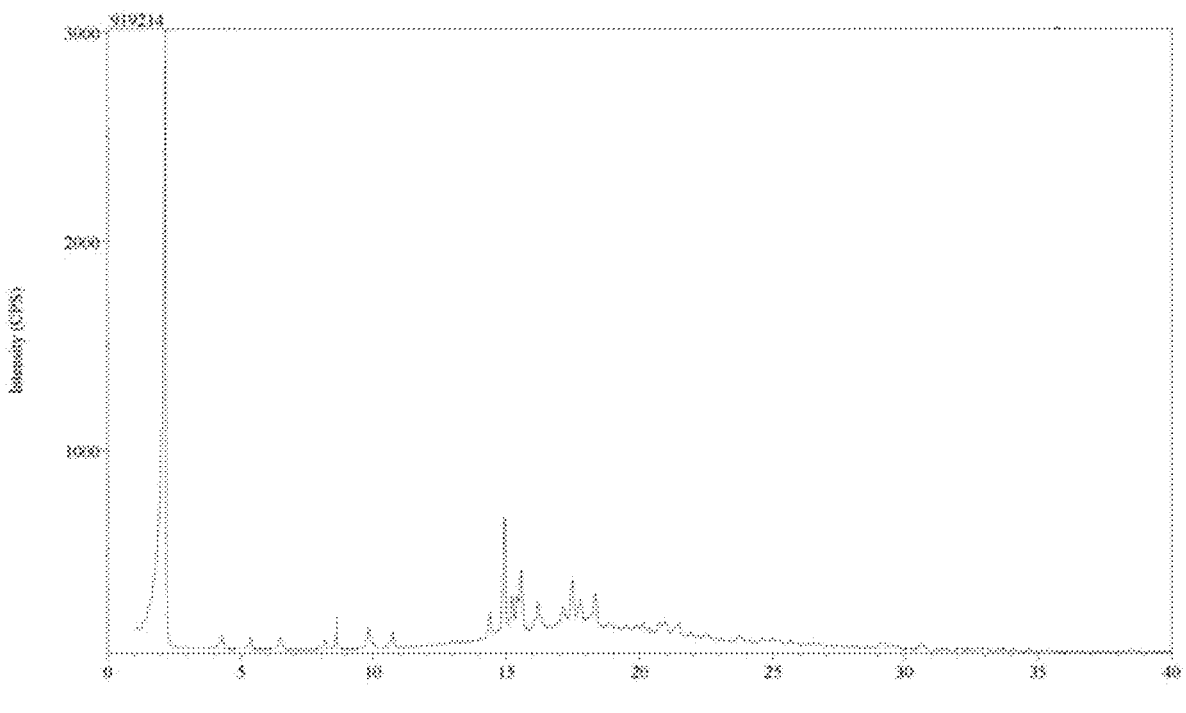

Figure 38 – Form 1 XRPD Diffractogram
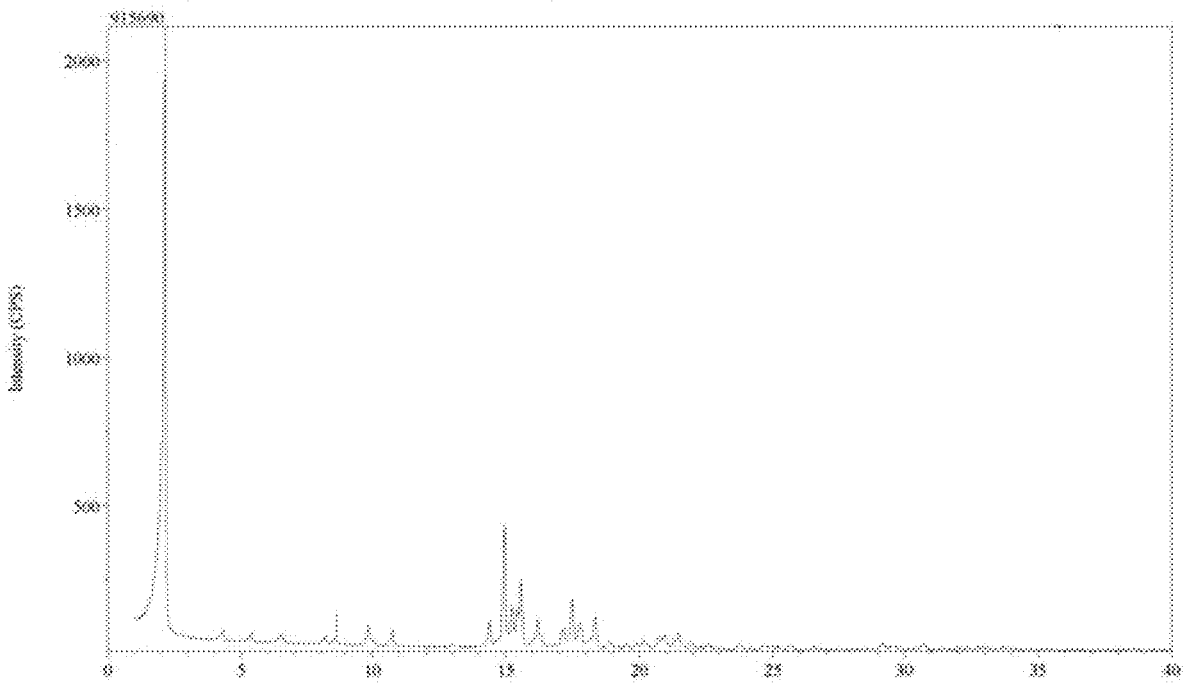

Figure 39 – XRPD Diffractograms of Form I and Form XIII
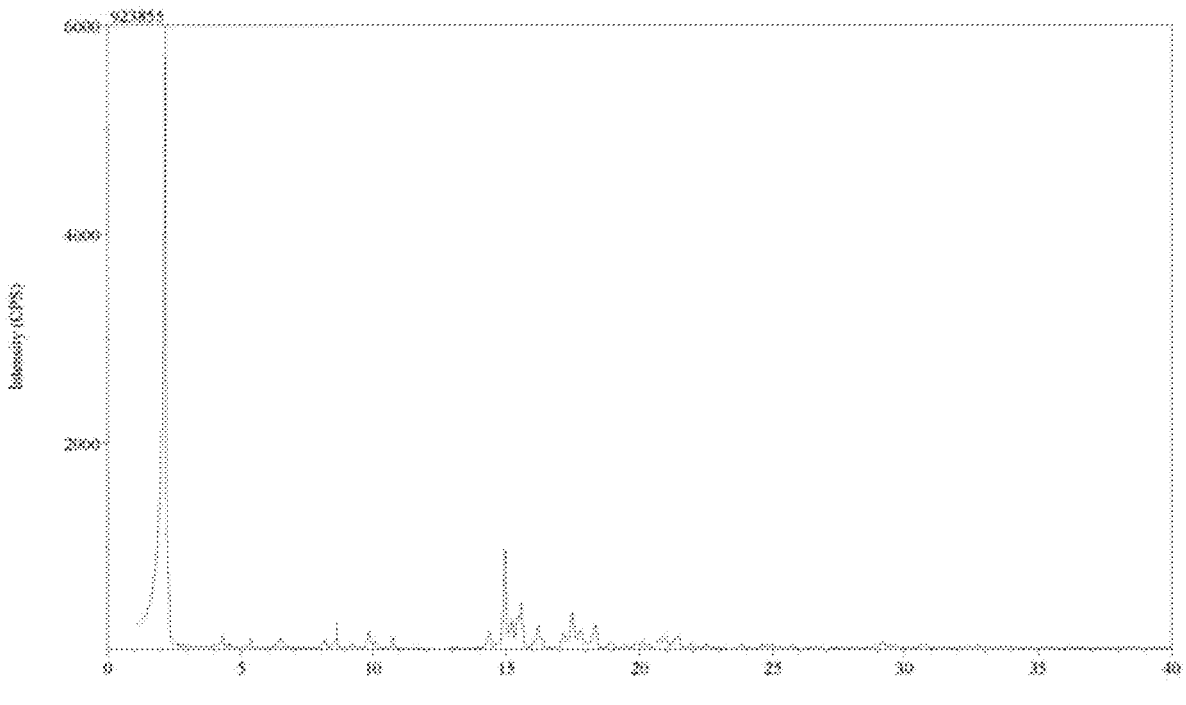

Figure 40 – Form XIII XRPD Diffractogram
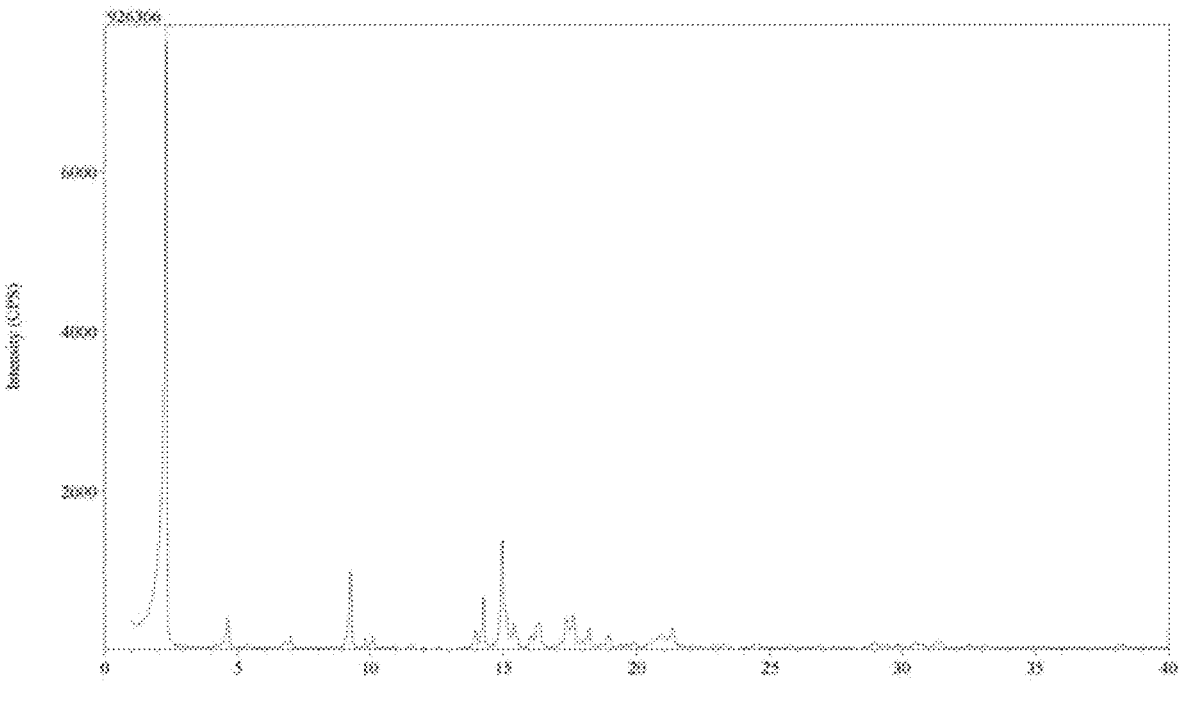

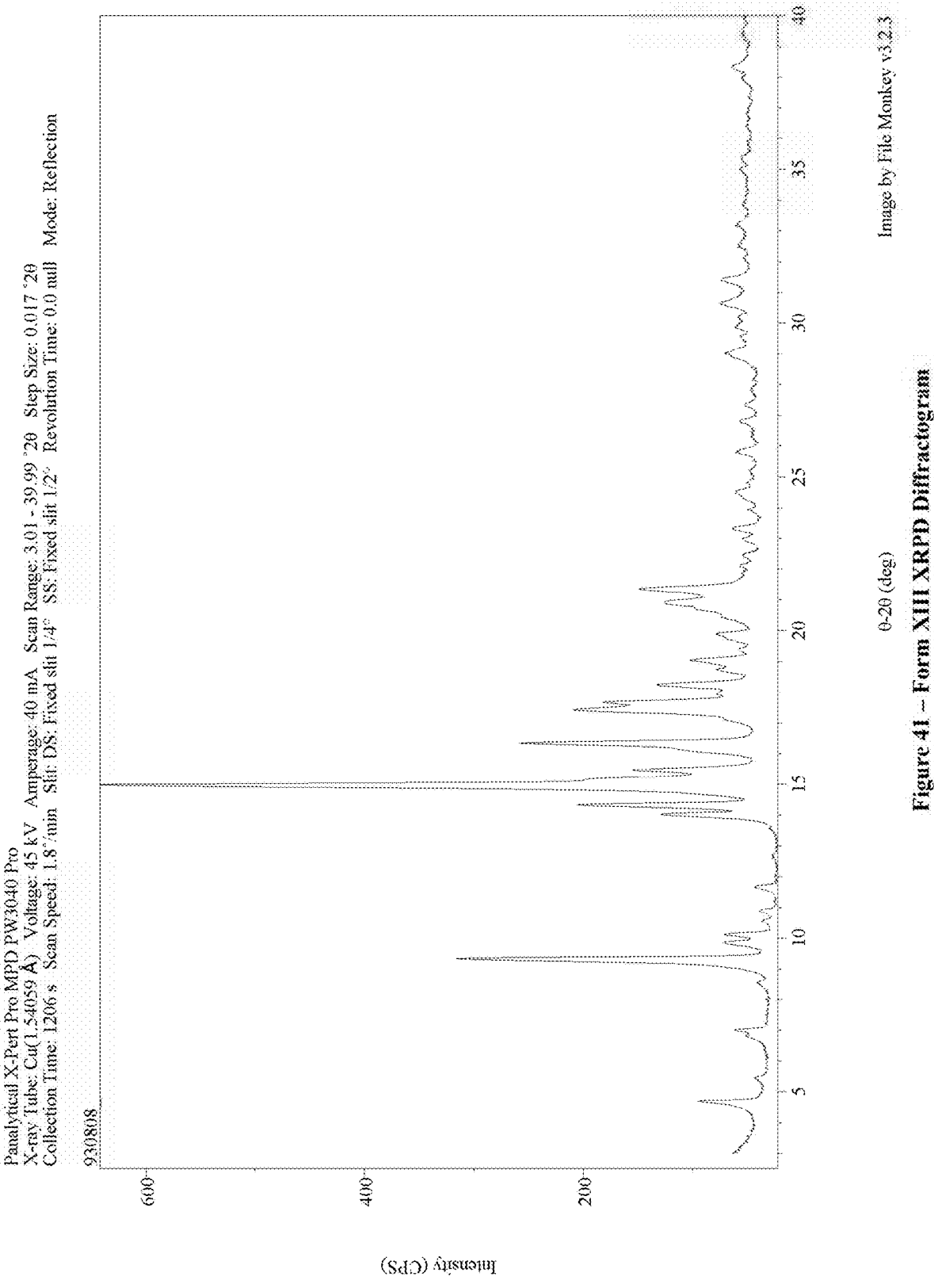
Figure 41 – Form XIII XRPD Diffractogram

Figure 42 – Form II XRPD Diffractogram
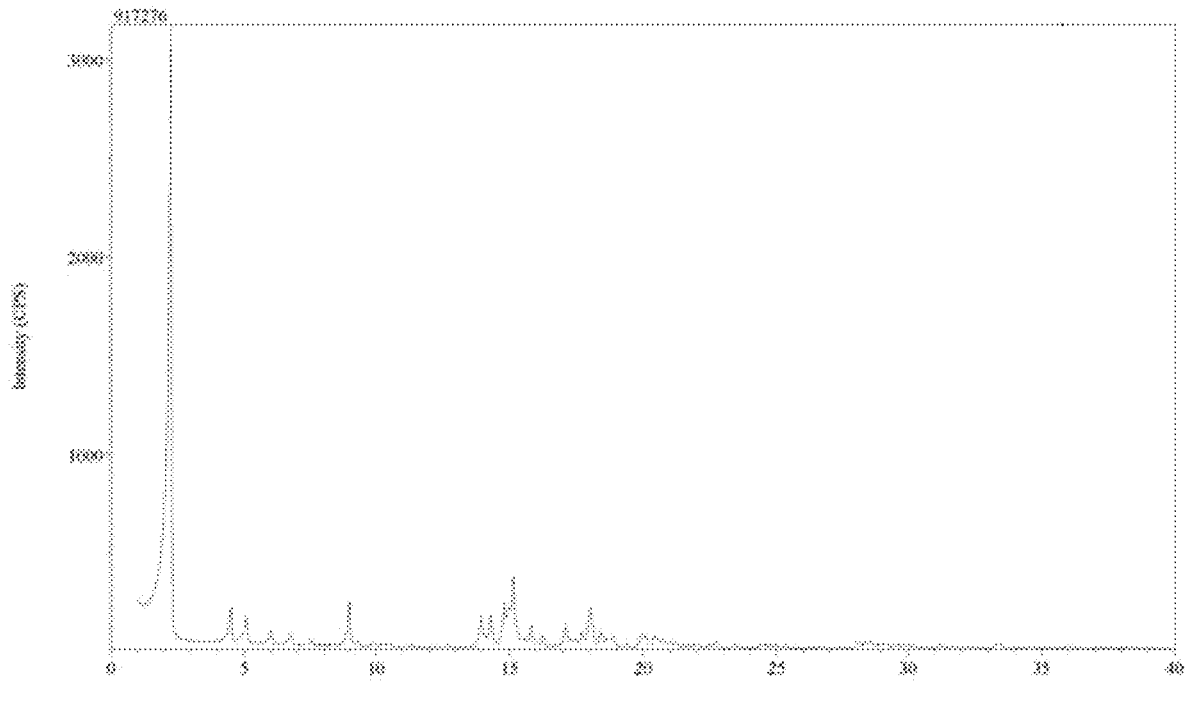

Figure 43 – Form II XRPD Diffractogram
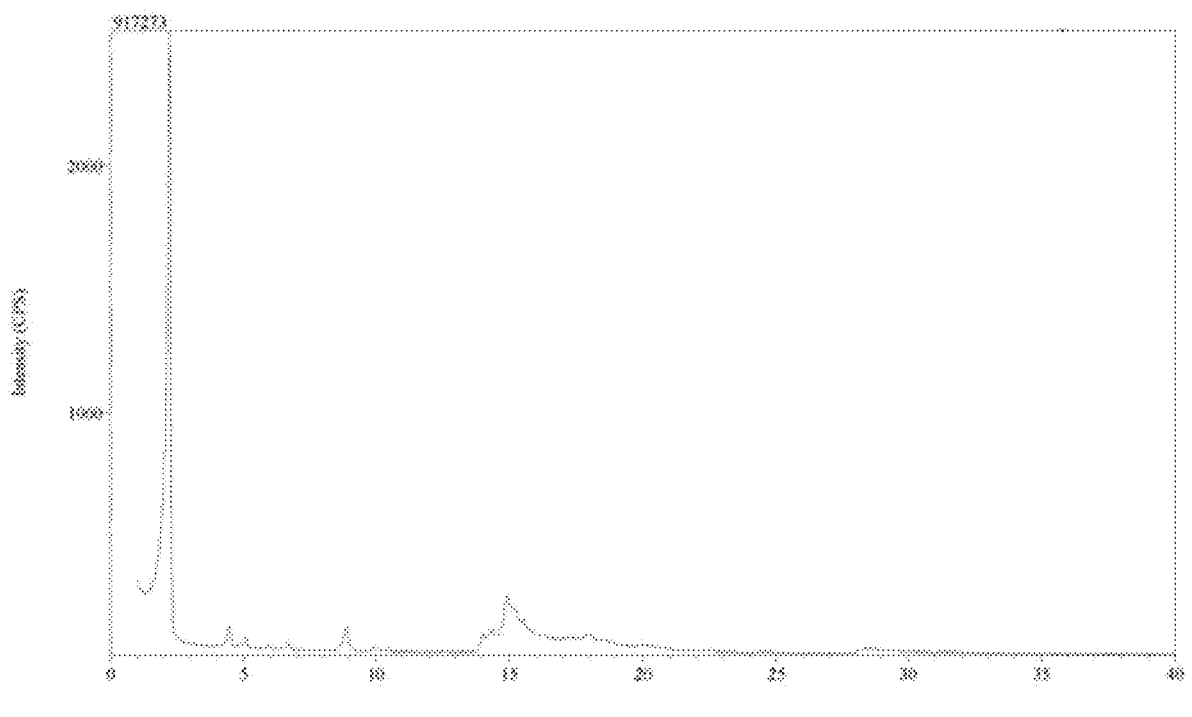

Figure 44 – Form II XRPD Diffractogram
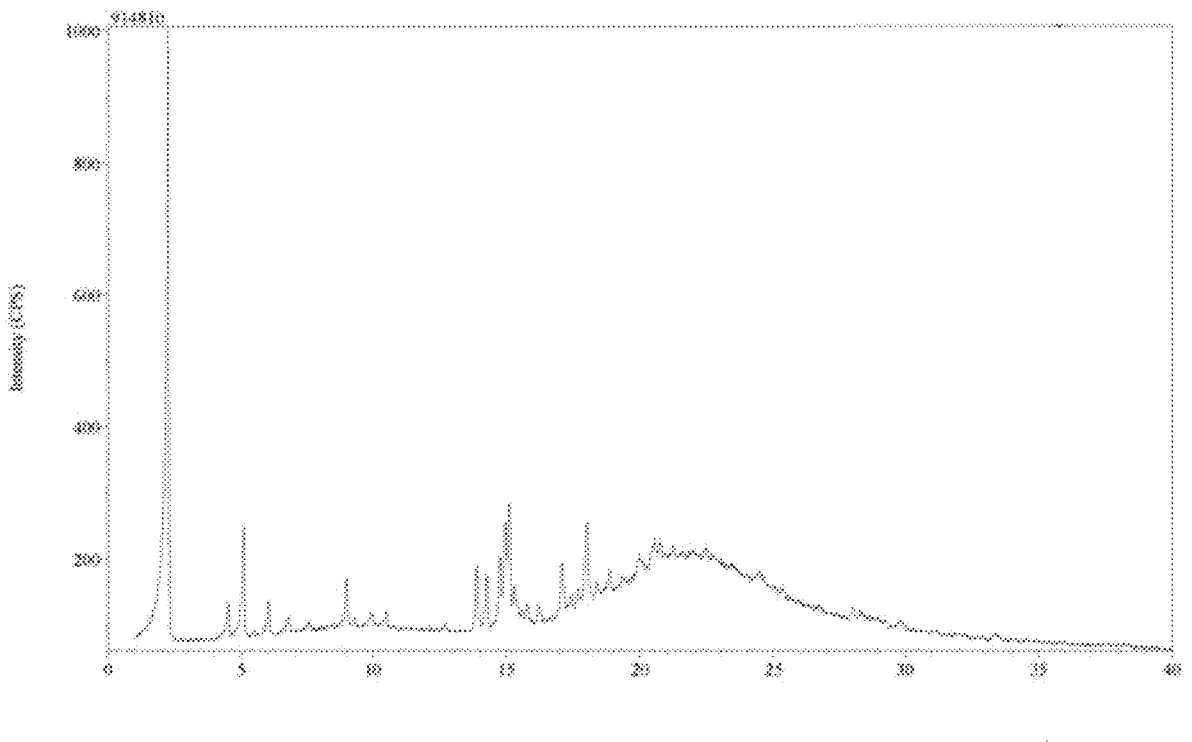

Figure 45 – XRPD Diffractogram of Form III and Form IX Mixture
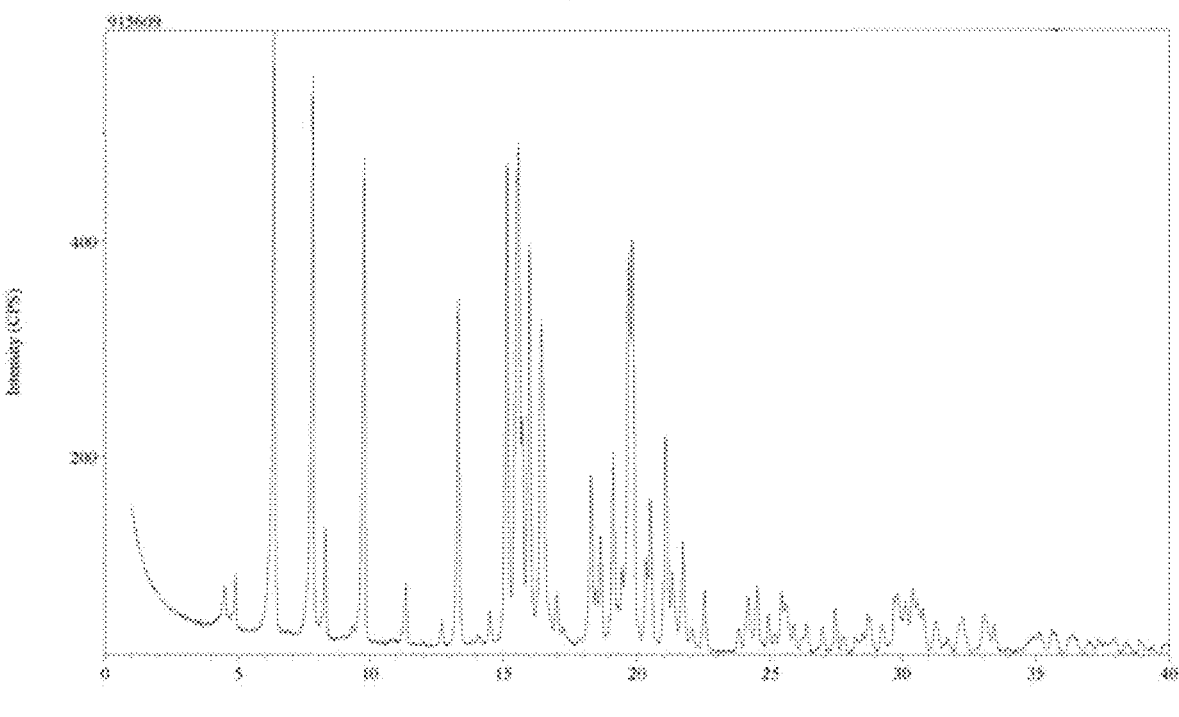

Figure 46 – Form II XRPD Diffractogram
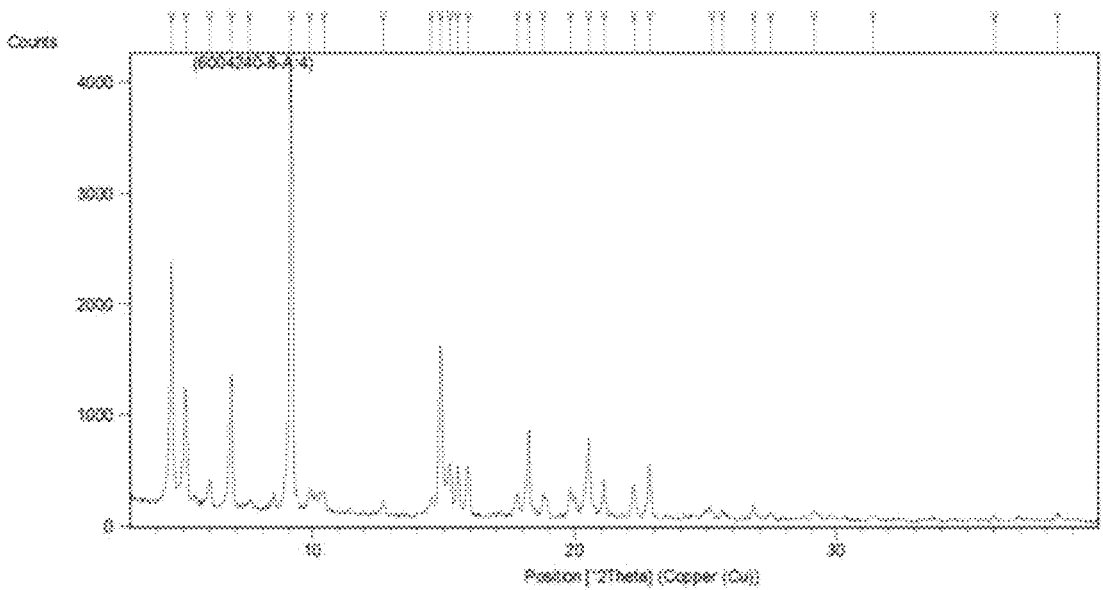

Figure 47 – Form V XRPD Diffractogram
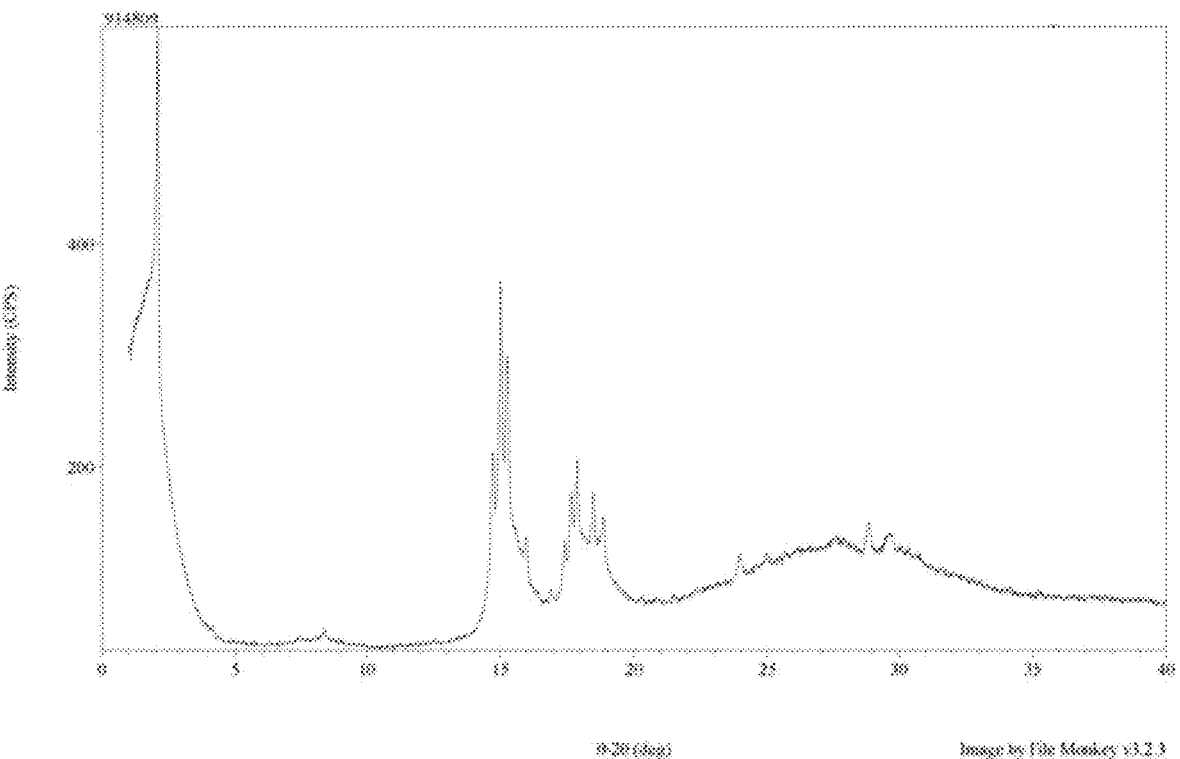

Figure 48 – Form V XRPD Diffractogram
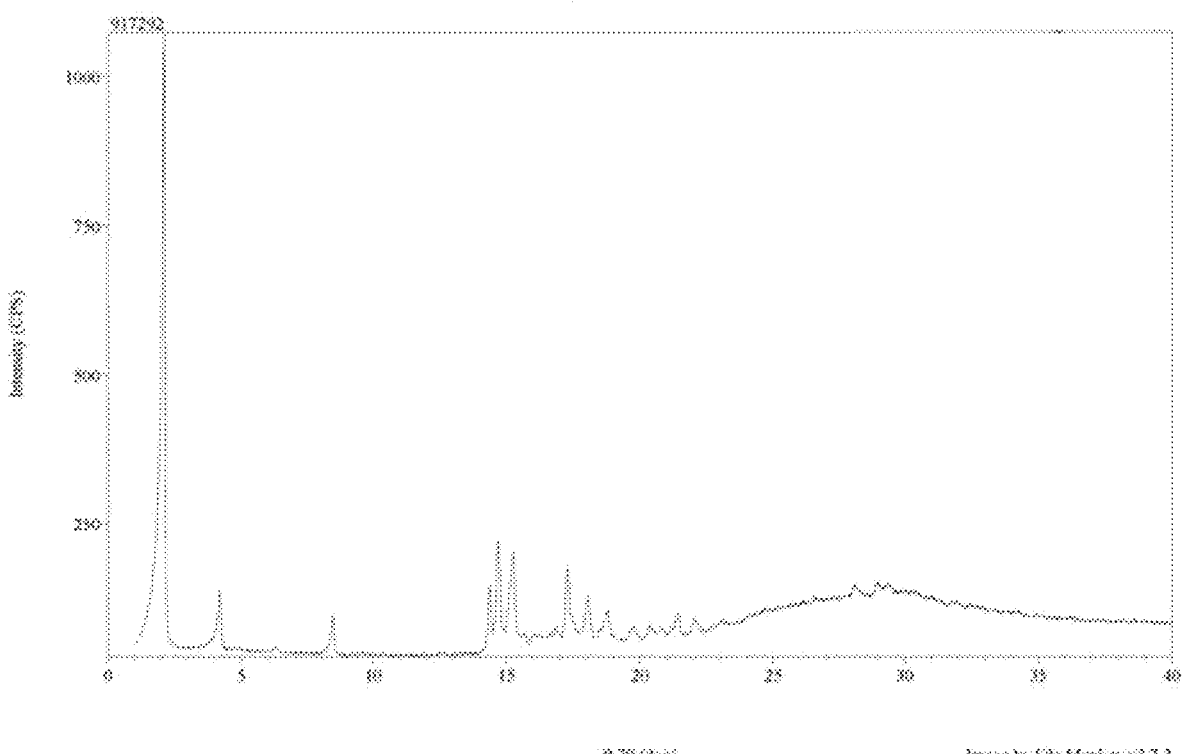

Figure 49 – Form III XRPD Diffractogram
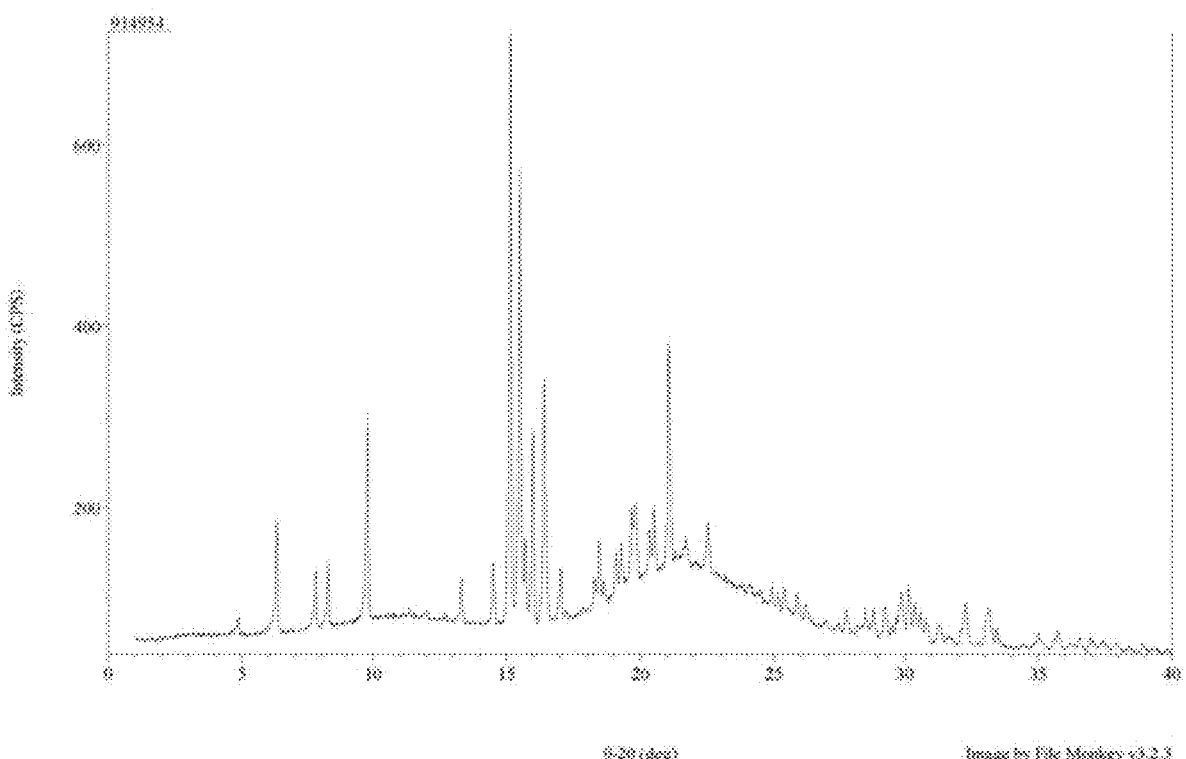

Figure 50 – Form III XRPD Diffractogram
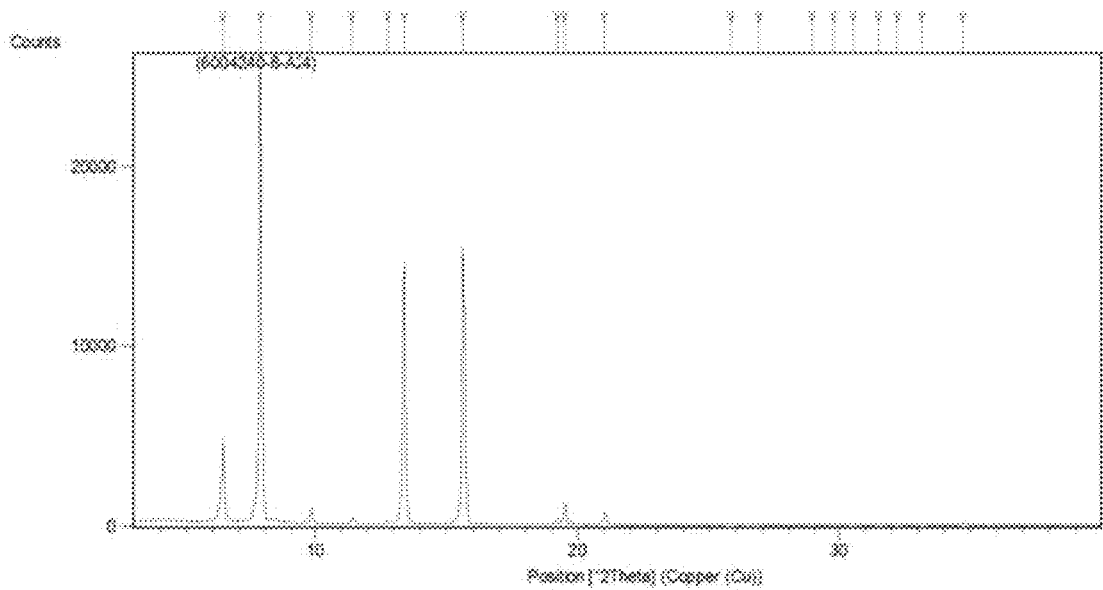

Figure 51 – Form IX XRPD Diffractogram
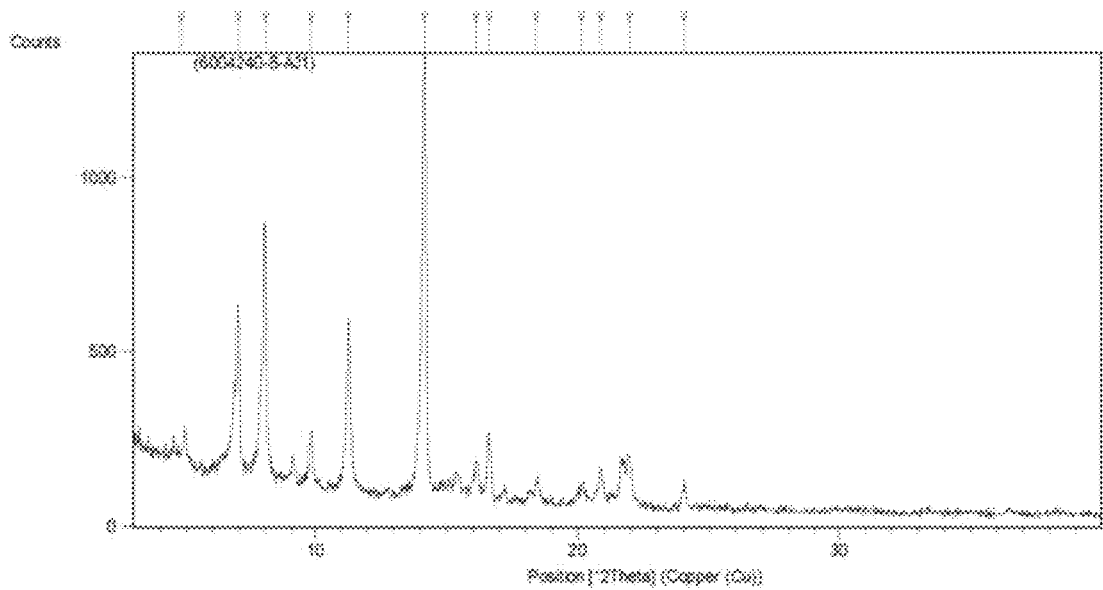

Figure 52 – Form III XRPD Diffractogram and Expanded
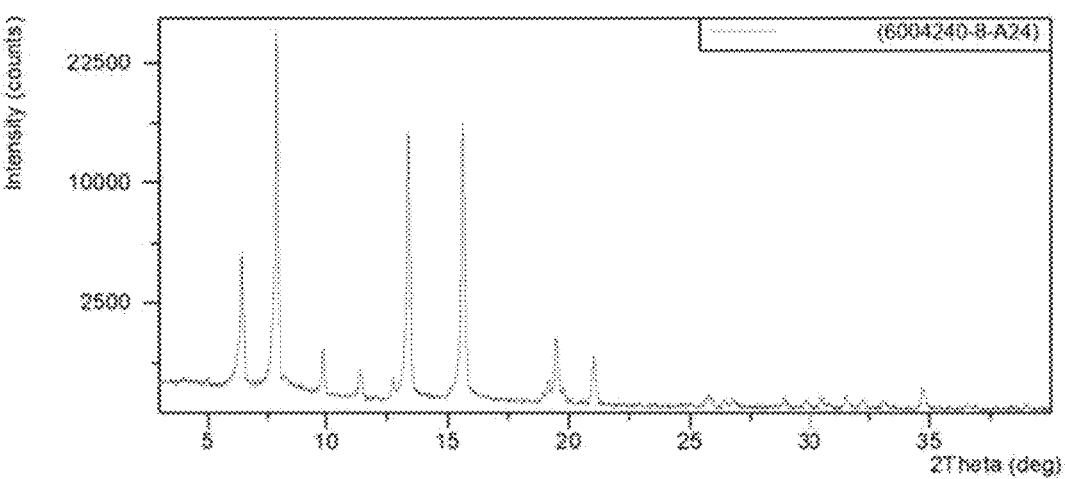
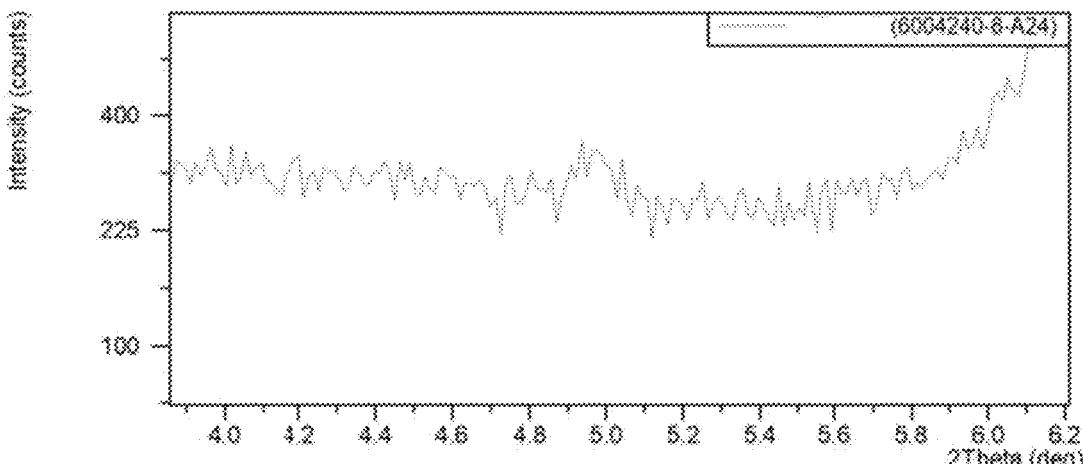
XRPD Results indicate that there is a small peak at 2θ ~ 4.9

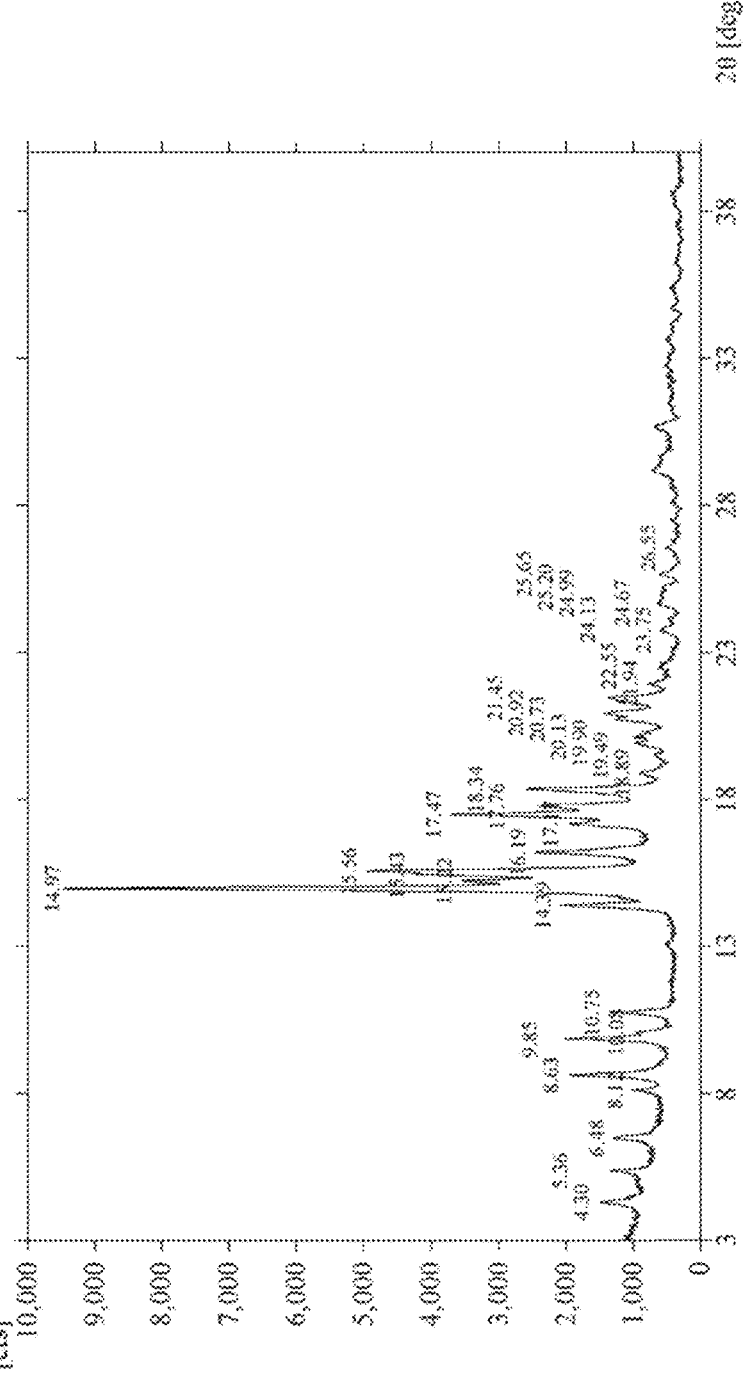
Figure 53 – Form I XRPD Diffractogram

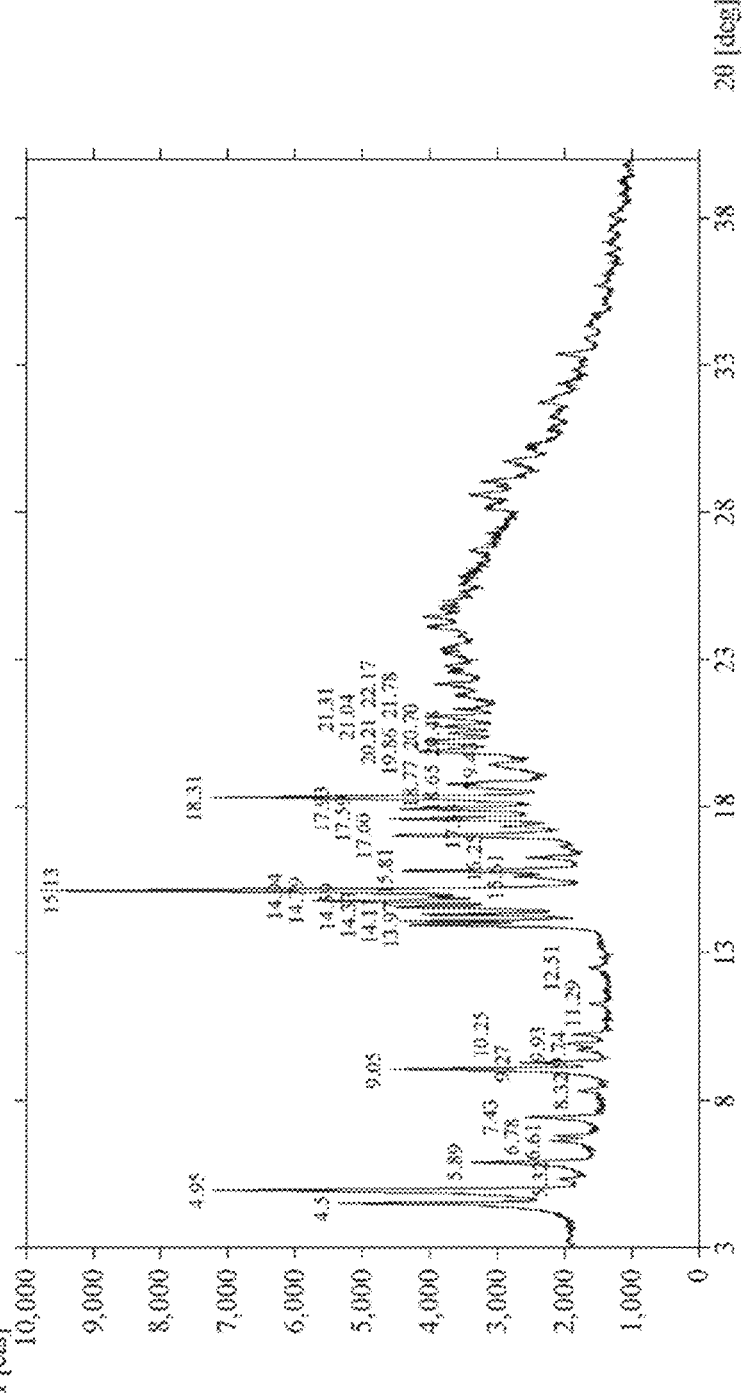
Figure 54 — Form II XRPD Diffractogram

Figure 55 – Form I XRPD Diffractogram
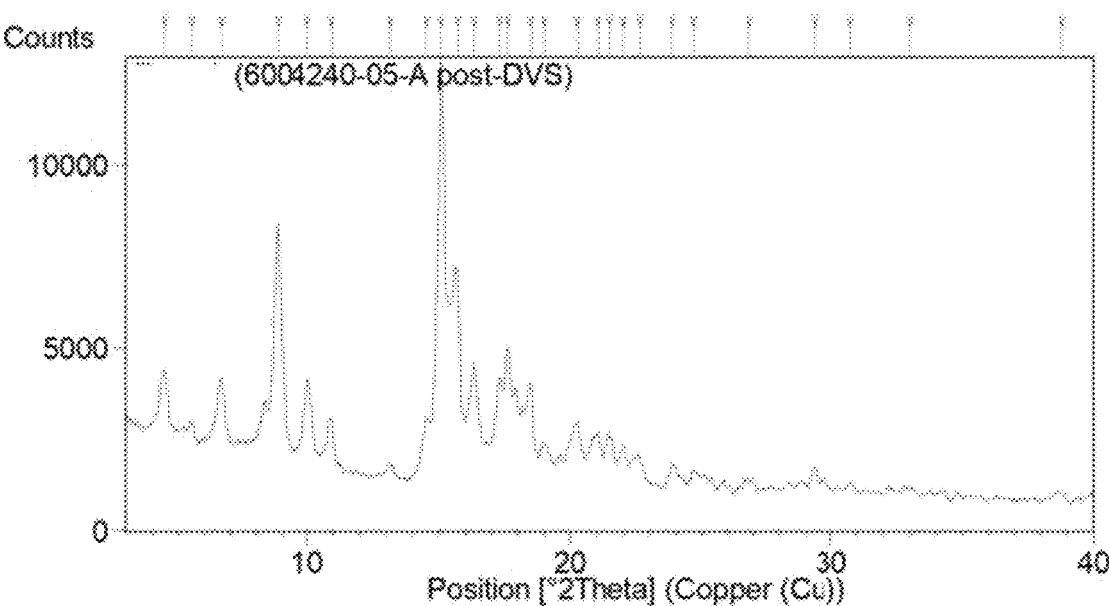

Figure 56 – Form V XRPD Diffractogram
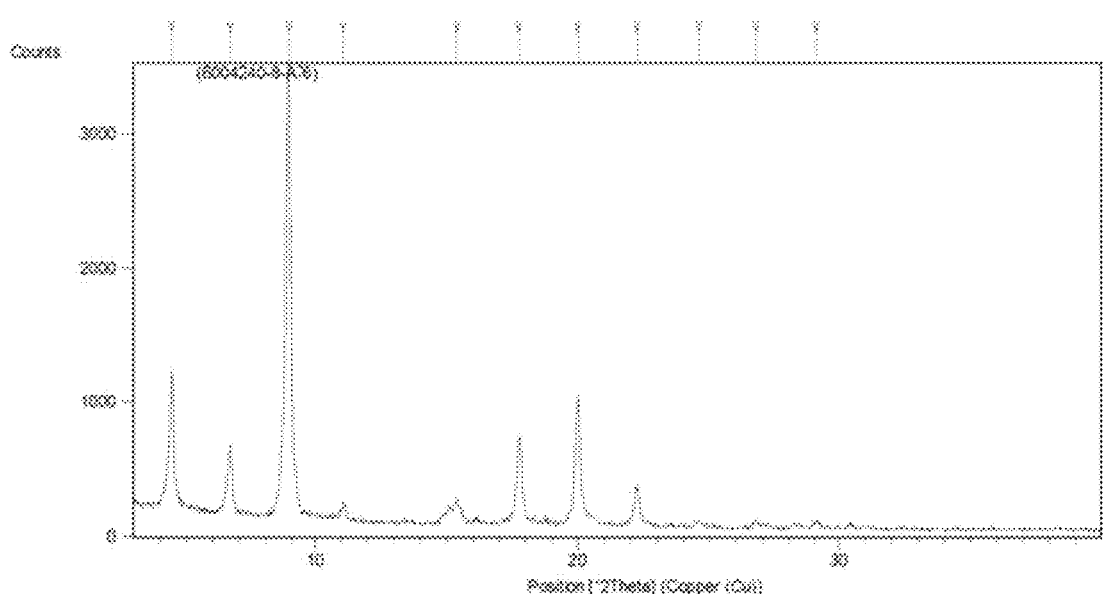

CRYSTALLINE AND LIQUID CRYSTALLINE 25-HYDROXY-CHOLEST-5-EN-3-SULFATE SODIUM AND METHODS FOR PREPARING SAME

CROSS-REFERENCE TO RELATED APPLICATION

This application claims the benefit of priority to U.S. Provisional Patent Application Ser. No. 62/954,279 filed on Dec. 27, 2019, the disclosure of which application is herein incorporated by reference.

INTRODUCTION

It has been shown previously that cholesterol metabolite, 5-cholesten-3β-25-diol-3-sulphate ("25HC3S"), decreases lipid biosynthesis and increases cholesterol secretion and degradation, and may be useful for the treatment and prevention of hypercholesterolemia, hypertriglyceridemia, and conditions related to fat accumulation and inflammation (e.g., non-alcoholic fatty liver disease (NAFLD), non-alcoholic steatohepatitis (NASH), alcoholic hepatitis, acute kidney injury (AKI), psoriasis, and atherosclerosis).

Cholesterol is used by the body for the manufacture and repair of cell membranes, and the synthesis of steroid hormones and vitamin D, and is transformed to bile acids in the liver. There are both exogenous and endogenous sources of cholesterol. The average American consumes about 450 mg of cholesterol each day and produces an additional 500 mg to 1,000 mg in the liver and other tissues. Another source is the 500 mg to 1,000 mg of biliary cholesterol that is secreted into the intestine daily, and about 50 percent is reabsorbed (enterohepatic circulation).

High serum lipid levels (hypercholesterolemia and hypertriglyceridemia) are associated with the accumulation of cholesterol in arterial walls, and can result in NAFLD and atherosclerosis. The plaques that characterize atherosclerosis inhibit blood flow and promote clot formation, and can ultimately cause death or severe disability via heart attacks and/or stroke. A number of therapeutic agents for the treatment of hyperlipidemia have been developed and are widely prescribed by physicians. Unfortunately, only about 35% of patients are responsive to the currently available therapies.

Non-alcoholic fatty liver disease (NAFLD) is the most common liver disease in the United States. This condition is associated with obesity, type-II adult onset diabetes, sedentary lifestyle, and diets high in fat. The earlier stage of NAFLD, fatty liver, is potentially reversible when proper treatment steps are taken. However, left unchecked, it can progress to inflammation of liver cells (non-alcoholic steatohepatitis, or NASH) which is much more difficult to treat. Without treatment, NASH can result in irreversible scarring of liver tissue (steatonecrosis), with the potential to cause cirrhosis, liver failure, and liver cancer.

25HC3S has been disclosed as a pharmaceutically acceptable salt, such as a sodium salt, for example (e.g., U.S. Pat. No. 10,144,759 and Ogawa et al., Steroids, 74, 81-87 (2009)). Crystalline solids tend to be more favorable for processing, storage, and stability than non-crystalline solids. However, energetics may not favor the ready formation of suitable crystalline solids and polymorphism may make creating stable crystalline solids of a particular active pharmaceutical ingredient impractical. Herein, the inventors disclose crystalline 25HC3S sodium including stable anhydrates, solvates, and hydrates as well as liquid crystal 25HC3S sodium. Methods for preparing 25HC3S are also provided.

SUMMARY

In some aspects of the present disclosure, crystalline 25HC3S sodium is provided.

In some aspects of the present disclosure, stable crystalline 25HC3S sodium is provided.

In further aspects of the present disclosure, hydrates of crystalline 25HC3S sodium are provided.

In yet further aspects of the present disclosure, monohydrates of crystalline 25HC3S sodium are provided.

In still further aspects of the present disclosure, dihydrates of crystalline 25HC3S sodium are provided.

In additional aspects of the present disclosure, variable hydrates of crystalline 25HC3S sodium are provided.

In some aspects of the present disclosure, anhydrous crystalline 25HC3S sodium is provided.

In additional aspects of the present disclosure, Form I, Form II, Form III, Form IX, Form XI, and Form XIII of crystalline 25HC3S sodium are provided.

In additional aspects of the present disclosure, liquid crystal 25HC3S sodium is provided.

In some aspects of the present disclosure, mesophases of 25HC3S sodium are provided.

In further aspects of the present disclosure, Form V 25HC3S sodium is provided.

In yet additional aspects of the present disclosure, mixtures of two or more of Form I of 25HC3S sodium, Form II of 25HC3S sodium, Form III of 25HC3S sodium, Form V of 25HC3S sodium, Form IX of 25HC3S sodium, Form XI of 25HC3S sodium, or Form XIII of 25HC3S sodium are provided.

In some aspects of the present disclosure, methods of treating one or more of hypercholesterolemia, hypertriglyceridemia, and conditions related to fat accumulation and inflammation, for example, non-alcoholic fatty liver disease (NAFLD), non-alcoholic steatohepatitis (NASH), alcoholic hepatitis, acute kidney injury (AKI), psoriasis, or atherosclerosis, comprising administering to a patient in need thereof an effective amount of a compound or pharmaceutical composition thereof of crystalline or liquid crystal mesophase 25HC3S sodium are provided.

In further aspects of the present disclosure, pharmaceutical compositions comprising crystalline 25HC3S sodium or liquid crystal 25HC3S sodium or both and at least one pharmaceutically acceptable excipient are provided.

In further aspects of the present disclosure, pharmaceutical compositions comprising mixtures of two or more of crystalline 25HC3S sodium Form I, crystalline 25HC3S sodium Form II, crystalline 25HC3S sodium Form III, liquid crystal 25HC3S sodium Form V, crystalline 25HC3S sodium Form IX, crystalline 25HC3S sodium Form XI, or crystalline 25HC3S sodium Form XIII and at least one pharmaceutically acceptable excipient are provided.

Aspects of the present disclosure also include methods for preparing 25HC3S. In some cases, methods include contacting 25-hydroxy-(3β)-cholest-5-en-3-ol with a sulfating agent to produce a 25-hydroxy-(3β)-cholest-5-en-3-sulfate organic cationic salt; and contacting the 25-hydroxy-(3β)-cholest-5-en-3-sulfate organic cationic salt with at least one metal salt to produce the 5-cholesten-3β,25-diol 3-sulfate metal salt.

In some cases, the sulfating agent is chosen from sulfur trioxide complexes, sulfuric acid compounds, sulfonic acid compounds, and sulfonate compounds. In some cases, the sulfating agent is a sulfur trioxide-pyridine complex. In some cases, the sulfating agent is chosen from sulfur trioxide dimethyl formamide, sulfur trioxide triethylamine, and sulfur trioxide trimethylamine. In some cases, the sulfating reagent is sulfuric acid and acetic anhydride and pyridine. In some cases, the sulfating reagent is sulfur trioxide triethylamine and pyridine. In some cases, the sulfating reagent is chosen from chlorosulfonic acid and pyridine and chlorosulfonic acid and 2,6-lutidine. In some cases, the sulfating reagent is ethyl chlorosulfonate. In some cases, the 25-hydroxy-(3β)-cholest-5-en-3-sulfate organic cationic salt is a 25-hydroxy-(3β)-cholest-5-en-3-sulfate pyridinium salt. In some cases, the sulfating reagent is contacted with an anhydride prior to contacting with the 25-hydroxy-(3β)-cholest-5-en-3-ol. In some cases, the anhydride is chosen from acetic anhydride, trifluoroacetic anhydride and triflic anhydride. In some cases, the sulfating reagent is contacted with 25-hydroxy-(3β)-cholest-5-en-3-ol in the presence of a 25-hydroxy-(3β)-cholest-5-en-3-sulfate organic cationic salt. In certain cases, the 25-hydroxy-(3β)-cholest-5-en-3-sulfate organic cationic salt is present as particles (e.g., seed crystals produced in a previous reaction or purified reaction batch).

In certain cases, the sulfating reagent is characterized prior to contacting with the 25-hydroxy-(3β)-cholest-5-en-3-ol. In certain cases, the sulfating reagent is characterized by $^1$H-NMR. In some cases, characterizing the sulfating reagent includes determining the extent of degradation of the sulfating reagent prior to contacting with the 25-hydroxy-(3β)-cholest-5-en-3-ol. In certain cases, determining the extent of degradation of the sulfating reagent includes determining the amount of impurity in the sulfating reagent prior to contacting with the 25-hydroxy-(3β)-cholest-5-en-3-ol.

In some cases, methods include quenching unreacted sulfating agent after producing the 25-hydroxy-(3β)-cholest-5-en-3-sulfate organic cationic salt. In some cases, quenching the unreacted sulfating agent includes adding water to the reaction mixture after producing the 25-hydroxy-(3β)-cholest-5-en-3-sulfate organic cationic salt. In certain cases, quenching the unreacted sulfating agent includes adding water to the reaction mixture followed by the addition of at least one base pyridine to the reaction mixture. In some cases, the at least one base is selected from a trialkylamine such as triethylamine or trimethylamine. In some cases, the at least one base is selected from 2,6-lutidine or pyridine. In certain casises the base is pyridine. In some cases, the unreacted sulfating agent in the reaction mixture is quenched under slow agitation.

In some cases, methods include purifying the 25-hydroxy-(3β)-cholest-5-en-3-sulfate organic cationic salt prior to contacting the 25-hydroxy-(3β)-cholest-5-en-3-sulfate organic cationic salt with the at least one metal salt. In some cases, the purified 25-hydroxy-(3β)-cholest-5-en-3-sulfate organic cationic salt has a purity of 70% or greater, such as 80% or greater, 90% or greater, 95% or greater, 98% or greater, or 99% or greater.

In certain cases, the purified 25-hydroxy-(3β)-cholest-5-en-3-sulfate organic cationic salt has one or more by-products of sulfation (e.g., by-products from sulfating the 25-hydroxy-(3β)-cholest-5-en-3-ol where the one or more by-products is present in an amount of 5% w/w or less, 4% w/w or less, 3% w/w or less, 2% w/w or less, or 1% w/w or less, relative to the 25-hydroxy-(3β)-cholest-5-en-3-sulfate organic cationic salt. In some cases, the bis-sulfated product (i.e., 5-cholesten-3β-25-diol-disulfate) is present in the purified 25-hydroxy-(3β)-cholest-5-en-3-sulfate organic cationic salt composition in an amount of 5% w/w or less, 4% w/w or less, 3% w/w or less, 2% w/w or less, or 1% w/w or less relative to the 25-hydroxy-(3β)-cholest-5-en-3-sulfate organic cationic salt.

In some cases, the 25-hydroxy-(3β)-cholest-5-en-3-sulfate organic cationic salt is purified by liquid chromatography. In some cases, purifying the 25-hydroxy-(3β)-cholest-5-en-3-sulfate organic cationic salt includes liquid chromatography employing a silica gel stationary phase and a mobile phase that includes at least one base. In some case, the at least one base is pyridine.

In some cases, one or more fractions collected from liquid chromatography may be combined. In some cases, the combined fractions may be concentrated. In certain cases, the combined fractions are concentrated by distillation. In certain cases, the combined fractions are concentrated under vacuum. In certain cases, the combined fractions are concentrated by distillation under vacuum. In some cases, the combined fractions are contacted with a 25-hydroxy-(3β)-cholest-5-en-3-sulfate organic cationic salt. In certain cases, the combined fractions are contacted with one or more particles of the 25-hydroxy-(3β)-cholest-5-en-3-sulfate organic cationic salt. In some cases, the 25-hydroxy-(3β)-cholest-5-en-3-sulfate organic cationic salt (e.g., particles of 25-hydroxy-(3β)-cholest-5-en-3-sulfate organic cationic salt) is contacted with the combined fractions by adding the 25-hydroxy-(3β)-cholest-5-en-3-sulfate organic cationic salt during distillation of the combined fractions. In some cases, the 25-hydroxy-(3β)-cholest-5-en-3-sulfate organic cationic salt is contacted with the combined fractions by adding the 25-hydroxy-(3β)-cholest-5-en-3-sulfate organic cationic salt after distillation of the combined fractions. In some cases, the combined fractions are concentrated and contacted with a composition containing particles of the 25-hydroxy-(3β)-cholest-5-en-3-sulfate organic cationic salt and at least one solvent.

In some cases, methods to produce the 25-hydroxy-(3β)-cholest-5-en-3-sulfate metal salt includes contacting the 25-hydroxy-(3β)-cholest-5-en-3-sulfate organic cationic salt with at least one sodium salt. In some cases, the at least one sodium salt is chosen from sodium acetate, sodium iodide, sodium chloride, sodium hydroxide and sodium methoxide. In certain cases, methods include contacting the 25-hydroxy-(3β)-cholest-5-en-3-sulfate pyridinium salt with sodium iodide to produce a 25-hydroxy-(3β)-cholest-5-en-3-sulfate sodium salt.

In some cases, methods for preparing 25-hydroxy-3β-cholesten-5-en-3-sulfate include contacting 25-hydroxy-(3β)-cholest-5-en-3-ol with a sulfur trioxide-pyridine complex to produce a 25-hydroxy-(3β)-cholest-5-en-3-sulfate pyridinium salt; and contacting the 25-hydroxy-(3β)-cholest-5-en-3-sulfate pyridinium salt with at least one sodium salt to produce the 5-cholesten-3β,25-diol 3-sulfate sodium salt.

In some cases, methods for preparing 25-hydroxy-3β-cholesten-5-en-3-sulfate include contacting (3β)-cholest-5-en-3-ol with a sulfating agent to produce a first (3β)-cholest-5-en-3-sulfate organic cationic salt; contacting the first (3β)-cholest-5-en-3-sulfate organic cationic salt with an organic base to produce a second (3β)-cholest-5-en-3-sulfate organic cationic salt; oxidizing the second (3β)-cholest-5-en-3-sulfate organic cationic salt in the presence of at least one surfactant to produce a 25-hydroxy-(3β)-cholest-(5,6-epoxy)-3-sulfate organic cationic salt; generating a 25-hydroxy-(3β)-cholest-5-en-3-sulfate organic cationic salt from the 25-hydroxy-(3β)-cholest-(5,6-epoxy)-3-sulfate organic cationic salt by deoxygenation; and contacting the 25-hydroxy-(3β)-cholest-5-en-3-sulfate organic cationic salt with at least one metal salt to produce the 5-cholesten-3β,25-diol 3-sulfate metal salt.

In some cases, the sulfating agent is chosen from sulfur trioxide complexes, sulfuric acid compounds, sulfonic acid compounds, and sulfonate compounds. In some cases, the sulfating agent is a sulfur trioxide-pyridine complex. In some cases, the sulfating agent is chosen from sulfur trioxide dimethyl formamide, sulfur trioxide triethylamine, and sulfur trioxide trimethylamine. In some cases, the sulfating agent is sulfuric acid and acetic anhydride and pyridine. In some cases, the sulfating agent is chosen from chlorosulfonic acid and pyridine. In some cases, the sulfating agent is chosen from chlorosulfonic acid and 2,6-lutidine. In some cases, the sulfating agent is chosen from ethyl chlorosulfonate. In some cases, the first (3β)-cholest-5-en-3-sulfate organic cationic salt is a (3β)-cholest-5-en-3-sulfate pyridinium salt.

In some cases, the organic base contacted with the first (3β)-cholest-5-en-3-sulfate organic cationic salt is chosen from a hydroxide base. In some cases, the hydroxide base is chosen from tetraethylammonium hydroxide, tetrabutylammonium hydroxide, tetrapropylammonium hydroxide and tetramethylammonium hydroxide. In some cases, the second (3β)-cholest-5-en-3-sulfate organic cationic salt is chosen from a tetraethylammonium cationic salt, a tetrabutylammonium cationic salt, a tetrapropylammonium cationic salt and a tetramethylammonium cationic salt.

In cases, the second (3β)-cholest-5-en-3-sulfate organic cationic salt is oxidized in the presence of at least one surfactant. In some cases, oxidizing the second (3β)-cholest-5-en-3-sulfate organic cationic salt includes contacting the second (3β)-cholest-5-en-3-sulfate organic cationic salt with a composition having an oxidizing agent and at least one surfactant. In certain cases, oxidizing the second (3β)-cholest-5-en-3-sulfate organic cationic salt to produce a 25-hydroxy-(3β)-cholest-(5,6-epoxy)-3-sulfate organic cationic salt includes contacting the second (3β)-cholest-5-en-3-sulfate organic cationic salt with a composition having potassium peroxymonosulfate in the presence of at least one surfactant. In some cases, the at least one surfactant is chosen from non-ionic surfactants, anionic surfactants, cationic surfactants and zwitterionic surfactants. Non-ionic surfactants may be chosen from polyoxyethylene glycol ether surfactants (e.g., polyoxyethylene glycol octylphenol ether), polyoxyethylene glycol sorbitan alkyl esters, sorbitan alkyl esters, block copolymers of polyethylene glycol and polypropylene glycol, among other non-ionic surfactants. Anionic surfactants may be chosen from surfactants having an anionic functional head group, such as a sulfonate, phosphate, sulfate or carboxylate head group-containing surfactant. For example, anionic surfactants may be chosen from alkyl sulfates such as ammonium lauryl sulfate, dioctyl sodium sulfosuccinate, perfluorooctanesulfonate, perfluorononanoate, perfluorooctanoate, a linear alkylbenzene sulfonate, an alkyl-aryl ether phosphate, sodium lauryl ether sulfate, lignosulfonate or sodium stearate, among other anionic surfactants. Cationic surfactants may be chosen from surfactants having a cationic functional head group, such as a pyridinium or a quarternary ammonium head group. For example, cationic surfactants may be chosen from cetyltrimethylammonium hydrogen sulfate, tetrabutylammonium hydrogen sulfate, cetyltrimethylammonium bromide, tetrabutylammonium bromide, tetrabutylammonium iodide, tetrabutylphosphonium bromide, tetraoctylammonium bromide, tetraoctylammonium iodide, benzyltriethylammonium chloride, benzyltriethylammonium bromide, benzylcetyldimethylammonium chloride and benzylcetyldimethylammonium bromide. Zwitterionic surfactants include both cationic and anionic centers, such as a sultaine (e.g., 3-[(3-cholamidopropyl)dimethylammonio]-1-propane-sulfonate) or a betaine (e.g., cocamidopropyl betaine). In certain cases, the surfactant is an Extran laboratory soap, La Parisienne soap or DL-α-tocopherol methoxypolyethylene glycol succinate (e.g., TPGS-750-M-2).

In some cases, the second (3β)-cholest-5-en-3-sulfate organic cationic salt is contacted with an oxidizing agent and at least one ketone in the presence of at least one surfactant. In some cases, methods include contacting the oxidizing agent (e.g., potassium peroxymonosulfate) with the at least one ketone in the presence of the at least one surfactant in a separate oxidative reaction mixture and contacting the oxidative reactive mixture with the second (3β)-cholest-5-en-3-sulfate organic cationic salt. In certain cases, methods include oxidizing the second (3β)-cholest-5-en-3-sulfate organic cationic salt in the presence of water. In some instances, the at least one ketone is chosen from tetrahydrothiopyran-4-one 1,1-dioxide and halogenated ketones. In some cases, the halogenated ketones are chosen from 1,1,1-trifluoro-2-butanone, 4,4-difluorocyclohexanone, 2-2-2-4'-tetrafluoroacetophenone, and 1,1,1-trifluoroacetone. In certain cases, the at least one ketone is 1,1,1-trifluoro-2-butanone.

In certain cases, oxidizing the second (3β)-cholest-5-en-3-sulfate organic cationic salt includes contacting the second (3β)-cholest-5-en-3-sulfate organic cationic salt with at leased one oxidative species. In some instances, the at least one oxidative species is chosen from dioxiranes. In some instances, the dioxiranes are generated in situ in a composition having the second (3β)-cholest-5-en-3-sulfate organic cationic salt. In some instances, the dioxiranes are generated separately (e.g., in a separate reaction container, e.g., flask) and then contacted with the composition having the second (3β)-cholest-5-en-3-sulfate organic cationic salt.

In certain cases, the second (3β)-cholest-5-en-3-sulfate organic cationic salt is oxidized in the presence of at least one base. In certain cases, the at least one base is chosen from weak bases. In some cases, the at least one base is chosen from potassium hydrogen carbonate, sodium hydrogen carbonate, potassium phenoxide, sodium citrate buffer, sodium phosphate buffer, potassium formate and potassium acetate. In certain cases, the at least one base is potassium hydrogen carbonate.

In some cases, generating the 25-hydroxy-(3β)-cholest-5-en-3-sulfate organic cationic salt from the 25-hydroxy-(3β)-cholest-(5,6-epoxy)-3-sulfate organic cationic salt includes deoxygenation by contacting the 25-hydroxy-(3β)-cholest-(5,6-epoxy)-3-sulfate organic cationic salt with zinc. In certain instances, the 25-hydroxy-(3β)-cholest-(5,6-epoxy)-3-sulfate organic cationic salt is contacted with zinc in the presence of at least one halide and at least one acid. In some cases, the at least one halide is chosen from iodine and metal halides. In some cases, the metal halide is chosen from sodium iodide and lithium iodide. In some cases, the at least one acid is chosen from weak acids. In some cases, the at least one acid is chosen from acetic acid, hydrochloric acid, citric acid, para-toluene sulfonic acid, formic acid, and methane sulfonic acid. In some cases, methods include contacting the 25-hydroxy-(3β)-cholest-(5,6-epoxy)-3-sulfate organic cationic salt with zinc in the presence of acetic acid to generate the 25-hydroxy-(3β)-cholest-5-en-3-sulfate organic cationic salt.

In some cases, methods to produce the 25-hydroxy-(3β)-cholest-5-en-3-sulfate metal salt includes contacting the 25-hydroxy-(3β)-cholest-5-en-3-sulfate organic cationic salt with at least one sodium salt. In some cases, the at least one sodium salt is chosen from sodium acetate, sodium iodide, sodium chloride, sodium hydroxide and sodium methoxide. In certain cases, methods include contacting the 25-hydroxy-(3β)-cholest-5-en-3-sulfate pyridinium salt with sodium iodide to produce a 25-hydroxy-(3β)-cholest-5-en-3-sulfate sodium salt.

BRIEF DESCRIPTION OF THE FIGURES

FIG. 1 is an XRPD Diffractogram of crystalline 25HC3S sodium Form I.

FIG. 2 is an XRPD Diffractogram of crystalline 25HC3S sodium Form II.

FIG. 3 is an XRPD Diffractogram of liquid crystal 25HC3S sodium Form V.

FIG. 4 is an XRPD Diffractogram of liquid crystal 25HC3S sodium Form V.

FIG. 5 is an XRPD Diffractogram of crystalline 25HC3S sodium Form IX.

FIG. 6 is an XRPD Diffractogram of crystalline 25HC3S sodium Form XI.

FIG. 7 is an XRPD Diffractogram of crystalline 25HC3S sodium Form XI.

FIG. 8 is an XRPD Diffractogram of crystalline 25HC3S sodium Form XIII

FIG. 9 is an XRPD Diffractogram of crystalline 25HC3S sodium Form XIII

FIG. 10 is indexing results for crystalline 25HC3S sodium Form I.

FIG. 11 is thermograms for crystalline 25HC3S sodium Form I.

FIG. 12 is a variable temperature XRPD experiment for crystalline 25HC3S sodium Form I.

FIG. 13 is a variable humidity XRPD experiment for crystalline 25HC3S sodium Form I and crystalline 25HC3S sodium Form XIII.

FIG. 14 is XRPD Diffractograms from the dehydration of crystalline 25HC3S sodium Form I.

FIG. 15 is XRPD Diffractograms from the dehydration of crystalline 25HC3S sodium Form I (expanded).

FIG. 16 is a DVS Isotherm for crystalline 25HC3S sodium Form II.

FIG. 17 is indexing results for crystalline 25HC3S sodium Form II (99:01 acetonitrile (ACN)/$H_2O$ slurry, 0.21 $a_w$, 3 days).

FIG. 18 is indexing results for crystalline 25HC3S sodium Form II (95:05 EtOH/$H_2O$ slurry, 0.30 $a_w$, 10 days).

FIG. 19 is indexing results for crystalline 25HC3S sodium Form II (Acetone slurry, 55° C., 1 day).

FIG. 20 is an XRPD peak position variability for crystalline 25HC3S sodium Form II for slurries indexed in FIGS. 17-19, shown from approximately 4°2θ to approximately 11°2θ.

FIG. 21 is an XRPD peak position variability for crystalline 25HC3S sodium Form II for slurries indexed in FIGS. 17-19, shown from approximately 13°2θ to approximately 21.5°2θ.

FIG. 22 is a variable humidity XRPD experiment for crystalline 25HC3S sodium Form II.

FIG. 23 is an XRPD peak position variability for crystalline 25HC3S sodium Form II observed by variable humidity XRPD, shown from approximately 7.5°2θ to approximately 10.2°2θ.

FIG. 24 is TGA thermograms for crystalline 25HC3S sodium Form II.

FIG. 25 is DSC thermograms for crystalline 25HC3S sodium Form II.

FIG. 26 is a cycling DSC experiment for crystalline 25HC3S sodium Form II.

FIG. 27 is a variable temperature XRPD experiment for crystalline 25HC3S sodium Form II.

FIG. 28 is a TGA thermogram for liquid crystal 25HC3S sodium Form V.

FIG. 29 is a DSC thermogram for liquid crystal 25HC3S sodium Form V.

FIG. 30 is indexing results for crystalline 25HC3S sodium Form XIII (generated from a mixture of crystalline 25HC3S sodium Form I and Form XIII exposed to 70° C. vacuum for 2 days).

Figure 31:
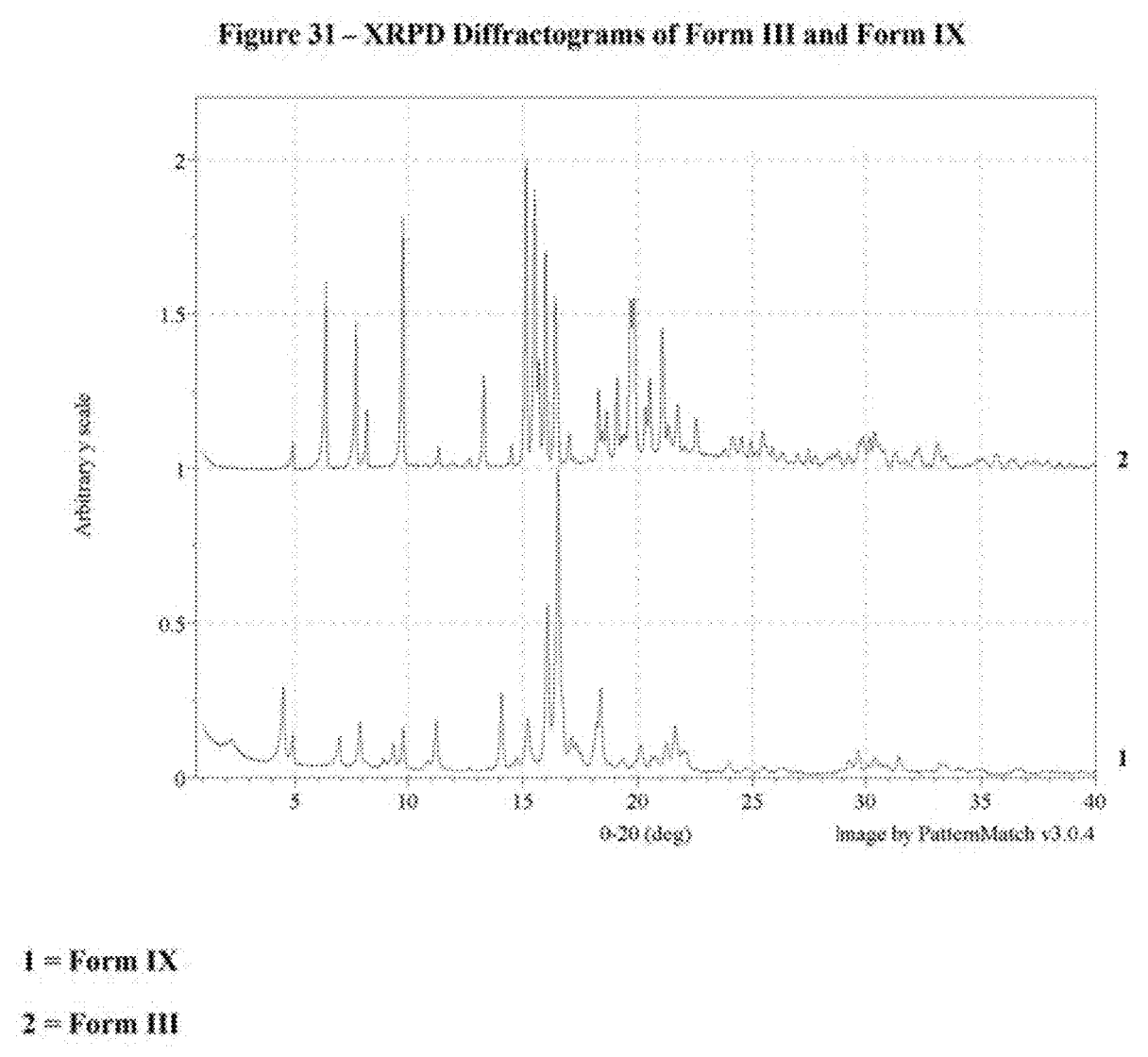

FIG. 31 is XRPD Diffractograms of crystalline 25HC3S sodium Form III and Form IX.

FIG. 32 is indexing results for crystalline 25HC3S sodium Form III.

FIG. 33 is a $^1$H-NMR spectrum of crystalline 25HC3S sodium Form IX in solution.

FIG. 34 is a $^1$H-NMR spectrum of 25HC3S sodium in solution.

FIG. 35 is an XRPD Diffractogram of crystalline 25HC3S sodium Form III.

FIG. 36 is an XRPD Diffractogram of crystalline 25HC3S sodium Form I.

FIG. 37 is an XRPD Diffractogram of crystalline 25HC3S sodium Form I.

FIG. 38 is an XRPD Diffractogram of crystalline 25HC3S sodium Form I.

FIG. 39 is an XRPD Diffractogram of crystalline 25HC3S sodium Form I and Form XIII FIG. 40 is an XRPD Diffractogram of crystalline 25HC3S sodium Form XIII.

FIG. 41 is an XRPD Diffractogram of crystalline 25HC3S sodium Form XIII.

FIG. 42 is an XRPD Diffractogram of crystalline 25HC3S sodium Form II.

FIG. 43 is an XRPD Diffractogram of crystalline 25HC3S sodium Form II.

FIG. 44 is an XRPD Diffractogram of crystalline 25HC3S sodium Form II.

FIG. 45 is an XRPD Diffractogram of crystalline 25HC3S sodium Form III and Form IX Mixture.

FIG. 46 is an XRPD Diffractogram of crystalline 25HC3S sodium Form II.

FIG. 47 is an XRPD Diffractogram of liquid crystalline 25HC3S sodium Form V.

FIG. 48 is an XRPD Diffractogram of liquid crystalline 25HC3S sodium Form V.

FIG. 49 is an XRPD Diffractogram of crystalline 25HC3S sodium Form III.

FIG. 50 is an XRPD Diffractogram of crystalline 25HC3S sodium Form III.

FIG. 51 is an XRPD Diffractogram of crystalline 25HC3S sodium Form IX.

FIG. 52 is an XRPD Diffractogram of crystalline 25HC3S sodium Form III and Expanded.

FIG. 53 is an XRPD Diffractogram of crystalline 25HC3S sodium Form I.

FIG. 54 is an XRPD Diffractogram of crystalline 25HC3S sodium Form II.

FIG. 55 is an XRPD Diffractogram of crystalline 25HC3S sodium Form I.

FIG. 56 is an XRPD Diffractogram of liquid crystalline 25HC3S sodium Form V.

Figure 57:
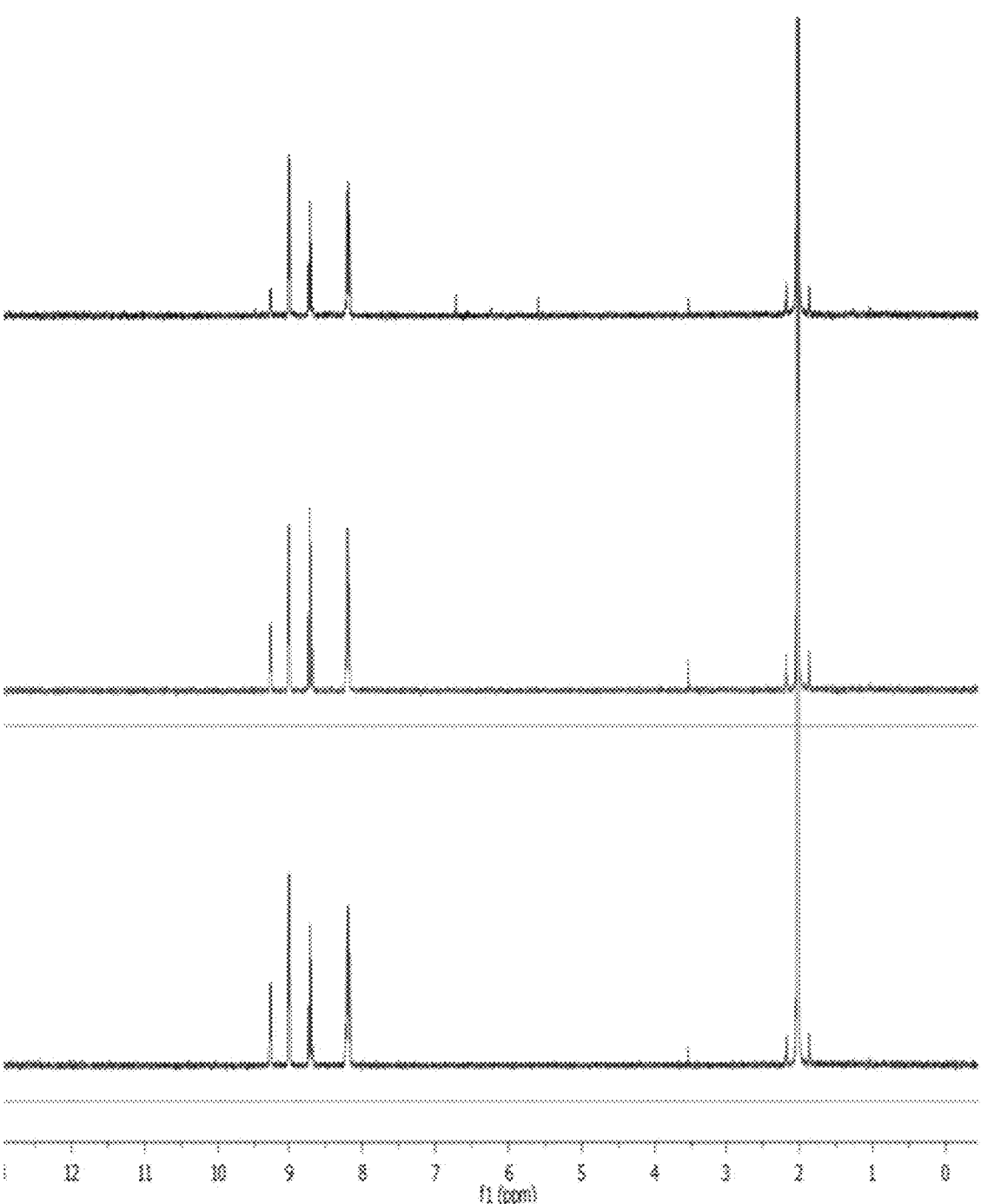

FIG. 57 is a $^1$H-NMR spectrum of three different samples of sulfur trioxide pyridine in deuterated acetone.

Figure 58A:
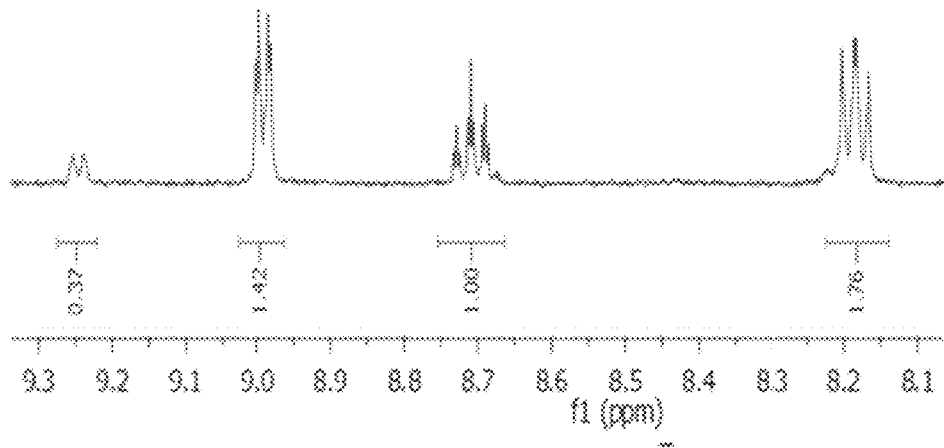

FIG. 58A is an enhancement of the region between 8.1 and 9.3 ppm of a $^1$H-NMR spectrum of a sample of sulfur trioxide-pyridine with 21% impurity in deuterated acetone.

Figure 58B:
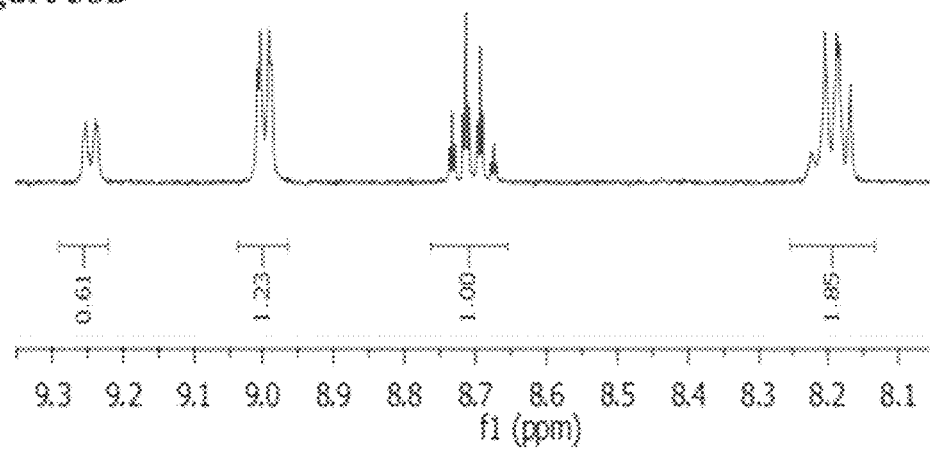
Figure 58C:
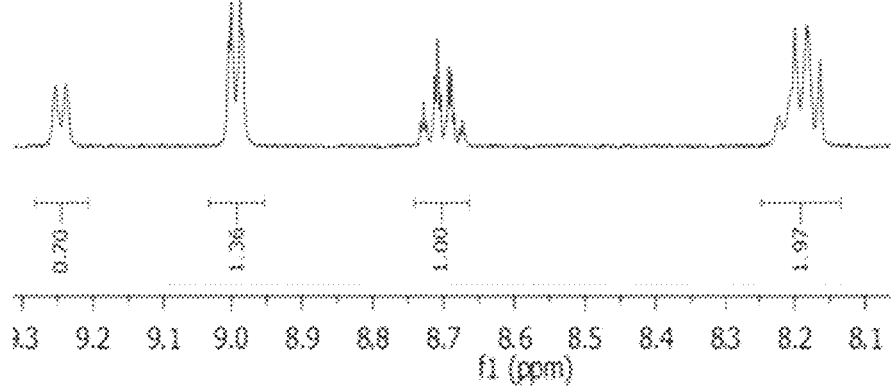

FIG. 58B is an enhancement of the region between 8.1 and 9.3 ppm of a $^1$H-NMR spectrum of a sample of sulfur trioxide-pyridine with 33% impurity in deuterated acetone. FIG. 58C is an enhancement of the region between 8.1 and 9.3 ppm of a $^1$H-NMR spectrum of a sample of sulfur trioxide-pyridine with 36% impurity in deuterated acetone.

DETAILED DESCRIPTION

Crystalline and Liquid Crystalline 25-hydroxy-3β-cholesten-5-en-3-sulfate (25HC3S)

Crystalline 25HC3S sodium and liquid crystalline 25HC3S are readily analyzed by x-ray powder diffraction. An x-ray powder diffraction pattern is an x-y graph with $^\circ$ 2θ (diffraction angle) on the x-axis and intensity on the y-axis. The x-axis can also be in the form of d-spacings which is related to the diffraction angle via the Bragg's law whereby $2d \sin\theta = n\lambda$ where d is the d-spacing and λ is the wavelength of the incident x-ray wave. The pattern contains peaks which may be used to characterize crystalline 25HC3S sodium. Unless otherwise specified, peaks are referred to by their position on the x-axis and not their y-axis intensity. It can also occur that due to sample orientation, a peak that is present in one sample on one instrument may not be present in another sample taken on a different instrument due to the orientation of the sample with respect to the instrument.

The data from x-ray powder diffraction may be used in multiple ways to characterize crystalline forms. For example, the entire x-ray powder diffraction pattern output from a diffractometer may be used to characterize 25HC3S sodium. A smaller subset of such data, however, may also be, and typically is, suitable for characterizing 25HC3S sodium. For example, a collection of one or more peaks from such a pattern may be used to characterize crystalline 25HC3S sodium. In the present application, all reported peak values are in $^\circ$ 2θ with Cu-Kα radiation as set forth in Example 16 and Example 17. Indeed, often even a single x-ray powder diffraction peak may be used to characterize such a crystalline form. When crystalline 25HC3S sodium herein is characterized by "one or more peaks" of an x-ray powder diffraction pattern and such peaks are listed, what is generally meant is that any combination of the peaks listed may be used to characterize crystalline 25HC3S sodium. Further, the fact that other peaks are present in the x-ray powder diffraction pattern, generally does not negate or otherwise limit that characterization.

In addition to the variability in peak intensity, there may also be variability in the position of peaks on the x-axis. This variability can, however, typically be accounted for when reporting the positions of peaks for purposes of characterization. Such variability in the position of peaks along the x-axis may derive from several sources (e.g., sample preparation, particle size, moisture content, solvent content, instrument parameters, data analysis software, and sample orientation). For example, samples of the same crystalline material prepared under different conditions may yield slightly different diffractograms, and different x-ray instruments may operate using different parameters, and these may lead to slightly different diffraction patterns from the same crystalline solid.

Due to such sources of variability, it is common to recite x-ray diffraction peaks using the word "about" prior to the peak value in $^\circ$ 2θ. For purposes of data reported herein, that value is generally ±0.1°2θ. This generally means that on a well-maintained instrument one would expect the variability in peak measurement to be ±0.1°2θ. Unless specified otherwise, x-ray powder diffraction peaks cited herein are generally reported with this variability of ±0.1°2θ and are generally intended to be reported with such a variability whenever disclosed herein whether the word "about" is present or not, however, variability may, in some instances, be as high as ±0.2°2θ or even higher depending on instrumentation conditions.

As described herein, the compound 25-hydroxy-3β-cholesten-5-en-3-sulfate (25HC3S) refers to [(3S,10R,13R,17R)-17-[(1R)-5-hydroxy-1,5-dimethyl-hexyl]-10,13-dimethyl-2,3,4,7,8,9,11,12,14,15,16,17-dodecahydro-1H-cyclopenta[a]phenanthren-3-yl] sulfate, the compound of Formula I:

Formula I

The present disclosure uses the term "Form" to identify different crystalline forms of crystalline 25HC3S sodium or liquid crystalline forms. The differences in the forms can be seen by structure, such as x-ray powder diffraction; properties such as hygroscopicity or thermal behaviors; and/or both. The use of the term "Form I" means crystalline 25HC3S sodium of Form I. Likewise, "Form II" means crystalline 25HC3S sodium of Form II. Similarly, Form III, Form IX, Form XI, and Form XIII mean crystalline 25HC3S sodium of Form III, Form IX, Form XI, and Form XIII, respectively. Form V means a form of 25HC3S sodium that is in a liquid crystalline phase.

The generated solids were observed by one or more of polarized light microscopy and x-ray powder diffraction. Materials exhibiting unique crystalline x-ray powder diffraction patterns, based on visual inspection of peaks associated with these materials, were given designations set forth in the present disclosure.

Table 1 summarizes some of the experiments performed to obtain the reported forms of 25HC3S sodium in the present disclosure, namely those experiments associated with Examples 1-36.

Cells in Table 1 with an asterisk (*) indicate a solid was identified which is not one of Form I, Form II, Form III, Form V, Form IX, Form XI, or Form XIII.

The times, temperatures, and humidity in Table 1 are approximate. The term "B" means birefringent and "NB" means non-birefringent when a sample is viewed by polarized light microscopy with cross polars. Solvent-based methods were used to screen for crystalline 25HC3S sodium using a diversity of solvents and conditions as set forth in Table 1. Methods using solvents or solvent mixtures included, for example, cooling a solution, evaporation, antisolvent addition, and suspensions (slurries). Variations on these methods can include changes in solvent, solvent mixtures, antisolvent, temperature, cooling rate, concentration, rate of addition, and order of mixing, to name a few possibilities.

TABLE 1

| A Screen of 25HC3S sodium | | | | |
|---|---|---|---|---|
| Solvent | | Method | Observation | Result |
| acetone | (i) | slurry, ambient, 14 days, dried under $N_2$ for <20 seconds | opaque fines, NB | II |
| | (ii) | (i) sub sample analyzed wet | — | II |
| | (iii) | slurry, 55° C., 1 day | opaque fines | II |
| ACN | (i) | slurry, ambient, 14 days, dried under $N_2$ for <20 seconds | opaque fines, NB | II |
| | (ii) | (i) sub sample analyzed wet | — | II |
| | (iii) | slurry, 55° C., 1 day, analyzed wet | plug formed at top isolated by tweezers very fine particles, wispy, B | II |
| | (iv) | slurry, 55° C., 1 day, dried under $N_2$ | — | II |
| | (v) | slurry, 55° C., 1 day, analyzed wet | — | II |
| | (vi) | slurry, 60° C., 1 day, $N_2$ dried | — | II |
| DCM | (i) | heated to reflux, filtered 1. fast evaporation 2. treated with heptane | 1. oily residue, fines, limited, B 2. hazy | — |
| | (ii) | slurry, ambient, 14 days | opaque fines, NB | I + II |
| diethyl ether | | slurry, ambient, 14 days 1. filtered 2. $N_2$ dried | 1. thick filter cake 2. collapsed, fines, B | XI |
| 1,4-dioxane | (i) | slurry, ambient, 14 days | opaque fines, NB limited recovery | * |
| | (ii) | slurry, ambient, 5 days | gel/plug translucent, B striations in solids | * + II |
| | (iii) | (ii) slurried ambient, 10 days | — | * |
| DMSO | (i) | solvent/anti-solvent 1. added to EtOAc 2. ambient, 3 days 3. decanted, chopped plug | 1. hazy followed by precipitates, NB, formed gel plug in suspension 2. gel plug remained 3. solvent displaced, slight opaqueness | limited re-flections |
| | (ii) | (i) dried w/$N_2$ | ¾ reduction in size gel/film with fines, B | * |
| DMSO | (iii) | (i) post XRPD 1. seeded with (ii) 2. EtOAc added 3. fast evaporation 4. DMSO drops added stored ambient | 1. gel + fines 2. gel "broke" no bulk crystallization 3. film, limited fines 4. bulk nucleated, dendritic, blades B | * |
| EtOH | (i) | fast evaporation partial analyzed wet | wispy, fine aciculars, B | II |
| | (ii) | (iii) bulk slurry fast evaporation, $N_2$ | — | III + peaks |
| | (iii) | slow evaporation partial 1. singles isolated 2. sub sample analyzed wet | 1. rosettes of blades and aciculars, B wouldn't elucidate 2. — | III |
| | (iv) | 1. 12 mg/mL suspension 2. capped, 5 min. 3. sub sampled, solvent flashed 4. sub sample analyzed wet | 1. faint haze 2. rosettes of fine aciculars 3. crystals turn opaque 4. — | III |

TABLE 1-continued

| | | A Screen of 25HC3S sodium | | |
|---|---|---|---|---|
| Solvent | | Method | Observation | Result |
| | (v) | 1. solvent added<br>2. heated on 75° C. plate<br>3. N₂ dried, 75° C.<br>plate for 15 minutes | 1. —<br>2. solvent absorbed<br>3. cake collapsed | III + IX |
| | (vi) | 1. solvent added<br>2. heated on 75° C. plate<br>3. filtered, EtOH rinse<br>and dried under N₂ | 1. —<br>2. thick slurry<br>3. fine blades and<br>aciculars, B | III + II |
| | (vii) | slurry, ambient, 5 days | large blades and fine<br>aciculars, B | III |
| EtOAc | | slurry, ambient, 5 days | paste/gel, decanted | II |
| IPA | (i) | slurry, ambient, 21 days | irregular fines, B | II |
| | (ii) | 1. slow cool from reflux<br>2. warmed to ambient | l. solid gel plug, NB<br>2. solution | — |
| | (iii) | (ii) solution<br>1. fast evaporation, ½<br>2. sonicated<br>3. fast evaporation | 1. gel plug, striations<br>of opaque regions,<br>NB, white wispy<br>B material in upper<br>regions<br>2. slurry, hazy<br>3. white fines, B | V |
| MeOH | (i) | 1. contacted with<br>MeOH<br>2. additional MeOH<br>3. fast evaporation | 1. faint haze<br>2. no changes<br>3. thin film, cracked,<br>striations, B | V |
| | (ii) | (i) reanalyzed after<br>7 days | appeared visually to<br>be more crystalline | V |
| | (iii) | slow cool to ambient<br>analyzed wet | irregular fines, B | * + V |
| | (iv) | cooling of solution<br>1. solvent added<br>2. filtered<br>3. freezer overnight<br>4. warmed ambient | 1. faint haze<br>2. difficult/slow to<br>filter<br>3. limited fines, B<br>4. clear solution | — |
| | (v) | slurry, ambient, 4 days | very fine aciculars, B | * + V |
| | (vi) | solvent/anti-solvent<br>1. heated MeOH<br>solution<br>2. filtered into EtO<br>3. filtered, N₂ dried | 1. clear<br>2. difficult to filter,<br>precipitation, NB<br>3. filter cake curled<br>as dried | V |
| | (vii) | solvent/anti-solvent<br>1. heated MeOH<br>solution<br>2. filtered into DCM<br>3. filtered | 1. clear<br>2. precipitation, gel<br>opaque, NB<br>3. gel cake isolated<br>4. gel crystallized<br>after isolating, B | I |
| | (viii) | (vii) sub sample<br>gel pressed between<br>filter paper | solvent expelled,<br>film, irregular<br>solids, B | V |
| toluene | (i) | fast evaporation | limited material, oil<br>fines, B | — |
| | (ii) | slurry, ambient,<br>21 days | irregular masses,<br>zones/particles B | I |
| water | (i) | slurry, ambient,<br>14 days dried<br>briefly under N₂ | very slow to filter<br>opaque masses when<br>pressed expelled<br>water, gel like<br>clumps, when<br>pressed further<br>between slide<br>film exhibited B,<br>mesophase like | V |
| | (ii) | (i) sub sample<br>analyzed wet | — | V |
| acetone/<br>H₂O<br>92:08<br>v/v<br>0.98 a_w | (i) | 1. slurry, acetone,<br>heated<br>2. removed, water<br>added<br>3. left at ambient,<br>4 days<br>4. filtered, N₂ dried for<br>10 minutes | 1. slurry<br>2. majority dissolved<br>3. limited flocculent,<br>gel deposits on<br>vial converted to<br>flocculent, then<br>dendritic<br>4. fines, B | I |
| | (ii) | (i) filtrate<br>fast evaporation | dendritic and fine<br>wispy aciculars | V |

TABLE 1-continued

| A Screen of 25HC3S sodium | | | | |
|---|---|---|---|---|
| Solvent | | Method | Observation | Result |
| ACN/ | (i) | slurry, ambient, 4 days analyzed wet cake | — | I + peak @ 9.0° |
| H$_2$O 97:03 | (ii) | (i) sub sampled 1.5 hrs after initial | — | I + peak @ 9.0° |
| v/v 0.50 a$_w$ | | solvent contact | | |
| | (iii) | (i) bulk dried under N$_2$ for 0.5 hrs | — | I + XIII |
| heptane/ DMSO 100:1 v/v | | slurry, ambient, 5 days | white fines, B | II |

The effect of water activity (a$_w$) on the hydration state can be investigated through competitive water activity trituration experiments (slurries) in various aqueous solvent mixtures. The resulting solid phase can be characterized by x-ray powder diffraction. The experiments can establish the physically stable form at various a$_w$. Water activity can also be related to relative humidity in that RH %=a$_w$×100. Therefore, it is possible to directly relate the stability of an anhydrous/hydrate system in slurry experiments to solid-state stability. The slurry technique at controlled water activities can provide an accurate method of rapidly predicting the physically stable form in anhydrous/hydrate systems. The results from water activity experiments are provided in Table 2 and were done at approximately room temperature. The times, temperatures, and humidity are approximate. As with Table 1, the term "B" means birefringent when viewed by polarized light microscopy with cross polars.

TABLE 2

| Water Activity Slurries of 25HC3S Sodium | | | |
|---|---|---|---|
| Water Activity (a$_w$) Solvent System (v:v)[1] | Duration | Observation | Result |
| 0.98 a$_w$ 92:08 H$_2$O/acetone | 10 days | irregular fines, B | V |
| 0.82 a$_w$ 92:08 ACN/H$_2$O | 10 days | irregular fines, B | V |
| 0.73 a$_w$ 94:06 ACN/H$_2$O | 8 days | fines, B | I + peak @ 9.0° |
| 0.70 a$_w$ 89:11 IPA/H$_2$O | 10 days | fine aciculars, B | I |
| 0.64 a$_w$ 92:08 acetone/H$_2$O | 10 days | irregular fines, B | I |
| 0.50 a$_w$ 97:03 ACN/H$_2$O | 3 days | irregular fines, B | I |
| 0.44 a$_w$ 97:03 acetone/H$_2$O | 7 days | irregular fines, B | I |
| 0.38 a$_w$ 98:02 ACN/H$_2$O | 3 days | irregular fines, B | I |
| 0.30 a$_w$ 95:05 EtOH/H$_2$O | 10 days | irregular fines, B | II |
| 0.21 a$_w$ 99:01 ACN/H$_2$O | 3 days | irregular fines, B | II |
| Combination of samples from 0.5 a$_w$ and 0.38 a$_w$ | 56 days | combined slurries filtered and dried under N$_2$ for 30 min. | I + XIII |

[1]Choy, B.; Reible, D. (1996). UNIFAC Activity Coefficient Calculator (Version 3.0) [Software]. University of Sydney, Australia and Louisiana State University, USA.

Several x-ray powder diffraction patterns were indexed. "Indexing," as used herein, generally refers to the process of determining the size and shape of the crystallographic unit cell given the peak positions in a diffraction pattern. The term gets its name from the assignment of Miller index labels to individual peaks. For example, if all of the peaks in a pattern are indexed by a single unit cell, this can be strong evidence that the sample contains a single crystalline phase. Given the indexing solution, the unit cell volume may be calculated directly and can be useful to determine their solvation states. Indexing may also be a description of a crystalline form and provides a concise summary of all available peak positions for that phase at a particular thermodynamic state point.

Multiple stable crystalline forms of crystalline 25HC3S sodium are herein reported—Forms I, II, IX, XI, and XIII, and one liquid crystal form, Form V. In the present disclosure, "stable" means that the Form does not readily interconvert to another Form under a given set of conditions. A metastable form, can, however, so readily convert when exposed to certain conditions. Thus, a form that is stable under one set of conditions (e.g., humidity) may not be stable under another set of conditions. Not all forms were able to be indexed herein. In addition, Form III is a metastable form which formed and can be a starting material for Form IX. Although metastable, Form III was sufficiently stable for isolation for XRPD.

In many cases, crystalline 25HC3S sodium is provided including stable crystalline 25HC3S sodium. Examples of crystalline 25HC3S sodium include anhydrous crystalline 25HC3S sodium, hydrates of crystalline 25HC3S sodium, and solvates of crystalline 25HC3S sodium.

The hydrates of crystalline 25HC3S sodium include monohydrates, dihydrates, and variable hydrates. Liquid crystal hydrates of 25HC3S sodium are also provided herein.

In some cases, hydrates of crystalline 25HC3S sodium may be characterized by an x-ray powder diffraction pattern comprising one or more of (i) a peak at less than about 2.8°2θ such as between about 2.1°2θ and about 2.6°2θ, (ii) a peak between about 4.3°2θ and about 4.6°2θ, (iii) a peak between about 5.0°2θ and about 5.5°2θ, (iv) a peak between about 8.6°2θ and about 9.1°2θ and (v) a peak between about 15.0°2θ and about 15.3°2θ. In these and other cases, hydrates of crystalline 25HC3S sodium may be characterized by an x-ray powder diffraction pattern comprising one or more of (i) a peak between about 2.1°2θ and about 2.3°2θ and (ii) a peak between about 9.9°2θ and about 10.0°2θ.

In some cases, anhydrous crystalline 25HC3S sodium may be characterized by an x-ray powder diffraction pattern comprising one or more of (i) a peak at between about 4.5°2θ and about 4.8°2θ, (ii) a peak between about 9.8°2θ and about 9.9°2θ, (iii) a peak at between about 14.1°2θ and about 14.3°2θ, and (iv) a peak at about 16.1°2θ.

In many cases, crystalline 25HC3S sodium Form I is provided for in the present disclosure. Form I is a dihydrate of crystalline 25HC3S sodium. Form I may be prepared as set forth in Table 1. For example, slurrying 25HC3S sodium in an acetone/H₂O solution, heating, removing the solution, adding water, and leaving at ambient results in Form I. Form I may also be prepared from methanol. Preparations of Form I are further described in Examples 20-23, and in a mixture with Form XIII in Example 24. The following Table 3 correlates the Examples producing Form I with the corresponding XRPD diffractogram figure.

TABLE 3

| Form 1 XRPD Examples/FIGS. | |
| --- | --- |
| Example # | FIG. |
| 20 | 36 |
| 21 | 37 |
| 22 | 38 |
| 23 | 55 |
| 24 | 39 |

Table 4 shows peaks found in FIG. 55, whereas peaks for the other figures in Table 3 are presented on the figures themselves.

TABLE 4

| FIG. 55 Peak List | | | | |
| --- | --- | --- | --- | --- |
| Pos. [°2Th.] | Height [cts] | FWHM Left [°2Th.] | d-spacing [Å] | Rel. Int. [%] |
| 4.482064 | 1692.179000 | 0.255840 | 19.71534 | 14.68 |
| 5.511474 | 425.857900 | 0.204672 | 16.03508 | 3.69 |
| 6.629832 | 1796.915000 | 0.204672 | 13.33249 | 15.59 |
| 8.788433 | 6365.006000 | 0.204672 | 10.06204 | 55.22 |
| 10.006760 | 2252.715000 | 0.179088 | 8.83955 | 19.54 |
| 10.919930 | 1279.297000 | 0.179088 | 8.10231 | 11.10 |
| 13.149270 | 330.143300 | 0.255840 | 6.73323 | 2.86 |
| 14.526540 | 1649.401000 | 0.230256 | 6.09780 | 14.31 |
| 15.105460 | 11525.940000 | 0.179088 | 5.86538 | 100.00 |
| 15.722710 | 5185.476000 | 0.204672 | 5.63648 | 44.99 |
| 16.343610 | 3132.548000 | 0.179088 | 5.42372 | 27.18 |
| 17.302730 | 2804.740000 | 0.179088 | 5.12517 | 24.33 |
| 17.632490 | 3663.537000 | 0.153504 | 5.03006 | 31.79 |
| 18.491410 | 2629.055000 | 0.153504 | 4.79831 | 22.81 |
| 19.006600 | 1076.854000 | 0.204672 | 4.66939 | 9.34 |
| 20.279930 | 1715.928000 | 0.409344 | 4.37900 | 14.89 |
| 21.076530 | 1403.260000 | 0.409344 | 4.21525 | 12.17 |
| 21.521580 | 1343.477000 | 0.204672 | 4.12908 | 11.66 |
| 22.042530 | 1077.881000 | 0.153504 | 4.03266 | 9.35 |
| 22.663660 | 768.489500 | 0.409344 | 3.92353 | 6.67 |
| 23.901110 | 634.608200 | 0.255840 | 3.72312 | 5.51 |
| 24.707990 | 481.575700 | 0.204672 | 3.60333 | 4.18 |
| 26.801360 | 243.341400 | 0.409344 | 3.32645 | 2.11 |
| 29.289260 | 693.492100 | 0.204672 | 3.04931 | 6.02 |
| 30.747140 | 292.114300 | 0.255840 | 2.90797 | 2.53 |
| 33.013470 | 203.217300 | 0.307008 | 2.71334 | 1.76 |
| 38.783180 | 201.201500 | 0.460512 | 2.32194 | 1.75 |

Form I of crystalline 25HC3S sodium may be characterized by various analytical techniques, including by x-ray powder diffraction. The x-ray powder diffraction pattern of Form I, or portions thereof, may be used to identify Form I. Form I contains various x-ray powder diffraction peaks which alone or together may help identify the presence of Form I. For example, in many cases, Form I may be characterized by an x-ray powder diffraction pattern comprising a peak at about 2.1°2θ (not all diffractograms herein display such low angle peaks). In addition to the peak at about 2.1°2θ, the x-ray powder diffraction pattern may comprise, for example, one or more peaks at about 5.4°2θ, about 6.5°2θ, about 10.8°2θ, and about 15.0°2θ.

In many cases, Form I may be characterized by an x-ray powder diffraction pattern comprising peaks at about 2.1°2θ, about 6.5'2θ, and about 10.8'2θ. The x-ray powder diffraction pattern may, in some cases, further comprise one or more peaks at about 9.9'2θ, about 15.0'2θ, and about 15.6°2θ.

FIG. 1 is an x-ray powder diffraction pattern of a representative sample of Form I where the x-axis begins at 0°2θ and goes to 40°2θ, whereas FIG. 53 shows the same pattern but between about 3°2θ and about 39°2θ. Either of FIG. 1 or FIG. 53 may, for example, be used to characterize Form I.

Form I appears to be stable at relative humidities at and between about 38% and about 70% RH. As such, Form I resulted from slurries in aqueous solvent mixtures with water activities at and between about 0.38 and about 0.70 $a_w$. Form I dehydrates to Form XIII when exposed to elevated temperatures or to humidity conditions near 0% RH. Form I is hygroscopic and is believed to form a liquid crystal called Form V at water activity conditions above 0.73 $a_w$.

The x-ray powder diffraction pattern of Form I was successfully indexed, indicating the pattern represents a single crystalline phase (FIG. 10). The indexing result has a monoclinic unit cell containing six molecules of 25HC3S sodium. The unit cell volume of 4544.7 Å³ (±5%) results in a formula unit volume of 757 Å³ (±5%) (6 molecules/cell) which would be consistent with a hydrate. The formula unit volume of Form I is larger than the formula unit for the anhydrous form, Form XIII, by approximately 52 Å³. The difference in volume provides sufficient room to accommodate up to 2 mol/mol of water. For reference, one water molecule occupies about 22 Å³.

Thermograms for Form I are shown in FIG. 11. The TGA thermogram provides an 8% weight loss up to 130° C. which occurs concurrently with broad dehydration endotherms in the DSC thermogram (FIG. 11). Assuming the loss is due to the volatilization water, the weight loss corresponds to approximately 2.4 mol/mol water. The DSC curve in FIG. 11 also shows endotherms near 168° C. and 182° C. These events are associated with decomposition.

The dehydration of Form I results in form conversion to Form XIII The conversion was confirmed with a variable temperature x-ray powder diffraction experiment (FIG. 12) which shows Form XIII when heating to 170° C. and then dropping to 135° C. (Pattern 5 of FIG. 12). During the same experiment, a decomposition product identified as trisodium hydrogen disulfate, $Na_3H(SO_4)_2$, was evident by 170° C. These results are consistent with the thermograms for Form I in FIG. 11.

A variable humidity x-ray powder diffraction experiment on a mixture composed predominately of Form I and a minor amount of Form XIII is presented in FIG. 13. The laboratory humidity in which the sample was prepared for analysis was 15% relative humidity ("RH"). The material was exposed to increasing and then decreasing humidity during x-ray powder diffraction analysis. The material was identified as Form I at humidity conditions spanning 25% to 85% RH. However, the material partially dehydrated back to Form XIII immediately upon exposure to 0% RH. Complete dehydration to Form XIII at 0% RH was evident after 20 minutes. Exposure to either 0% RH or 70° C. under vacuum dehydrated Form I to Form XIII FIG. 14 and FIG. 15 compare the x-ray powder diffraction patterns of the material as Form I dehydrates to Form XIII Substantially pure Form I is further disclosed. "Substantially pure," as described herein, generally refers to a form herein that is present without any appreciable amounts, other than potentially trace levels of other forms of crystalline 25HC3S sodium, liquid crystalline form of 25HC3S sodium, or non-crystalline 25HC3S such as amorphous 25HC3S sodium. Examples of trace levels include not more than about 10%, 5%, 2%, 1.5%, 1%, 0.5%, 0.25%, 0.1%, or less in total relative to the total amount (based on weight) of 25HC3S sodium present.

Form II crystalline 25HC3S sodium, including substantially pure Form II crystalline 25HC3S sodium, is provided for in many cases of the present disclosure. Form II is a variable hydrate of crystalline 25HC3S sodium. The water content is typically present at no greater than about 3 moles of water per mole of 25HC3S sodium. In some cases, the molar content of water to 25HC3S sodium is from about 1 to 3, including, for example, from about 2 to 3. Form II may be prepared as set forth in Table 1. For example, slurrying 25HC3S sodium in acetone and drying under nitrogen results in Form II. Form II may also be prepared as set forth in Examples 27-30. The following Table 5 correlates the Examples producing Form II with the corresponding XRPD diffractogram Figure.

TABLE 5

Form II XRPD Examples/FIGS.

| Example # | FIG. |
|---|---|
| 27 | 42 |
| 28 | 43 |
| 29 | 44 |
| 30 | 46 |

Table 6 show peaks found in FIG. 46, whereas peaks for the other figures in Table 5 are presented on the figures themselves.

TABLE 6

FIG. 46 Peak List

| Pos. [°2Th.] | Height [cts] | FWHM Left [°2Th.] | d-spacing [Å] | Rel. Int. [%] |
|---|---|---|---|---|
| 4.568637 | 2176.180000 | 0.076752 | 19.34194 | 52.97 |
| 5.093186 | 1019.875000 | 0.089544 | 17.35102 | 24.83 |
| 6.024972 | 222.111200 | 0.102336 | 14.66954 | 5.41 |
| 6.833070 | 1157.846000 | 0.089544 | 12.93639 | 28.19 |
| 7.500985 | 52.534870 | 0.307008 | 11.78592 | 1.28 |
| 9.102928 | 4107.982000 | 0.089544 | 9.71510 | 100.00 |
| 9.924992 | 200.682800 | 0.102336 | 8.91219 | 4.89 |
| 10.444960 | 185.467200 | 0.204672 | 8.46967 | 4.51 |
| 12.706730 | 118.823500 | 0.102336 | 6.96672 | 2.89 |
| 14.530520 | 182.929600 | 0.102336 | 6.09614 | 4.45 |
| 14.887640 | 1538.703000 | 0.127920 | 5.95070 | 37.46 |
| 15.254160 | 464.882600 | 0.127920 | 5.80854 | 11.32 |
| 15.526900 | 453.899600 | 0.115128 | 5.70711 | 11.05 |
| 15.920180 | 454.991900 | 0.089544 | 5.56700 | 11.08 |
| 17.796940 | 219.076700 | 0.127920 | 4.98395 | 5.33 |
| 18.224860 | 795.017100 | 0.076752 | 4.86788 | 19.35 |
| 18.779150 | 200.652400 | 0.102336 | 4.72543 | 4.88 |
| 19.831570 | 259.643200 | 0.102336 | 4.47697 | 6.32 |
| 20.525570 | 726.830800 | 0.063960 | 4.32714 | 17.69 |
| 21.123060 | 313.674400 | 0.089544 | 4.20607 | 7.64 |
| 22.241580 | 301.102600 | 0.102336 | 3.99702 | 7.33 |
| 22.828300 | 485.040800 | 0.127920 | 3.89560 | 11.81 |
| 25.218110 | 42.303550 | 0.818688 | 3.53159 | 1.03 |

TABLE 6-continued

FIG. 46 Peak List

| Pos. [°2Th.] | Height [cts] | FWHM Left [°2Th.] | d-spacing [Å] | Rel. Int. [%] |
|---|---|---|---|---|
| 25.606150 | 71.888400 | 0.204672 | 3.47895 | 1.75 |
| 26.769420 | 121.605300 | 0.153504 | 3.33035 | 2.96 |
| 27.429070 | 64.946410 | 0.153504 | 3.25174 | 1.58 |
| 29.066220 | 74.634100 | 0.153504 | 3.07220 | 1.82 |
| 31.423480 | 44.097820 | 0.255840 | 2.84691 | 1.07 |
| 36.048690 | 33.706900 | 0.204672 | 2.49155 | 0.82 |
| 38.425090 | 58.863040 | 0.204672 | 2.34275 | 1.43 |

Form II may be characterized by various analytical techniques, including by x-ray powder diffraction. The x-ray powder diffraction pattern of Form II, or portions thereof, may be used to identify Form II. Form II contains various x-ray powder diffraction peaks which alone or together may help identify the presence of Form II. In many cases, Form II may be characterized by an x-ray powder diffraction pattern comprising a peak at about 2.3°2θ. In addition to the peak at about 2.3°2θ, the x-ray powder diffraction pattern may comprise, for example, one or more peaks at about 4.5°2θ, a peak at and between about 5.0°2θ and about 5.1°2θ, a peak at and between about 5.9°2θ and about 6.1°2θ, and at least one peak at and between about 14.8°2θ and about 15.1°2θ.

In many cases, Form II may be characterized by an x-ray powder diffraction pattern comprising peaks at about 2.3°2θ and about 5.0°2θ. The x-ray powder diffraction pattern may, in some cases, comprise one or more peaks at about 4.5°2θ, about 5.9°2θ, about 9.1°2θ, and about 15.1°2θ.

FIG. 2 is an x-ray powder diffraction pattern of Form II where the x-axis begins at about 0°2θ and goes to about 40°2θ, whereas FIG. 54 shows the same pattern but between about 3°2θ and about 39°2θ. Either of FIG. 2 or FIG. 54 may be used to characterize Form II.

Form II is stable under various conditions of temperature and humidity. Both Form II and substantially pure Form II are described herein. Form II is stable at relative humidities ranging from about 21% to about 30% RH. As such, Form II was generated from slurries in aqueous solvent mixtures with water activities at and between 0.21 and 0.30 $a_w$. Variable hydrates so prepared appear kinetically stable. Form II has been seen to dehydrate to an anhydrous state without form conversion when exposed to elevated temperatures or low humidity conditions. In a fully hydrated state, Form II appears to accommodate approximately 3 mol/mol of water (FIG. 16 shows the DVS sorption isotherm at 85% RH of Form I). Upon extended exposure to an RH of 75% or greater, Form II converts to liquid crystalline Form V of 25HC3S sodium.

Multiple x-ray powder diffraction patterns of Form II obtained from various experiments were successfully indexed (FIG. 17, FIG. 18, and FIG. 19). These indices show that the unit cell volume of Form II changes to accommodate varying amounts of water and thus Form II is a variable hydrate. Differences in these patterns, attributed to variation in the positions of peaks, suggest that a range exists for the observed peaks (FIGS. 18 and 19). FIGS. 20 and 21 are expanded regions of the x-ray powder diffraction patterns of the slurries. Given that x-ray powder diffraction peak positions are a direct result of the unit cell parameters, one x-ray powder diffraction pattern is not necessarily representative of the crystal form under all conditions due to the variable hydration and its effect on lattice parameters. The x-ray powder diffraction patterns should be considered discrete states of the same crystalline phase of Form II. The general trend is for peaks to shift toward smaller scattering angles with increased cell volume. Anisotropic strain can cause some peaks to shift toward higher scattering angles with increased cell volume. Some peak positions are more sensitive than others to changes in cell volume. Peaks that are sensitive to changes in cell volume can be useful for determining the cell volume for a particular specimen. Peaks that move result in x-ray powder diffraction patterns that appear to be qualitatively different by visual inspection, but do not indicate a change in crystalline phase.

Multiple x-ray powder diffraction patterns were acquired for Form II at ambient temperature and different RH conditions spanning 0% to 85% RH through an in situ variable humidity x-ray powder diffraction experiment performed in general accordance with Example 18. The experiment provides a systematic approach to determine the variation in unit cell volume dictated by water sorption, where the cell expands/contracts to accommodate water. As expected, a form change did not occur; however, peak shifts between the patterns are observed, due to unit cell volume differences (FIG. 22 and FIG. 23). The peaks shift toward smaller scattering angles at higher humidity, suggesting that the unit cell volume is directly proportional to relative humidity and likely increases to incorporate water.

The DVS isotherm, provided in FIG. 16, shows water content variability for Form II at the same relative humidity conditions in which kinetic form stability was demonstrated by variable humidity x-ray powder diffraction. Form II gained approximately 3.5 wt % from 5 to 55% RH (1 mol/mol water), 7 wt % from 55 to 85% RH (2 mol/mol water), and another 7 wt % from 85 to 95% RH. The instrument timed-out above 85% RH, suggesting that additional water sorption may be possible if left longer at this condition. Hysteresis was observed upon desorption. The material was recovered and identified as a mixture of Form II and Form V. Form II remained unchanged, by x-ray powder diffraction, under dry nitrogen for up to 4 days or stored at 0% RH for up to 35 days. Conversion to Form V occurred within 35 days upon exposure to 75% RH.

Of the three indexing solutions obtained, the largest unit cell volume observed from an indexing result for Form II is provided in FIG. 17. Assuming the orthorhombic unit cell contains 12 molecules of 25HC3S sodium, the formula unit volume of 756 $Å^3$ would be larger than the formula unit for the anhydrous form, Form XIII, by approximately 50 $Å^3$. This corresponds to a unit cell volume of 9066.5 $Å^3$ ($\pm5\%$). The difference in volume provides sufficient room to accommodate up to 2 mol/mol of water.

Thermally, up to 150° C., weight losses of 5 and 6% are observed by TGA (See FIG. 24). Assuming the losses are due to the volatilization water, the weight losses correspond to approximately 1.5 and 1.8 mol/mol water, respectively. The losses occur concurrently with the broad dehydration endotherms in the DSC (FIG. 25). The DSC curves also show endotherms near 167° C. and 189° C. These events are associated with decomposition.

A cycling DSC experiment for Form II is shown in FIG. 26. Broad desolvation endotherms are observed during the first heating cycle up to 130° C. (trace 1), as expected for the hydrate. However, no events are observed upon cooling (trace 2) or upon the second heating (trace 3) up to 130° C. This suggests that a form change did not occur upon dehydration and, once heated again to 130° C., the material does not contain water. The sample then proceeds through decomposition as evidenced by the endotherms near 167° C. and 188° C. The kinetic stability of Form II through dehydration at elevated temperatures was confirmed with a variable temperature x-ray powder diffraction experiment done in general accordance with Example 19 (FIG. 27). Form II is still observed by x-ray powder diffraction at 135° C. Therefore, the results from both variable temperature x-ray powder diffraction and cycling DSC experiments show that Form II can be maintained through complete dehydration. During the same variable temperature x-ray powder diffraction experiment, a decomposition product identified as trisodium hydrogen disulfate, $Na_3H(SO_4)_2$, was evident by 170° C.

In some cases, Form XI, including substantially pure Form XI, is provided of crystalline 25HC3S sodium. Form XI is a hydrate of crystalline 25HC3S sodium which may be prepared as set forth in Table 1. For example, Form XI may be prepared by slurrying in diethyl ether and exposing to ambient conditions for 14 days, filtering, and drying under nitrogen. It may thus be prepared in a stable form. In addition, Example 37 shows a preparation of Form XI. Form XI may be characterized by various analytical techniques, including by x-ray power diffraction. The x-ray powder diffraction pattern of Form XI, or portions thereof, may be used to identify Form XI. Form XI contains various x-ray powder diffraction peaks which alone or together may help identify the presence of Form XI.

In many cases, Form XI may be characterized by an x-ray powder diffraction pattern comprising a peak at about 2.6°2θ. In addition to the peak at about 2.6°2θ, the x-ray powder diffraction pattern may comprise, for example, one or more peaks at about 3.1°2θ, about 3.5°2θ, and about 14.5°2θ. The x-ray powder diffraction patterns for Form XI are at FIG. 6 and FIG. 7. Either FIG. 6 or FIG. 7 may be used to characterize Form XI.

In some cases, Form V, a lyotropic mesophase (also known as a liquid crystal) of 25HC3S sodium, including substantially pure Form V, is provided herein. Lyotropic mesophases are induced by the presence of solvent. In addition, concentration and temperature are determining factors in their phase transitions. Form V may be prepared as set forth in Table 1. For example, transparent and viscous gels were formed from water, aqueous solvent mixtures with a water activity above 0.73 $a_w$, methanol, and DMSO. Form V formed as gels specifically from water, aqueous solvent systems with water activity above 0.73 $a_w$, and methanol exhibited disordered x-ray powder diffraction patterns. Form V also formed when either Forms I or II were exposed to relative humidity at or above 75% RH. These gels did not typically exhibit birefringence under polarized light microscopy until a shear force, such as sliding between two glass slides, was applied. Optical birefringence is suggestive of an ordered phase having at least one-dimension of order. Flow of the material was also observed. In addition, Form V may be prepared as set forth, for example, in Examples 34, 35, and 36.

A mesophase is characterized by its birefringence, which is absent in amorphous solids or isotropic liquids and present in almost all cases for crystalline solids. Further, the material flows like a liquid when pressed upon, rather than break and fracture like a solid. As typical for mesophases, the x-ray powder diffraction patterns of Form V exhibit few peaks superimposed on a diffuse background (FIG. 3).

In many cases, Form V may be characterized by an x-ray powder diffraction pattern comprising a peak at about 2.2°2θ. In addition to the peak at about 2.2°2θ, the x-ray powder diffraction pattern may comprise, for example, one or more peaks at about 4.4°2θ, about 6.6°2θ, and about 8.8°2θ.

In many cases, Form V may be characterized by an x-ray powder diffraction pattern comprising peaks at about 2.2'2θ, about 6.6'2θ, and a single peak at and between about 4.0'2θ and about 6.0°2θ. The x-ray powder diffraction, in some cases, may further comprise one or more peaks at about 8.8°2θ, about 9.9°2θ, and about 14.9°2θ. The x-ray powder diffraction patterns for Form V are at FIG. 3 and FIG. 4. Either of FIG. 3 or FIG. 4 may be used to characterize Form V.

Form V exhibits a 7% weight loss up to 147° C. by TGA (FIG. 28) which occurs concurrently with a broad dehydration endotherm in the DSC (FIG. 29). Events associated with decomposition are evident above 148° C.

The physical stability of Form V showed no changes observed by x-ray powder diffraction on storage at ambient conditions for 25 days. In addition, the material remained Form V upon exposure to 55° C. and vacuum for 1 day. Thus, disclosed herein is also stable Form V. The following Table 7 correlates the Examples producing Form V with the corresponding XRPD diffractogram Figure.

TABLE 7

Form V XRPD Examples/FIGS.

| Example # | FIG. |
|---|---|
| 34 | 47 |
| 35 | 48 |
| 36 | 56 |

Table 8 shows peaks found in FIG. 56, whereas peaks for the other figures in Table 8 are presented on the figures themselves.

TABLE 8

FIG. 56 Peak List

| Pos. [°2Th.] | Height [cts] | FWHM Left [°2Th.] | d-spacing [Å] | Rel. Int. [%] |
|---|---|---|---|---|
| 4.456570 | 1011.928000 | 0.102336 | 19.82806 | 30.00 |
| 6.670990 | 515.763400 | 0.102336 | 13.25033 | 15.29 |
| 8.883880 | 3372.782000 | 0.140712 | 9.95415 | 100.00 |
| 11.079420 | 116.481300 | 0.153504 | 7.98604 | 3.45 |
| 15.392700 | 171.999000 | 0.255840 | 5.75657 | 5.10 |
| 17.756100 | 662.088400 | 0.153504 | 4.99532 | 19.63 |
| 19.986240 | 896.322600 | 0.127920 | 4.44267 | 26.58 |
| 22.239050 | 304.758100 | 0.153504 | 3.99747 | 9.04 |
| 24.583640 | 42.981330 | 0.307008 | 3.62128 | 1.27 |
| 26.762670 | 66.577970 | 0.204672 | 3.33117 | 1.97 |
| 29.038120 | 41.789920 | 0.307008 | 3.07511 | 1.24 |

In many cases, Form XIII crystalline 25HC3S sodium is provided, including substantially pure Form XIII crystalline 25HC3S sodium. Form XIII is anhydrous and was observed through the dehydration of Form I upon exposure to 130° C., 70° C. and vacuum, or to humidity conditions near 0% RH. Under ambient conditions, Form XIII quickly hydrates to Form I. Form XIII was also seen by dissolving in an acetonitrile/H₂O solution and drying as set forth in Table 1. Form XIII may also, for example, be prepared as set forth in Examples 25 and 26.

The x-ray powder diffraction pattern of Form XIII was successfully indexed, indicating the pattern represents a single crystalline phase (FIG. 30). The indexing result has a monoclinic unit cell containing six molecules of 25HC3S sodium. Consequently, the formula unit volume of 705 Å³ (±5%) would be consistent with an anhydrous form and is not capable of accommodating any additional solvent or water molecules, with a unit cell volume of 4230.8 Å³ (±5%).

In many cases, Form XIII may be characterized by an x-ray powder diffraction pattern comprising a peak at about 2.3°2θ. In addition to the peak at about 2.3°2θ, the x-ray powder diffraction pattern may comprise, for example, one or more peaks at about 4.6°2θ, about 9.3°2θ, about 14.3°2θ, and about 15.0°2θ (FIG. 8 and FIG. 9).

In many cases, Form XIII may be characterized by an x-ray powder diffraction pattern comprising peaks at about 2.3°2θ, about 5.4°2θ, about 9.3°2θ, and about 11.6°2θ. The x-ray powder diffraction pattern, in some cases, may further comprise one or more peaks at about 4.6°2θ and about 15.0°2θ. Either FIG. 8 or FIG. 9 may be used to characterize Form XIII.

A variable humidity x-ray powder diffraction experiment on a mixture composed predominately of Form I and a minor amount of Form XIII is presented in FIG. 13. The material was exposed to increasing and then decreasing humidity during x-ray powder diffraction analysis. These results provide evidence that Forms I and XIII quickly interconvert. A mixture of Forms I and XIII was evident at 14% RH. Form XIII was shown to hydrate to Form I before reaching 25% RH. Conversely, Form I was shown to dehydrate within minutes to Form XIII upon exposure to 0% RH, remaining stable under those conditions.

In many cases of the present disclosure, solvates of crystalline 25HC3S sodium are provided, including substantially pure crystalline solvates of 25HC3S sodium.

In many cases, Form III crystalline 25HC3S sodium is provided, including substantially pure Form III crystalline 25HC3S sodium. Form III is an ethanol solvate of crystalline 25HC3S sodium. X-ray powder diffraction patterns for Form III are set forth in FIG. 35, FIG. 49, and FIG. 50. Form III crystallized only from experiments involving ethanol. Form III is metastable and desolvates to Form II at ambient conditions. When exposed to 58° C. and vacuum overnight, or a temperature of 130° C., it desolvates to another anhydrous form, Form IX (FIG. 31). Preparations of Form III are further described in Examples 38-39.

Table 9 shows peaks found in FIG. 50, whereas peaks for FIGS. 35 and 49 are presented on the figure itself.

TABLE 9

FIG. 50 Peak List (Form III)

| Pos. [°2Th.] | Height [cts] | FWHM Left [°2Th.] | d-spacing [Å] | Rel. Int. [%] |
|---|---|---|---|---|
| 6.387487 | 4693.291000 | 0.051168 | 13.83778 | 17.97 |
| 7.814675 | 26117.580000 | 0.051168 | 11.31351 | 100.00 |
| 9.872075 | 811.450200 | 0.076752 | 8.95984 | 3.11 |
| 11.401980 | 342.370700 | 0.076752 | 7.76083 | 1.31 |
| 12.764300 | 213.323200 | 0.076752 | 6.93542 | 0.82 |
| 13.379850 | 14526.280000 | 0.063960 | 6.61771 | 55.62 |
| 15.621830 | 15172.540000 | 0.089544 | 5.67265 | 58.09 |
| 19.173970 | 227.941600 | 0.102336 | 4.62901 | 0.87 |
| 19.474080 | 1176.151000 | 0.102336 | 4.55834 | 4.50 |
| 21.008570 | 719.226400 | 0.089544 | 4.22874 | 2.75 |
| 25.810620 | 93.194700 | 0.204672 | 3.45185 | 0.36 |
| 26.862540 | 34.265340 | 0.614016 | 3.31902 | 0.13 |
| 28.882870 | 63.145900 | 0.153504 | 3.09129 | 0.24 |
| 29.799090 | 42.999270 | 0.153504 | 2.99829 | 0.16 |
| 30.535120 | 65.048610 | 0.153504 | 2.92768 | 0.25 |
| 31.510870 | 84.185980 | 0.153504 | 2.83921 | 0.32 |
| 32.225590 | 48.569530 | 0.204672 | 2.77786 | 0.19 |
| 33.137800 | 47.258860 | 0.153504 | 2.70345 | 0.18 |
| 34.683980 | 171.839700 | 0.102336 | 2.58639 | 0.66 |

The x-ray powder diffraction pattern of Form III was successfully indexed, indicating the pattern represents a single crystalline phase as seen in FIG. 32. The indexing result has a triclinic unit cell containing two molecules of 25HC3S sodium. Consequently, the formula unit volume of 768 Å$^3$ is consistent with a monoethanolate. The volume is larger than the formula unit for the anhydrous form, Form XIII, by approximately 63 Å$^3$. The difference in volume provides sufficient room to accommodate up to 1 mol/mol of ethanol which further suggests Form III is a monoethanolate.

In many cases, Form III may be characterized by an x-ray powder diffraction pattern comprising a peak at about 4.9°2θ. Although no peak at about 4.9°2θ appears in Table 9, an expanded view of that diffractogram in FIG. 52 shows the presence of a peak at about 4.9°2θ. In addition to the peak at about 4.9°2θ, the x-ray powder diffraction pattern may comprise, for example, one or more peaks at about 6.3°2θ, about 7.8°2θ, and about 9.8°2θ.

In many cases, Form III may be characterized by peaks at about 4.9°2θ and about 6.3°2θ. The x-ray powder diffraction pattern, in some cases, may further comprise one or more peaks at about 7.8°2θ, about 9.8°2θ, about 13.3°2θ, and about 15.5°2θ. Form III may be characterized by the x-ray powder diffraction pattern of FIG. 35.

With respect to Form IX, in many cases, Form IX may be characterized by an x-ray powder diffraction pattern comprising a peak at about 4.9°2θ. The x-ray powder diffraction pattern may comprise for example, one or more peaks at about 7.9°2θ, about 11.2°2θ, about 14.1°2θ, about 16.1°2θ, and about 16.6°2θ.

In many cases, Form IX may be characterized by an x-ray powder diffraction pattern comprising peaks at about 2.2°2θ, about 4.9°2θ, and about 7.9°2θ. The x-ray diffraction pattern may, in some cases, may further comprise one or more peaks at about 14.1°2θ, about 16.1°2θ, and about 16.6°2θ. Form IX may further be characterized by FIG. 5.

Residual organic solvent, such as ethanol, was not observed. A 1.6% weight loss observed up to 145° C. by TGA is likely due to the volatilization of water. Congruent dehydration endotherms are evident by DSC, and events above 150° C. are associated with decomposition. Form IX may be prepared as set forth in Example 32 and Example 33. FIG. 5 corresponds to Example 32 and FIG. 51 to Example 33.

Table 10 shows peaks found in FIG. 51, whereas the peaks of FIG. 5 are presented on that Figure.

TABLE 10

| FIG. 51 Peak List | | | | |
|---|---|---|---|---|
| Pos. [°2Th.] | Height [cts] | FWHM Left [°2Th.] | d-spacing [Å] | Rel. Int. [%] |
| 4.811323 | 45.357440 | 0.614016 | 18.36685 | 3.59 |
| 6.984234 | 453.736100 | 0.089544 | 12.65673 | 35.92 |
| 8.010692 | 655.509800 | 0.102336 | 11.03711 | 51.90 |
| 9.860124 | 152.477100 | 0.102336 | 8.97068 | 12.07 |
| 11.274460 | 472.185700 | 0.127920 | 7.84832 | 37.39 |
| 14.158540 | 1263.031000 | 0.127920 | 6.25545 | 100.00 |
| 16.117560 | 95.677850 | 0.204672 | 5.49927 | 7.58 |
| 16.601830 | 183.637300 | 0.127920 | 5.33994 | 14.54 |
| 18.391860 | 51.683560 | 0.409344 | 4.82405 | 4.09 |
| 20.142210 | 46.117470 | 0.307008 | 4.40862 | 3.65 |
| 20.881010 | 103.616700 | 0.153504 | 4.25428 | 8.20 |
| 21.966780 | 142.983300 | 0.153504 | 4.04639 | 11.32 |
| 24.041400 | 57.026530 | 0.307008 | 3.70171 | 4.52 |

The present disclosure also relates to pharmaceutical compositions containing crystalline 25HC3S sodium as disclosed herein. Such pharmaceutical compositions are comprised of one or more pharmaceutically acceptable excipients and crystalline 25HC3S sodium as set forth in the present disclosure. Such pharmaceutical compositions may be administered orally or configured to be delivered as any effective conventional dosage unit forms, including, for example, immediate, slow and timed-release oral preparations, parenterally, topically, nasally, ophthalmically, optically, sublingually, rectally, vaginally, and the like.

The present disclosure further includes mixtures of forms of 25HC3S sodium such as crystalline 25HC3S sodium forms with each other and/or with lyotropic forms of 25HC3S sodium. For examples, mixtures of two or more of crystalline 25HC3S sodium Form I, crystalline 25HC3S sodium Form II, liquid crystal 25HC3S sodium Form V, crystalline 25HC3S sodium Form IX, crystalline 25HC3S sodium Form XI, or crystalline 25HC3S sodium Form XIII are provided. The amount of each form present in such mixtures ranges from, for example, about 0.01% to about 99.9% by weight. Other ranges include about 0.1% to about 95%, about 0.1% to about 90%, about 0.1% to about 85%, about 0.1% to about 80%, about 0.1% to about 75%, about 0.1% to about 70%, about 0.1% to about 65%, about 0.1% to about 60%, about 0.1% to about 55%, about 0.1% to about 50%, about 0.1% to about 45%, about 0.1% to about 40%, about 0.1% to about 35%, about 0.1% to about 30%, about 0.1% to about 25%, about 0.1% to about 20%, about 0.1% to about 15%, about and 0.1% to about 10% by weight. Other ranges include about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1% by weight. Additional ranges include about 0.1% to about 0.9%, about 0.1% to about 0.8%, about 0.1% to about 0.7%, about 0.1% to about 0.6%, about 0.1% to about 0.5%, about 0.1% to about 0.4%, about 0.1% to about 0.3%, and about 0.1% to about 0.2% by weight. Further ranges include between about 0.01% and about 0.1% by weight. Additional ranges include between about 0.01% and about 0.09%, about 0.01% to about 0.08%, about 0.01% to about 0.07%, about 0.01% to about 0.06%, about 0.01% to about 0.05%, about 0.01% to about 0.04%, about 0.01% to about 0.03% and about 0.01% to about 0.02% by weight. Such mixtures may also be present in pharmaceutical compositions comprising one or more pharmaceutically acceptable excipients.

The present disclosure further includes methods and uses for treating diseases in humans such as one or more of hypercholesterolemia, hypertriglyceridemia, and conditions related to fat accumulation and inflammation (e.g., non-alcoholic fatty liver disease (NAFLD), non-alcoholic steatohepatitis (NASH), alcoholic hepatitis, acute kidney injury (AKI), psoriasis, and atherosclerosis) with effective amounts crystalline 25HC3S sodium and/or pharmaceutical compositions comprising crystalline 25HC3S sodium of the present disclosure.

Methods for Preparing
25-hydroxy-cholesten-5-en-3-sulfate (25HC3S)

As summarized above, the present disclosure also provides methods for preparing 25-hydroxy-cholesten-5-en-3-sulfate, such as 25-hydroxy-3β-cholesten-5-en-3-sulfate (25HC3S). Although many of the teachings herein involve a sulfate in the 3β position, the teachings of the present disclosure are also generally applicable to a sulfate in the 3α position. The components used in each step of the subject methods for preparing 25-hydroxy-3β-cholesten-5-en-3-sulfate described herein may be a purified composition or a crude composition as desired. The term "purified" is used in its conventional sense to refer to a composition where at least some isolation or purification process has been conducted, such as for example, filtration or aqueous workup of a reaction mixture. In certain instances, purification includes at least one of liquid chromatography, recrystallization, distillation (e.g., azeotropic distillation) and other type of compound purification. For example, compounds as described herein may be purified by chromatographic means, such as high performance liquid chromatography (HPLC), supercritical fluid chromatography (SFC), thin layer chromatography, flash column chromatography and ion exchange chromatography. Any suitable stationary phase can be used, including normal and reversed phases as well as ionic resins. Mobile phases may be chosen from polar solvents and non-polar solvents. In some cases, the mobile phase includes a polar solvent. In some cases, the polar solvent is chosen from chloroform, dichloromethane, tetrahydrofuran, dichloroethane, acetone, dioxane, ethyl acetate, dimethylsulfoxide, aniline, diethylamine, nitromethane, acetonitrile, pyridine, isopropanol, ethanol, methanol, ethylene glycol, acetic acid and water. In some cases, the mobile phase includes a non-polar solvent. In some cases, the non-polar solvent is chosen from diethyl ether, toluene, benzene, pentane, hexanes, cyclohexane, petroleum ether and carbon tetrachloride. See, e.g., Introduction to Modern Liquid Chromatography, 2nd Edition, ed. L. R. Snyder and J. J. Kirkland, John Wiley and Sons, 1979; and Thin Layer Chromatography, ed. E. Stahl, Springer-Verlag, New York, 1969.

In some cases, a reaction mixture is used in a subsequent step in the methods described herein as a crude mixture where no purification or other workup of the reaction mixture has been conducted. In certain instances, the crude mixture includes the compound of interest in sufficient purity such as where the reaction mixture includes the compound of interest in a purity of 70% or greater, such as 75% or greater, such as 80% or greater, such as 85% or greater, such as 90% or greater, such as 95% or greater, such as 97% or greater, such as 99% or greater, such as 99.5% or greater, such as 99.9% or greater, such as 99.99% or greater and including 99.999% or greater, relative to the crude reaction mixture (apart from solvent when present), as determined by chromatography (e.g., HPLC or SFC), nuclear magnetic resonance spectroscopy (e.g., $^1$H NMR or $^{13}$C NMR) or a combination thereof. In some cases, the compound of interest is present in the reaction mixture in an amount that is 30% by weight or greater relative to the crude reaction mixture (apart from solvent when present), such as 40% by weight or greater, such as 50% by weight or greater, such as 60% by weight or greater, such as 70% by weight or greater, such as 75% by weight or greater, such as by 80% by weight or greater, such as 85% by weight or greater, such as 90% by weight or greater, such as 95% by weight or greater, such as 97% by weight or greater, such as 99% by weight or greater, such as 99.5% by weight or greater, such as 99.9% by weight or greater, such as 99.99% by weight or greater and including 99.999% by weight or greater relative to the crude reaction mixture, and may range from 5% by weight to 99.999% by weight, such as 30% by weight to 99.99% by weight, 40% by weight to 99.9% by weight, 50% by weight to 99% by weight, 70% by weight to 95% by weight, 75% by weight to 90% by weight, 80% by weight to 99% by weight, or 80% by weight to 95% by weight. In some cases, the compound of interest is present at 30 mol % or greater in the crude reaction mixture (apart from solvent when present), such as 40 mol % or greater, such as 50 mol % or greater, such as 60 mol % or greater, such as 70 mol % or greater, such as 75 mol % or greater, such as by 80 mol % or greater, such as 85 mol % or greater, such as 90 mol % or greater, such as 95 mol % or greater, such as 97 mol % or greater, such as 99 mol % or greater, such as 99.5 mol % or greater, such as 99.9 mol % or greater, such as 99.99 mol % or greater and including 99.999 mol % or greater relative to the crude reaction mixture, and may range from 30 mol % to 99.999 mol %, such as 50 mol % to 99 mol %, 70 mol % to 95 mol %, 75 mol % to 90 mol %, 80 mol % to 99 mol %, or 80 mol % to 95 mol %.

Methods for preparing a metal salt of 25-hydroxy-3β-cholesten-5-en-3-sulfate ([(3S,10R,13R,17R)-17-[(1R)-5-hydroxy-1,5-dimethyl-hexyl]-10,13-dimethyl-2,3,4,7,8,9,11,12,14,15,16,17-dodecahydro-1H-cyclopenta[a]phenanthren-3-yl] sulfate metal salt) according to the present disclosure include contacting 25-hydroxy-(3β)-cholest-5-en-3-ol with a sulfating agent to produce a 25-hydroxy-(3β)-cholest-5-en-3-sulfate organic cationic salt; and contacting the 25-hydroxy-(3β)-cholest-5-en-3-sulfate organic cationic salt with at least one metal salt to produce the 5-cholesten-3β,25-diol 3-sulfate metal salt (Scheme Ia).

Scheme Ia

Scheme IA1 sulfation
→

25HC

25HC3S

The 25-hydroxy-(3β)-cholest-5-en-3-ol is sulfated by contacting with a sulfating agent (Scheme IA1). In some cases, the sulfating reagent is chosen from sulfur trioxide complexes, sulfuric acid compounds, sulfonic acid compounds, and sulfonate compounds. In some cases, the sulfating reagent is chosen from sulfur trioxide dimethyl formamide, sulfur trioxide triethylamine, and sulfur trioxide trimethylamine. In some cases, the sulfating reagent includes from sulfuric acid and acetic anhydride and pyridine. In some cases, the sulfating reagent includes sulfur trioxide triethylamine and pyridine. In some cases, the sulfating reagent is chosen from 1) chlorosulfonic acid and pyridine and 2) chlorosulfonic acid and 2,6-lutidine. In some cases, the sulfating reagent is ethyl chlorosulfonate.

The 25-hydroxy-(3β)-cholest-5-en-3-ol may be sulfated at a temperature that ranges from –10° C. to 50° C., such as from –5° C. to 45° C., such as from –4° C. to 40° C., such as from –3° C. to 35° C., such as from –2° C. to 30° C., such as from –1° C. to 25° C., and including from 0° C. to 20° C. The reaction may be carried out for a duration that ranges from 0.1 hours to 72 hours, such as from 0.2 hours to 48 hours, such as from 0.3 hours to 24 hours, such as from 0.4 hours to 21 hours, such as from 0.5 hours to 20 hours, such as from 0.6 hours to 19 hours, such as from 0.7 hours to 18 hours, such as from 0.8 hours to 17 hours, such as from 0.9 hours to 16 hours and including from 1 hour to 15 hours. The amount of sulfating agent used relative to the 25-hydroxy-(3β)-cholest-5-en-3-ol may vary and may be 0.001 equivalents or more, such as 0.01 equivalents or more, such as 0.1 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more, and may range from 0.001 equivalents to 10 equivalents, such as 0.1 equivalents to 10 equivalents, 0.1 equivalents to 8 equivalents, 0.1 equivalents to 5 equivalents, 0.5 equivalents to 10 equivalents, 0.5 equivalents to 8 equivalents, 0.5 equivalents to 5 equivalents, 0.9 equivalents to 10 equivalents, 0.9 equivalents to 8 equivalents, 0.9 equivalents to 5 equivalents, 1.3 equivalents to 10 equivalents, 1.3 equivalents to 8 equivalents, 1.3 equivalents to 5 equivalents, 1.5 equivalents to 10 equivalents, 1.5 equivalents to 8 equivalents, 1.5 equivalents to 5 equivalents, 2 equivalents to 10 equivalents, 2 equivalents to 8 equivalents, 2 equivalents to 5 equivalents, or 1 equivalent to 2 equivalents, 1 equivalent to 1.5 equivalents, or 1.1 to 1.2 equivalents, relative to the 25-hydroxy-(3β)-cholest-5-en-3-ol.

In some cases, methods include sulfating the 25-hydroxy-(3β)-cholest-5-en-3-ol in at least one solvent where the 25-hydroxy-(3β)-cholest-5-en-3-sulfate product exhibits low solubility. In some cases, the 25-hydroxy-(3β)-cholest-5-en-3-ol is sulfated in at least one solvent where the 25-hydroxy-(3β)-cholest-5-en-3-sulfate product exhibits a solubility of 100 mmol/L or less, such as 90 mmol/L or less, such as 80 mmol/L or less, such as 70 mmol/L or less, such as 60 mmol/L or less, such as 50 mmol/L or less, such as 40 mmol/L or less, such as 30 mmol/L or less, such as 20 mmol/L or less, such as 10 mmol/L or less, and including sulfating the 25-hydroxy-(3β)-cholest-5-en-3-ol in at least one solvent where the 25-hydroxy-(3β)-cholest-5-en-3-sulfate product exhibits a solubility of 5 mmol/L or less. In some cases, the 25-hydroxy-(3β)-cholest-5-en-3-ol is sulfated in at least one solvent where 25-hydroxy-(3β)-cholest-5-en-3-sulfate product precipitates after formation. In some cases, the at least one solvent is chosen from chloroform, methylene chloride, acetone, acetonitrile, toluene, tetrahydrofuran, and methyltetrahydrofuran.

In some cases, methods include sulfating the 25-hydroxy-(3β)-cholest-5-en-3-ol in a manner sufficient to reduce or eliminate bis-sulfation of the 25-hydroxy-(3β)-cholest-5-en-3-ol. In some instances, the 25-hydroxy-(3β)-cholest-5-en-3-ol is sulfated and a bis-sulfate product (i.e., 5-cholesten-3β-25-diol-disulfate, Structure IA) is formed in an amount that is 10% by weight or less of the reaction product formed by contacting the 25-hydroxy-(3β)-cholest-5-en-3-ol with the sulfating agent, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less, and including where the 25-hydroxy-(3β)-cholest-5-en-3-ol is sulfated and the bis-sulfate product is formed in an amount that is 0.0001% by weight or less, and may range from 10% by weight to 0.001% by weight, such as 10% by weight to 0.1% by weight, 10% by weight to 1% by weight, 10% by weight to 2% by weight, 8% by weight to 0.001% by weight, 8% by weight to 0.1% by weight, 8% by weight to 1% by weight, 8% by weight to 2% by weight, 6% by weight to 0.001% by weight, 6% by weight to 0.1% by weight, 6% by weight to 1% by weight, 6% by weight to 2% by weight, 4% by weight to 0.001% by weight, 4% by weight to 0.1% by weight, 4% by weight to 1% by weight, 4% by weight to 2% by weight, 3% by weight to 0.001% by weight, 3% by weight to 0.1% by weight, 3% by weight to 1% by weight, 2% by weight to 0.001% by weight, 2% by weight to 0.1% by weight, or 2% by weight to 1% by weight.

In some cases, the ratio by weight of the 25-hydroxy-(3β)-cholest-5-en-3-sulfate to the 5-cholesten-3β-25-diol-disulfate formed is 10:1 or more, such as 25:1 or more, such as 50:1 or more, such as 100:1 or more, such as such as 250:1 or more, such as 500:1 or more, such as 1000:1 or more, such as 2500:1 or more, such as 5000:1 or more, such as 10,000:1 or more, such as 25,000:1 or more, such as 50,000:1 or more, such as 100,000:1 or more, such as $10^6$:1 or more, such as $10^7$:1 or more, such as $10^8$:1 or more, and including where the ratio by weight of the 25-hydroxy-(3β)-cholest-5-en-3-sulfate to the 5-cholesten-3β-25-diol-disulfate formed is $10^9$:1 or more, and may range from a ratio by weight of 10:1 to a ratio by weight of $10^9$:1, such as a ratio of weight of 10:1 to a ratio of weight of $10^6$:1, a ratio of weight of 10:1 to a ratio of weight of $10^3$:1, a ratio of weight of 10:1 to a ratio of weight of 100:1, a ratio of weight of 100:1 to a ratio of weight of $10^9$:1, a ratio of weight of 100:1 to a ratio of weight of $10^6$:1, a ratio of weight of 100:1 to a ratio of weight of $10^3$:1, a ratio of weight of 250:1 to a ratio of weight of $10^9$:1, a ratio of weight of 250:1 to a ratio of weight of $10^6$:1, a ratio of weight of 250:1 to a ratio of weight of $10^3$:1, a ratio of weight of 500:1 to a ratio of weight of $10^9$:1, a ratio of weight of 500:1 to a ratio of weight of $10^6$:1, a ratio of weight of 500:1 to a ratio of weight of $10^3$:1, a ratio of weight of $10^3$:1 to a ratio of weight of $10^9$:1, a ratio of weight of $10^3$:1 to a ratio of weight of $10^6$:1, or a ratio of weight of 250:1 to a ratio of weight of $10^3$:1.

IA

In some cases, the 5-cholesten-3β-25-diol-disulfate formed when sulfating 25-hydroxy-(3β)-cholest-5-en-3-ol remains solubilized in the at least one solvent. In some cases, the 5-cholesten-3β-25-diol-disulfate has high solubility in the at least one solvent. In some instances, the 5-cholesten-3β-25-diol-disulfate exhibits a solubility of 500 mmol/L or more in the at least one solvent, such as 600 mmol/L or more, such as 700 mmol/L or more, such as 800 mmol/L or more, such as 900 mmol/L, or more and including a solubility of 1 mol/L or more in the at least one solvent.

In certain cases, methods further include separating the 25-hydroxy-(3β)-cholest-5-en-3-sulfate product from the bis-sulfate product (i.e., 5-cholesten-3β-25-diol-disulfate). In some cases, the 25-hydroxy-(3β)-cholest-5-en-3-sulfate product is separated from the bis-sulfate product by vacuum filtration. In some cases, the 25-hydroxy-(3β)-cholest-5-en-3-sulfate product is separated from the bis-sulfate product by recrystallization of the 25-hydroxy-(3β)-cholest-5-en-3-sulfate product. In some cases, the 25-hydroxy-(3β)-cholest-5- en-3-sulfate product is separated from the bis-sulfate product by chromatography (e.g., silica column).

In some cases, the 25-hydroxy-(3β)-cholest-5-en-3-ol is sulfated in a reaction mixture having a pH that ranges from 5.0 to 8.0, such as a pH from 5.1 to 7.9, such as a pH from 5.2 to 7.8, such as a pH from 5.3 to 7.7, such as a pH from 5.4 to 7.6, such as a pH from 5.5 to 7.5, such as a pH from 5.6 to 7.4, such as a pH from 5.7 to 7.3, such as a pH from 5.8 to 7.2, such as a pH from 5.9 to 7.1, and including sulfating the 25-hydroxy-(3β)-cholest-5-en-3-ol in a reaction mixture having a pH of from 6.0 to 7.0.

In some cases, 25-hydroxy-(3β)-cholest-5-en-3-ol is sulfated in the presence of a 25-hydroxy-(3β)-cholest-5-en-3-sulfate organic cationic salt. In certain cases, the 25-hydroxy-(3β)-cholest-5-en-3-sulfate organic cationic salt is present as particles (e.g., seed crystals of 25-hydroxy-(3β)-cholest-5-en-3-sulfate organic cationic salt produced in a previous reaction or purified reaction batch). In some cases, sulfating 25-hydroxy-(3β)-cholest-5-en-3-ol in the presence of 25-hydroxy-(3β)-cholest-5-en-3-sulfate organic cationic salt (e.g., as particles) is sufficient to reduce the solubility of 25-hydroxy-(3β)-cholest-5-en-3-sulfate organic cationic salt produced by reaction of the sulfating agent with 25-hydroxy-(3β)-cholest-5-en-3-ol as compared to the solubility when the 25-hydroxy-(3β)-cholest-5-en-3-sulfate organic cationic salt is not present. In certain cases, the solubility of 25-hydroxy-(3β)-cholest-5-en-3-sulfate organic cationic salt produced in the reaction mixture is reduced as compared to the solubility when the added 25-hydroxy-(3β)-cholest-5-en-3-sulfate organic cationic salt is not present by 5% or more, such as by 10% or more, such as by 25% or more, such as by 50% or more, such as by 75% or more, such as by 90% or more and including by reducing the solubility of the produced 25-hydroxy-(3β)-cholest-5-en-3-sulfate organic cationic salt by 99% or more. The size of the particles of 25-hydroxy-(3β)-cholest-5-en-3-sulfate organic cationic salt added to the reaction mixture may vary and may have a dimension (e.g., length, width or diameter) of 0.01 mm or more, such as 0.025 mm or more, such as 0.05 mm or more, such as 0.075 mm or more, such as 0.1 mm or more, such as 0.25 mm or more, such as 0.5 mm or more, such as 0.75 mm or more, such as 1 mm or more, such as 2 mm or more, such as 3 mm or more, such as 4 mm or more and including 5 mm or more. In some cases, the particles of 25-hydroxy-(3β)-cholest-5-en-3-sulfate organic cationic salt are added to the reaction mixture immediately after contacting the sulfating agent with the 25-hydroxy-(3β)-cholest-5-en-3-ol. In some cases, the particles of 25-hydroxy-(3β)-cholest-5-en-3-sulfate organic cationic salt are added to the reaction mixture 1 minute or more after contacting the sulfating agent with the 25-hydroxy-(3β)-cholest-5-en-3-ol, such as 5 minutes or more, such as 10 minutes or more, such as 15 minutes or more, such as 20 minutes or more, such as 30 minutes or more, such as 40 minutes or more, such as 50 minutes or more and including adding the particles of 25-hydroxy-(3β)-cholest-5-en-3-sulfate organic cationic salt to the reaction mixture 60 minutes or more after contacting the sulfating agent with the 25-hydroxy-(3β)-cholest-5-en-3-ol.

In certain cases, the sulfating agent is characterized prior to contacting with the 25-hydroxy-(3β)-cholest-5-en-3-ol. In some cases, characterizing the sulfating agent includes determining the extent of degradation of the sulfating agent prior to contacting with the 25-hydroxy-(3β)-cholest-5-en-3-ol. In certain cases, determining the extent of degradation of the sulfating reagent includes determining the amount of impurity in the sulfating reagent prior to contacting with the 25-hydroxy-(3β)-cholest-5-en-3-ol.

In some instances, the degradation of the sulfating agent is determined by proton nuclear magnetic resonance spectroscopy ('H-NMR). Proton NMR spectroscopy of the sulfating agent may be conducted in at least one deuterated solvent. In certain cases, the at least one deuterated solvent is deuterated acetone ($(CD_3)_2CO$). In certain cases, the at least one deuterated solvent is not deuterated benzene ($C_6D_6$). In certain cases, the at least one deuterated solvent is not deuterated acetonitrile ($CD_3CN$). In certain cases, the at least one deuterated solvent is not deuterated chloroform ($CD_3Cl$).

In some instances, methods for determining the extent of degradation include integrating one or more peaks in the $^1$H-NMR spectrum at a chemical shift of from 9.2 ppm to 9.3 ppm and calculating the impurity level of the sulfating agent based on the integrated peaks. In certain instances, methods for determining the extent of degradation include integrating one or more peaks in the $^1$H-NMR spectrum at a chemical shift of about 9.25 ppm and calculating the impurity level of the sulfating agent based on the integrated peaks. In some cases, the sulfating agent is contacted with the 25-hydroxy-(3β)-cholest-5-en-3-ol when the impurity level of the sulfating agent is below a predetermined threshold, such as where the impurity level is 25% or less as determined by integrating one or more peaks in the proton NMR spectrum at a chemical shift of from 9.2 ppm to 9.3 ppm, such as 24% or less, such as 23% or less, such as 22% or less, such as 21% or less, such as 20% or less, such as 19% or less, such as 18% or less, such as 17% or less, such as 16% or less, such as 15% or less, such as 14% or less such as 13% or less, such as 12% or less, such as 11% or less, such as 10% or less, such as 9% or less, such as 8% or less, such as 7% or less, such as 6% or less, such as 5% or less, such as 4% or less, such as 3% or less such as 2% or less and including where the impurity level is 1% or less as determined by integrating one or more peaks in the proton NMR spectrum at a chemical shift of from 9.2 ppm to 9.3 ppm. In some cases, the sulfating agent is not contacted with the 25-hydroxy-(3β)-cholest-5-en-3-ol when the impurity level is above a predetermined threshold, such as where the impurity level is 25% or more as determined by integrating one or more peaks in the proton NMR spectrum at a chemical shift of from 9.2 ppm to 9.3 ppm, such as 26% or more, such as 27% or more, such as 28% or more, such as 29% or more, such as 30% or more, such as 31% or more, such as 32% or more, such as 33% or more, such as 34% or more and including where the impurity level is 35% or more as determined by integrating one or more peaks in the proton NMR spectrum at a chemical shift of from 9.2 ppm to 9.3 ppm.

In certain cases, the generated 25-hydroxy-(3β)-cholest-5-en-3-sulfate product includes one or more byproducts. In some cases, the byproduct is 5-cholesten-3β-25-diol-disulfate. In some cases, 5-cholesten-3β-25-diol-disulfate byproduct is present in the composition produced by sulfation of 25-hydroxy-(3β)-cholest-5-en-3-ol in an amount relative to the 25-hydroxy-(3β)-cholest-5-en-3-sulfate of 10% by weight or less, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less, and including where 5-cholesten-3β-25-diol-disulfate byproduct is present in the composition produced by sulfation of 25-hydroxy-(3β)-cholest-5-en-3-ol in an amount of 0.001% by weight or less, and may range from 0.1% by weight to 50% by weight, such as 0.5% by weight to 20% by weight or 1% by weight to 12% by weight. In some cases, the ratio by weight of the 25-hydroxy-(3β)-cholest-5-en-3-sulfate to the 5-cholesten-3β-25-diol-disulfate byproduct formed is 10:1 or more, such as 25:1 or more, such as 50:1 or more, such as 100:1 or more, such as such as 250:1 or more, such as 500:1 or more, such as 1000:1 or more, such as 2500:1 or more, such as 5000:1 or more, such as 10,000:1 or more, such as 25,000:1 or more, such as 50,000:1 or more, such as 100,000:1 or more, such as $10^6$:1 or more, such as $10^7$:1 or more, such as $10^8$:1 or more, and including where the ratio by weight of the 25-hydroxy-(3β)-cholest-5-en-3-sulfate to the 5-cholesten-3β-25-diol-disulfate formed is $10^9$:1 or more. In some cases, the ratio by weight of the 25-hydroxy-(3β)-cholest-5-en-3-sulfate and the 5-cholesten-3β-25-diol-disulfate formed ranges from 10:1 to $10^9$:1, such as from 100:1 to $10^8$:1, such as from 1000:1 to $10^7$:1, and including from 10000:1 to $10^6$:1.

Aspects of the present disclosure also include compositions having 25-hydroxy-(3β)-cholest-5-en-3-sulfate and 5-cholesten-3β-25-diol-disulfate that is present in the composition in an amount relative to the 25-hydroxy-(3β)-cholest-5-en-3-sulfate of 10% by weight or less, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less, and including 0.001% by weight or less, and may range from 10% by weight to 0.001% by weight, such as 10% by weight to 0.1% by weight, 10% by weight to 1% by weight, 10% by weight to 2% by weight, 8% by weight to 0.001% by weight, 8% by weight to 0.1% by weight, 8% by weight to 1% by weight, 8% by weight to 2% by weight, 6% by weight to 0.001% by weight, 6% by weight to 0.1% by weight, 6% by weight to 1% by weight, 6% by weight to 2% by weight, 4% by weight to 0.001% by weight, 4% by weight to 0.1% by weight, 4% by weight to 1% by weight, 4% by weight to 2% by weight, 3% by weight to 0.001% by weight, 3% by weight to 0.1% by weight, 3% by weight to 1% by weight, 2% by weight to 0.001% by weight, 2% by weight to 0.1% by weight, or 2% by weight to 1% by weight.

In some cases, compositions include a ratio by weight of the 25-hydroxy-(3β)-cholest-5-en-3-sulfate and the 5-cholesten-3β-25-diol-disulfate of 10:1 or more, such as 25:1 or more, such as 50:1 or more, such as 100:1 or more, such as such as 250:1 or more, such as 500:1 or more, such as 1000:1 or more, such as 2500:1 or more, such as 5000:1 or more, such as 10,000:1 or more, such as 25,000:1 or more, such as 50,000:1 or more, such as 100,000:1 or more, such as $10^6$:1 or more, such as $10^7$:1 or more, such as $10^8$:1 or more, and including where the ratio by weight of the 25-hydroxy-(3β)-cholest-5-en-3-sulfate to the 5-cholesten-3β-25-diol-disulfate in the composition is $10^9$:1 or more. In some cases, compositions include a ratio by weight of the 25-hydroxy-(3β)-cholest-5-en-3-sulfate and the 5-cholesten-3β-25-diol-disulfate that ranges from 10:1 to $10^9$:1, such as from 100:1 to $10^8$:1, such as from 1000:1 to $10^7$:1, and including from 10000:1 to $10^6$:1.

In some cases, the byproduct is sulfated desmosterol (Structure IB).

IB

-O₃SO

In some cases, sulfated desmosterol ([(3S,8S,9S,10R, 13R,14S,17R)-17-[(1R)-1,5-dimethylhex-4-enyl]-10,13-di-methyl-2,3,4,7,8,9,11,12,14,15,16,17-dodecahydro-1H-cy-clopenta[a]phenanthren-3-yl] sulfate) is present in the composition produced by sulfation of 25-hydroxy-(3β)-cholest-5-en-3-ol in an amount relative to the 25-hydroxy-(3β)-cholest-5-en-3-sulfate of 10% by weight or less, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less, and including where sulfated desmosterol is present in the composition produced by sulfation of 25-hydroxy-(3β)-cholest-5-en-3-ol in an amount relative to the 25-hydroxy-(3β)-cholest-5-en-3-sul-fate of 0.001% by weight or less, and may range from 0.1% by weight to 10% by weight, such as 0.2% by weight to 5% by weight or 0.3% by weight to 3% by weight. In some cases, the ratio by weight of the 25-hydroxy-(3β)-cholest-5-en-3-sulfate to the sulfated desmosterol formed is 10:1 or more, such as 25:1 or more, such as 50:1 or more, such as 100:1 or more, such as such as 250:1 or more, such as 500:1 or more, such as 1000:1 or more, such as 2500:1 or more, such as 5000:1 or more, such as 10,000:1 or more, such as 25,000:1 or more, such as 50,000:1 or more, such as 100,000:1 or more, such as 10⁶:1 or more, such as 10⁷:1 or more, such as 10⁸:1 or more, and including where the ratio by weight of the 25-hydroxy-(3β)-cholest-5-en-3-sulfate to the sulfated desmosterol formed is 10⁹:1 or more. In some cases, the ratio by weight of the 25-hydroxy-(3β)-cholest-5-en-3-sulfate and the sulfated desmosterol formed ranges from 10:1 to 10⁹:1, such as from 100:1 to 10⁸:1, such as from 1000:1 to 10⁷:1 and including from 10000:1 to 10⁶:1.

Aspects of the present disclosure also include compositions having 25-hydroxy-(3β)-cholest-5-en-3-sulfate and sulfated desmosterol that is present in the composition in an amount relative to the 25-hydroxy-(3β)-cholest-5-en-3-sul-fate of 10% by weight or less, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less, and including 0.001% w/w or less relative to the 25-hydroxy-(3β)-cholest-5-en-3-sulfate, and may range from 10% by weight to 0.001% by weight, such as 10% by weight to 0.1% by weight, 10% by weight to 1% by weight, 10% by weight to 2% by weight, 8% by weight to 0.001% by weight, 8% by weight to 0.1% by weight, 8% by weight to 1% by weight, 8% by weight to 2% by weight, 6% by weight to 0.001% by weight, 6% by weight to 0.1% by weight, 6% by weight to 1% by weight, 6% by weight to 2% by weight, 4% by weight to 0.001% by weight, 4% by weight to 0.1% by weight, 4% by weight to 1% by weight, 4% by weight to 2% by weight, 3% by weight to 0.001% by weight, 3% by weight to 0.1% by weight, 3% by weight to 1% by weight, 2% by weight to 0.001% by weight, 2% by weight to 0.1% by weight, or 2% by weight to 1% by weight.

In some cases, compositions include a ratio by weight of the 25-hydroxy-(3β)-cholest-5-en-3-sulfate and the sulfated desmosterol of 10:1 or more, such as 25:1 or more, such as 50:1 or more, such as 100:1 or more, such as such as 250:1 or more, such as 500:1 or more, such as 1000:1 or more, such as 2500:1 or more, such as 5000:1 or more, such as 10,000:1 or more, such as 25,000:1 or more, such as 50,000:1 or more, such as 100,000:1 or more, such as 10⁶:1 or more, such as 10⁷:1 or more, such as 10⁸:1 or more, and including where the ratio by weight of the 25-hydroxy-(3β)-cholest-5-en-3-sulfate to the sulfated desmosterol in the composition is 10⁹:1 or more. In some cases, compositions include a ratio by weight of the 25-hydroxy-(3β)-cholest-5-en-3-sulfate and the sulfated desmosterol that ranges from 10:1 to 10⁹:1, such as from 100:1 to 10⁸:1, such as from 1000:1 to 10⁷:1 and including from 10000:1 to 10⁶:1.

In some cases, the byproduct of sulfating the 25-hydroxy-(3β)-cholest-5-en-3-ol that is present in the 25-hydroxy-(3β)-cholest-5-en-3-sulfate composition is a thermal degra-dation product. In some cases, the byproduct is identified by relative retention time when the components of the 25-hy-droxy-(3β)-cholest-5-en-3-sulfate composition are sepa-rated by liquid chromatography (e.g., HPLC). In certain cases, the byproduct is sulfated desmosterol, a compound having a retention time of about 18.3 minutes when the components of the 25-hydroxy-(3β)-cholest-5-en-3-sulfate composition are separated by HPLC operating at about 45° C. with a C8 stationary phase and separates the components of the composition with a first mobile phase comprising a buffer (e.g., an aqueous buffer of sodium phosphate) and a second mobile phase comprising one or more organic sol-vents (see e.g., Tables 13 and 14 below). In some cases, the first mobile phase is an aqueous buffer. In certain cases, the first mobile phase includes sodium phosphate. In some cases, the second mobile phase is chosen from one or more of methoxypropyl acetate, acetonitrile and methanol. In some cases, the flow rate of the first mobile phase is about 1.0 mL/minute. In some cases, the flow rate of the second mobile phase is about 1.0 mL/minute or more. In some cases, 25-hydroxy-(3β)-cholest-5-en-3-sulfate has a reten-tion time of about 7.7 minutes under the same HPLC conditions. In some cases, the byproduct is a compound having a retention time of about 37.7 minutes when the components of the 25-hydroxy-(3β)-cholest-5-en-3-sulfate composition are separated by HPLC operating at about 45° C. with a C8 stationary phase and separates the components of the composition with a first mobile phase comprising a buffer (e.g., an aqueous buffer of sodium phosphate) and a second mobile phase comprising one or more organic sol-vents (see e.g., Tables 13 and 14 below). While not wishing to be bound by theory, it is believed that the compound having a retention time of about 37.7 minutes is desmos-terol. In some cases, the first mobile phase is an aqueous buffer. In certain cases, the first mobile phase includes sodium phosphate. In some cases, the second mobile phase is chosen from one or more of methoxypropyl acetate, acetonitrile and methanol. In some cases, the flow rate of the first mobile phase is about 1.0 mL/minute. In some cases, the flow rate of the second mobile phase is about 1.0 mL/minute or more. In some cases, and 25-hydroxy-(3β)-cholest-5-en-3-sulfate has a retention time of about 7.7 minutes under the same HPLC conditions such that sulfated desmosterol has a relative retention time of about 2.4 (=18.3/7.7) and the compound believed to be desmosterol has a relative retention time of about 4.9 (=37.7/7.7).

Aspects of the present disclosure also include compositions having 25-hydroxy-(3β)-cholest-5-en-3-sulfate and one or more byproducts of sulfating the 25-hydroxy-(3β)-cholest-5-en-3-ol. In some cases, the one or more byproducts are present in the composition in an amount relative to the 25-hydroxy-(3β)-cholest-5-en-3-sulfate of 10% by weight or less, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less, and including 0.001% by weight or less, and may range from 0.1% by weight to 5% by weight, such as 0.2% by weight to 10% by weight or 0.3% by weight to 15% by weight. In some cases, compositions include 25-hydroxy-(3β)-cholest-5-en-3-sulfate and the one or more byproducts in an amount relative to the 25-hydroxy-(3β)-cholest-5-en-3-sulfate that ranges from 0.0001% by weight to 10% by weight, such as from 0.005% by weight to 9.5% by weight, such as from 0.001% to 9.0% by weight, such as from 0.05% by weight to 8.5% by weight, such as from 0.1% by weight to 8.0% by weight, such as from 0.5% by weight to 7.5% by weight, such as from 1% by weight to 7% by weight, such as from 1.5% by weight to 6.5% by weight, and including from 2% by weight to 6% by weight.

In some cases, the ratio by weight of the 25-hydroxy-(3β)-cholest-5-en-3-sulfate to the one or more byproducts formed is 10:1 or more, such as 25:1 or more, such as 50:1 or more, such as 100:1 or more, such as such as 250:1 or more, such as 500:1 or more, such as 1000:1 or more, such as 2500:1 or more, such as 5000:1 or more, such as 10,000:1 or more, such as 25,000:1 or more, such as 50,000:1 or more, such as 100,000:1 or more, such as $10^6$:1 or more, such as $10^7$:1 or more, such as $10^8$:1 or more, and including where the ratio by weight of the 25-hydroxy-(3β)-cholest-5-en-3-sulfate to the one or more byproducts formed is $10^9$:1 or more. In some cases, the ratio by weight of the 25-hydroxy-(3β)-cholest-5-en-3-sulfate and the one or more byproducts formed ranges from 10:1 to $10^9$:1, such as from 100:1 to $10^8$:1, such as from 1000:1 to $10^7$:1, and including from 10000:1 to $10^6$:1.

In some cases, the 25-hydroxy-(3β)-cholest-5-en-3-sulfate organic cationic salt is a 25-hydroxy-(3β)-cholest-5-en-3-sulfate pyridinium salt (Scheme IA2).

Scheme IA2

25HC

-continued

25HC3S pyridinium salt

In certain cases, the sulfating agent is contacted with an anhydride prior to contacting with the 25-hydroxy-(3β)-cholest-5-en-3-ol. In some cases, the anhydride is chosen from acetic anhydride, trifluoroacetic anhydride and triflic anhydride. The amount of anhydride relative to the 25-hydroxy-(3β)-cholest-5-en-3-ol may vary and may be 0.001 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more, and may range from 0.001 equivalents to 10 equivalents, such as 0.1 equivalents to 10 equivalents, 0.1 equivalents to 8 equivalents, 0.1 equivalents to 5 equivalents, 0.5 equivalents to 10 equivalents, 0.5 equivalents to 8 equivalents, 0.5 equivalents to 5 equivalents, 0.9 equivalents to 10 equivalents, 0.9 equivalents to 8 equivalents, 0.9 equivalents to 5 equivalents, 1.3 equivalents to 10 equivalents, 1.3 equivalents to 8 equivalents, 1.3 equivalents to 5 equivalents, 1.5 equivalents to 10 equivalents, 1.5 equivalents to 8 equivalents, 1.5 equivalents to 5 equivalents, 2 equivalents to 10 equivalents, 2 equivalents to 8 equivalents, 2 equivalents to 5 equivalents, 0.1 equivalent to 1.5 equivalents, 0.5 equivalents to 1.1 equivalents, or 0.1 equivalent to 1 equivalent relative to the 25-hydroxy-(3β)-cholest-5-en-3-ol.

In some cases, methods include quenching (i.e., deactivating) unreacted sulfating agent after producing the 25-hydroxy-(3β)-cholest-5-en-3-sulfate organic cationic salt. In some cases, quenching the sulfating agent includes adding water to the reaction mixture. The amount of water added to the reaction mixture relative to the amount of sulfating agent contacted with the 25-hydroxy-(3β)-cholest-5-en-3-ol may vary and may be 1 equivalent or more, such as 2 equivalents or more, such as 3 equivalents or more, such as 4 equivalents or more, such as 5 equivalents or more, such as 6 equivalents or more, such as 7 equivalents or more, such as 8 equivalents or more, such as 9 equivalents or more, such as 10 equivalents or more, such as 15 equivalents or more, such as 20 equivalents or more and including 25 equivalents or more.

In certain cases, quenching the reactivity of unreacted sulfating agent includes adding water to the reaction mixture followed by the addition of at least one base. In some cases, the at least one base is a trialkyamine, such as trimethylamine or triethylamine. In some cases, the at least one base is 2,6-lutidine. In certain cases, the at least one base is pyridine. The pyridine may be added to the reaction mixture 1 minute or more after adding the water, such as 5 minutes or more, such as 10 minutes or more, such as 15 minutes or more, such as 30 minutes or more, such as 45 minutes or more, such as 60 minutes or more, such as 90 minutes or more, such as 120 minutes or more, such as 150 minutes or more, such as 180 minutes or more, such as 210 minutes or more and including 240 minutes or more after adding the water to the reaction mixture. In certain cases, pyridine is added to the reaction mixture 60 minutes after adding the water. The amount of pyridine added to the reaction mixture relative to the amount of sulfating agent may vary and may be 0.001 equivalents or more, such as 0.005 equivalents or more, such as 0.01 equivalents or more, such as 0.05 equivalents or more, such as 0.1 equivalents or more, such as 0.5 equivalents or more, such as 1 equivalent or more, such as 2 equivalents or more, such as 3 equivalents or more, such as 4 equivalents or more, such as 5 equivalents or more, such as 6 equivalents or more and including 10 equivalents or more.

In some cases, the unreacted sulfating agent in the reaction mixture is quenched under slow agitation. In certain cases, quenching the unreacted sulfating agent under slow agitation includes stirring the reaction mixture in a manner sufficient to maintain agglomerates of the unreacted sulfating agent in the reaction mixture. In some cases, slow agitation of the reaction mixture is sufficient such that agglomerates of unreacted sulfating agent reduce in size during quenching by 10% or less, such as by 9% or less, such as by 8% or less, such as by 7% or less, such as by 6% or less, such as by 5% or less, such as by 4% or less, such as by 3% or less, such as by 2% or less, such as by 1% or less and including where the reaction mixture is slowly agitated such that agglomerates of unreacted sulfating agent reduce in size during quenching by 0.1% or less. In certain cases, slow agitation of the reaction mixture is sufficient such that agglomerates of unreacted sulfating agent remain at the bottom of the reaction flask during quenching. In certain cases, slow agitation of the reaction mixture is sufficient such that little to no agglomerates of unreacted sulfating agent is present in the stirring vortex of the agitated reaction mixture.

In some cases, methods include purifying the 25-hydroxy-(3β)-cholest-5-en-3-sulfate organic cationic salt prior to contacting the 25-hydroxy-(3β)-cholest-5-en-3-sulfate organic cationic salt with the at least one metal salt. In some cases, the purified 25-hydroxy-(3β)-cholest-5-en-3-sulfate organic cationic salt has a purity of 97% or greater, such as a purity of 98% or greater, such as a purity of 99% or greater, such as purity of 99.5% or greater, such as purity of 99.7% or greater, such as a purity of 99.9% or greater and including a purity of 99.99% or greater. In certain cases, the purified 25-hydroxy-(3β)-cholest-5-en-3-sulfate organic cationic salt has one or more by-products of sulfation (e.g., by-products from sulfating the 25-hydroxy-(3β)-cholest-5-en-3-ol) where the one or more by-products is present in an amount of 5% w/w or less relative to the 25-hydroxy-(3β)-cholest-5-en-3-sulfate organic cationic salt, such as 4% w/w or less, such as 3% w/w or less, such as 2% w/w or less, such as 1% w/w or less, such as in an amount of 0.9% w/w or less, such as 0.8% w/w or less, such as 0.7% w/w or less, such as 0.6% w/w or less, such as 0.5% w/w or less, such as 0.4% w/w or less, such as 0.3% w/w or less, such as 0.2% w/w or less, such as 0.1% w/w or less, such as 0.05% w/w or less, such as 0.01% w/w or less and including being present in an amount of 0.001% w/w or less relative to the 25-hydroxy-(3β)-cholest-5-en-3-sulfate organic cationic salt. In some cases, the bis-sulfated product (i.e., 5-cholesten-3β-25-diol-disulfate) is present in the purified 25-hydroxy-(3β)-cholest-5-en-3-sulfate organic cationic salt composition in an amount of 1% w/w or less relative to the 25-hydroxy-(3β)-cholest-5-en-3-sulfate organic cationic salt, such as in an amount of 0.9% w/w or less, such as 0.8% w/w or less, such as 0.7% w/w or less, such as 0.6% w/w or less, such as 0.5% w/w or less, such as 0.4% w/w or less, such as 0.3% w/w or less, such as 0.2% w/w or less, such as 0.1% w/w or less, such as 0.05% w/w or less, such as 0.01% w/w or less and including being present in an amount of 0.001% w/w or less relative to the 25-hydroxy-(3β)-cholest-5-en-3-sulfate organic cationic salt.

In some cases, the 25-hydroxy-(3β)-cholest-5-en-3-sulfate organic cationic salt is purified by liquid chromatography. In some cases, purifying the 25-hydroxy-(3β)-cholest-5-en-3-sulfate organic cationic salt includes liquid chromatography using a silica gel stationary phase (e.g., a silica gel plug column, ≥5 mass equivalents). In some cases, the 25-hydroxy-(3β)-cholest-5-en-3-sulfate organic cationic salt is purified using the silica gel stationary phase and a mobile phase that includes pyridine. In certain cases, the mobile phase includes methylene chloride, methanol, and pyridine. In certain cases, the mobile phase includes a mixture of methylene chloride-methanol (85:15) and pyridine (1%).

In some cases, one or more fractions collected from the stationary phase may be combined. In some cases, the combined fractions may be concentrated. In certain cases, the combined fractions are concentrated by distillation. In certain cases, the combined fractions are concentrated under vacuum. In certain cases, the combined fractions are concentrated by distillation under vacuum.

In some cases, the combined fractions are contacted with one or more particles of the 25-hydroxy-(3β)-cholest-5-en-3-sulfate organic cationic salt (e.g., particles from a previously purified sample of the 25-hydroxy-(3β)-cholest-5-en-3-sulfate organic cationic salt). In some cases, contacting the particles of the 25-hydroxy-(3β)-cholest-5-en-3-sulfate organic cationic salt with the combined fractions is sufficient to precipitate 25-hydroxy-(3β)-cholest-5-en-3-sulfate organic cationic salt in the combined fractions. In some cases, contacting particles of the 25-hydroxy-(3β)-cholest-5-en-3-sulfate organic cationic salt with the combined fractions includes adding the particles during distillation of the combined fractions. In some cases, the particles of 25-hydroxy-(3β)-cholest-5-en-3-sulfate organic cationic salt are added to the combined fractions before distilling the combined fractions. In some cases, the particles of 25-hydroxy-(3β)-cholest-5-en-3-sulfate organic cationic salt are added to the combined fractions while distilling the combined fractions, such as 1 minute or more after beginning the distillation, such as 5 minutes or more, such as 10 minutes or more, such as 15 minutes or more, such as 20 minutes or more, such as 30 minutes or more, such as 40 minutes or more, such as 50 minutes or more and including adding the particles of 25-hydroxy-(3β)-cholest-5-en-3-sulfate organic cationic salt to the combined fractions 60 minutes or more after beginning the distillation of the combined fractions. In certain cases, the combined fractions are distilled under constant pressure, such as where the pressure changes by 10% or less, such as by 9% or less, such as by 8% or less, such as by 7% or less, such as by 6% or less, such as by 5% or less, such as by 4% or less, such as by 3% or less, such as by 2% or less, such as by 1% or less and including by 0.1% or less. In some cases, the pressure during distillation changes by 10 inHg or less, such as by 9 inHg or less, such as by 8 inHg or less, such as by 7 inHg or less, such as by 6 inHg or less, such as by 5 inHg or less, such as by 4 inHg or less, such as by 3 inHg or less, such as by 2 inHg or less, such as by 1 inHg or less, such as by 0.5 inHg or less, such as by 0.1 inHg or less, such as by 0.05 inHg or less and including by 0.01 inHg or less. In some cases, the combined fractions are distilled under a reduced pressure wherein the pressure is maintained between 15 inHg to 30 inHg, such as from 17.5 inHg to 27.5 inHg, such as from 20 inHg to 25 inHg, such as from 21 inHg and 24 inHg and including maintained at a pressure of from 22 inHg to 23 inHg.

In some cases, the combined fractions are concentrated under vacuum and the concentrated combined fractions are contacted with a composition containing particles of the 25-hydroxy-(3β)-cholest-5-en-3-sulfate organic cationic salt. In certain cases, the concentrated combined fractions are contacted with a composition containing particles of the 25-hydroxy-(3β)-cholest-5-en-3-sulfate organic cationic salt and at least one solvent. In certain cases, the at least one solvent is chosen from tetrahydrofurans, such as 2-methyltetrahydrofuran. The concentrated combined fractions may be contacted with the composition containing the particles of the 25-hydroxy-(3β)-cholest-5-en-3-sulfate organic cationic salt over a duration of 0.001 minutes or more, such as over 0.005 minutes or more, such as over 0.01 minutes or more, such as over 0.05 minutes or more, such as over 0.1 minutes or more, such as over 0.5 minutes or more, such as over 1 minute or more, such as over 2 minutes or more, such as over 3 minutes or more, such as over 4 minutes or more, such as over 5 minutes or more, such as over 10 minutes or more, such as over 15 minutes or more, such as over 30 minutes or more, such as over 45 minutes or more and including over 60 minutes or more. In certain cases, the combined fractions are added dropwise to a composition containing 25-hydroxy-(3β)-cholest-5-en-3-sulfate organic cationic salt in 2-methyltetrahydrofuran.

In some cases, the 25-hydroxy-(3β)-cholest-5-en-3-sulfate organic cationic salt is contacted with a metal salt to produce the 25-hydroxy-(3β)-cholest-5-en-3-sulfate metal salt (Scheme IB1).

Scheme IB1

25HC3S organic salt

-continued

25HC3S metal salt

In some cases, methods to produce the 25-hydroxy-(3β)-cholest-5-en-3-sulfate metal salt includes contacting the 25-hydroxy-(3β)-cholest-5-en-3-sulfate organic cationic salt with at least one sodium salt. In some cases, the at least one sodium salt is chosen from sodium acetate, sodium iodide, sodium chloride, sodium hydroxide and sodium methoxide. The 25-hydroxy-(3β)-cholest-5-en-3-sulfate organic cationic salt may be contacted with the metal salt at a temperature that ranges from −10° C. to 75° C., such as from −5° C. to 70° C., such as from −4° C. to 65° C., such as from −3° C. to 60° C., such as from −2° C. to 55° C., such as from −1° C. to 50° C., such as from 0° C. to 45° C., such as from 5° C. to 40° C., and including from 10° C. to 35° C.

The reaction may be carried out for a duration that ranges from 0.1 hours to 72 hours, such as from 0.2 hours to 48 hours, such as from 0.3 hours to 24 hours, such as from 0.4 hours to 21 hours, such as from 0.5 hours to 20 hours, such as from 0.6 hours to 19 hours, such as from 0.7 hours to 18 hours, such as from 0.8 hours to 17 hours, such as from 0.9 hours to 16 hours, and including from 1 hours to 15 hours. The amount of metal salt used relative to the 25-hydroxy-(3β)-cholest-5-en-3-sulfate organic cationic salt may vary and may be 0.0001 equivalents or more, such as 0.001 equivalents or more, such as 0.01 equivalents or more, such as 0.1 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more, and may range from 0.001 equivalents to 10 equivalents, such as 0.1 equivalents to 10 equivalents, 0.1 equivalents to 8 equivalents, 0.1 equivalents to 6 equivalents, 0.1 equivalents to 4 equivalents, 0.1 equivalents to 3 equivalents, 1 equivalents to 10 equivalents, 1 equivalents to 8 equivalents, 1 equivalents to 6 equivalents, 1 equivalents to 4 equivalents, 1 equivalents to 3 equivalents, 1.5 equivalents to 10 equivalents, 1.5 equivalents to 8 equivalents, 1.5 equivalents to 6 equivalents, 1.5 equivalents to 4 equivalents, 1.5 equivalents to 3 equivalents, 2 equivalents to 10 equivalents, 2 equivalents to 8 equivalents, 2 equivalents to 6 equivalents, 2 equivalents to 4 equivalents, or 2 equivalents to 3 equivalents, 1 equivalent to 100 equivalents, 1 equivalent to 5 equivalents, 1 equivalent to 2 equivalents.

In some cases, methods include contacting the 25-hydroxy-(3β)-cholest-5-en-3-sulfate pyridinium salt with sodium iodide to produce a 25-hydroxy-(3β)-cholest-5-en-3-sulfate sodium salt (Scheme IB2).

Scheme IB2

25HC3S pyridinium salt

NaI

25HC3S sodium salt

In some cases, methods for preparing 25-hydroxy-3β-cholesten-5-en-3-sulfate include contacting 25-hydroxy-(3β)-cholest-5-en-3-ol with a sulfur trioxide-pyridine complex to produce a 25-hydroxy-(3β)-cholest-5-en-3-sulfate pyridinium salt; and contacting the 25-hydroxy-(3β)-cholest-5-en-3-sulfate pyridinium salt with a sodium salt to produce the 5-cholesten-3β,25-diol 3-sulfate sodium salt (Scheme Ib).

Scheme Ib

SO₃-pyridine

-continued

Sodium Salt

In some cases, methods for preparing 25-hydroxy-3β-cholesten-5-en-3-sulfate include contacting (3β)-cholest-5-en-3-ol with a sulfating agent to produce a first (3β)-cholest-5-en-3-sulfate organic cationic salt; contacting the first (3β)-cholest-5-en-3-sulfate organic cationic salt with an organic base to produce a second (3β)-cholest-5-en-3-sulfate organic cationic salt; oxidizing the second (3β)-cholest-5-en-3-sulfate organic cationic salt in the presence of at least one surfactant to produce a 25-hydroxy-(3β)-cholest-(5,6-epoxy)-3-sulfate organic cationic salt; generating a 25-hydroxy-(3β)-cholest-5-en-3-sulfate organic cationic salt from the 25-hydroxy-(3β)-cholest-(5,6-epoxy)-3-sulfate organic cationic salt by deoxygenation; and contacting the 25-hydroxy-(3β)-cholest-5-en-3-sulfate organic cationic salt with at least one metal salt to produce the 5-cholesten-3β,25-diol 3-sulfate metal salt (Scheme IIa).

Scheme IIa

-continued pounds, sulfonic acid compounds, and sulfonate compounds. In some cases, the sulfating agent is a sulfur trioxide-pyridine complex. In some cases, the sulfating agent is chosen from sulfur trioxide dimethyl formamide, sulfur trioxide triethylamine, and sulfur trioxide trimethylamine. In some cases, the sulfating agent is sulfuric acid and acetic anhydride and pyridine. In some cases, the sulfating agent is chosen from chlorosulfonic acid and pyridine. In some cases, the sulfating agent is chosen from chlorosulfonic acid and 2,6-lutidine. In some cases, the sulfating agent is chosen from ethyl chlorosulfonate.

Cholesterol may be sulfated at a temperature that ranges from 0° C. to 100° C., such as from 5° C. to 95° C., such as from 10° C. to 90° C., such as from 15° C. to 85° C., such as from 20° C. to 80° C., such as from 25° C. to 75° C., and including from 30° C. to 70° C. The reaction may be carried out for a duration that ranges from 0.1 hours to 72 hours, such as from 0.2 hours to 48 hours, such as from 0.3 hours to 24 hours, such as from 0.4 hours to 21 hours, such as from 0.5 hours to 20 hours, such as from 0.6 hours to 19 hours, and including from 0.7 hours to 18 hours. The amount of sulfating agent used relative to cholesterol may vary and may be 0.0001 equivalents or more, such as 0.001 equivalents or more, such as 0.01 equivalents or more, such as 0.1 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more, and may range from 0.001 equivalents to 10 equivalents, such as 0.1 equivalents to 10 equivalents, 0.1 equivalents to 8 equivalents, 0.1 equivalents to 6 equivalents, 0.1 equivalents to 4 equivalents, 0.1 equivalents to 3 equivalents, 1 equivalents to 10 equivalents, 1 equivalents to 8 equivalents, 1 equivalents to 6 equivalents, 1 equivalents to 4 equivalents, 1 equivalents to 3 equivalents, 1.5 equivalents to 10 equivalents, 1.5 equivalents to 8 equivalents, 1.5 equivalents to 6 equivalents, 1.5 equivalents to 4 equivalents, 1.5 equivalents to 3 equivalents, 2 equivalents to 10 equivalents, 2 equivalents to 8 equivalents, 2 equivalents to 6 equivalents, 2 equivalents to 4 equivalents, 2 equivalents to 3 equivalents, 1 equivalent to 30 equivalents, 1 equivalent to 5 equivalents, or 1 equivalent to 2 equivalents.

Scheme IIA1

Sulfation

Cholesterol

In some cases, cholesterol is sulfated with a sulfating agent (Scheme IIA1). In some cases, the sulfating agent is chosen from sulfur trioxide complexes, sulfuric acid com- -continued Cholesterol Sulfate In some cases, the first (3β)-cholest-5-en-3-sulfate organic cationic salt is a (3β)-cholest-5-en-3-sulfate pyridinium salt (Scheme IIA2).

Scheme IIA2

Cholesterol

SO₃-pyridine →

Cholesterol sulfate pyridinium salt

In some cases, the first (3β)-cholest-5-en-3-sulfate organic cationic salt (Structure IIA) is contacted with an organic base to produce a second (3β)-cholest-5-en-3-sulfate organic cationic salt (Structure IIB) (Scheme IIB1).

Scheme VB1

IIA organic base →

IIB

In some cases, the organic base contacted with the first (3β)-cholest-5-en-3-sulfate organic cationic salt is chosen from a hydroxide base. In some cases, the hydroxide base is chosen from tetraethylammonium hydroxide, tetrabutylammonium hydroxide, tetrapropylammonium hydroxide and tetramethylammonium hydroxide. In some cases, the second (3β)-cholest-5-en-3-sulfate organic cationic salt is chosen from a tetraethylammonium cationic salt, a tetrabutylammonium cationic salt, a tetrapropylammonium cationic salt and a tetramethylammonium cationic salt. In some cases, the organic base is contacted with the first (3β)-cholest-5-en-3-sulfate organic cationic salt at a temperature that ranges from −10° C. to 75° C., such as from −5° C. to 70° C., such as from −4° C. to 65° C., such as from −3° C. to 60° C., such as from −2° C. to 55° C., such as from −1° C. to 50° C. and including from 0° C. to 15° C. The reaction may be carried out for a duration that ranges from 0.1 hours to 72 hours, such as from 0.2 hours to 48 hours, such as from 0.3 hours to 24 hours, such as from 0.4 hours to 21 hours, such as from 0.5 hours to 20 hours, such as from 0.6 hours to 19 hours, such as from 0.7 hours to 18 hours, such as from 0.8 hours to 17 hours, such as from 0.9 hours to 16 hours, and including from 1 hour to 15 hours. The amount of the organic base used relative to the first (3β)-cholest-5-en-3-sulfate organic cationic salt may vary and may be 0.0001 equivalents or more, such as 0.001 equivalents or more, such as 0.01 equivalents or more, such as 0.1 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more, and may range from 0.001 equivalents to 10 equivalents, such as 0.1 equivalents to 10 equivalents, 0.1 equivalents to 8 equivalents, 0.1 equivalents to 6 equivalents, 0.1 equivalents to 4 equivalents, 0.1 equivalents to 3 equivalents, 1 equivalents to 10 equivalents, 1 equivalents to 8 equivalents, 1 equivalents to 6 equivalents, 1 equivalents to 4 equivalents, 1 equivalents to 3 equivalents, 1.5 equivalents to 10 equivalents, 1.5 equivalents to 8 equivalents, 1.5 equivalents to 6 equivalents, 1.5 equivalents to 4 equivalents, 1.5 equivalents to 3 equivalents, 2 equivalents to 10 equivalents, 2 equivalents to 8 equivalents, 2 equivalents to 6 equivalents, 2 equivalents to 4 equivalents, 2 equivalents to 3 equivalents, 1 equivalent to 10 equivalents, 1 equivalent to 5 equivalents, or 1 equivalent to 2 equivalents.

In certain cases, methods include contacting the first (3β)-cholest-5-en-3-sulfate organic cationic salt with tetra-butylammonium hydroxide to generate a (3β)-cholest-5-en-3-sulfate tetrabutylammonium cationic salt (Structure IIB1) (Scheme IIB2).

In some cases, the second (3β)-cholest-5-en-3-sulfate organic cationic salt is oxidized to produce a 25-hydroxy-(3β)-cholest-(5,6-epoxy)-3-sulfate organic cationic salt (Structure IIC) (Scheme IIC1).

Scheme IIC1

Scheme VB1

51

-continued

IIC

In some cases, oxidizing the second (3β)-cholest-5-en-3-sulfate organic cationic salt includes contacting the second (3β)-cholest-5-en-3-sulfate organic cationic salt with a composition having an oxidizing agent and at least one surfactant.

In some cases, the at least one surfactant is chosen from non-ionic surfactants, anionic surfactants, cationic surfactants and zwitterionic surfactants. Non-ionic surfactants may be chosen from polyoxyethylene glycol ethers (e.g., polyoxyethylene glycol octylphenol ether), polyoxyethylene glycol sorbitan alkyl esters, sorbitan alkyl esters, block copolymers of polyethylene glycol and polypropylene glycol, among other non-ionic surfactants. Anionic surfactants may be chosen from surfactants having an anionic functional head group, such as a sulfonate, phosphate, sulfate or carboxylate head group-containing surfactant. For example, anionic surfactants may be chosen from alkyl sulfates such as ammonium lauryl sulfate, dioctyl sodium sulfosuccinate, perfluorooctanesulfonate, perfluorononanoate, perfluorooctanoate, a linear alkylbenzene sulfonate, an alkyl-aryl ether phosphate, sodium lauryl ether sulfate, lignosulfonate or sodium stearate, among other anionic surfactants. Cationic surfactants may be chosen from surfactants having a cationic functional head group, such as a pyridinium or a quarternary ammonium head group. For example, cationic surfactants may be chosen from cetyltrimethylammonium hydrogen sulfate, tetrabutylammonium hydrogen sulfate, cetyltrimethylammonium bromide, tetrabutylammonium bromide, tetrabutylammonium iodide, tetrabutylphosphonium bromide, tetraoctylammonium bromide, tetraoctylammonium iodide, benzyltriethylammonium chloride, benzyltriethylammonium bromide, benzylcetyldimethylammonium chloride or benzylcetyldimethylammonium bromide. Zwitterionic surfactants include both cationic and anionic centers, such as a sultaine (e.g., 3-[(3-cholamidopropyl)dimethylammonio]-1-propanesulfonate) or a betaine (e.g., cocamidopropyl betaine). In certain cases, the at least one surfactant is an Extran laboratory soap, La Parisienne soap or DL-α-tocopherol methoxypolyethylene glycol succinate (e.g., TPGS-750-M-2).

The amount of surfactant used relative to the second (3β)-cholest-5-en-3-sulfate organic cationic salt may vary, where in some instances, 0.0001 equivalents or more of the surfactant is used, such as 0.001 equivalents or more, such as 0.01 equivalents or more, such as 0.1 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more of the surfactant, and may range from 0.001 equivalents to 10 equivalents, such as 0.1 equivalents to 10 equivalents, 0.1 equivalents to 8 equivalents, 0.1 equivalents to 6 equivalents, 0.1 equivalents to 4 equivalents, 0.1 equivalents to 3 equivalents, 1 equivalents to 10 equivalents, 1 equivalents to 8 equivalents, 1 equivalents to 6 equivalents, 1 equivalents to 4 equivalents, 1 equivalents to 3 equivalents, 1.5 equivalents to 10 equivalents, 1.5 equivalents to 8 equivalents, 1.5 equivalents to 6 equivalents, 1.5 equivalents to 4 equivalents, 1.5 equivalents to 3 equivalents, 2 equivalents to 10 equivalents, 2 equivalents to 8 equivalents, 2 equivalents to 6 equivalents, 2 equivalents to 4 equivalents, 2 equivalents to 3 equivalents, 0.1 equivalent to 5 equivalents, 0.15 equivalents to 1 equivalent, or 0.2 equivalents to 0.3 equivalents.

In some cases, oxidizing the second (3β)-cholest-5-en-3-sulfate organic cationic salt includes contacting the second (3β)-cholest-5-en-3-sulfate organic cationic salt with an oxidizing agent and at least one ketone in the presence of at least one surfactant.

In some instances, the at least one ketone is chosen from tetrahydrothiopyran-4-one 1,1-dioxide and halogenated ketones. In some cases, the halogenated ketones are chosen from 1,1,1-trifluoro-2-butanone, 4,4-difluorocyclohexanone, 2-2-2-4'-tetrafluoroacetophenone, and 1,1,1-trifluoroacetone. In certain cases, the at least one ketone is 1,1,1-trifluoro-2-butanone. The amount of ketone used relative to the oxidizing agent in the subject reaction may vary, and may be 1 equivalent or more, such as 2 equivalents or more, such as 3 equivalents or more, such as 4 equivalents or more, such as 5 equivalents or more, such as 6 equivalents or more, such as 7 equivalents or more, such as 8 equivalents or more, such as 9 equivalents or more, such as 10 equivalents or more, such as 15 equivalents or more, such as 20 equivalents or more, such as 25 equivalents or more, such as 30 equivalents or more, such as 35 equivalents or more, and including 50 equivalents or more of the ketone, and may range from 1 equivalent to 50 equivalents, such as 1 equivalent to 35 equivalents, 1 equivalent to 25 equivalents, 1 equivalent to 15 equivalents, 1 equivalent to 10 equivalents, 1 equivalent to 8 equivalents, 1 equivalent to 5 equivalents, 2 equivalent to 50 equivalents, 2 equivalent to 35 equivalents, 2 equivalent to 25 equivalents, 2 equivalent to 15 equivalents, 2 equivalent to 10 equivalents, 2 equivalent to 8 equivalents, 2 equivalent to 5 equivalents, 4 equivalent to 50 equivalents, 4 equivalent to 35 equivalents, 4 equivalent to 25 equivalents, 4 equivalent to 15 equivalents, 4 equivalent to 10 equivalents, 4 equivalent to 8 equivalents, 1 equivalent to 50 equivalents, 2 equivalent to 25 equivalents, or 5 equivalents to 10 equivalents.

In certain cases, the ketone is further purified before use. For example, the ketone may be purified by distillation prior to use. In some instances, the reactivity of the ketone is tested (e.g., tested for impurities by $^1$H-NMR) in order to determine whether purification may be required.

In certain cases, oxidizing the second (3β)-cholest-5-en-3-sulfate organic cationic salt includes contacting the second (3β)-cholest-5-en-3-sulfate organic cationic salt with an oxidizing agent and at least one ketone in the presence of at least one surfactant and water. The amount of water present may vary, ranging from 0.0000001% w/v or more of the reaction mixture, such as 0.000001% w/v or more, such 0.00001% w/v or more, such as 0.0001% w/v or more, such as 0.001% w/v, such as 0.01% w/v or more, such as 0.1% w/v, such as 0.05% w/v or more, such as 0.1% w/v or more, such as 0.5% w/v or more, such as 1% w/v or more, such as 5% w/v or more, such as 10% w/v or more, such as 15% w/v or more, and including 25% w/v or more of the reaction mixture, and may range from 0.0000001% w/v to 25% w/v, such as 0.0000001% w/v to 15% w/v, 0.0000001% w/v to 10% w/v, 0.0000001% w/v to 5% w/v, 0.0000001% w/v to 1% w/v, 0.001% w/v to 25% w/v, 0.001% w/v to 15% w/v, 0.001% w/v to 10% w/v, 0.001% w/v to 5% w/v, 0.001% w/v to 1% w/v, 0.1% w/v to 25% w/v, 0.1% w/v to 15% w/v, 0.1% w/v to 10% w/v, 0.1% w/v to 5% w/v, 0.1% w/v to 1% w/v, 1% w/v to 25% w/v, 1% w/v to 15% w/v, 1% w/v to 10% w/v, 1% w/v to 5% w/v, 0.1% w/v to 50% w/v, 0.1% w/v to 10% w/v, or 0.5% w/v to 1% w/v.

The second (3β)-cholest-5-en-3-sulfate organic cationic salt may be oxidized at a temperature that ranges from –25° C. to 50° C., such as from –20° C. to 45° C., such as from –15° C. to 40° C., such as from –10° C. to 35° C., such as from –5° C. to 30° C., such as from –1° C. to 25° C., and including from 0° C. to 15° C. In certain cases, the second (3β)-cholest-5-en-3-sulfate organic cationic salt is oxidized at a temperature of from 0° C. to 5° C. Where the reaction mixture includes an amount of water, the reaction may be conducted at a temperature that is from –10° C. to 50° C., such as from –5° C. to 45° C., such as from 0° C. to 40° C., such as from 0° C. to 35° C., such as from 0° C. to 30° C., such as from 0° C. to 25° C., such as from 0° C. to 20° C., such as from 0° C. to 15° C., and including from 0° C. to 10° C.

The second (3β)-cholest-5-en-3-sulfate organic cationic salt may be oxidized at a pH that ranges from 5 to 7.5, such as a pH of from 5.5 to 7.0 and including a pH of from 5.5 to 6.5. In some cases, where the reaction mixture contains water (e.g., in a biphasic solvent system), the pH ranges from 5.0 to 6.0, such as a pH of from 5.0 to 5.9, such as a pH of from 5.0 to 5.8, such as a pH of from 5.0 to 5.7, such as a pH from 5.0 to 5.6, and including a pH of from 5.0 to 5.5.

The reaction may be carried out for a duration that ranges from 0.1 hours to 72 hours, such as from 0.2 hours to 48 hours, such as from 0.3 hours to 24 hours, such as from 0.4 hours to 21 hours, such as from 0.5 hours to 20 hours, such as from 0.6 hours to 19 hours, such as from 0.7 hours to 18 hours, such as from 0.8 hours to 17 hours, such as from 0.9 hours to 16 hours, and including from 1 hours to 15 hours.

In some instances, the second (3β)-cholest-5-en-3-sulfate organic cationic salt is contacted in situ with a composition having potassium peroxymonosulfate and at least one ketone in the presence of at least one surfactant. In some cases, methods include contacting the potassium peroxymonosulfate with at least one ketone in the presence of at least one surfactant to form a separate oxidative reactive mixture and adding the oxidative reactive mixture to the second (3β)-cholest-5-en-3-sulfate organic cationic salt. In these cases, the potassium peroxymonosulfate may be contacted with the at least one ketone in the presence of the at least one surfactant for a duration of 0.1 minute or more before contacting the oxidative reactive mixture with the second (3β)-cholest-5-en-3-sulfate organic cationic salt, such as 1 minute or more, such as 2 minutes or more, such as 3 minutes or more, such as 5 minutes or more, and including 10 minutes or more, and the time may range from 2 minutes to 180 minutes, such as 3 minutes to 120 minutes or 4 minutes to 60 minutes. In certain instances, the potassium peroxymonosulfate may be contacted with the at least one ketone in the presence of the at least one surfactant to form a separate oxidative reactive mixture and immediately contacting the oxidative reactive mixture with the second (3β)-cholest-5-en-3-sulfate organic cationic salt. The oxidative reactive mixture may be formed at a temperature that ranges from –10° C. to 50° C., such as from –5° C. to 45° C., such as from –4° C. to 40° C., such as from –3° C. to 35° C., such as from –2° C. to 30° C., such as from –1° C. to 25° C. and including from 0° C. to 15° C. Where the oxidative reactive mixture is not immediately contacted with the second (3β)-cholest-5-en-3-sulfate organic cationic salt, the oxidative reactive mixture may be maintained at a temperature that ranges from –10° C. to 50° C., such as from –5° C. to 45° C., such as from –4° C. to 40° C., such as from –3° C. to 35° C., such as from –2° C. to 30° C., such as from –1° C. to 25° C., and including from 0° C. to 15° C.

In some cases, methods further include adding the oxidative reactive mixture to the second (3β)-cholest-5-en-3-sulfate organic cationic salt. In some instances, methods include adding dropwise the oxidative reactive mixture to the second (3β)-cholest-5-en-3-sulfate organic cationic salt. In some instances, the oxidative reactive mixture is added to the second (3β)-cholest-5-en-3-sulfate organic cationic salt in metered amounts. The metered amounts may be added continuously or at predetermined time intervals (e.g., every 30 seconds, 1 minute, 2 minutes, 3 minutes, 5 minutes, or some other interval). In some instances, the oxidative reactive mixture is added to the second (3β)-cholest-5-en-3-sulfate organic cationic salt by controlled addition, such as with a mechanically or computer controlled pump, e.g., syringe pump. In some cases, methods include generating the oxidative reactive mixture and adding a composition containing the second (3β)-cholest-5-en-3-sulfate organic cationic salt to the oxidative reactive mixture. In some instances, methods include adding dropwise the second (3β)-cholest-5-en-3-sulfate organic cationic salt to the oxidative reactive mixture. In some instances, the second (3β)-cholest-5-en-3-sulfate organic cationic salt is added to the oxidative reactive mixture in metered amounts. The metered amounts may be added continuously or at predetermined time intervals (e.g., every 30 seconds, 1 minute, 2 minutes, 3 minutes, 5 minutes, or some other interval). In some instances, the second (3β)-cholest-5-en-3-sulfate organic cationic salt is added to the oxidative reactive mixture by controlled addition, such as with a mechanically or computer-controlled pump, e.g., syringe pump.

In certain cases, oxidizing the second (3β)-cholest-5-en-3-sulfate organic cationic salt includes contacting the second (3β)-cholest-5-en-3-sulfate organic cationic salt with at least one oxidative species. In some instances, the at least one oxidative species is chosen from dioxiranes. In some instances, the dioxiranes are generated in situ in a composition having the second (3β)-cholest-5-en-3-sulfate organic cationic salt. In some instances, the dioxiranes are generated separately (e.g., in a separate reaction container, e.g., flask) and added to the composition having the second (3β)-cholest-5-en-3-sulfate organic cationic salt.

In certain cases, the second (3β)-cholest-5-en-3-sulfate organic cationic salt is oxidized in the presence of at least one base. In certain cases, the at least one base is chosen from weak bases. In some cases, the at least one base is chosen from potassium hydrogen carbonate, sodium hydrogen carbonate, potassium phenoxide, sodium citrate buffer, sodium phosphate buffer, potassium formate and potassium acetate. In certain cases, the at least one base is potassium hydrogen carbonate. In some cases, the at least one base may be added to the reaction mixture over time, such as in metered amounts where the base is added at predetermined time intervals (e.g., every 30 seconds, 1 minute, 2 minutes, 3 minutes, 5 minutes, or some other interval). In some cases, the at least one base may be a composition having water where the base present in the composition may be 0.0000001% w/v or more of the composition, such as 0.000001% w/v or more, such as 0.00001% w/v or more, such as 0.0001% w/v or more, such as 0.001% w/v or more, such as 0.01% w/v or more, such as 0.05% w/v or more, such as 0.1% w/v or more, such as 0.5% w/v or more, such as 1% w/v or more, such as 5% w/v or more, such as 10% w/v or more, such as 15% w/v or more, and including 25% w/v or more of the composition, and may range from 0.0000001% w/v to 25% w/v, such as 0.0000001% w/v to 15% w/v, 0.0000001% w/v to 10% w/v, 0.0000001% w/v to 5% w/v, 0.0000001% w/v to 1% w/v, 0.001% w/v to 25% w/v, 0.001% w/v to 15% w/v, 0.001% w/v to 10% w/v, 0.001% w/v to 5% w/v, 0.001% w/v to 1% w/v, 0.1% w/v to 25% w/v, 0.1% w/v to 15% w/v, 0.1% w/v to 10% w/v, 0.1% w/v to 5% w/v, 0.1% w/v to 1% w/v, 1% w/v to 25% w/v, 1% w/v to 15% w/v, 1% w/v to 10% w/v, 1% w/v to 5% w/v, 0.1% w/v to 20% w/v, 0.2% w/v to 15% w/v, or 0.3% w/v to 10% w/v. In certain cases, the at least one base may be an aqueous potassium hydrogen carbonate composition.

In certain cases, the second (3β)-cholest-5-en-3-sulfate organic cationic salt is oxidized by contacting with oxone in the presence of cetyltrimethylammonium hydrogen sulfate (CTAHS) followed by adding trifluorobutanone and potassium hydrogen sulfate to form 25-hydroxy-(3β)-cholest-(5,6-epoxy)-3-sulfate organic cationic salt (Scheme IIC2).

Scheme IIC2

IIB

Oxone
CF₃-butanone
CTAHS
KHCO₃

IIC

In certain instances, methods include forming an oxidative species in situ with the second (3β)-cholest-5-en-3-sulfate organic cationic salt, such as by contacting potassium peroxymonosulfate and trifluorobutanone in the presence of cetyltrimethylammonium hydrogen sulfate (CTAHS) in a reaction mixture with the second (3β)-cholest-5-en-3-sulfate organic cationic salt. In certain cases, forming an oxidative species in situ with the second (3β)-cholest-5-en-3-sulfate organic cationic salt includes forming a dioxirane in situ with the second (3β)-cholest-5-en-3-sulfate organic cationic salt.

In certain cases, methods include forming a dioxirane in a separate reaction and adding the dioxirane to the second (3β)-cholest-5-en-3-sulfate organic cationic salt. In these cases, the potassium peroxymonosulfate may be contacted with the trifluorobutanone in the presence of cetyltrimethylammonium hydrogen sulfate (CTAHS) for a duration of 0.1 minute or more before contacting the reactive composition with the second (3β)-cholest-5-en-3-sulfate organic cationic salt, such as 1 minute or more, such as 2 minutes or more, such as 3 minutes or more, such as 5 minutes or more, and including 10 minutes or more), and the time may range from 0.01 minutes to 120 minutes, such as 0.1 minutes to 90 minutes or 0.5 minutes to 60 minutes. In certain instances, the potassium peroxymonosulfate may be contacted with trifluorobutanone in the presence of cetyltrimethylammonium hydrogen sulfate (CTAHS) to form the oxidative reactive composition, which is immediately contacted with the second (3β)-cholest-5-en-3-sulfate organic cationic salt.

The 25-hydroxy-(3β)-cholest-(5,6-epoxy)-3-sulfate organic cationic salt is deoxygenated to produce a 25-hydroxy-(3β)-cholest-5-en-3-sulfate organic cationic salt (Structure IID) (Scheme IID1).

Scheme IID1

IIC deoxygenation

IID

In some cases, generating 25-hydroxy-(3β)-cholest-5-en-3-sulfate organic cationic salt from the 25-hydroxy-(3β)-cholest-(5,6-epoxy)-3-sulfate organic cationic salt includes deoxygenation by contacting the 25-hydroxy-(3β)-cholest-(5,6-epoxy)-3-sulfate organic cationic salt with zinc. In certain instances, the 25-hydroxy-(3β)-cholest-(5,6-epoxy)-3-sulfate organic cationic salt is contacted with zinc in the presence of at least one halide and at least one acid. In some cases, the at least one halide is chosen from iodine and metal halides. In some cases, the metal halide is chosen from sodium iodide and lithium iodide. In some cases, the at least one acid is chosen from weak acids. In some cases, the at least one acid is chosen from acetic acid, hydrochloric acid, citric acid, para-toluene sulfonic acid, formic acid and methane sulfonic acid.

The amount of reagent used to deoxygenate the 25-hydroxy-(3β)-cholest-(5,6-epoxy)-3-sulfate organic cationic salt may vary, where in some instances, 0.0001 equivalents or more of reagent relative to the 25-hydroxy-(3β)-cholest-(5,6-epoxy)-3-sulfate organic cationic salt is used, such as 0.001 equivalents or more, such as 0.01 equivalents or more, such as 0.1 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more, and may range from 0.001 equivalents to 10 equivalents, such as 0.1 equivalents to 10 equivalents, 0.1 equivalents to 8 equivalents, 0.1 equivalents to 6 equivalents, 0.1 equivalents to 4 equivalents, 0.1 equivalents to 3 equivalents, 1 equivalents to 10 equivalents, 1 equivalents to 8 equivalents, 1 equivalents to 6 equivalents, 1 equivalents to 4 equivalents, 1 equivalents to 3 equivalents, 1.5 equivalents to 10 equivalents, 1.5 equivalents to 8 equivalents, 1.5 equivalents to 6 equivalents, 1.5 equivalents to 4 equivalents, 1.5 equivalents to 3 equivalents, 2 equivalents to 10 equivalents, 2 equivalents to 8 equivalents, 2 equivalents to 6 equivalents, 2 equivalents to 4 equivalents, 2 equivalents to 3 equivalents, 1 equivalent to 20 equivalents, 1 equivalent to 10 equivalents, or 4 equivalents to 6 equivalents.

The 25-hydroxy-(3β)-cholest-(5,6-epoxy)-3-sulfate organic cationic salt may be deoxygenated at a temperature that ranges from −10° C. to 75° C., such as from −5° C. to 70° C., such as from −4° C. to 65° C., such as from −3° C. to 60° C., such as from −2° C. to 55° C., such as from −1° C. to 50° C. and including from 0° C. to 25° C. The reaction may be carried out for a duration that ranges from 0.1 hours to 72 hours, such as from 0.2 hours to 48 hours, such as from 0.3 hours to 24 hours, such as from 0.4 hours to 21 hours, such as from 0.5 hours to 20 hours, such as from 0.6 hours to 19 hours, such as from 0.7 hours to 18 hours, such as from 0.8 hours to 17 hours, such as from 0.9 hours to 16 hours, and including from 1 hours to 15 hours.

In certain instances, methods include contacting the 25-hydroxy-(3β)-cholest-(5,6-epoxy)-3-sulfate organic cationic salt with zinc in the presence of iodine and acetic acid to generate the 25-hydroxy-(3β)-cholest-5-en-3-sulfate organic cationic salt (Scheme IID2).

Scheme IID2

IIC

Zn, I₂, AcOH

IID

In some cases, the 25-hydroxy-(3β)-cholest-5-en-3-sulfate organic cationic salt (Structure IID) is contacted with a metal salt to produce the 25-hydroxy-(3β)-cholest-5-en-3-sulfate metal salt (Structure IIE) (Scheme IIE1)

Scheme IIE1

IID metal salt

IIE

In some cases, methods to produce the 25-hydroxy-(3β)-cholest-5-en-3-sulfate metal salt include contacting the 25-hydroxy-(3β)-cholest-5-en-3-sulfate organic cationic salt with at least one sodium salt. In some cases, the at least one sodium salt is chosen from sodium acetate, sodium iodide, sodium chloride, sodium hydroxide and sodium methoxide. The 25-hydroxy-(3β)-cholest-5-en-3-sulfate organic cationic salt may be contacted with the metal salt at a temperature that ranges from −10° C. to 75° C., such as from −5° C. to 70° C., such as from −4° C. to 65° C., such as from −3° C. to 60° C., such as from −2° C. to 55° C., such as from −1° C. to 50° C., such as from 0° C. to 45° C., such as from 5° C. to 40° C., and including from 10° C. to 35° C.

The reaction may be carried out for a duration that ranges from 0.1 hours to 72 hours, such as from 0.2 hours to 48 hours, such as from 0.3 hours to 24 hours, such as from 0.4 hours to 21 hours, such as from 0.5 hours to 20 hours, such as from 0.6 hours to 19 hours, such as from 0.7 hours to 18 hours, such as from 0.8 hours to 17 hours, such as from 0.9 hours to 16 hours, and including from 1 hours to 15 hours. The amount of metal salt used relative to the 25-hydroxy-(3β)-cholest-5-en-3-sulfate organic cationic salt may vary and may be 0.0001 equivalents or more, such as 0.001 equivalents or more, such as 0.01 equivalents or more, such as 0.1 equivalents or more, such as 0.2 equivalents or more, such as 0.3 equivalents or more, such as 0.4 equivalents or more, such as 0.5 equivalents or more, such as 0.6 equivalents or more, such as 0.7 equivalents or more, such as 0.8 equivalents or more, such as 0.9 equivalents or more, such as 1 equivalent or more, such as 1.1 equivalents or more, such as 1.2 equivalents or more, such as 1.3 equivalents or more, such as 1.4 equivalents or more, such as 1.5 equivalents or more, such as 1.6 equivalents or more, such as 1.7 equivalents or more, such as 1.8 equivalents or more, such as 1.9 equivalents or more, such as 2 equivalents or more, such as 3 equivalents or more, such as 4 equivalents or more, such as 5 equivalents or more, and including 10 equivalents or more, and may range from 0.001 equivalents to 10 equivalents, such as 0.1 equivalents to 10 equivalents, 0.1 equivalents to 8 equivalents, 0.1 equivalents to 6 equivalents, 0.1 equivalents to 4 equivalents, 0.1 equivalents to 3 equivalents, 1 equivalents to 10 equivalents, 1 equivalents to 8 equivalents, 1 equivalents to 6 equivalents, 1 equivalents to 4 equivalents, 1 equivalents to 3 equivalents, 1.5 equivalents to 10 equivalents, 1.5 equivalents to 8 equivalents, 1.5 equivalents to 6 equivalents, 1.5 equivalents to 4 equivalents, 1.5 equivalents to 3 equivalents, 2 equivalents to 10 equivalents, 2 equivalents to 8 equivalents, 2 equivalents to 6 equivalents, 2 equivalents to 4 equivalents, 2 equivalents to 3 equivalents, 1 equivalent to 20 equivalents, 1 equivalent to 10 equivalents, or 1 equivalent to 7 equivalents.

In some cases, methods include contacting the 25-hydroxy-(3β)-cholest-5-en-3-sulfate pyridinium salt with sodium iodide to produce a 25-hydroxy-(3β)-cholest-5-en-3-sulfate sodium salt (Scheme IIE2).

Scheme IIE2

25HC3S pyridinium salt

-continued

25HC3S sodium salt

CLAUSES

The present disclosure may be further described by one or more of the non-limiting clauses that follow.

Clause 1. Crystalline 25HC3S sodium.

Clause 1. Crystalline 25HC3S sodium.

Clause 2. A hydrate of crystalline 25HC3S sodium.

Clause 3. A monohydrate of crystalline 25HC3S sodium.

Clause 4. A dihydrate of crystalline 25HC3S sodium.

Clause 5. A variable hydrate of crystalline 25HC3S sodium.

Clause 6. Form I of crystalline 25HC3S sodium.

Clause 7. The crystalline hydrate of any one of clauses 2-6, having an x-ray powder diffraction pattern comprising a peak at about 2.1°2θ.

Clause 8. The crystalline hydrate of clause 1 or 7, further comprising one or more peaks at about 5.4°2θ, about 6.5°2θ, about 10.8°2θ, and about 15.0°2θ.

Clause 9. The crystalline hydrate of any one of clauses 7-8 and 85-86, wherein the crystalline hydrate has a weight loss of about 8% when heated from ambient to 130° C. at a rate of 10° C./min.

Clause 10. The substantially pure crystalline hydrate of 25HC3S sodium of any one of clauses 2-9 and clauses 85-86.

Clause 11. The crystalline hydrate of any one of clauses 2-10 and clauses 85-86, having a unit cell volume of about 4544.7 Å$^3$±5%.

Clause 12. The crystalline hydrate of any one of clauses 2-11 and clauses 85-86, having a monoclinic unit cell.

Clause 13. A stable crystalline hydrate of any one of clauses 2-12 and clauses 85-86.

Clause 14. The stable crystalline hydrate of clause 13, wherein the stable crystalline hydrate is stable at a relative humidity from about 38% to about 70%.

Clause 15. Form II of crystalline 25HC3S sodium.

Clause 16. The crystalline hydrate of clause 2 or 5, wherein the water content is not greater than about 3 moles of water per mole of 25HC3S sodium.

Clause 17. The crystalline hydrate of clause 2 or 5, wherein the water content is from about 2 moles of water to about 3 moles of water per mole of 25HC3S sodium.

Clause 18. The crystalline hydrate of clause 2 or 5, wherein the water content is from about 1 mole of water to about 3 moles of water per one mole of 25HC3S sodium.

Clause 19. The crystalline hydrate of any one of clauses 15-18, having an x-ray pattern comprising a peak at about 2.3°2θ.

Clause 20. The crystalline hydrate of clause 2 or 19, further comprising an x-ray pattern comprising one or more peaks at about 4.5°2θ, a peak at and between about 5.0°2θ and about 5.1°2θ, a peak at and between about 5.9°2θ and about 6.1°2θ, and a peak at and between about 14.8°2θ and about 15.1°2θ.

Clause 21. The substantially pure crystalline hydrate of 25HC3S sodium of any one of clauses 15-20 and clauses 87-88.

Clause 22. A stable crystalline hydrate of any one of clauses 15-21 and clauses 87-88.

Clause 23. The stable crystalline hydrate of clause 22, wherein the stable crystalline hydrate is stable at a relative humidity ranging from about 21% to about 30%.

Clause 24. Form XI of crystalline 25HC3S sodium.

Clause 25. The crystalline hydrate of 25HC3S sodium of any one of clauses 2 and 24 having an x-ray powder diffraction pattern comprising a peak at about 2.6°2θ.

Clause 26. The crystalline hydrate of clause 2 or 25, having an x-ray powder diffraction pattern further comprising one or more peaks at about 3.1°2θ, about 3.5°2θ, and about 14.5°2θ.

Clause 27. The substantially pure crystalline hydrate of 25HC3S sodium of any one of clauses 24-26.

Clause 28. A stable crystalline hydrate of any one of clauses 24-27.

Clause 29. Anhydrous crystalline 25HC3S sodium.

Clause 30. Form XIII crystalline 25HC3S sodium.

Clause 31. The crystalline 25HC3S sodium of clause 1, 29, or 30 having an x-ray powder diffraction pattern comprising a peak at about 2.3°2θ.

Clause 32. The crystalline 25HC3S sodium of clause 1 or 31, having an x-ray powder diffraction pattern comprising one or more peaks at about 4.6°2θ, about 9.3°2θ, about 14.3°2θ, and about 15.0°2θ.

Clause 33. The crystalline 25HC3S sodium of clause 1, 29, or 30, wherein the unit cell has a volume of about 4230.8 $Å^3$±5%.

Clause 34. Stable crystalline 25HC3S sodium of any one of clauses 29-33 and clauses 91-92.

Clause 35. The crystalline 25HC3S sodium of any one of clauses 29-34 and clauses 91-92, wherein the crystalline 25HC3S is stable at a relative humidity ranging from about 0% to about 14% RH.

Clause 36. The crystalline 25HC3S sodium of any one of clauses 29-35 and clauses 91-92, wherein the crystalline 25HC3S is stable at a temperature of 70° C. or greater.

Clause 37. The crystalline 25HC3S sodium of any one of clauses 29-36 and clauses 91-92, wherein the unit cell is monoclinic.

Clause 38. The substantially pure crystalline 25HC3S sodium of any one of clauses 30-37 and clauses 91-92.

Clause 39. Form IX crystalline 25HC3S sodium.

Clause 40. The crystalline 25HC3S sodium of clause 1 or 39, having an x-ray powder diffraction pattern comprising a peak at about 4.9°2θ.

Clause 41. The crystalline 25HC3S sodium of clause 1 or 39, further comprising one or more peaks at about 7.9°2θ, about 11.2°2θ, about 14.1°2θ, about 16.1°2θ, and about 16.6°2θ.

Clause 42. A liquid crystal of 25HC3S sodium.

Clause 43. A mesophase of 25HC3S sodium.

Clause 44. Form V of 25HC3S sodium.

Clause 45. The liquid crystalline material of clause 1 or 44, having an x-ray powder diffraction pattern comprising a peak at about 2.2°2θ.

Clause 46. The crystalline material of clause 1 or 45, further comprising one or more peaks at about 4.4°2θ, about 6.6°2θ, and about 8.8°2θ.

Clause 47. The substantially pure crystalline 25HC3S sodium of any one of clauses 42-46 and clauses 89-90.

Clause 48. Stable crystalline 25HC3S sodium of any one of clauses 42-46 and clauses 89-90.

Clause 49. The crystalline 25HC3S sodium of clause 1 or 6, having at least one of substantially the same x-ray powder diffraction pattern as FIG. 1 and a TGA thermogram substantially the same as shown in FIG. 11.

Clause 50. The crystalline 25HC3S sodium of clause 1 or 6, having at least one of substantially the same x-ray powder diffraction pattern as FIG. 53 and a TGA thermogram substantially the same as shown in FIG. 11.

Clause 51. The crystalline 25HC3S sodium of clause 1 or 15, having at least one of substantially the same x-ray powder diffraction pattern as FIG. 2 and a TGA thermogram substantially the same as shown in FIG. 24.

Clause 52. The crystalline 25HC3S sodium of clause 1 or 15, having at least one of substantially the same x-ray powder diffraction pattern as FIG. 54 and a TGA thermogram substantially the same as shown in FIG. 24.

Clause 53. The crystalline 25HC3S sodium of clause 1 or 44, having at least one of substantially the same x-ray powder diffraction pattern as FIG. 3 and a TGA thermogram substantially the same as shown in FIG. 28.

Clause 54. The crystalline 25HC3S sodium of clause 1 or 44, having at least one of substantially the same x-ray powder diffraction pattern as FIG. 4 and a TGA thermogram substantially the same as shown in FIG. 28.

Clause 55. The crystalline 25HC3S sodium of clause 1 or 39, having substantially the same x-ray powder diffraction pattern as FIG. 5.

Clause 56. The crystalline 25HC3S sodium of clause 1 or 24, having substantially the same x-ray powder diffraction pattern as FIG. 6.

Clause 57. The crystalline 25HC3S sodium of clause 1 or 24, having substantially the same x-ray powder diffraction pattern as FIG. 7.

Clause 58. The crystalline 25HC3S sodium of clause 1 or 30, having substantially the same x-ray powder diffraction pattern as FIG. 8.

Clause 59. The crystalline 25HC3S sodium of clause 1 or 35, having substantially the same x-ray powder diffraction pattern as FIG. 9.

Clause 60. A method of treating one or more of hypercholesterolemia, hypertriglyceridemia, and conditions related to fat accumulation and inflammation comprising administering to a patient in need thereof an effective amount of a compound of 25HC3S sodium of any one of clauses 1-59 or 64.

Clause 61. A pharmaceutical composition comprising 25HC3S sodium of any one of clauses 1-59, 64, 68-83, and 85-96, and at least one pharmaceutically acceptable excipient.

Clause 62. A method of treating one or more of hypercholesterolemia, hypertriglyceridemia, and conditions related to fat accumulation and inflammation, comprising administering to a patient in need thereof an effective amount of a pharmaceutical composition of 25HC3S sodium of clause 61.

Clause 63. The method of clause 60 or 62 wherein the condition related to fat accumulation and inflammation comprises nonalcoholic fatty liver disease (NAFLD).

Clause 64. Stable crystalline 25HC3S sodium.

Clause 65. A method of clause 60 for treating nonalcoholic fatty liver disease (NAFLD), nonalcoholic steatohepatitis (NASH), alcoholic hepatitis, acute kidney injury (AKI), psoriasis, and atherosclerosis, comprising administering to a patient in need thereof an effective amount of a compound of 25HC3S sodium of any one of clauses 1-59, 64, 68-83, and 85-96.

Clause 66. The method of clause 65 for treating nonalcoholic fatty liver disease (NAFLD), nonalcoholic steatohepatitis (NASH), alcoholic hepatitis, acute kidney injury (AKI), psoriasis, and atherosclerosis, comprising administering to a patient in need thereof an effective amount of a pharmaceutical composition of 25HC3S sodium of clause 61.

Clause 67. A composition comprising two or more of Form I 25HC3S sodium, Form II 25HC3S sodium, Form III 25HC3S sodium, Form V 25HC3S sodium, Form IX 25HC3S sodium, Form XI 25HC3S sodium, and Form XIII 25HC3S sodium.

Clause 68. Form I of 25HC3S sodium having substantially the same x-ray powder diffraction pattern as FIG. 1.

Clause 69. Form I of 25HC3S sodium having substantially the same x-ray powder diffraction pattern as FIG. 53.

Clause 70. Form II of 25HC3S sodium having substantially the same x-ray powder diffraction pattern as FIG. 2.

Clause 71. Form II of 25HC3S sodium having substantially the same x-ray powder diffraction pattern as FIG. 54.

Clause 72. Form XI of 25HC3S sodium having substantially the same x-ray powder diffraction pattern as FIG. 6 or FIG. 7.

Clause 73. Form V of 25HC3S sodium having substantially the same x-ray powder diffraction pattern as FIG. 3.

Clause 74. Form V of 25HC3S sodium having substantially the same x-ray powder diffraction pattern as FIG. 4.

Clause 75. Form XIII of 25HC3S sodium having substantially the same x-ray powder diffraction pattern as FIG. 8.

Clause 76. Form XIII of 25HC3S sodium having substantially the same x-ray powder diffraction pattern as FIG. 9.

Clause 77. Form III of 25HC3S sodium having substantially the same x-ray powder diffraction pattern as FIG. 35.

Clause 78. Form IX of 25HC3S sodium having substantially the same x-ray powder diffraction pattern as FIG. 5.

Clause 79. Form III of crystalline 25HC3S sodium.

Clause 80. A solvate of crystalline 25HC3S sodium.

Clause 81. An ethanol solvate of crystalline 25HC3S sodium.

Clause 82. The crystalline solvate of clause 1 or 79 having an x-ray powder diffraction pattern comprising a peak at about 4.9°2θ.

Clause 83. The crystalline material of clause 1 or 82, further comprising one or more peaks at about 6.3°2θ, about 7.8°2θ, and about 9.8°2θ.

Clause 84. A pharmaceutical composition comprising two or more of Form I 25HC3S sodium, Form II 25HC3S sodium, Form III 25HC3S sodium, Form V 25HC3S sodium, Form IX 25HC3S sodium, Form XI 25HC3S sodium, and Form XIII 25HC3S sodium and at least one pharmaceutically acceptable excipient.

Clause 85. Form I of crystalline 25HC3S sodium having an x-ray powder diffraction pattern comprising peaks at about 2.1°2θ, about 6.5°2θ, and about 10.8°2θ.

Clause 86. Form I of crystalline 25HC3S sodium of clause 85 further comprising one or more peaks at about 9.9°2θ, about 15.0'20, and about 15.6°2θ.

Clause 87. Form II of crystalline 25HC3S sodium having an x-ray powder diffraction pattern comprising peaks at about 2.3°2θ and about 5.0°2θ.

Clause 88. Form II of crystalline 25HC3S sodium of clause 87 further comprising one or more peaks at about 4.5°2θ, about 5.9°2θ, about 9.1°2θ, and about 15.1°2θ.

Clause 89. Form V of crystalline 25HC3S sodium having an x-ray powder diffraction pattern comprising peaks at about 2.2°2θ, about 6.6°2θ, and a single peak at and between about 4.0°2θ and about 6.0°2θ.

Clause 90. Form V of crystalline 25HC3S sodium of clause 89 further comprising one or more peaks at about 8.8°2θ, about 9.9°2θ, and about 14.9°2θ.

Clause 91. Form XIII of crystalline 25HC3S sodium having an x-ray powder diffraction pattern comprising peaks at about 2.3°2θ, about 5.4°2θ, about 9.3°2θ, and about 11.6°2θ.

Clause 92. Form XIII of crystalline 25HC3S sodium of clause 91 further comprising one or more peaks at about 4.6°2θ and about 15.0°2θ.

Clause 93. Form III of crystalline 25HC3S sodium having an x-ray powder diffraction pattern comprising peaks at about 4.9°2θ and about 6.3°2θ.

Clause 94. Form III of crystalline 25HC3S sodium of clause 93 further comprising one or more peaks at 7.8°2θ, about 9.8°2θ, about 13.3°2θ, and about 15.5°2θ.

Clause 95. Form IX of crystalline 25HC3S sodium having an x-ray powder diffraction pattern comprising peaks at about 2.2°2θ, about 4.9°2θ, and about 7.9°2θ.

Clause 96. Form IX of crystalline 25HC3S sodium of clause 95 further comprising one or more peaks at about 14.1°2θ, about 16.1°2θ, and about 16.6°2θ.

Clause 97. A pharmaceutical composition comprising crystalline 25HC3S sodium or liquid crystal 25HC3S sodium or both and at least one pharmaceutically acceptable excipient.

Clause 98. The pharmaceutical composition of clause 97, the crystalline 25HC3S sodium or liquid crystal 25HC3S sodium comprising any one of clauses 1-59, 64, 68-83, and 85-96.

Clause 99. The pharmaceutical composition of clause 97, wherein the crystalline 25HC3S sodium or liquid crystal 25HC3S sodium comprises a mixture of Form I of 25HC3S sodium and Form II of 25HC3S sodium.

Clause 100. A method of producing a 5-cholesten-3β,25-diol-3-sulfate metal salt, the method comprising: contacting 25-hydroxy-(3β)-cholest-5-en-3-ol with at least one sulfating agent in at least one solvent to produce a 25-hydroxy-(3β)-cholest-5-en-3-sulfate organic cationic salt, wherein the 25-hydroxy-(3β)-cholest-5-en-3-sulfate organic cationic salt has low solubility in the at least one solvent; and contacting the 25-hydroxy-(3β)-cholest-5-en-3-sulfate organic cationic salt with at least one metal salt to produce the 5-cholesten-3β,25-diol 3-sulfate metal salt.

Clause 101. The method according to clause 100, wherein the at least one sulfating agent is a sulfur trioxide complex.

Clause 102. The method according to clause 101, wherein the at least one sulfating agent is a sulfur trioxide-pyridine complex.

Clause 103. The method according to any one of clauses 100-102, wherein the at least one metal salt is sodium acetate.

Clause 104. The method according to any one of clauses 100-102, wherein the at least one metal salt is sodium iodide.

Clause 105. The method according to any one of clauses 100-104, wherein the at least one sulfating agent is contacted with acetic anhydride prior to contacting with 25-hydroxy-(3β)-cholest-5-en-3-ol.

Clause 106. A method of producing a 5-cholesten-3β,25-diol 3-sulfate sodium salt, the method comprising: contacting 25-hydroxy-(3β)-cholest-5-en-3-ol with a sulfur trioxide-pyridine complex in at least one solvent to produce a 25-hydroxy-(3β)-cholest-5-en-3-sulfate pyridinium salt, wherein the 25-hydroxy-(3β)-cholest-5-en-3-sulfate pyridinium salt has low solubility in the at least one solvent; and contacting the 25-hydroxy-(3β)-cholest-5-en-3-sulfate pyridinium salt with a sodium salt to produce the 5-cholesten-3β,25-diol 3-sulfate sodium salt.

Clause 107. The method according to clause 106, wherein the sodium salt is sodium acetate.

Clause 108. The method according to clause 106, wherein the sodium salt is sodium iodide.

Clause 109. A method of producing a 5-cholesten-3β,25-diol 3-sulfate metal salt, the method comprising: contacting (3β)-cholest-5-en-3-ol with at least one sulfating agent to produce a first (3β)-cholest-5-en-3-sulfate organic cationic salt; contacting the first (3β)-cholest-5-en-3-sulfate organic cationic salt with an organic base to produce a second (3β)-cholest-5-en-3-sulfate organic cationic salt; oxidizing the second (3β)-cholest-5-en-3-sulfate organic cationic salt in the presence of at least one surfactant to produce a 25-hydroxy-(3β)-cholest-(5,6-epoxy)-3-sulfate organic cationic salt; generating a 25-hydroxy-(3β)-cholest-5-en-3-sulfate organic cationic salt from the 25-hydroxy-(3β)-cholest-(5,6-epoxy)-3-sulfate organic cationic salt by deoxygenation; and contacting the 25-hydroxy-(3β)-cholest-5-en-3-sulfate organic cationic salt with at least one metal salt to produce the 5-cholesten-3β,25-diol 3-sulfate metal salt.

Clause 110. The method according to clause 109, wherein the at least one sulfating agent is a sulfur trioxide complex.

Clause 111. The method according to clause 110, wherein the at least one sulfating agent is a sulfur trioxide-pyridine complex.

Clause 112. The method according to any one of clauses 109-111, wherein the organic base is tetraethylammonium hydroxide.

Clause 113. The method according to any one of clauses 109-112, wherein oxidizing the second (3β)-cholest-5-en-3-sulfate organic cationic salt comprises contacting the second (3β)-cholest-5-en-3-sulfate organic cationic salt with a composition comprising an oxidizing agent in the presence of at least one surfactant.

Clause 114. The method according to clause 113, wherein the method comprises contacting the second (3β)-cholest-5-en-3-sulfate organic cationic salt with a composition comprising the oxidizing agent and at least one ketone in the presence of the at least one surfactant.

Clause 115. The method according to clause 114, wherein the at least one ketone is 1,1,1-trifluoro-2-butanone.

Clause 116. The method according to any one of clauses 114-115, wherein the composition comprising the oxidizing agent and the at least one ketone further comprises the second (3β)-cholest-5-en-3-sulfate organic cationic salt and the at least one surfactant.

Clause 117. The method according to any one of clauses 114-116, wherein oxidizing the second (3β)-cholest-5-en-3-sulfate organic cationic salt comprises contacting the composition comprising the oxidizing agent and the at least one ketone with a second composition comprising the second (3β)-cholest-5-en-3-sulfate organic cationic salt in the presence of the at least one surfactant.

Clause 118. The method according to any one of clauses 114-117, wherein the method comprises contacting the second (3β)-cholest-5-en-3-sulfate organic cationic salt with the oxidizing agent in the presence of at least one base.

Clause 119. The method according to clause 118, wherein the at least one base is potassium hydrogen carbonate.

Clause 120. The method according to any one of clauses 113-119, wherein the oxidizing agent is potassium peroxymonosulfate.

Clause 121. The method according to any one of clauses 109-120, wherein the at least one surfactant is cetyltrimethylammonium hydrogen sulfate.

Clause 122. The method according to any one of clauses 109-121, wherein generating the 25-hydroxy-(3β)-cholest-5-en-3-sulfate organic cationic salt from the 25-hydroxy-(3β)-cholest-(5,6-epoxy)-3-sulfate organic cationic salt comprises contacting the 25-hydroxy-(3β)-cholest-(5,6-epoxy)-3-sulfate organic cationic salt with zinc.

Clause 123. The method according to clause 122, wherein the method comprises contacting the 25-hydroxy-(3β)-cholest-(5,6-epoxy)-3-sulfate organic cationic salt with zinc in the presence of at least one halide and at least one acid.

Clause 124. The method according to clause 123, wherein the at least one acid is acetic acid.

Clause 125. The method according to any one of clauses 123-124, wherein the at least one halide is iodine.

Clause 126. The method according to any one of clauses 109-125, wherein the at least one metal salt is sodium acetate.

Clause 127. The method according to any one of clauses 109-125, wherein the at least one metal salt is sodium iodide.

Clause 128. A composition comprising: 25-hydroxy-(3β)-cholest-5-en-3-sulfate; and sulfated desmosterol.

Clause 129. The composition according to clause 128, wherein the ratio by weight of the 25-hydroxy-(3β)-cholest-5-en-3-sulfate to the sulfated desmosterol is from 100:1 to 10000:1.

Clause 130. The composition according to clause 128, wherein the ratio by weight of the 25-hydroxy-(3β)-cholest-5-en-3-sulfate to the sulfated desmosterol is from 100:1 to 1000:1.

Clause 131. A composition comprising: 25-hydroxy-(3β)-cholest-5-en-3-sulfate; and 5-cholesten-3β-25-diol-disulfate.

Clause 132. The composition according to clause 131, wherein the ratio by weight of the 25-hydroxy-(3β)-cholest-5-en-3-sulfate to the 5-cholesten-3β-25-diol-disulfate is from 100:1 to 10000:1.

Clause 133. The composition according to clause 131, wherein the ratio by weight of the 25-hydroxy-(3β)-cholest-5-en-3-sulfate to the 5-cholesten-3β-25-diol-disulfate is from 100:1 to 1000:1.

Clause 134. The composition according to clause 133, wherein the ratio by weight of the 25-hydroxy-(3β)-cholest-5-en-3-sulfate to the 5-cholesten-3β-25-diol-disulfate is from 250:1 to 500:1.

Clause 135. A method comprising: sulfating 25-hydroxy-(3β)-cholest-5-en-3-ol to produce 25-hydroxy-(3β)-cholest-5-en-3-sulfate in at least one solvent, wherein 25-hydroxy-(3β)-cholest-5-en-3-sulfate has low solubility in the at least one solvent; and precipitating 25-hydroxy-(3β)-cholest-5-en-3-sulfate in the solvent.

Clause 136. The method according to clause 135, wherein 25-hydroxy-(3β)-cholest-5-en-3-sulfate has a solubility of 100 mmol/L or less in the at least one solvent.

Clause 137. The method according to clause 136, wherein 25-hydroxy-(3β)-cholest-5-en-3-sulfate has a solubility of 10 mmol/L or less in the at least one solvent.

Clause 138. The method according to any one of clauses 135-137, wherein the at least one solvent is chosen from chloroform, methylene chloride, acetone, acetonitrile, toluene, tetrahydrofuran and methyltetrahydrofuran.

Clause 139. The method according to any one of clauses 135-138, wherein sulfating 25-hydroxy-(3β)-cholest-5-en-3-ol generates 5-cholesten-3β-25-diol-disulfate that remains solubilized in the at least one solvent.

Clause 140. The method according to clause 139, wherein the ratio by weight of the 25-hydroxy-(3β)-cholest-5-en-3-sulfate to 5-cholesten-3β-25-diol-disulfate generated is from 100:1 to 10000:1.

Clause 141. The method according to clause 140, wherein the ratio by weight of the 25-hydroxy-(3β)-cholest-5-en-3-sulfate to 5-cholesten-3β-25-diol-disulfate generated is from 100:1 to 1000:1.

Clause 142. The method according to any one of clauses 139-141, wherein 5-cholesten-3β-25-diol-disulfate has high solubility in the at least one solvent.

Clause 143. The method according to clause 142, wherein 5-cholesten-3β-25-diol-disulfate has a solubility of 500 mmol/L or more in the at least one solvent.

Clause 144. A composition comprising: 25-hydroxy-(3β)-cholest-5-en-3-sulfate; and byproducts from sulfating 25-hydroxy-(3β)-cholest-5-en-3-ol comprising a first compound comprising a high-pressure liquid chromatography (HPLC) retention time of about 18.3 minutes, a second compound comprising a HPLC retention time of about 37.7 minutes, or any combination thereof, and the 25-hydroxy-(3β)-cholest-5-en-3-sulfate comprising a HPLC retention time of about 7.7 minutes, wherein the first compound, the second compound and the 25-hydroxy-(3β)-cholest-5-en-3-sulfate are capable of being separated by HPLC comprising a C8 stationary phase operating at about 45° C. with a first mobile phase comprising a buffer and a second mobile phase comprising one or more organic solvents.

Clause 145. The composition according to clause 144, wherein the ratio by weight of the 25-hydroxy-(3β)-cholest-5-en-3-sulfate to the byproducts is from 100:1 to 10000:1.

Clause 146. The composition according to clause 144, wherein the ratio by weight of the 25-hydroxy-(3β)-cholest-5-en-3-sulfate to the byproducts is from 100:1 to 1000:1.

Clause 147. The composition according to any one of clauses 144-146, wherein the flow rate of the first mobile phase is about 1.0 mL/minute Clause 148. The composition according to any one of clauses 144-147, wherein the flow rate of the second mobile phase is about 1.0 mL/minute.

Clause 149. The composition according to any one of clauses 144-148, wherein the first mobile phase comprises sodium phosphate.

Clause 150. The composition according to any one of clauses 144-149, wherein the second mobile phase is chosen from one or more of methoxypropyl acetate, acetonitrile and methanol.

Clause 151. A composition comprising: 25-hydroxy-(3β)-cholest-5-en-3-sulfate; and byproducts from sulfating 25-hydroxy-(3β)-cholest-5-en-3-ol comprising sulfated desmosterol, a second compound comprising a HPLC retention time of about 37.7 minutes, or any combination thereof, and the 25-hydroxy-(3β)-cholest-5-en-3-sulfate comprising a HPLC retention time of about 7.7 minutes, wherein the sulfated desmosterol, the second compound and the 25-hydroxy-(3β)-cholest-5-en-3-sulfate are capable of being separated by HPLC comprising a C8 stationary phase operating at about 45° C. with a first mobile phase comprising a buffer and a second mobile phase comprising one or more organic solvents.

Clause 152. The composition according to clause 151, wherein the ratio by weight of the 25-hydroxy-(3β)-cholest-5-en-3-sulfate to the byproducts is from 100:1 to 10000:1.

Clause 153. The composition according to clause 151, wherein the ratio by weight of the 25-hydroxy-(3β)-cholest-5-en-3-sulfate to the byproducts is from 100:1 to 1000:1.

Clause 154. The composition according to any one of clauses 151-152, wherein the flow rate of the first mobile phase is about 1.0 mL/minute Clause 155. The composition according to any one of clauses 151-154, wherein the flow rate of the second mobile phase is about 1.0 mL/minute.

Clause 156. The composition according to any one of clauses 151-155, wherein the first mobile phase comprises sodium phosphate.

Clause 157. The composition according to any one of clauses 151-156, wherein the second mobile phase is chosen from one or more of methoxypropyl acetate, acetonitrile and methanol.

Clause 158. The composition according to any one of clauses 151-157, wherein the second compound is desmosterol.

Clause 159. A method of producing a 5-cholesten-3β,25-diol-3-sulfate metal salt, the method comprising: contacting 25-hydroxy-(3β)-cholest-5-en-3-ol with at least one sulfating agent in at least one solvent to produce a 25-hydroxy-(3β)-cholest-5-en-3-sulfate organic cationic salt, wherein the 25-hydroxy-(3β)-cholest-5-en-3-sulfate organic cationic salt has low solubility in the at least one solvent; and contacting the 25-hydroxy-(3β)-cholest-5-en-3-sulfate organic cationic salt with at least one metal salt to produce the 5-cholesten-3β,25-diol 3-sulfate metal salt.

Clause 160. The method according to clause 159, wherein the sulfating reagent is characterized by $^1$H-NMR (proton nuclear magnetic resonance) spectroscopy prior to contacting with the 25-hydroxy-(3β)-cholest-5-en-3-ol.

Clause 161. The method according to clause 160, wherein the method comprises determining the extent of degradation of the sulfating reagent prior to contacting with the 25-hydroxy-(3β)-cholest-5-en-3-ol by determining the amount of impurity present in the sulfating reagent.

Clause 162. The method according to clause 161, wherein the extent of degradation of the sulfating reagent is determined by proton nuclear magnetic resonance spectroscopy by integrating one or more peaks in the $^1$H-NMR spectrum at a chemical shift indicative of the presence of impurities in the sulfating reagent.

Clause 163. The method according to clause 162, wherein proton nuclear magnetic resonance spectroscopy of the sulfating agent is conducted in at least one deuterated solvent.

Clause 164. The method according to clause 163, wherein the at least one deuterated solvent is deuterated acetone.

Clause 165. The method according to clause 164, wherein the at least one deuterated solvent is not deuterated benzene, deuterated acetonitrile, or deuterated chloroform.

Clause 166. The method according to any one of clauses 162-165, wherein the method comprises integrating one or more peaks in the proton NMR spectrum at a chemical shift of from 9.2 ppm to 9.3 ppm and calculating the impurity level of the sulfating agent based on the integrated peaks.

Clause 167. The method according to clause 166, wherein the method comprises integrating one or more peaks in the proton NMR spectrum at a chemical shift of about 9.25 ppm.

Clause 168. The method according to any one of clauses 159-167, wherein 25-hydroxy-(3β)-cholest-5-en-3-ol is contacted with the sulfating agent in the presence of particles of a 25-hydroxy-(3β)-cholest-5-en-3-sulfate organic cationic salt.

Clause 169. The method according to clause 168, wherein the particles of the 25-hydroxy-(3β)-cholest-5-en-3-sulfate organic cationic salt have an average particle width of 0.1 mm or greater.

Clause 170. The method according to any one of clauses 159-169, wherein the method further comprises quenching unreacted sulfating agent.

Clause 171. The method according to clause 170, wherein quenching unreacted sulfating agent comprises contacting the reaction mixture with water.

Clause 172. The method according to clause 171, wherein 1 equivalent or more of water is contacted with the reaction mixture.

Clause 173. The method according to any one of clauses 171-172, wherein quenching unreacted sulfating agent comprises contacting the reaction mixture with water and pyridine.

Clause 174. The method according to clause 173, wherein the pyridine is contacted with the reaction mixture after a predetermined period of time after contacting the reaction mixture with the water.

Clause 175. The method according to any one of clauses 170-174, wherein the reactivity of the unreacted sulfating agent is quenched under slow agitation.

Clause 176. The method according to any one of clauses 159-175, wherein the method further comprises purifying the 25-hydroxy-(3β)-cholest-5-en-3-sulfate organic cationic salt.

Clause 177. The method according to clause 176, wherein the 25-hydroxy-(3β)-cholest-5-en-3-sulfate organic cationic salt is purified by liquid chromotography.

Clause 178. The method according to clause 177, wherein the 25-hydroxy-(3β)-cholest-5-en-3-sulfate organic cationic salt is purified by liquid chromatography comprising a silica gel stationary phase and a mobile phase comprising pyridine.

Clause 179. The method according to clause 178, wherein the mobile phase comprises methylene chloride, methanol, and pyridine.

Clause 180. The method according to any one of clauses 178-179, wherein fractions collected from the liquid chromatography are combined and concentrated by distillation.

Clause 181. The method according to any one of clauses 178-179, wherein fractions collected from the liquid chromatograph are combined and concentrated under vacuum.

Clause 182. The method according to any one of clauses 180-181, wherein the concentrated fractions are contacted with one or more particles of the 25-hydroxy-(3β)-cholest-5-en-3-sulfate organic cationic salt.

Clause 183. The method according to clause 182, wherein the particles of the 25-hydroxy-(3β)-cholest-5-en-3-sulfate organic cationic salt are contacted during distillation of the combined fractions.

Clause 184. The method according to clause 182, wherein the method comprises:

concentrating the combined fractions under vacuum; and contacting the concentrated fractions with particles of the 25-hydroxy-(3β)-cholest-5-en-3-sulfate organic cationic salt and at least one solvent.

Clause 185. The method according to clause 184, wherein the at least one solvent is chosen from 2-methyl tetrahydrofuran, heptane, or a combination thereof.

Clause 186. The method according to any one of clauses 184-185, wherein the at least one solvent is 2-methyl tetrahydrofuran.

Clause 187. The hydrate of crystalline 25HC3S sodium of clause 2, having an x-ray powder diffraction pattern comprising a peak at less than about 2.8°2θ.

Clause 188. The hydrate of crystalline 25HC3S sodium of clause 187, having a diffraction pattern comprising a peak at between about 2.1°2θ and about 2.6°2θ.

Clause 189. The hydrate of crystalline 25HC3S sodium of clause 188, having a diffraction pattern comprising a peak between about 2.1°2θ and about 2.3°2θ.

Clause 190. The hydrate of crystalline 25HC3S sodium of any one of clauses 2, 187, or 188, having an x-powder diffraction pattern comprising a peak between about 4.3°2θ and about 4.6°2θ.

Clause 191. The hydrate of crystalline 25HC3S sodium of any one of clauses 2, 187, 188, 189, or 190 having an x-ray powder diffraction pattern comprising a peak between about 5.0°2θ and about 5.5°2θ.

Clause 192. The hydrate of crystalline 25HC3S sodium of any one of clauses 2, 187-191, having an x-ray diffraction pattern comprising a peak between about 8.6°2θ and about 9.1°2θ.

Clause 193. The hydrate of crystalline 25HC3S sodium of any one of clauses 2, 187-192, having an x-ray powder diffraction pattern comprising a peak between about 15.0°2θ and about 15.3°2θ.

Clause 194. The hydrate of crystalline 25HC3S sodium of any one of clauses 2 or 188 having an x-ray powder diffraction pattern comprising a peak at between about 9.9°2θ and about 10.0°2θ.

Clause 195. The anhydrous crystalline 25HC3S sodium of any one of clauses 29, 30, or 39, having an x-ray powder diffraction pattern comprising a peak at between about 4.5°2θ and about 4.8°2θ.

Clause 196. The anhydrous crystalline 25HC3S sodium of any one of clauses 29, 30, 39, or 195 having an x-ray powder diffraction pattern comprising a peak between about 9.8°2θ and about 9.9°2θ.

Clause 197. The anhydrous crystalline 25HC3S sodium of any one of clauses 29, 30, 39, 195, or 196 having an x-ray powder diffraction pattern comprising a peak at between about 14.1°2θ and about 14.3°2θ.

Clause 198. The anhydrous crystalline 25HC3S sodium of any one of clauses 29, 30, 39, 195, 197, or 197 having an x-ray powder diffraction pattern comprising a peak at about 16.1°2θ.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for.

Examples 1-19 are associated with samples prepared in accordance with Table 1 and Examples 20, 21, 22, 24, 25, 26, 27, 28, 29, 31, 32, 34, 35, 37, and 38. Examples 23, 30, 33, 36 and 39 were prepared as written; XRPD patterns were collected in accordance with Example 40, and no other analytical data are reported in the disclosure for these examples.

Example 1—Analysis of 25HC3S Sodium Used in the Screen

Approximately 10 grams of 25HC3S sodium were used for screening. X-ray powder diffraction analysis identifies the material as a physical mixture of hydrates (Form I and Form II). The solution $^1$H-NMR spectrum is consistent with the chemical structure (See FIG. 34 as an example of a $^1$H-NMR structure of 25HC3S). The mixture contained 6.1 wt % water by Karl Fischer titration. This corresponds to approximately 1.8 mol/mol of water. The DVS isotherm suggests that the material is hygroscopic. The mixture gained approximately 5 wt % from 5 to 25% RH (1.5 mol/mol water), 6 wt % from 25 to 85% RH (1.8 mol/mol water), and another 6 wt % from 85 to 95% RH. The material was recovered and identified as predominantly Form I with an additional peak near 8.8° (2θ) by x-ray powder diffraction. The peak is believed to be due to Form V.

TGA provided a 5.4% weight loss up to 128° C. which occurred concurrently with broad dehydration endotherms in the DSC. The DSC curve also showed endotherms near 167° C. and 184° C. These events were associated with decomposition. Hot stage microscopy was consistent with dehydration between 58° C. and 112° C., followed by decomposition near 163° C.

Briefly exposing the mixture to 130° C. resulted in a mixture of Forms I, II, and XIII In addition, the peaks associated with Form II were shifted. Exposure to 75% RH for 10 days resulted in predominately Form I and two additional peaks near 4.4°2θ and 8.8°2θ by x-ray powder diffraction, and the peaks were believed to be due to Form V.

Example 2—General Screening Methods

Methods using solvents or solvent mixtures include cooling a solution, evaporation, antisolvent addition, and suspensions (slurries). Variations on these methods can include changes in solvent, solvent mixtures, antisolvent, temperature, cooling rate, concentration, rate of addition, and order of mixing, to name a few possibilities. The generated solids were observed by Polarized light microscopy and/or analyzed by x-ray powder diffraction.

Specific methods of screening are set forth in Examples 3-7. Methods and results are summarized, e.g., in Table 1 and the Figures of the present disclosure.

Example 3—Anti-Solvent Additions

Solutions were contacted with anti-solvents. These anti-solvent additions were added to help lower the solubility of the solvent system and induce crystallization.

Example 4—Cooling and Slow Cools

Solutions were prepared in the selected solvent or solvent/anti-solvent system. These solutions were chilled below room temperature within a refrigerator for varying lengths of time in an attempt to induce nucleation. The presence or absence of solids was noted. Upon observation of solids, in quantities sufficient for analysis, isolation of material was conducted. If insufficient quantities were present, further cooling was performed in a freezer. Samples were isolated for analysis either wet or as dry powders.

Example 5—Fast Evaporation

Solutions were prepared in selected solvents and agitated between aliquot additions to assist in dissolution. Once a mixture reached complete dissolution, as judged by visual observation, the solution was filtered through a 0.2-μm nylon filter and allowed to evaporate at ambient conditions in an uncapped vial or at ambient temperature under nitrogen. The solids that formed were isolated for evaluation.

Example 6—Slow Evaporation

Solutions were prepared in selected solvents and agitated between aliquot additions to assist in dissolution. Once a mixture reached complete dissolution, as judged by visual observation, the solution was filtered through a 0.2-μm nylon filter into a sample vial. The vial opening was covered with foil and pierced 3× and allowed to evaporate at ambient conditions. The solids that formed were isolated for evaluation.

Example 7—Slurry

Solutions were prepared by adding enough solids to a given solvent so that excess solids were present. The mixture was then agitated in a sealed vial at either ambient or elevated temperature. After a given amount of time, the solids were isolated for analysis.

Example 8—Differential Scanning Calorimetry (DSC)

Differential scanning calorimetry analyses were performed using a Mettler-Toledo DSC3+ differential scanning calorimeter. Temperature calibration was performed using octane, phenyl salicylate, indium, tin, and zinc. The sample was placed into a hermetically sealed or an open aluminum DSC pan, and the weight was recorded. A weighed aluminum pan configured as the sample pan was placed on the reference side of the cell. The samples were analyzed from −30 to 250° C. at a ramp rate of 10° C./min. Although thermograms were plotted by reference temperature (x-axis), results were reported according to sample temperatures.

Example 9—Dynamic Vapor Sorption/Desorption (DVS)

Moisture sorption/desorption data were collected on a VTI SGA-100 Vapor Sorption Analyzer. NaCl and PVP were used as calibration standards. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Example 10—Hot Stage Microscopy

Hot stage microscopy was performed using a Linkam hot stage (FTIR 600) mounted on a Leica DM LP microscope equipped with a SPOT Insight™ color digital camera.

Temperature calibrations were performed using USP melting point standards. Samples were placed on a cover glass, prepared either neat or with mineral oil, and a second cover glass was placed on top of the sample. As the stage was heated, each sample was visually observed using a 10×0.22 or 20×0.40 numerical aperture objective with crossed polarizers and a first order red compensator. Images were captured using SPOT software (v. 4.5.9).

Example 11—Karl Fischer

Coulometric Karl Fischer (KF) analysis for water determination was performed using a Mettler Toledo DL39 KF titrator. A NIST-traceable water standard (Hydranal Water Standard 1.0) was analyzed to check the operation of the coulometer. A blank titration was carried out prior to sample analyses. The sample was prepared at ambient conditions, where a weighed amount of sample was dissolved in approximately 1 mL Hydranal-Coulomat AD in a pre-dried vial. The entire solution was added to the KF coulometer through a septum and mixed for 10 seconds. The sample was then titrated by means of a generator electrode, which produces iodine by electrochemical oxidation: $2 I-\rightarrow I_2+ 2e-$. Two replicates were obtained to ensure reproducibility.

Example 12—Polarized Light Microscopy

Polarized light microscopy was performed using a Motic SMZ-168. Each sample was observed using a 10× objective at 0.75 up to 5.0× magnification with crossed polarizers.

Example 13—$^1$H NMR Spectroscopy

The solution $^1$H NMR spectra were obtained at Spectral Data Solutions.

Example 14—Thermogravimetric Analysis (TGA)

Thermogravimetric analyses were performed using a Mettler Toledo TGA/DSC3+ analyzer. Temperature calibration was performed using phenyl salicylate, indium, tin, and zinc. The sample was placed in an aluminum pan. The open pan was inserted into the TG furnace. The furnace was heated under nitrogen. Each sample was heated from ambient temperature to 350° C. at 10° C./min. Although thermograms were plotted by reference temperature (x-axis), results were reported according to sample temperatures.

Example 15—X-Ray Powder Diffraction (XRPD)

XRPD patterns (also called diffractograms) were collected in either transmission or reflection mode.

Example 16—Transmission

X-ray powder diffraction patterns were collected with a PANalytical X'Pert PRO MPD or PANalytical Empyrean diffractometer using an incident beam of Cu radiation produced using a long, fine-focus source. An elliptically graded multilayer mirror was used to focus Cu Kα x-rays through the specimen and onto the detector. Prior to the analysis, a silicon specimen (NIST SRM 640e) was analyzed to verify the observed position of the Si 111 peak was consistent with the NIST-certified position. A specimen of the sample was sandwiched between 3-μm-thick films and analyzed in transmission geometry. A beam-stop, short anti-scatter extension, and anti-scatter knife edge were used to minimize the background generated by air. Soller slits for the incident and diffracted beams were used to minimize broadening and asymmetry from axial divergence. Diffraction patterns were collected using a scanning position-sensitive detector (X'Celerator) located 240 mm from the specimen and Data Collector software v. 2.2b or 5.5. All images were produced with the instrument labeled as X'Pert PRO MPD regardless of the instrument used.

Example 17—Reflection

X-ray powder diffraction patterns were collected with a PANalytical X'Pert PRO MPD diffractometer using an incident beam of Cu Kα radiation produced using a long, fine-focus source and a nickel filter. The diffractometer was configured using the symmetric Bragg—Brentano geometry. Prior to the analysis, a silicon specimen (NIST SRM 640e) was analyzed to verify that the observed position of the Si 111 peak was consistent with the NIST-certified position. A specimen of the sample was packed in a well. Anti-scatter slits were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

Example 18—Variable Humidity (VH-XRPD)

X-ray powder diffraction patterns were collected with a PANalytical X'Pert PRO MPD diffractometer using an incident beam of Cu Kα radiation produced using a long, fine-focus source and a nickel filter. The diffractometer was configured using the symmetric Bragg—Brentano geometry. Data were collected and analyzed using Data Collector software v. 2.2b. Prior to the analysis, a silicon specimen (NIST SRM 640e) was analyzed to verify that the observed position of the Si 111 peak was consistent with the NIST-certified position. A specimen of the sample was packed in a nickel-coated copper well. Antiscatter slits were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

An Anton Paar temperature-humidity chamber (THC) was used to collect in-situ x-ray powder diffraction patterns as a function of humidity. The temperature of the specimen was controlled with a Peltier thermoelectric device located directly under the specimen holder and monitored with a platinum-100 resistance sensor located in the specimen holder. The thermoelectric device was powered and controlled by an Anton Paar TCU 50 interfaced with Data Collector software.

The humidity was generated with an RH-200 manufactured by VTI Inc. and carried by a flow of nitrogen gas. The humidity and temperature were monitored by a Rotronic HygroClip sensor located next to the specimen inside the THC.

Example 19—Variable Temperature (VT-XRPD)

X-ray powder diffraction patterns were collected with a PANalytical X'Pert PRO MPD diffractometer using an incident beam of Cu Kα radiation produced using a long, fine-focus source and a nickel filter. The diffractometer was configured using the symmetric Bragg—Brentano geometry. Data were collected and analyzed using Data Collector software v. 2.2b. Prior to the analysis, a silicon specimen (NIST SRM 640e) was analyzed to verify that the observed position of the Si 111 peak was consistent with the NIST-certified position. A specimen of the sample was packed in a nickel-coated copper well. Antiscatter slits were used to minimize the background generated by air scattering. Soller slits for the incident and diffracted beams were used to minimize broadening from axial divergence. Diffraction patterns were collected using a scanning position-sensitive detector (X'Celerator) located 240 mm from the sample.

An Anton Paar TTK 450 stage was used to collect in-situ x-ray powder diffraction patterns as a function of temperature. The sample was heated with a resistance heater located directly under the sample holder, and the temperature was monitored with a platinum-100 resistance sensor located in the specimen holder. The heater was powered and controlled by an Anton Paar TCU 100 interfaced with Data Collector software.

Example 20—Form I—Preparation 1

25HC3S sodium (164.6 mg) and methanol (2 mL) were heated on a hot plate set at 75° C. until a clear solution was achieved. The solution was filtered through a 0.2-μm nylon filter into 20 mL of dichloromethane. This resulted in immediate precipitation of a gel, which was harvested by water-aspirated vacuum filtration. The gel crystallized to Form I after isolation. FIG. 36 is an XRPD diffractogram of this preparation.

Example 21—Form I—Preparation 2

A slurry was obtained with 64.5 mg of 25HC3S sodium and 1 mL of toluene. The slurry was magnetically stirred at approximately 400 RPM at room temperature for 21 days. Form I was obtained by allowing the suspended solids to settle and decanting the excess solution from the solids. FIG. 37 is an XRPD diffractogram of this preparation.

Example 22—Form I—Preparation 3

A slurry was obtained with 41.9 mg of 25HC3S sodium and 12 mL of acetone. The slurry was briefly heated on a hot plate set at 85° C. and magnetically stirred at approximately 200 RPM. The slurry was removed from the heat source, and 1 mL of water was added while magnetically stirring at approximately 400 RPM. Nearly complete dissolution was followed by the formation of a flocculent suspension which then nucleated to fine dendrites. The slurry was left to stir for 4 days. Form I was harvested by water-aspirated vacuum filtration and dried under nitrogen for approximately 10 minutes. FIG. 38 is an XRPD diffractogram of this preparation.

Example 23—Form I—Preparation 4

Form I was obtained by performing the following Dynamic Vapor Sorption Test:

Dynamic Vapor Sorption (DVS) was measured using an SMS (Surface Measurement Systems) DVS Intrinsic. Parameters for the DVS test are listed in Table 11.

TABLE 11

| Parameters for DVS | |
| --- | --- |
| Parameters | Values |
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 360 min |
| RH range | 40% RH-95% RH-0% RH-95% RH |
| RH step size | 10% (0% RH-90% RH) |
| | 5% (90% RH-95% RH) |

From the above DVS test, the compound was found to be hygroscopic, and the starting material reversibly absorbed 7.0% moisture below 30% RH and 8.5% water by 95% RH. FIG. 355 is an XRPD diffractogram of this preparation.

Example 24—Form I+XIII

A slurry was obtained with 586.6 mg of 25HC3S sodium and 10 mL of 97:03 v/v acetonitrile/water. The slurry was magnetically stirred at approximately 250 RPM for 4 days at room temperature. A mixture of Forms I+XIII was harvested by water-aspirated vacuum filtration and dried under nitrogen for approximately 30 minutes. FIG. 39 is an XRPD diffractogram of this mixture.

Example 25—Form XIII—Preparation 1

Form XIII was obtained by exposing a mixture of Forms I+XIII (obtained from Example 24) to 70° C. under vacuum for 2 days. FIG. 40 is an XRPD diffractogram of this preparation.

Example 26—Form XIII—Preparation 2

A mixture of Forms I+XIII (obtained from Example 24) isolated at 15% RH was exposed to 25%, 55%, 75%, 85%, 75%, 25%, and 0% RH, successively. The material was held at each RH condition for a minimum of one hour before proceeding to the next condition. The mixture converted to Form I once exposed to 25% RH and remained Form I at 55%, 75%, 85%, 75%, and 25% RH. Form I converted to a mixture of Form I+XIII upon reaching 0% RH. The mixture of Form I+XIII converted to Form XIII within 20 minutes of continued exposure to 0% RH. FIG. 41 is an XRPD diffractogram of this preparation.

Example 27—Form II—Preparation 1

A slurry was obtained with 75.4 mg of 25HC3S sodium and 20 mL of acetone. The slurry was magnetically stirred at approximately 400 RPM for 14 days at room temperature. Form II was harvested by water-aspirated vacuum filtration and briefly dried under nitrogen. FIG. 42 is an XRPD diffractogram of this preparation.

Example 28—Form II—Preparation 2

A slurry was obtained with 66.9 mg of 25HC3S sodium and 19 mL of acetonitrile. The slurry was magnetically stirred at approximately 400 RPM for 14 days at room temperature. Form II was harvested by water-aspirated vacuum filtration and briefly dried under nitrogen. FIG. 43 is an XRPD diffractogram of this preparation.

Example 29—Form II—Preparation 3

A slurry was obtained with 75.4 mg of 25HC3S sodium and 8 mL of ethanol. The slurry was filtered through a 0.2-µm nylon filter resulting in a clear solution. A 4-mL aliquot of the clear solution was allowed to evaporate at ambient conditions until solids were evident and approximately 0.1 mL of the mother liquor remained. Form II was harvested by decantation. FIG. 44 is an XRPD diffractogram of this preparation.

Example 30—Form II—Preparation 4

Form II was obtained from anti-solvent addition (dimethylacetamide (DMA) solvent and methyl isobutyl ketone (MIBK) antisolvent). The anti-solvent method was as follows: a concentrated stock of starting material was prepared in DMA. The solution was stirred and MIBK added quickly to induce precipitation. Solids isolated for XRPD analysis after centrifugation and filtration yielded Form II. FIG. 46 is an XRPD diffractogram of this preparation.

Example 31—Form III+Form IX

A slurry was obtained with 46.6 mg of 25HC3S sodium and 0.5 mL of ethanol. The slurry was heated briefly on a hot plate set at 75° C., resulting in sorption of solvent. The mixture of Forms III+IX was removed from the heat source and dried under nitrogen for approximately 15 minutes. FIG. 45 is an XRPD diffractogram of a mixture of Form III and Form IX.

Example 32—Form IX—Preparation 1

Form IX was obtained by exposing a mixture of Forms III+IX (obtained from Example 31) to 58° C. under vacuum for 1 day. FIG. 5 is an XRPD diffractogram of this preparation.

Example 33—Form IX—Preparation 2

20.3 mg of 25HC3S sodium was weighed into a 3-mL vial. This 3-mL vial was placed inside a 20 mL vial containing 3 to 4 mL of ethanol, and the outer vial was sealed. The system was kept at room temperature for 12 hours, and the isolated solids were analyzed by XRPD. FIG. 51 is an XRPD diffractogram of this preparation.

Example 34—Form V—Preparation 1

A turbid suspension was obtained with 85.1 mg of 25HC3S sodium and 7 mL of methanol. The suspension was filtered through a 0.2-µm nylon filter to provide a clear solution. Form V was provided by evaporating the solution until visually dry at ambient conditions. FIG. 47 is an XRPD diffractogram of this preparation.

Example 35—Form V—Preparation 2

A slurry was obtained with 70.4 mg of 25HC3S sodium and 20 mL of water. The slurry was magnetically stirred at approximately 400 RPM for 14 days. An opaque gel was harvested by water-aspirated vacuum filtration. The gel transformed to Form V after isolation. FIG. 48 is an XRPD diffractogram of this preparation.

Example 36—Form V—Preparation 3

Form V was obtained by anti-solvent addition (MeOH solvent and EtOAc antisolvent). The anti-solvent method was as follows: a concentrated stock of starting material was prepared in MeOH. The solution was stirred and EtOAC added quickly to induce precipitation. Solids isolated for XRPD analysis after centrifugation and filtration yielded Form V. FIG. 56 is an XRPD diffractogram of this preparation.

Example 37—Form XI

A slurry was obtained with 97.5 mg of 25HC3S sodium and 20 mL of diethyl ether. The slurry was magnetically stirred at approximately 400 RPM for 14 days. Form XI was harvested by water-aspirated vacuum filtration and dried under nitrogen. FIGS. 6 and 7 are XRPD diffractograms of this preparation.

Example 38—Form III—Preparation I

A turbid suspension was obtained with 97 mg of 25HC3S sodium and 8 mL of ethanol. The suspension was left to settle at ambient temperature for ~1 day. The suspension was centrifuged, and the wet solids were harvested by decantation. FIG. 49 is an XRPD diffractogram of this preparation.

Example 39—Form III—Preparation 2

25HC3S sodium (1.98 mg) was weighed into a 3-mL glass vial. EtOH (3 mL) was added into the glass vial to produce a suspension at room temperature and heated to 50° C. The solution was filtered at 50° C. with a 0.45-µm PTFE filter, and the filtrates were collected into clean vials. The solutions were cooled to room temperature and then stored at −20° C. Solids were isolated by centrifuging at 14,000 RPM for 5 minutes, then collected and analyzed by XRPD. FIG. 50 is an XRPD diffraction of this preparation.

Example 40—XRPD Analyses for Examples 23, 30, 33, 35, and 36

XRPD was performed with Panalytical X'Pert³ Powder XRPD on a Si zero-background holder. The 2θ position was calibrated against a Panalytical 640 Si powder standard. The 4-min method was used for most samples. Spray-dried dispersion stability samples were analyzed using the 80-min method. Details of XRPD used in the experiments are listed in Table 12 below.

TABLE 12

| XRPD parameters | |
| --- | --- |
| Parameters for Reflection Mode | |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Fixed slit | ¼° (0.38 mm height) |
| Divergence slit | ⅛° (0.19 mm height) |
| Scan mode | Continuous |
| Scan range (°2TH) | 3° -40° |
| Step size (°2TH) | 0.0131 (4-min method), 0.0033 (80-min method) |
| Scan speed (°/s) | 0.16 (4-min method), 0.0075 (80-min method) |

General Synthetic Procedures for Preparing 25-hydroxy-(3β)-cholest-5-en-3-sulfate 25HC3S may be prepared by various methods. Enclosed herein are exemplary methods of making 25HC3S.

All temperatures are in degrees Celsius (° C.) and are uncorrected. Reagent grade chemicals and anhydrous solvents were purchased from commercial sources and, unless otherwise mentioned, used without further purification. The names of the products were determined using the naming software included in Biovia electronic lab notebook. Silica gel chromatography was performed on Teledyne Isco instruments using pre-packaged disposable $SiO_2$ stationary phase columns with eluent flow rates of 15 to 200 mL/min. The analytical HPLC chromatograms were performed using an Agilent 1100 series instrument with DAD detector (190 nm to 300 nm). The mass spectra were recorded with a Waters Micromass ZQ detector at 130° C. The mass spectrometer was equipped with an electrospray ion source (ESI) operated in a positive ion mode and was set to scan between m/z 150-750 with a scan time of 0.3 s. Products and intermediates were analyzed by HPLC/MS on a Gemini-NX (5 μM, 2.0×30 mm) using a high pH buffer gradient of 5% to 100% of MeCN in $H_2O$ (0.03% $(NH_4)_2CO_3$/0.375% $NH_4OH$) over 2.5 min at 1.8 mL/min for a 3.5 min run (B05), and EVO C18 (5 μM, 3.0×50 mm) using a low pH buffer gradient of 5% to 100% of MeCN in $H_2O$ (0.1% HCOOH) over 2.5 min at 2.2 mL/min for a 3.5 min run (A05). The $^1H$ NMR spectra were recorded on a Bruker UltraShield 500 MHz/54 mm instrument (BZH 43/500/70B, D221/54-3209). The chemical shifts are referenced to solvent peaks which, in $^1H$ NMR, appear at 7.26 ppm for $CDCl_3$, 2.50 ppm for DMSO-$d_6$, and 3.31 ppm for $CD_3OD$.

Synthesis of Sodium [(3S,10R,13R,17R)-17-[(1R)-5-hydroxy-1,5-dimethyl-hexyl]-10,13-dimethyl-2,3,4,7,8,9,11,12,14,15,16,17-dodecahydro-1H-cyclopenta[a]phenanthren-3-yl] sulfate A dry 3-necked flask was charged with pyridine sulfur trioxide complex (12.45 g, 78 mmol), and the solid was suspended in toluene (1.5 L) and acetic anhydride (7.2 mL, 74.5 mmol). The mixture was stirred at 20° C. for 40 min, and pyridine (60 mL, 745 mmol) was added. The mixture was stirred at 20° C. for 20 min. (3S,8S,9S,10R,13R,14S,17R)-17-[(1R)-5-hydroxy-1,5-dimethyl-hexyl]-10,13-dimethyl-2,3,4,7,8,9,11,12,14,15,16,17-dodecahydro-1H-cyclopenta[a]phenanthren-3-ol (30 g, 74.5 mmol) was added in a single portion as a solid. The mixture was stirred at 20° C. for 23 h. Aqueous sodium acetate solution (10 wt %, 123 mL, 149 mmol) was added dropwise with vigorous stirring over 5 min. The resultant mixture was stirred at 20° C. for 1 h. The solvent was pumped out of the reactor, collecting any solids onto a glass frit. ACN (700 mL) was added, and the slurry was stirred vigorously for 3 h. The slurry was pumped out of the reactor onto the same frit, and the remaining solids in the reactor were again suspended in ACN (700 mL) and stirred for 1 h before pumping out of the reactor to the glass frit. The solids in the frit were rinsed with diethyl ether (750 mL) and then suspended in DMF (800 mL). The mixture was stirred for 1 h at 20° C. The suspension was filtered, and the filtrate collected. To the filtrate, with stirring, was added diethyl ether (3.2 L). The resulting solids were collected by vacuum filtration, and the filter cake rinsed with diethyl ether (1 L). The solids were dried under reduced pressure to provide the title compound as a solid (15 g, 40%). $^1H$ NMR (500 MHz, MeOD) δ 5.56-5.32 (m, 1H), 4.17 (tt, J=11.5, 4.8 Hz, 1H), 2.55 (dd, J=4.9, 2.2 Hz, 1H), 2.47-2.29 (m, 1H), 2.14-2.06 (m, 2H), 2.01 (ddd, J=12.4, 7.7, 5.1 Hz, 1H), 1.97-1.85 (m, 2H), 1.73-1.22 (m, 15H), 1.20 (s, 6H), 1.19-1.08 (m, 4H), 1.07 (s, 3H), 1.04-0.95 (m, 1H), 1.00 (d, J=6.5 Hz, 3H), 0.76 (s, 3H); m/z: ES– [M]$^-$ 481.3; LCMS (B05); $t_R$=1.18 m.

Synthesis of Sodium [(3S,10R,13R,17R)-17-[(1R)-5-hydroxy-1,5-dimethyl-hexyl]-10,13-dimethyl-2,3,4,7,8,9,11,12,14,15,16,17-dodecahydro-1H-cyclopenta[a]phenanthren-3-yl] sulfate A dry 3-necked flask was charged with sulfur trioxide pyridine complex (4.74 g, 29.8 mmol). The solid was suspended in toluene (500 mL), and acetic anhydride (2.61 mL, 27.67 mmol) was added in a single portion. The resultant mixture stirred at 23° C. for 1 h. Pyridine (20 mL, 248.4 mmol) was added, and the mixture was stirred at 23° C. for 5 min. (3S,10R,13R,17R)-17-[(1R)-5-hydroxy-1,5-dimethyl-hexyl]-10,13-dimethyl-2,3,4,7,8,9,11,12,14,15,16,17-dodecahydro-1H-cyclopenta[a]phenanthren-3-ol (10 g, 24.83 mmol) was added in a single portion as a solid. The mixture stirred at 23° C. for 23 h. The reaction was diluted with MeOH (2.01 mL, 49.7 mmol) and stirred at 23° C. for 1 h. The suspension was filtered, and the solids washed with toluene (2×200 mL). The solids were collected and dried under high vacuum to provide a solid. The solids were partially dissolved in ACN (600 mL), and sodium iodide (14.9 g, 99.3 mmol) was added. The mixture was stirred at 23° C. for 10 min before being cooled to 0° C. with an ice-bath and stirred for 1.5 h. The suspension was filtered, and the solids washed with cold ACN (2×275 mL) and acetone (2×200 mL). The solids were collected and dried under high vacuum to provide the title compound as a solid (7.24 g, 57%). $^1H$ NMR (500 MHz, MeOD) δ 5.56-5.32 (m, 1H), 4.17 (tt, J=11.5, 4.8 Hz, 1H), 2.55 (dd, J=4.9, 2.2 Hz, 1H), 2.47-2.29 (m, 1H), 2.14-2.06 (m, 2H), 2.01 (ddd, J=12.4, 7.7, 5.1 Hz, 1H), 1.97-1.85 (m, 2H), 1.73-1.22 (m, 15H), 1.20 (s, 6H), 1.19-1.08 (m, 4H), 1.07 (s, 3H), 1.04-0.95 (m, 1H), 1.00 (d, J=6.5 Hz, 3H), 0.76 (s, 3H); m/z: ES– [M]$^-$ 481.3; LCMS (B05); $t_R$=1.18 m.

81

Synthesis of Sodium [(3S,10R,13R,17R)-17-[(1R)-
5-hydroxy-1,5-dimethyl-hexyl]-10,13-dimethyl-2,3,
4,7,8,9,11,12,14,15,16,17-dodecahydro-1H-cyclo-
penta[a]phenanthren-3-yl] sulfate A 15 L jacketed reactor was heated to 60° C. and purged
with nitrogen for 1.5 h. The jacket temperature was set to
30° C. and 2-MeTHF (7 L) was charged. (3S,10R,13R,17R)-
17-[(1R)-5-hydroxy-1,5-dimethyl-hexyl]-10,13-dimethyl-2,
3,4,7,8,9,11,12,14,15,16,17-dodecahydro-1H-cyclopenta[a]
phenanthren-3-ol (495 g, 1.23 mol) was charged, and the
manway/glassware was rinsed with 2-MeTHF (6 L). The
solution was cooled to 25° C., additional 2-MeTHF (1 L)
was added, and sulfur trioxide pyridine complex (234.8 g,
1.47 mol) was added. The mixture was stirred at 28° C. for
24 h. 2-MeTHF (2 L) was added, the mixture was stirred for
a further 16 h, cooled to 20° C. and filtered. The solids were
rinsed with 2-MeTHF (3.5 L). The solids were taken up in
a solution of NaOH (118 g, 2.95 mmol) in MeOH (6 L). The
mixture was stirred at 25° C. for 1 h and then filtered on a
plug of Celite. The filtrate was concentrated to 3.5 L and
diluted with diethyl ether (8 L). The suspension was chilled
to 15° C. and filtered to provide the title compound as a solid
(146.8 g, 24%). The filtrate was concentrated to 1 L and
again mixed with diethyl ether (4 L). The solids were
collected by vacuum filtration to provide the title compound
as a solid (68.5 g, 11%). The Celite was extracted with
MeOH (2 L), which was concentrated to 500 mL and diluted
with diethyl ether (3 L) and the solids were collected by
vacuum filtration to provide the title compound as a solid
(53.3 g, 8.6%). A fourth crop was isolated from the filtrates
(11.88 g, 2%). Total yield: 280.5 g, 45%. $^1$H NMR (500
MHz, MeOD) δ 5.56-5.32 (m, 1H), 4.17 (tt, J=11.5, 4.8 Hz,
1H), 2.55 (dd, J=4.9, 2.2 Hz, 1H), 2.47-2.29 (m, 1H),
2.14-2.06 (m, 2H), 2.01 (ddd, J=12.4, 7.7, 5.1 Hz, 1H),
1.97-1.85 (m, 2H), 1.73-1.22 (m, 15H), 1.20 (s, 6H), 1.19-
1.08 (m, 4H), 1.07 (s, 3H), 1.04-0.95 (m, 1H), 1.00 (d, J=6.5
Hz, 3H), 0.76 (s, 3H); m/z: ES– [M]⁻ 481.3; LCMS (B05);
$t_R$=1.18 m.

Synthesis of Ammonium [(3S,10R,13R,17R)-17-
[(1R)-5-hydroxy-1,5-dimethyl-hexyl]-10,13-dim-
ethyl-2,3,4,7,8,9,11,12,14,15,16,17-dodecahydro-
1H-cyclopenta[a]phenanthren-3-yl] sulfate

82

Sulfur trioxide dimethyl formamide complex (42 mg,
0.273 mmol) was added to a stirred solution of (3S,10R,
13R,17R)-17-(5-hydroxy-1,5-dimethyl-hexyl)-10,13-dim-
ethyl-2,3,4,7,8,9,11,12,14,15,16,17-dodecahydro-1H-cyclo-
penta[a]phenanthren-3-ol (100 mg, 0.25 mmol) in
anhydrous DCM (20 mL) at 0° C. The mixture was stirred
at 0° C. for 5 h, and then the reaction was warmed to 20° C.
The mixture was concentrated under reduced pressure to
afford a crude solid which was purified by column chroma-
tography on silica gel (12 g cartridge) eluting with mixtures
of DCM and MeOH (0-20%) to afford impure title com-
pound. m/z: ES– [M–H]⁻ 481.

Synthesis of Pyridin-1-ium [(3S,8S,9S,10R,13R,
14S,17R)-17-[(1R)-1,5-dimethylhexyl]-10,13-dim-
ethyl-2,3,4,7,8,9,11,12,14,15,16,17-dodecahydro-
1H-cyclopenta[a]phenanthren-3-yl] sulfate In an oven-dried round-bottom flask, sulfur trioxide pyri-
dine complex (4.53 g, 28.5 mmol) was suspended in toluene
(240 mL). Acetic anhydride (2.44 mL) was added, followed
by pyridine (20.8 mL). The reaction was stirred at 23° C. for
1 h, and cholesterol (10 g, 25.9 mmol) was added in a single
portion as a solid. The suspension was stirred at 23° C. for
18 h and, filtered on a glass frit, and the solids rinsed with
toluene (100 mL) followed by hexanes (100 mL). The solids
were suspended in chloroform (400 mL) and filtered on the
same frit. The frit was rinsed with chloroform (200 mL) and
the filtrate collected. The filtrate was diluted to 1.8 L with
hexanes and refrigerated for 1 h. The suspension was
filtered; the solids were rinsed with diethyl ether (100 mL)
and dried under high vacuum to provide the title compound
as a solid (10.06 g, 71%). $^1$H NMR (500 MHz, MeOD) δ
8.89 (dd, J=6.6, 1.4 Hz, 2H), 8.79-8.61 (m, 1H), 8.27-8.05
(m, 2H), 5.38 (d, J=5.3 Hz, 1H), 4.13 (tt, J=11.5, 4.7 Hz,
1H), 2.53 (ddd, J=13.3, 5.0, 2.3 Hz, 1H), 2.43-2.28 (m, 1H),
2.12-2.02 (m, 2H), 2.01-1.94 (m, 1H), 1.94-1.80 (m, 2H),
1.70-0.83 (m, 20H), 1.03 (s, 3H), 0.95 (d, J=6.6 Hz, 3H),
0.88 (dd, J=6.6, 1.9 Hz, 6H), 0.72 (s, 3H); m/z: ES– [M]⁻
465.3; LCMS (B05); $t_R$=1.40 m.

US 12,692,288 B2

83

Synthesis of Pyridin-1-ium [(3S,8S,9S,10R,13R,
14S,17R)-17-[(1R)-1,5-dimethylhexyl]-10,13-dim-
ethyl-2,3,4,7,8,9,11,12,14,15,16,17-dodecahydro-
1H-cyclopenta[a]phenanthren-3-yl] sulfate Cholesterol sulfate pyridinium salt was prepared by add-
ing sulfur trioxide pyridine complex (4.53 g, 28.5 mmol) to
a solution of cholesterol (10 g, 25.9 mmol) in 2-MeTHF
(250 mL) at 30° C. and stirring the mixture for 16 h. The
suspension was then filtered, and the solids rinsed with
2-MeTHF (50 mL) to afford the title compound.

Synthesis of Sodium [(3S,8S,9S,10R,13R,14S,17R)-
17-[(1R)-1,5-dimethylhexyl]-10,13-dimethyl-2,3,4,7,
8,9,11,12,14,15,16,17-dodecahydro-1H-cyclopenta
[a]phenanthren-3-yl] sulfate Chlorosulfonic acid (0.03 mL, 0.45 mmol) was added to
a solution of 2,6-lutidine (0.08 mL, 0.69 mmol) in acetone
(2.5 mL) over molecular sieves. The solution was stirred at
20° C. for 2 min before being cooled to 0° C. A solution of
cholesterol (100 mg, 0.26 mmol) in acetone (5 mL), which
was previously dried over molecular sieves, was added
dropwise. The mixture stirred at 0° C. for 2 h before
warming to 20° C. over 16 h. The mixture was filtered and
the solid was collected. The solid was then suspended in
acetone (10 mL) and aqueous sodium bicarbonate was added
until bubbling subsided. The suspension was filtered and the
solid triturated with MeOH (10 mL) and DCM (10 mL). The
solvent was removed under reduced pressure to afford a
solid. The solid was triturated with ACN (30 mL), filtered,
and the filtrate was lyophilized to afford the title compound
as a solid (7.3 mg, 5.8%). ¹H NMR (500 MHz, DMSO) δ
5.31-5.19 (m, 1H), 4.10 (s, 1H), 3.87-3.78 (m, 1H), 2.42-
2.31 (m, 1H), 2.13 (dd, J=14.5, 7.6 Hz, 1H), 2.02-1.69 (m,
5H), 1.62-0.95 (m, 20H), 0.94 (s, 3H), 0.89 (d, J=6.5 Hz,
4H), 0.84 (dd, J=6.6, 2.5 Hz, 7H), 0.65 (s, 3H).

84

Synthesis of Ammonium [(3S,5S,8R,9S,10S,13R,
14S,17R)-17-[(1R)-1,5-dimethylhexyl]-10,13-dim-
ethyl-2,3,4,5,6,7,8,9,11,12,14,15,16,17-tetradeca-
hydro-1H-cyclopenta[a]phenanthren-3-yl] sulfate Sulfur trioxide pyridine complex (300 mg, 1.88 mmol)
was added to a solution of cholestanol (300 mg, 0.772
mmol) in pyridine (5.00 mL), and the suspension was stirred
at 20° C. for 16 h. The residue was purified by silica gel
chromatography (24 g cartridge) with MeOH (5% NH₄OH)
in DCM eluting with mixtures of DCM and MeOH (0-30%)
to afford the title compound as a solid (314 mg, 84%). ¹H
NMR (500 MHz, DMSO-d₆) δ 7.08 (s, 4H), 3.97-3.86 (m,
1H), 1.91 (dd, J=12.5, 3.5 Hz, 1H), 1.86-1.71 (m, 2H),
1.69-1.55 (m, 3H), 1.55-1.41 (m, 3H), 1.38-1.25 (m, 5H),
1.25-0.90 (m, 15H), 0.88 (d, J=6.6 Hz, 4H), 0.84 (dd, J=6.6,
2.4 Hz, 7H), 0.74 (s, 3H), 0.62 (s, 3H); m/z: ES [M−NH₄]⁻
467.3; HPLC (BEH Ambicarb/ACN 5-100%) $t_R$=7.48 min.

Synthesis of Ammonium [(3R,8S,9S,10R,13R,14S,
17R)-17-[(1R)-1,5-dimethylhexyl]-10,13-dimethyl-
2,3,4,7,8,9,11,12,14,15,16,17-dodecahydro-1H-cy-
clopenta[a]phenanthren-3-yl] sulfate Sulfur trioxide pyridine complex (206 mg, 1.29 mmol)
was added to a solution of (3R,8S,9S,10R,13R,14S,17R)-
17-[(1R)-1,5-dimethylhexyl]-10,13-dimethyl-2,3,4,7,8,9,
11,12,14,15,16,17-dodecahydro-1H-cyclopenta[a]
phenanthren-3-ol (200 mg, 0.517 mmol) in pyridine (5.00
mL). The suspension was stirred at 20° C. for 16 h, then
concentrated under reduced pressure. The residue was puri-
fied by silica gel chromatography (24.0 g cartridge) eluting
with mixtures of DCM and 5% NH₄OH in MeOH (0-30%)
to afford the title compound as a solid (160 mg, 64%). ¹H
NMR (500 MHz, DMSO) δ 7.07 (s, 4H), 5.18-5.14 (m, 1H),
4.32-4.27 (m, 1H), 2.40-2.29 (m, 1H), 2.16 (dt, J=14.9, 2.4
Hz, 1H), 2.01-1.72 (m, 4H), 1.60-0.96 (m, 22H), 0.94 (s,
3H), 0.90 (d, J=6.5 Hz, 3H), 0.84 (dd, J=6.6, 2.4 Hz, 6H),
0.65 (s, 3H); m/z: ES [M−NH₄]⁻ 465.6; HPLC (BEH
AmForm/ACN 5-100%) $t_R$=2.76 min.

Synthesis of Pyridinium [(3S,8S,9S,10R,13R,14S, 17R)-17-[(1R)-5-hydroxy-1,5-dimethyl-hexyl]-10, 13-dimethyl-2,3,4,7,8,9,11,12,14,15,16,17-dodeca-hydro-1H-cyclopenta[a]phenanthren-3-yl] sulfate Acetic anhydride (0.0704 mL, 0.745 mmol) was added to a suspension of sulfur trioxide pyridine complex (125 mg, 0.782 mmol) in anhydrous toluene (15.0 mL). The suspension was stirred at 20° C. for 40 min, and pyridine (0.600 mL) was added. The suspension was stirred at 20° C. for 20 min. (3S,8S,9S,10R,13R,14S,17R)-17-[(1R)-5-hydroxy-1, 5-dimethyl-hexyl]-10,13-dimethyl-2,3,4,7,8,9,11,12,14,15, 16,17-dodecahydro-1H-cyclopenta[a]phenanthren-3-ol (300 mg, 0.745 mmol) was added in a single portion as a solid. The suspension was stirred at 20° C. for 20 h. The mixture was filtered on a glass frit to afford title compound as a solid (329 mg, 92% purity, 72% yield). $^1$H NMR (500 MHz, DMSO-d$_6$) δ 8.99-8.88 (m, 2H), 8.65-8.53 (m, 1H), 8.13-7.97 (m, 2H), 5.30-5.20 (m, 1H), 3.93-3.71 (m, 1H), 2.41-2.32 (m, 1H), 2.18-2.08 (m, 1H), 2.02-1.71 (m, 5H), 1.59-0.95 (m, 20H), 1.05 (s, 6H), 0.94 (s, 3H), 0.90 (d, J=6.4 Hz, 3H), 0.65 (s, 3H); m/z ES$^+$ [M+H]$^+$ 481.32; HPLC (DUR B) t$_R$=1.36 min.

Synthesis of 3β-25-hydroxycholest-5-ene sulfate (1, as sodium salt)

-continued

NaOH, ACN

Preparation of 3β-25-hydroxycholest-5-ene sulfate—Route 1

3β,25-dihydroxycholest-5-ene (4.6 g, 0.011 mol) and triethylamine (1.7 ml, 0.023 mol) were suspended in pyridine (57 ml) and heated to 50° C. The sulfur trioxide trimethylamine complex (3.2 g, 0.023 mol) was added and the mixture agitated for 24 hours. A further charge of sulfur trioxide trimethylamine complex (0.77 g, 0.006 mol) was made and the mixture agitated for an additional 4 hours. With jacket at 50° C., the reaction mixture was distilled to −20% of initial volume. The residue was purified by silica gel chromatography (110 g), eluting with an ethyl acetate/methanol/triethylamine (90/9/1 v/v) mixture; fractions were analyzed by TLC (4:1 methylene chloride:methanol) using a phosphomolybdic acid stain. Fractions containing the 3- and 25-sulfate regioisomers were combined and evaporated (bath temp <35° C.). The residue (4.2 g, 0.0072 mol) was slurried in acetonitrile (25 g), treated with 1 N sodium hydroxide (7.2 ml, diluted from 30% sodium hydroxide solution) for 1 hour, and then filtered. Solids were rinsed through with aceotnitrile (25 g) and dried to a constant weight (2.77 g). The solids, containing a mixture of 3- and 25-sodium sulfate salts (2.77 g), were triturated with ethanol (27.7 g, 10S) at 50° C. for 1 hour and then filtered at 5° C. The isolated solids were dried to a constant weight (1.2 g). The solids (1.2 g) were suspended in 6:1 acetonitrile/water (10 S) at 30° C. for 30 minutes and then filtered. Filtration required about 40 minutes. Solids were dried to a constant weight (0.86 g) and analyzed.

Preparation of 3β-25-hydroxycholest-5-ene
sulfate—Route 2—Excess sulfating agent An excess of sulfur trioxide trimethylamine complex was
used to drive the reaction toward formation of the disulfate.
The 3-hydroxy group of 3β,25-dihydroxycholest-5-ene is
about 6 times more reactive towards sulfation than the
25-hydroxyl. Providing excess sulfating agent and allowing
the reaction to proceed to high conversion will provide
monosulfate of higher regioisomeric purity. This result was
observed during this synthesis. A solution of 3β, 25-dihy-
droxycholest-5-ene (4.1 g) in pyridine (75 ml) was vacuum
distilled to reduce the volume to 50 ml. This was performed
to remove isopropanol (from the recrystallization of the diol)
and any moisture present. Triethylamine (2 equivalents) and
then a total of 1.75 equivalents of sulfur trioxide trimethyl-
amine complex was added in portions (1.0, 0.5 and 0.25
equivalents) to the reaction at 50° C. cover a period of 18
hours and the reaction was allowed run for a total of 43
hours. The reaction mixture was concentrated by vacuum
distillation and the residue was absorbed onto $SiO_2$ (10 g).
The loaded $SiO_2$ was placed on a $SiO_2$ column and eluted with 2-50% methanol/ethyl acetate/1% triethylamine. The
appropriate fractions from the column were combined and
evaporated to yield the disulfate (3.1 g, 39.7%) and the
monosulfate (2.6 g, 44.7%). The monosulfate was obtained
as a 22:1 mixture of the 3-sulfate and 25-sulfate. The solids
were suspended in acetonitrile (25 g), treated with 1 N
sodium hydroxide (4.44 ml), and then filtered. A thick gel
formed, which was difficult to manipulate and was not
filtered. The product was a suspension in acetonitrile/water.
The solvents were removed by rotary evaporation at 40° C.
and the residue was dried in a vacuum oven at 40° C.
Trituration of the solid with acetone yielded a white solid:
1.27 g, 24.9%. This product showed only the 3β-sulfated
product, but was contaminated with peaks at RRT 8.18
(unknown, 2.0%), RRT 15.17 (diol, 2.2%) and RRT 16.70
(unknown, 1.8%).

Preparatory Scale Synthesis

Synthesis of 3β-25-hydroxycholest-5-ene sulfate (1,
as sodium salt)

34

34.1

-continued 1
3β-25dihydroxycholesteral sulfate

A 2 L, three-necked, round-bottomed flask with an over-head stirrer was charged with 3β,25-dihydroxycholest-5-ene (34) (30 g, 74.5 mmol) and dry pyridine (500 mL, Sigma-Aldrich, cat. #270970-1L, lot #SHBC6287V). Sulfur triox-ide-trimethylamine complex (12.2 g, 89.4 mmol, Sigma-Aldrich, cat. #135879-100G, lot #MKBH5585V) was added in one portion. The suspension was stirred at room tempera-ture overnight. The reaction mixture was concentrated and the residue was purified by column chromatography to give 25.9 g (59%) of white solid as the triethylamine salt (HPLC: 98.6% purity). To a suspension of triethylamine salt 34.1 (64 g, 110.1 mmol) in ACN (1 L) was added 1 N NaOH (110 mL, 110.1 mmol, NaOH, Fisher, cat. #S318-3, lot #034906), and the mixture was stirred for 1 h at room temperature. The solid was filtered, washed with ACN (1 L), and dried under vacuum ($P_2O_5$) overnight, yield: 51.5 g, 93% (HPLC: 98.6% purity).

After overnight stirring, the reaction was a gel-like mix-ture. TLC showed the expected product as the major spot (TLC: 20% MeOH in DCM, $R_f$=0.4), with both the starting material ($R_f$>0.9) and 3b-25-hydroxycholesterol disulfate ($R_f$<0.1) as minor spots. Silica gel (1 kg, Sorbent Technolo-gies, cat. #40930-2.5 kg) was packed to form a column of dimension 10 cm×42 cm. The column equilibration was accomplished with 1% triethylamine ($Et_3N$, Fisher, cat #04885-4, lot #062833) in DCM (2.8 L). The crude residue was dissolved in DCM (200 mL) and $Et_3N$ (20 mL), which was directly loaded into the column. Triethylamine was used at this stage to avoid decomposition of the product and of the disulfate (which forms an olefin that is then very difficult to remove from the product). Initial elution was DCM (1% $Et_3N$) (2 L), followed by 1% MeOH in DCM (1% $Et_3N$)(1 L), 2% MeOH in DCM (1% $Et_3N$)((3 L), 5% MeOH in DCM (1% $Et_3N$)((1 L). The product began to elute in 2% MeOH in $CH_2Cl_2$ (1% $Et_3N$). The collected fractions were concentrated via rotary evaporation below 36° C. (if the temperature is higher than 45° C., decomposition of the product in the presence of MeOH is observed). Both TLC and NMR were checked for the selected fractions. HPLC (Zorbax SB-18, 4.6×150 mm, 5 μm, 202 nm, flow rate 0.8 mL/min): Solvent A: MeOH/5% ACN/7.4 mM $NH_4OAc$; Solvent B: $H_2O$/5% ACN/7.4 mM $NH_4OAc$. Gradient 75% A and 25% B to 100% A. Product: 98.6% purity; 1.4% (starting material 34). HPLC: Durashell C18 (Agela Tech-nologies, 4.6×50 mm, 3 mm, 100 Å); Solvent A: MeOH/5% ACN/7.4 mM $NH_4OAc$; Solvent B: $H_2O$/5% ACN/7.4 mM $NH_4OAc$. Product: 98.6% purity; 1.4% (starting material 34).

Large Scale Synthesis

Synthesis of 313-25-hydroxycholest-5-ene sulfate
(1, as sodium salt)

34

1. $SO_3$—$NMe_3$,
   pyr
   chromatography

NaOH,
ACN

-continued

1

Summary of Kilogram-Scale Preparation

3β,25-dihydroxycholest-5-ene (34) (2.6 kg) and pyridine (39.2 kg) was combined and the mixture heated to 40° C. with agitation in two 50 L reactors. Sulfur trioxide-trimethylamine (1.1 kg) was added to the mixture and stirred at 40° C. for 6-12 hours until the reaction was complete. The mixture was concentrated to minimum stir volume under vacuum distillation and then diluted with methylene chloride and triethylamine.

The crude reaction mixture in methylene chloride was loaded onto a 2.33 ft³ stainless steel column (C-105) packed with silican gel and eluted with methylene chloride (containing 1% methanol and 1% triethylamine). Fractions containing undesired product were collected in waste drums. Fractions containing desired product are collected and concentrated in the reactor.

Acetonitrile, water and sodium hydroxide were added to the reactor containing the desired product and the mixture was agitated until the reaction was deemed complete. The resulting slurry was cooled to 10-15° C. and filtered to isolate compound 1. The cake of isolated compound 1 was washed with acetonitrile and then dried at 40° C. under vacuum until a constant weight was achieved.

The solid was filtered, washed with acetonitrile (1 L), and dried under vacuum (P₂O₅) overnight, yield: 51.5 g, 93% (HPLC: 98.6% purity).

Discussion

Analysis of the reaction mixture by HPLC after 6 h showed 44.1% remaining starting material. The reaction was considered complete and distilled under vacuum to a minimum stir volume (Step 5.3). To the resulting thick residue were added methylene chloride and triethylamine, and the solution was transferred to a clean 5 gallon glass carboy. Thick solids precipitated in the glass carboy after holding the solution overnight. The solids were filtered away using the benchtop filter. Approximately ⅓ of the clear filtrate was charged to the top of a C-105 column. The silica in the C-105 column was previously flushed with ethyl acetate and methanol, and then equilibrated with 1% triethylamine in methylene chloride eluent.

Once the crude solution was loaded to the top of the column, eluent was charged to maintain a pressure of ~10 psi. Eluent was sampled as it exited the column every 10-15 minutes. Pyridine and 3β,25-dihydroxycholest-5-ene were present in the first two samples, but the 3β-triethylamine salt and 25-sulfate regioisomer were detected in the third sample in addition to pyridine and 3β,25-dihydroxycholest-5-ene. Since minimal separation occurred, all remaining material was eluted from the column using the polar eluent (1% MeOH, 1% NEt3, and 98% DCM). The filtrate was concentrated and combined with the remaining two-thirds of the crude solution from the carboy. After distillation, the crude solution was transferred to a clean carboy. The eluent exiting the column was analyzed and contained 1.7% methanol (¹H NMR area %). The column was equilibrated with eluent (1% triethylamine in methylene chloride) and analyzed for methanol (0.25% methanol, ¹H NMR area %). Solids began to form in the carboy during this time. The slurry was filtered, and the filtrate was collected in a clean carboy.

Approximately one-third of the crude solution was loaded onto a second C-105 column. Eluent was charged to the column to maintain <5 psi. Analysis of the eluent leaving the column by thin layer chromatography (TLC) showed that separation was taking place. Once 3β, 25-dihydroxycholest-5-ene was no longer detected by TLC, the eluent was analyzed by ¹H NMR to ensure that the 3β-triethylamine salt was separated from the 25-sulfate regioisomer. A sample was removed from the eluent containing drum, and the purity of the 3β-triethylamine salt was 85% with 15% 25-sulfate regioisomer present (¹H NMR). An HPLC weight percentage assay showed that 127 g of 3β-triethylamine salt/25-sulfate regioisomer was collected in the drum (85% 3β-triethylamine salt). The purified material was set aside and the remaining two-thirds of the crude solution was purified by chromatography. The silica in the C-105 column was flushed with methanol and then equilibrated with 1% triethylamine in methylene chloride (0.2% methanol by ¹H NMR area % in the eluent after regeneration).

The solids that precipitated from the carboy were analyzed by ¹H NMR and identified as the quaternary ammonium salt produced from the reaction of methylene chloride with triethylamine (from the SO₃NMe₃ reagent) and methylene chloride with triethylamine. The methylene chloride-triethylamine complex was separated by filtration, while methylene chloride-triethylamine complex was formed in the chromatography. Formation of the salt occurred under ambient conditions and was rapid in certain instances in a pressurized environment. The establishment of an equilibrium in which the triethylammonium moiety of the 3β-triethylamine salt may be exchanging for the quaternary ammonium salt to give the quaternary ammonium complex and the triethylamine hydrochloride. Equilibrium favors the formation of the quaternary ammonium complex since there is more methylene chloride-triethylamine complex present. Triethylamine hydrochloride was isolated and characterized.

34

1. SO₃—NMe₃, pyr
chromatography

NaOH,
ACN

1

NEt₃ + CH₂Cl₂ ⟶

+ NEt₃HCl

Of the remaining two-thirds of the crude mixture in the carboy, one-third was subjected to chromatography on a fourth column. Pressure was maintained at 0-1 psi during the entire purification. Separation of 3β-triethylamine salt from the 25-sulfate regioisomer was successful: The purity of the 3β-triethylamine salt in the drum was 99.79% by HPLC. Approximately 0.050 kg of 34.1 was isolated from the column (HPLC weight percent assay). The silica gel was cleaned with methanol and regenerated with 1% triethylamine in methylene chloride. The amount of methanol present after regeneration was 0.44% ('H NMR area %). No separation occurred for this column. No further purifications were done with the material from the fourth column. Eluent from the third column (~50 g of the 3β-triethylamine salt)

was subjected to the cation exchange beginning with a solvent swap to acetonitrile. After the addition of acetonitrile, water, and 30% sodium hydroxide, the slurry was agitated and then held overnight. Solids were present in the reactor after the post-stir. The mixture was cooled and filtered using a new 8.5" benchtop filter. The cake was washed with fresh acetonitrile and dried. A sample was analyzed by ¹H NMR and peaks consistent with a quaternary ammonium salt were present in the spectrum. The 25-sulfate regioisomer was present by HPLC.

Eluent from the second column was concentrated under vacuum and dried to a constant weight. Analysis of the yellow powder (540 g) by ¹H NMR showed a ratio (3:1) of the methylene chloride-triethylamine quaternary ammonium salt to the monosulfate compound. All of the crude material (540 g) was charged to a 3 L jacketed reactor. Acetonitrile (1400 g) was charged, and the slurry was heated to 50±5° C. for 30 min. The slurry was cooled to 26° C. and then filtered. The wet cake was analyzed and the ratio of 3β-triethylamine salt/25-sulfate regioisomer to quaternary ammonium salt was ~1:1. The purified solids and fresh acetonitrile (1400 g) were charged back to the reactor. Water (200 g) was charged after 45 min, agitated for 15 min, and then filtered. The granular powder was dried in a vacuum oven at 40° C. overnight. The filtrate was concentrated to dryness, and the residue was combined with the dried material and both were charged to a 3 L reactor. Acetonitrile (1500 g), 1 N sodium hydroxide (600 g), and 30% sodium hydroxide (40 g) were sequentially charged to the reactor. The slurry was agitated for 48 hours and then filtered at ambient temperature. The cake was dried to a constant weight (173 g) and analyzed by HPLC.

Purification to Separate the 25-Sulfate Regioisomer from Compound 1

Several solvents were explored to purge the 25-sulfate sodium salt from compound 1. No solids were recovered after dissolving impure compound 1 in polar solvents and then charging anti-solvents (Entries 1 and 2, Table 13). Minimal solids were formed after dissolving the material in methanol and then adding acetonitrile (Entry 3, Table 13). Using 2-propanol (Entry 4, Tabl 13) and a mixture of methanol and water resulted in a form change, which caused the material to become a thick paste that would not transfer or filter. Trituration of impure compound 1 with ethanol at 40-50° C. was sufficient to purge the majority of the 25-sulfate regioisomer (Entry 6, Table 13). A mixture of compound 1 (1 g) and ethanol (10 mL) was heated to reflux, cooled, and filtered. The isolated material (55% recovery) was 99.6% pure with the 25-sulfate and 3β,25-dihydroxycholest-5-ene products reduced to 0.1% and 0.3%, respectively.

SO$_3$NMe$_3$ complex. Following the final charge of the SO$_3$NMe$_3$ complex, the vial was allowed to stir at 50° C. for a total of 24 h. (Table 14). Approximately 1.75 equivalents of SO$_3$NMe$_3$ complex were sufficient to consume 86.6% of starting material 3β,25-dihydroxycholest-5-ene (Sample 7, Table 14). 3β,25-dihydroxycholest-5-ene was completely consumed after 2.5 equivalents of SO$_3$NMe$_3$ complex were added. Formation of the bis-sulfate will out-compete mono-sulfation of 3β,25-dihydroxycholest-5-ene as the reaction progresses. The 3β-triethylamine salt was completely converted to the bis-sulfate after 24 h.

TABLE 14

| | Equivalents of sulfur trioxide-trimethylamine complex | | | |
|---|---|---|---|---|
| Sample | Equvalients of SO$_3$NMe$_3$ | 3β-triethylamine salt | 3β, 25-dihydroxycholest-5-ene | Bis-sulfate |
| 1 | 0.25 | 18.0 | 75.9 | 6.1 |
| 2 | 0.5 | 28.6 | 71.4 | 0.0 |
| 3 | 0.75 | 39.8 | 60.2 | 0.0 |
| 4 | 1.00 | 48.6 | 46.7 | 4.7 |
| 5 | 1.25 | 53.1 | 39.4 | 7.4 |
| 6 | 1.50 | 58.4 | 28.6 | 12.9 |
| 7 | 1.75 | 68.1 | 13.4 | 18.5 |
| 8 | 2.00 | 60.9 | 13.1 | 26.0 |
| 9 | 2.30 | 58.3 | 7.2 | 34.4 |
| 10 | 2.60 | 49.6 | 1.0 | 49.4 |
| 11 | 2.90 | 46.6 | 0.0 | 53.4 |
| 12 | 3.20 | 37.7 | 0.0 | 62.3 |
| 13 | 3.50 | 32.3 | 0.0 | 67.7 |

One-Hundred Gram Scale Synthesis of 3β-25-Hydroxycholest-5-Ene Sulfate (1, as Sodium Salt)

A slurry of 3β,25-dihydroxycholest-5-ene (100 g, 1.0 S) and triethylamine (0.5 S) in pyridine (15.6 S) was heated to 50° C. The SO$_3$NMe$_3$ complex (1.75 equivalents, 0.6 S) was

TABLE 13

| | | Trituration/recrystallization of Compound 1 | | | | |
|---|---|---|---|---|---|---|
| Sample | Solvent | Unpurified Compound 1 (g) | Compound 1 Purity | 25-sulfate regioisomer | 3β, 25-dihydroxycholest-5-ene | Comment |
| 1 | Ethyl acetate/methanol | 0.5 | N/A | N/A | N/A | No Solids |
| 2 | Dimethyl sulfoxide/isopropanol | 0.5 | N/A | N/A | N/A | No Solid |
| 3 | Methanol/acetonitrile | 0.1 | N/A | N/A | N/A | Minimal Solids |
| 4 | Isopropanol | 0.1 | N/A | N/A | N/A | Gel/paste |
| 5 | Methanol/water | 0.5 | 96.3 | 1.8 | 1.9 | Gel/paste |
| 6 | Ethanol | 0.1 | 97.0 | 0.4 | 2.6 | Trituration |
| 7 | ethanol | 1.0 | 99.6 | 0.1 | 0.3 | 55% recovery |

Purification of the 3β-Triethylamine Salt

The 3β-triethylamine salt was purified to eliminate methylene chloride due to reactivity with trimethylamine and triethylamine. Purification was achieved using an isocratic solvent system that includes 90% ethyl acetate, 9% methanol and 1% triethylamine.

Optimization of SO$_3$NMe$_3$ Equivalents

The amount of added SO$_3$NMe$_3$ complex needed to either completely consume 3β,25-dihydroxycholest-5-ene or arrive at a point at which the bis-sulfate and unreacted starting material byproducts were minimal was determined. A solution of 3β,25-dihydroxycholest-5-ene (0.5 g, 1.0 S) in pyridine (18.6 S) containing triethyl amine (0.5 S) was heated to 50° C. A sample was removed from the reaction every 30 min, which was followed by the addition of the charged in one portion. The mixture was agitated for 5 hours and then analyzed for reaction completion by HPLC (Sample 1-3β-triethylamine salt/25-sulfate regioisomer (67.1%); 3β,25-dihydroxycholest-5-ene (12.2%); bis-sulfate (20.8%)). The jacket was set to 70° C. and the reaction was concentrated to <20% of the initial volume. A sample was removed and analyzed by HPLC for stability (Sample 2-3β-triethylamine salt/25-sulfate regioisomer (60.5%); 3β,25-dihydroxycholest-5-ene (10.0%); bis-sulfate (29.5%)). The amount of monosulfate decreased from 67.1% to 60.5% during the distillation, while the amount of bisulfate increased ~9%. The amount of 3β,25-dihydroxycholest-5-ene did not decrease much during the distillation.

Solids were present in the reactor following a 48 h post stir, and the addition of methanol (0.5 S) did not dissolve the solids. The crude material (300 g) was subjected to purification by silica gel chromatography eluting with 90% ethyl acetate, 9% methanol, and 1% triethylamine. Silica gel (2.4 kg) was slurried in the eluent and packed to form a 5.25"× 28" column. The crude mixture was transferred to the column, and the purification was carried on over three days. The eluent was collected in 1 L fractions. Fractions 1-7 contained no material detected by TLC; Fractions 8-11 contained pyridine and 3β,25-dihydroxycholest-5-ene; Fractions 12-20 contained no material detected by TLC; Fractions 21-22 contained an undetermined compound and Fractions 23-59 contained 3β-triethylamine salt/25-sulfate regioisomer.

Approximately 82 g of 3β-triethylamine salt/25-sulfate regioisomer (56.5% yield) was isolated after the column determined by weight percentage analysis. After chromatography, the eluent containing a mixture of 3β-triethylamine salt/25-sulfate regioisomer was concentrated to a slurry and transferred to a 2 liter reactor. The solvent was swapped to acetonitrile, the slurry was cooled to 10° C., and 1 N sodium hydroxide (1.8S, 1 equivalent based on 82 g of 3β-triethylamine salt/25-sulfate regioisomer) was charged over 10 minutes. The slurry was agitated for 1 hour and then filtered. The filtration was very fast, requiring <5 minutes. The solids were dried at 40° C. under vacuum to a constant weight (70 g, 99% yield for the cation exchange). A sample was analyzed by HPLC (Sample 1, Table 15) which indicated that the 25-sulfate regioisomer was present at 5.1%. The white powder (70 g) was transferred to a 2 liter reactor and slurried with ethanol (700 g) at 50° C. for 1 hour. A form change was observed after 30 minutes of stirring by the thickening of the slurry mixture. The slurry was cooled to 10° C., stirred for 1 hour, and then filtered at 10° C. The reactor was rinsed with ethanol (170 g), cooled to 10° C. and then transferred to the filter as a cake wash. The solids were dried to a constant weight (64.6 g, 92.3% recovery) and analyzed by HPLC (Sample 2, Table 15). After trituration, the purity of compound 1 improved to 97.4%, but the 25-sulfate regioisomer was 1.6%. Impure compound 1 (64.6 g, 1.0 S) was slurried in ethanol (581 g, 9 S) at 55° C. for 1.5 hours. The slurry was cooled to 10° C. and then filtered. The reactor and cake were rinsed with ethanol (84 g) at 10° C., and the resulting solid was dried at 40° C. under vacuum to a constant weight (60.4 g, ethanol present at 5.9%, 87.9% recovery).

A sample of compound 1 following ethanol trituration was analyzed by HPLC (Sample 3, Table 15). The 25-sulfate regioisomer was purged, but the amount of unknown 1 increased to 0.9%. The purified material (56.8 g) was slurried in acetonitrile (5 S) and water (0.9 S) at 30° C. for 30 minutes in a 1 liter reactor. The slurry formed stiff peaks during this time, but the paste was easily transferred to the filtration setup using an FMI pump. The reactor and cake were rinsed with fresh acetonitrile (30 g), and the material was dried to a constant weight (54.5 g, 90.2% recovery). Analysis by $^1$H NMR showed that ethanol was absent, but water was present at 1.2% by weight. The purity of the final material improved to ≥99% (Sample 4, Table 15). The unknown impurities at RRT 1.68 and 1.85 were present at 0.6% and 0.2%, respectively. Taking into account the residual water, the final isolated yield of compound 1 in the 100 g demonstration run was 43.2%.

TABLE 15

| | Purification of Crude Compound 1 | | | | |
| --- | --- | --- | --- | --- | --- |
| Sample | 25-sulfate regioisomer (%) RRT 0.78 | 3β-triethylamine salt (%) RRT 1.00 | Unknown 1 (%) RRT 1.68 | Unknown 2 (%) RRT 1.85 | Unknown 3 (%) RRT 1.99 |
| 1 | 5.1 | 93.1 | 0.9 | 0.6 | 0.3 |
| 2 | 1.6 | 97.4 | 0.6 | 0.4 | ND |
| 3 | ND | 98.9 | 0.9 | 0.2 | ND |
| 4 | ND | 99.2 | 0.6 | 0.2 | ND |

Azeotropic Removal of Water from 3β,25-dihydroxycholest-5-ene

A slurry of 3β,25-dihydroxycholest-5-ene (5 g, 1.0 S) and pyridine (15.6S, 0.016% water, Entry 1, Table 16) was heated to 50° C. A sample of the reaction was removed for water content analysis (0.29%, Entry 2, Table 16). The reaction volume was reduced 50% and sampled for water content (0.042%, Entry 3, Table 16). The amount of pyridine that was collected in the distillate (39 g) was replaced with fresh pyridine in the reactor and sampled again for water (0.027%, Entry 4, Table 16). Once the internal temperature reached 50° C., triethylamine (0.5 S) and SO₃NMe₃ (0.6 S) were charged to the reactor. The thin white slurry became a clear solution within 15 minutes, and the reaction was agitated at 50° C. A sample was removed at 2 hours and 3 hours for IPC analysis (Entries 1 and 2, Table 17). Only 7.1% 3β,25-dihydroxycholest-5-ene remained after 2 h. Azeotropically removing the water prior to the addition of SO₃NMe₃ improves the consumption of starting material.

TABLE 16

| | Water content analysis | |
| --- | --- | --- |
| Sample | Comment | % Water |
| 1 | Pyridine solvent | 0.016 |
| 2 | Reaction solution before pyridine distillation | 0.285 |
| 3 | Reaction solution after pyridine distillation | 0.042 |
| 4 | Reaction solution after addition of pyridine | 0.027 |

TABLE 17

| | Reaction completion profile by HPLC | | |
| --- | --- | --- | --- |
| Sample | 25-sulfate regioisomer (%) | 3β-triethylamine salt/25-sulfate regioisomer (%) | 3β, 25-dihydroxycholest-5-ene (%) |
| 1 | 30.8 | 62.2 | 7.1 |
| 2 | 38.9 | 55.6 | 5.6 |

Ethanol Trituration of Crude Compound 1

Crude Compound 1

1. Ethanol
   trituration
2. Water,
   ACN

Purified Compound 1

Crude compound 1 was suspended in ethanol and heated to 55° C. and stirred for 1 hour. The slurry mixture is cooled, filtered and washed with ethanol. The resulting cake is dried overnight at 50° C. The cake was charged back into the reactor and suspended in acetonitrile and water. The mixture is heated to 30° C. and stirred for 1 hour. The mixture is then cooled to 15° C., filtered and washed with acetonitrile and water (90:10). The resulting cake is dried for not longer than 24 hours at 50° C. until a constant weight is achieved. Impurity content in purified compound 1 was determined by HPLC. (RRT 0.67<0.05%; RRT 0.77<0.05%; RRT 0.79<0.05%; RRT 0.95<0.05%; RRT 1.13<0.05%; RRT 1.22<0.05%; RRT 1.31<0.05%; RRT 1.95=0.09%; RRT 2.09<0.05%; RRT 2.67<0.05%; RRT 2.75=0.05%; RRT 3.04<0.05%; RRT 3.23=0.09%; RRT 3.64=0.3%; RRT 5.00<0.05%; Total impurities=1.1%.

Identification of Byproducts from Sulfating 25-hydroxy-(3β)-cholest-5-en-3-ol to produce 25-hydroxy-(3β)-cholest-5-en-3-sulfate A composition of 25-hydroxy-(3β)-cholest-5-en-3-ol was sulfated with a sulfur-trioxide pyridine complex in toluene at 23° C. for 1 h to produce 25-hydroxy-(3β)-cholest-5-en-3-sulfate. Compounds formed in a reaction mixture when preparing the 25-hydroxy-(3β)-cholest-5-en-3-sulfate product were analyzed by high performance liquid chromatography. Tables 13 and 14 provide the HPLC chromatography conditions. Table 15 lists retention times of compounds identified as being formed in the reaction mixture when sulfating 25-hydroxy-(3β)-cholest-5-en-3-ol with a sulfur-trioxide pyridine complex.

TABLE 17

| Chromatographic Conditions | |
|---|---|
| Column | Aglient Zorbax Eclipse XDB-C8, 3.5 μm (4.6 × 150) mm |
| Mobile Phase A | 2.5 mM sodium phosphate, pH 2.1 with 0.2% SDS |
| Mobile Phase B | 10:85:5 MPA:ACN:MeOH |
| Detection | Impurities and calculated purity: 205 nm; Assay: 220 nm |
| Column Temperature | 45° C. |
| Injection Volume | 25.0 μL |
| Flow Rate | 1.0 mL/min |
| Acquisition Time | 50.0 minutes (including 5.0 min. re-equilibration) |

TABLE 18

| Chromatographic Conditions - Gradient | | |
|---|---|---|
| Time (minutes) | % A | % B |
| 0.0 | 62 | 38 |
| 35 | 0 | 100 |
| 45 | 0 | 100 |
| 45.1 | 62 | 38 |
| 50.0 | 62 | 38 |

TABLE 19

| Retention Times | |
|---|---|
| Compound | Retention Time (min) |
| Pyridine | 3.2 |
| 25-sulfated cholesterol | 6.6 |
| 25-hydroxy-(3β)-cholest-5-en-3-sulfate | 7.7 |
| Unknown Byproduct #1 | 18.3 |
| 25-hydroxy-(3β)-cholest-5-en-3-ol | 26.5 |
| Unknown Byproduct #2 | 37.7 |

Determining Purity of Sulfur Trioxide Pyridine Sulfating Agent

Proton nuclear magnetic resonance spectroscopy ($^1$H-NMR) was conducted on samples of sulfur trioxide pyridine in a deuterated solvent. Sulfur trioxide pyridine is a colorless solid that can degrade due to the presence of moisture, which can impact the overall yield and reproducibility of sulfating 25-hydroxy-(3β)-cholest-5-en-3-ol. A sample of sulfur trioxide pyridine from three lots (A-C) was dissolved in deuterated acetone (($CD_3)_2CO$) and proton NMR spectra were recorded using a 500 MHz Bruker spectrometer (FIG. 57). An enhancement of the region between 8.1 and 9.3 ppm in the NMR spectra is shown in FIGS. 58A-58C. The NMR spectrum of lot A in FIG. 58A exhibits a smaller set of peaks at 9.25 ppm than the NMR spectrum of lots B and C in FIGS. 58B and 58C, respectively. Based on the integrated peak at 9.25 ppm in each spectrum, an impurity level of 21% was calculated for the sulfating agent of lot A (FIG. 58A), an impurity level of 33% was calculated for the sulfating agent of lot B (FIG. 58B) and an impurity level of 36% was calculated for the sulfating agent of lot C (FIG. 58C).

Process Parameters for Sulfating 25-hydroxy-(3β)-cholest-5-en-3-ol

A sulfation reaction study to minimize and control the formation of bis-sulfated product 5-cholesten-3β-25-diol-disulfate was conducted.

Sulfation with Particles of 25-Hydroxy-(3β)-Cholest-5-En-3-Ol in Reaction Mixture During the sulfation reaction, it was observed that the 25-hydroxy-(3β)-cholest-5-en-3-sulfate organic cationic salt precipitates as a gel-like solid during the reaction. Some of this colloidal material may be solubilized in the reaction mixture due to its particle size. To minimize this solubility effect, the addition of seed crystals of 25-hydroxy-(3β)-cholest-5-en-3-sulfate organic cationic salt to the reaction to modify the product crystal shape was tested. As the reaction proceeds by charging the sulfur trioxide-pyridine complex, the gel-like solids of 25-hydroxy-(3β)-cholest-5-en-3-sulfate organic cationic salt produced during the sulfation reaction turned into an amorphous slurry with a larger particle size. This allowed for control of the solubility of the generated 25-hydroxy-(3β)-cholest-5-en-3-sulfate organic cationic salt in the reaction mixture. This also resulted in minimizing the formation of bis-sulfated product 5-cholesten-3β-25-diol-disulfate in the reaction mixture.

25-hydroxy-(3β)-cholest-5-en-3-ol was dissolved with 2-methyl tetrahydrofuran (30V); and heated to about 35-40° C. The solution was cooled to about 20±5° C. and seed crystals of 25-hydroxy-(3β)-cholest-5-en-3-sulfate organic cationic salt were added. The sulfating agent sulfur-trioxide-pyridine complex was added in four portions held 2 hours 4 of Table 20, the holding time was extended to mimic time expansion. To control the competition reactions between reagent hydrolysis and bis-sulfation, reagent hydrolysis was evaluated by adding water and holding it for one hour. This approach maximized excess hydrolysis. Pyridine was then added to minimize product hydrolysis (items, Table 20). As summarized in Table 20, the addition of water for 1 hour followed by mixing with pyridine overnight afforded the highest yield of the 25-hydroxy-(3β)-cholest-5-en-3-sulfate organic cationic salt product and the lowest amount of bis-sulfated product and desmosterol impurity.

During quenching of excess unreacted sulfation reagent, it was determined that the agitation speed can play a role in competition between formation of bis-sulfated product 5-cholesten-3β-25-diol-disulfate and reagent quench. At high agitation speed, the unquenched sulfur trioxide-pyridine complex agglomerates brake apart, allowing further reaction with the 25-hydroxy-(3β)-cholest-5-en-3-sulfate organic cationic salt product. At slow agitation speed agglomerated complex remains at the bottom of the reactor minimizing this side reaction. Bis-sulfated product 5-cholesten-3β-25-diol-disulfate formation is observed under these reaction conditions in a range of 2-5%. Isolated crude 25-hydroxy-(3β)-cholest-5-en-3-sulfate organic cationic salt product was stable enough for further purification.

TABLE 20

Quenching of unreacted Sulfur Trioxide-Pyridine Sulfation Reagent

| | HPLC area (%) | | | | | |
|---|---|---|---|---|---|---|
| Item | Bis-sulfated product 5-cholesten-3β-25-diol-disulfate | 25-hydroxy-(3β)-cholest-5-en-3-sulfate organic cationic salt | Desmosterol sulfate | 25-hydroxy-(3β)-cholest-5-en-3-ol | Stage | Time |
| 1 | 4.4 | 92.9 | 1.329 | 1.26 | IPC | 1 h |
| | 5.0 | 92.0 | 1.46 | 1.54 | Solid | |
| 2 | 1.4 | 97.3 | 0.58 | 0.67 | IPC | 1 h |
| | 2.8 | 94.3 | 0.68 | 2.16 | Solid | |
| 3 | 1.9 | 96.6 | 0.79 | 0.61 | IPC | 1 h |
| | 2.6 | 95.8 | 0.46 | 1.11 | Solid | |
| 4 | 1.1 | 96.4 | 0.77 | 1.67 | IPC | overnight |
| | 3.5 | 95.4 | 0.27 | 0.86 | Solid | |
| 5 | 1.8 | 97.0 | 0.69 | 0.57 | IPC | Water 1 h, pyridine overnight |
| | 2.6 | 96.1 | 0.62 | 0.59 | Solid | |

*IPC-in process control apart from each other. Water (2 equivalents) was added to the slurry and held for 1 hour. At this point, agitation was reduced to a minimum vortex deep. Pyridine (2 equivalents) in 2-methyl tetrahydrofuran was added and the slurry was held for 12 hours or longer. Crude 25-hydroxy-(3β)-cholest-5-en-3-sulfate organic cationic salt product was collected by filtration and washed with 2-methyl tetrahydrofuran—pyridine (5%). The presence of bis-sulfated product 5-cholesten-3β-25-diol-disulfate was estimated to be about 2-5% in the crude product.

Quenching of Unreacted Sulfur Trioxide-Pyridine Sulfation Reagent

Quenching excess unreacted sulfur-trioxide pyridine sulfation reagent was evaluated using two equivalents of water and pyridine to keep basic conditions and to avoid hydrolysis of the 25-hydroxy-(3β)-cholest-5-en-3-sulfate organic cationic salt product. In Items 1-3 of Table 20, water and pyridine were added simultaneously and held for one hour; then, the product was isolated by vacuum filtration. In item Liquid Chromatography and Recrystallization of 25-hydroxy-(3β)-cholest-5-en-3-sulfate Organic Cationic Salt Product The 25-hydroxy-(3β)-cholest-5-en-3-sulfate organic cationic salt product was purified using a plug column emplying a silica gel (≥mass equivalent) stationary phase and a mixture of methylene chloride-methanol (85:15) and pyridine (1%) mobile phase. The chromatographic column was prepared with silica gel (≥mass-eq)/DCM-Pyridine (1%), with a 1:2 ratio diameter-silica gel. The column was carefully prepared to avoid disturbing the silica gel top layer. Crude 25-hydroxy-(3β)-cholest-5-en-3-sulfate organic cationic salt product was dissolved in methylene chloride-methanol (1:1)-pyridine (1%) (2.4V), the solution charged to the column, and rinsed with methylene chloride-methanol (15%)-Pyridine (1%) (2V). The column was eluted with methylene chloride-methanol (15%)-Pyridine (1%) (~75V). Samples of about 10V were taken and monitored by thin layer chromatography (mobile phase methylene chloride-methanol 7:3 one drop pyridine and CAM stain). Fractions containing the 25-hydroxy-(3β)-cholest-5-en-3-sulfate organic cationic salt product were combined and the fractions containing bis-sulfated product were excluded.

The 25-hydroxy-(3β)-cholest-5-en-3-sulfate organic cationic salt product was isolated and purified from collected fractions by two different processes:

Isolation and Recrystallization Process (IP)-A. Fractions with the product from the plug column were concentrated under the constant volume technique. The 25-hydroxy-(3β)-cholest-5-en-3-sulfate organic cationic salt product solution was added to the initial constant volume (28V) mixture of 2-methyl tetrahydrofuran-heptane (1:2)—Particle seeds of 25-hydroxy-(3β)-cholest-5-en-3-sulfate organic cationic salt product were added while synchronizing distillation and addition. Pressure was maintained between 20-25 in. Hg. Under these conditions, the product precipitated out immediately and remains as a slurry during the distillation. The slurry temperature is adjusted to 2β-25° C. and held for a minimum of 1 hour. The product is collected by filtration and rinsed with 2-methyl tetrahydrofuran-heptane (1:2) followed by heptane. The collected material was dried at 30-35° C. under vacuum for 24 hours.

Isolation Process (IP)-B. Fractions with the product from the plug column are concentrated under vacuum to ~7V. If the solution remained or turned cloudy or solids were observed, methylene chloride was added until a clear solution was obtained. This concentrated 25-hydroxy-(3β)-cholest-5-en-3-sulfate organic cationic salt product solution was added dropwise to a mixture of 2-methyl tetrahydro-furan-heptane (1:3) containing seeds of the 25-hydroxy-(3β)-cholest-5-en-3-sulfate organic cationic salt for about 1 hour to 1.5 hours. The product was rinsed in the container with methylene chloride-methanol (1:1) (0.5V) for 1 hour at 2β-25° C. After aging the slurry, the product was collected by filtration and rinsed with 2-methyl tetrahydrofuran-heptane (1:3), followed by heptane. The solids were dried at 30-35° C. under vacuum for 24 hours.

The purity of 25-hydroxy-(3β)-cholest-5-en-3-sulfate organic cationic salt product obtained by each isolation and recrystallization process is summarized in Table 21.

3. The crystalline form of 25HC3S sodium of claim 1, wherein the crystalline form is Form I of crystalline 25HC3S sodium.

4. The crystalline form of 25HC3S sodium of claim 1, wherein the crystalline form is Form II of crystalline 25HC3S sodium.

5. The crystalline form of 25HC3S sodium of claim 1, wherein the crystalline form is Form XI of crystalline 25HC3S sodium.

6. The crystalline form of 25HC3S sodium of claim 1, wherein the crystalline form is a crystalline anhydrate of crystalline 25HC3S sodium.

7. The crystalline form of 25HC3S sodium of claim 1, wherein the crystalline form is Form XIII of crystalline 25HC3S sodium.

8. The crystalline form of 25HC3S sodium of claim 1, wherein the crystalline form is Form III of crystalline 25HC3S sodium.

9. The crystalline form of 25HC3S sodium of claim 1, wherein the crystalline form is Form V of crystalline 25HC3S sodium.

10. The crystalline form of 25HC3S sodium of claim 1, wherein the crystalline form is Form IX of crystalline 25HC3S sodium.

11. A method of treating one or more of hypercholesterolemia, hypertriglyceridemia, nonalcoholic fatty liver disease (NAFLD), nonalcoholic steatohepatitis (NASH), alcoholic hepatitis, acute kidney injury (AKI), psoriasis, and atherosclerosis, comprising administering to a patient in need thereof an effective amount of a crystalline form of 25HC3S sodium of claim 1.

12. The method of claim 11, wherein the crystalline form of 25HC3S sodium is the hydrate of crystalline 25HC3S sodium.

13. The method of claim 11, wherein the crystalline form of 25HC3S sodium is Form I of crystalline 25HC3S sodium.

14. The method of claim 11, wherein the crystalline form of 25HC3S sodium is Form II of crystalline 25HC3S sodium.

15. A pharmaceutical composition comprising a crystalline form of 25HC3S sodium of claim 1, and at least one pharmaceutically acceptable excipient.

TABLE 21

| | | Purity 25-hydroxy-(3β)-cholest-5-en-3-sulfate organic cationic salt product after Isolation and recrystallization | | | | | |
| | | HPLC area (%) | | | | | |
| Step | Scale (g) | Bis-sulfated product 5-cholesten-3β-25-diol-disulfate | 25-hydroxy-(3β)-cholest-5-en-3-sulfate organic cationic salt | Desmosterol sulfate | 25-hydroxy-(3β)-cholest-5-en-3-ol | Isolation Process | Yield |
|---|---|---|---|---|---|---|---|
| Sulfation | 430 | 3.89 | 95.23 | 0.40 | 0.43 | — | — |
| Purified | 540 | ND | 99.88 | 0.12 | ND | (IP)-A | 75.1 |
| Sulfation | 40 | 2.28 | 96.83 | 0.75 | 0.14 | — | — |
| Purified | 45 | ND | 99.45 | 0.51 | ND | (IP)-B | 84.0 |

What is claimed is:

1. A crystalline form of 5-cholesten-3β-25-diol-3-sulphate (25HC3S) sodium, selected from Form I, Form II, Form III, Form V, Form IX, Form XI, Form XIII, a hydrate form and an anhydrate form.

2. The crystalline form of 25HC3S sodium of claim 1, wherein the crystalline form is a crystalline hydrate of crystalline 25HC3S sodium.

16. The pharmaceutical composition of claim 15, wherein the crystalline form of 25HC3S sodium is the hydrate of crystalline 25HC3S sodium.

17. The pharmaceutical composition of claim 15, wherein the crystalline form of 25HC3S sodium is Form I of crystalline 25HC3S sodium.

18. The pharmaceutical composition of claim 15, wherein the crystalline form of 25HC3S sodium is Form II of crystalline 25HC3S sodium.

19. A method of treating one or more of hypercholesterolemia, hypertriglyceridemia, nonalcoholic fatty liver disease (NAFLD), nonalcoholic steatohepatitis (NASH), alcoholic hepatitis, acute kidney injury (AKI), psoriasis, and atherosclerosis, comprising administering to a patient in need thereof an effective amount of a pharmaceutical composition of 25HC3S sodium of claim 15.

20. A composition comprising the crystalline form of 25HC3S sodium of claim 1, wherein the composition comprises two or more of Form I of 25HC3S sodium, Form II of 25HC3S sodium, Form III of 25HC3S sodium, Form V of 25HC3S sodium, Form IX of 25HC3S sodium, Form XI of 25HC3S sodium, and Form XIII of 25HC3S sodium.

\* \* \* \* \*